US007709454B2

(12) United States Patent
Ruiz I Altaba et al.

(10) Patent No.: US 7,709,454 B2
(45) Date of Patent: May 4, 2010

(54) METHODS AND COMPOSITIONS FOR INHIBITING TUMORIGENESIS

(75) Inventors: Ariel Ruiz I Altaba, Geneva (CH); Barbara Stecca, Geneva (CH)

(73) Assignee: New York University, New York, NY (US)

(*) Notice: Subject to any disclaimer, the term of this patent is extended or adjusted under 35 U.S.C. 154(b) by 263 days.

(21) Appl. No.: 11/407,702

(22) Filed: Apr. 20, 2006

(65) Prior Publication Data

US 2007/0009530 A1 Jan. 11, 2007

Related U.S. Application Data

(63) Continuation-in-part of application No. 10/930,723, filed on Aug. 31, 2004, and a continuation-in-part of application No. 10/927,951, filed on Aug. 29, 2004, now abandoned, which is a continuation-in-part of application No. 10/456,954, filed on Jun. 6, 2003, now abandoned, which is a continuation-in-part of application No. 09/825,155, filed on Apr. 3, 2001, now abandoned, which is a continuation of application No. 09/102,491, filed on Jun. 22, 1998, now Pat. No. 6,238,876, said application No. 10/927,951 is a continuation-in-part of application No. 10/414,267, filed on Apr. 15, 2003, now abandoned.

(60) Provisional application No. 60/050,286, filed on Jun. 20, 1997, provisional application No. 60/372,508, filed on Apr. 15, 2002.

(51) Int. Cl.
*A01N 43/04* (2006.01)
*C12Q 1/68* (2006.01)
*C12N 5/00* (2006.01)
*C12P 19/34* (2006.01)
*C07H 21/04* (2006.01)

(52) U.S. Cl. ............... 514/44; 435/6; 435/91.31; 435/375; 435/455; 536/23.1; 536/24.5

(58) Field of Classification Search .......... 435/6, 435/91.31, 455, 91.1, 375; 514/1, 2, 44; 536/23.1, 24.5
See application file for complete search history.

(56) References Cited

U.S. PATENT DOCUMENTS

| 5,247,007 | A | | 9/1993 | Nitta et al. | |
|---|---|---|---|---|---|
| 5,734,039 | A | * | 3/1998 | Calabretta et al. | 536/24.5 |
| 6,238,876 | B1 | | 5/2001 | Altaba | |
| 6,329,203 | B1 | | 12/2001 | Bennett et al. | |
| 6,506,559 | B1 | | 1/2003 | Fire et al. | |
| 2004/0248094 | A1 | | 12/2004 | Ford et al. | |
| 2005/0054568 | A1 | * | 3/2005 | Ling et al. | 514/12 |

FOREIGN PATENT DOCUMENTS

WO   WO 2004/020599   * 3/2004

OTHER PUBLICATIONS

Peracchi, A. et al., Rev. Med. Virol., vol. 14, pp. 47-64 (2004).*
Chirila, T. et al, Biomaterials, vol. 23, pp. 321-342 (2002).*
Agrawal, S. et al., Molecular Med. Today, vol. 6, pp. 72-81 (2000).*
Branch, A., Trends in Biochem. Sci., vol. 23, pp. 45-50 (1998).*
Opalinska, J.B., et al., Nature Rev., vol. 1, pp. 503-514 (2002).*
Crooke, S.T., Annu. Rev. Med., vol. 55, pp. 61-95 (2004).*
Dahmane, N. et al., Nature, vol. 389, pp. 876-881 (1997).*
Reynolds, A., et al., Nature Biotech., vol. 22, No. 3, pp. 326-330 (2004).*
Ackerman, et al., Neoplasms with follicular differntiation. Philadelphia Lea and Febinger (1993).
Alexandre, et al., Genes and Dev. 10, 2003-2013 (1996).
Belloni, et al. Nature Genetics 14, 353-356 (1996).
Blessing, et al. Genese Dev. 7, 204-215 (1993).
Bitgood, et al., Dev. Biol. 172, 126-138 (1996).
Byrne, et al., Development 120, 2369-2383 (1994).
Cerroni, et al., J. Cutan Pathol 21,398-403 (1994).
Chen, et al., Cell 87, 553-563 (1996).
Chiang, et al., Nature 383, 407-413 (1996).
Concordet, et al., Development 122, 2835-2846 (1996).
Cotsarelis, et al., Cell 61, 1329-1337 (1990).
Dominguez, et al., Science 272, 1621-1625 (1996).
Echelard, et al., Cell 75, 1417-1430 (1993).
Ekker, et al., Development 121, 2337-2347 (1995).
Elder, Ed. in chief, Lever's Histopathology of the skin, 8th Edition, Philadelphia, Lippincott-Raven (1997).
Epstein, et al., Development 122, 2885-2894 (1996).
Ericson, et al., cell 87, 661-673 (1996).
Forbes, et al., Mutation Research 276, 299-306 (1992).
Fuller, et al., Mutation Research 276, 299-306 (1992).
Gailani, et al., Nature Genet. 14, 78-81 (1996).
Goodrich, et al., Genes Dev. 10, 301-312 (1996).
Grimwood, et al., Society for Invest. Derm. 86, 191-194 (1986).
Hahn, et al., Cell 85, 841-851 (1996).
Hammerschmidt, et al, Genes and Dev. 10, 647-658 (1996).
Hepker, et al., Develooment 124 549-558 (1997).
Hui, et al., Development Biology 162, 402-413 (1994).
Hynes et al., Neuron 15, 35-34 (1995).
Iseki, et al., Biochem, Biophys. res. Commun. 218, 688-693 (1996).

(Continued)

*Primary Examiner*—Jane Zara
(74) *Attorney, Agent, or Firm*—Klauber & Jackson LLC

(57) ABSTRACT

The present invention relates to compounds, small interfering RNAs and compositions and methods of inhibiting tumorigenesis and methods of inhibiting tumor cell growth and proliferation using agents that inhibit the hedgehog and Gli signaling pathway, including agents that inhibit GLI synthesis and/or function. The present invention also relates to particular biomarkers that can be used in the diagnosis and prognosis of melanomas. Methods of treating cancer, including melanoma are also provided using small organic compounds, siRNAs and blocking antibodies that inhibit or block the SHH/GLI pathway. In addition, the use of agents that inhibit other signaling pathways is contemplated for use as second agents to be used in conjunction with the inhibitors of the GLI pathway.

5 Claims, 32 Drawing Sheets

OTHER PUBLICATIONS

Johnson, et al., Science 272, 1668-1671 (1996).
Kelsey-Motzny, et al., Mechanisms of Development 52, 137-150 (1995).
Kinzler, et al., Mol. Cell Biol. 10, 634-642 (1990).
Kinzler, et al., Science 236, 70-73 (1987).
Krauss, et al., Cell 75, 1431-1444 (1993).
Lai, et al., Development 121, 2349-2360 (1995).
Liem, et al., cell 82, 969-979 (1995).
Marigo, et al., Dev. Biol. 180, 273-283 (1996).
Marigo, et al., Proc. Natl. Acad. Sci, USA 93, 9346-9351 (1996).
Marti, et al., Nature 375, 322-325 (1995).
Mullor, et al., Development 124, 1227-1237 (1997).
Nohno, et al., Biphys Res Comm. 206, 33-39 (1995).
Oro, et al. Science 276: 817-21 (1997).
Platt, et al., Mech. Dev. in press (1997).
Roberts, et al., Cancer Research 49, 5407-5413 (1989).
Roelink, et al., Cell 76, 761-775 (1994).
Roessler, et al., Nature Genetics 14, 357-360 (1996).
Riddle, et al., Cell 75, 1401-1418 (1993).
Ruppert, et al., Mol. Cell Biol 11, 1724-1728 (1991).
Ruppert, et al., Mol. Cell Biol. 10, 54088-5415 (1990).
Ruiz i Altaba, et al., Natl. Acad. Sci. USA 90, 8268-8272 (1993).
Ruiz i Altaba, et al., Mech. Dev. 44, 91-108 (1993).
Ruiz i Altaba, et al, Mol. Cell. Neurosci. 6, 106-121 (1995).
Ruiz i Altaba, In Essential Developmental Bioilogy—A Practical Approach, (C. Stern and P.W.H. Holland) IRL Press, Oxford (1993).
Salgaller, et al., Cancer Letters 57, 243-253 (1991).
Scharen-Wiemers, et al., Histochemistry 100, 431-440 (1993).
Shimizu, et al., J. Dermatol 14, 359-363 (1987).
St. Jacques, et al., Curr Biol. 8:1058-68 (1998).
Stone, et al., Nature 384, 129-134 (1996).
Urano, et al., Society for Invest. Derm. 104, 928-932 (1995).
van der Schroeff, et al., Society for Invest. Derm. 94, 423-425 (1990).
von Ohnen, et al., Proc. Natl. Acad. Sci. USA. 94, 2404-2409 (1997).
Wallace, et al. Arch. pathol 50, 199 (1950).
Walterhouse, et al., Development Dyn. 196, 91-102 (1993).
Wilson, et al., Nature 376, 331-333 (1995).
Xiao, et al., Pediatr Neurosurg 20, 178-182 (1994).
Dahmane, et al., Development & disease, 128, 5201-5212 (2001).
Palma, et al., Development, 131, 337-345 (2004).
Ruiz i Altaba, et al., Nat Rev cancer, 2, 361-372 (2002).
Ruiz i Altaba, et al., Cancer Letters, 204, 145-157 (2004).
Sanchez, et al, Mech. dev. 122, 223-230 (2005).
Sanchez, et al., cancer Res., 65, 2990-2992 (2005).
Sanchez, et al., PNAS, 101, 12561-12566 (2004).
Stecca, et al., J. Neurobiol. 64, 476-490 (2005).
Stecca, et al., Trends Mol. Med., 11, 199-203 (2005).
Pai, et al., Gene Therapy 13, 464-477 (2006).
Ryther, et al., Gene Therapy 12, 5-11 (2005).
Schiffelers, et al., Nucleic Acids Research 2004; 32: e49.
Elbashir, et al., Nature, 2001, 411:494-498.
Holen, et al. (Nucleic Acids Research, vol. 30(8); 1757-1766, 2002).
Hammond, et al. (Nature, 2001, vol. 2, pp. 110-119).
Opalinska, et al., Nature Reviews 1, 503-514 (2002).
Caplen, N.J. Trends in Biotechnology vol. 20 (2), 49-51 (2002).
Gura (Science, v. 278, 1997, pp. 1041-1042).
Bellone, et al., (Immunology Today, v20(10), 1999, pp. 457-462).
Gaiger, et al., (Blood, vol. 96, No. 4, Aug. 2000, pp. 1480-1489).

* cited by examiner

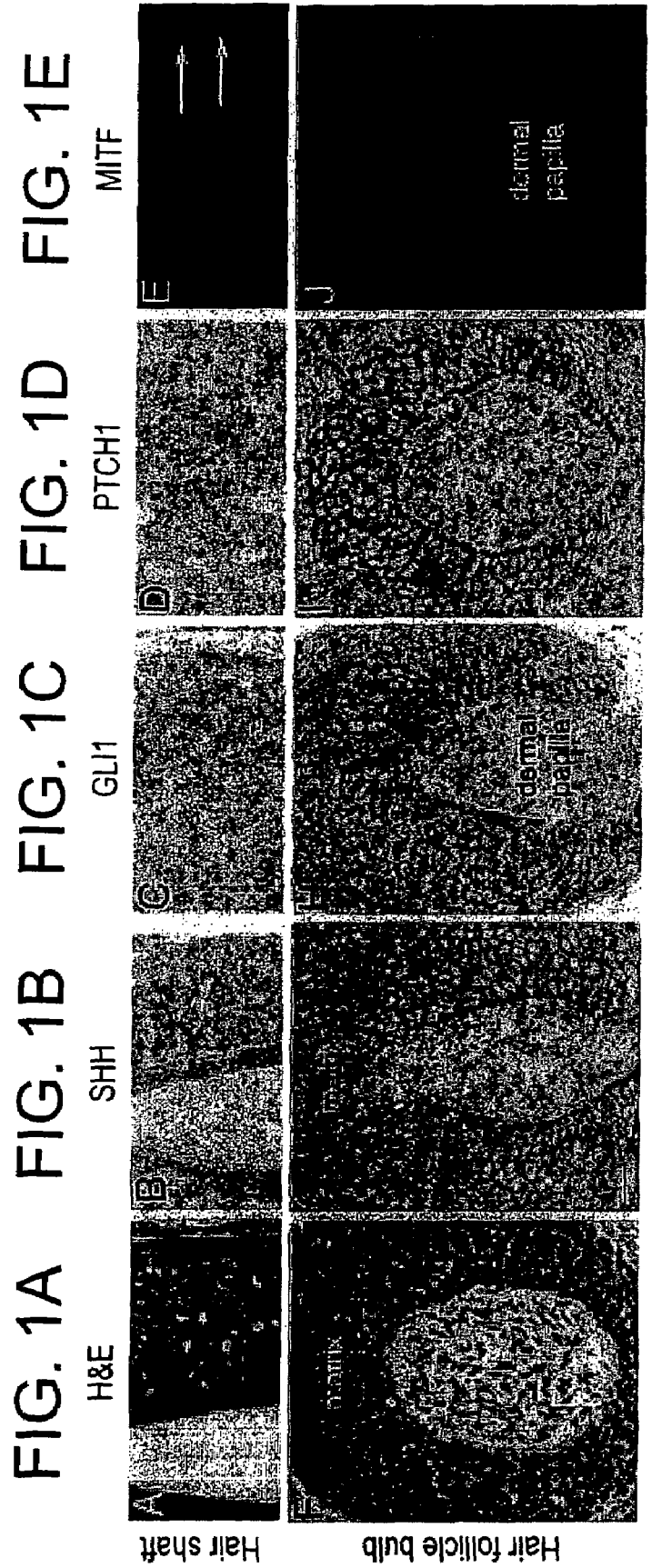

BrdU+DAPI

BrdU+DAPI control cyclopamine cyclopamine control cyclopamine

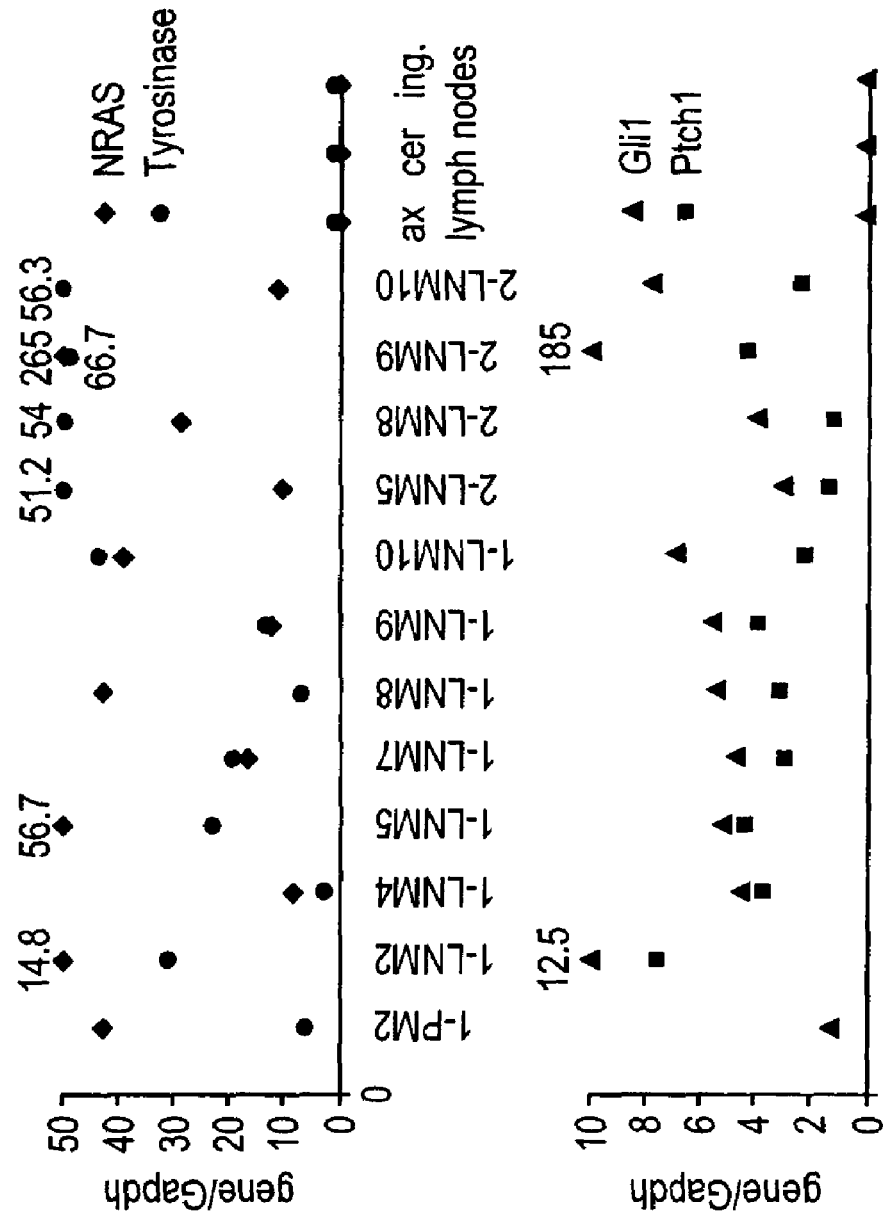
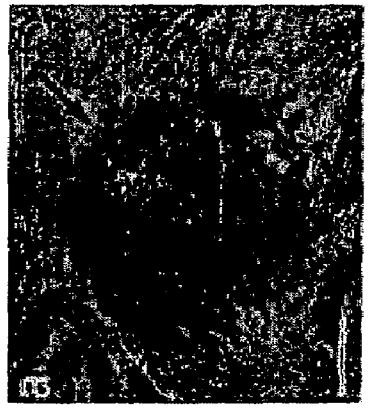

SK-MEL2

COS7

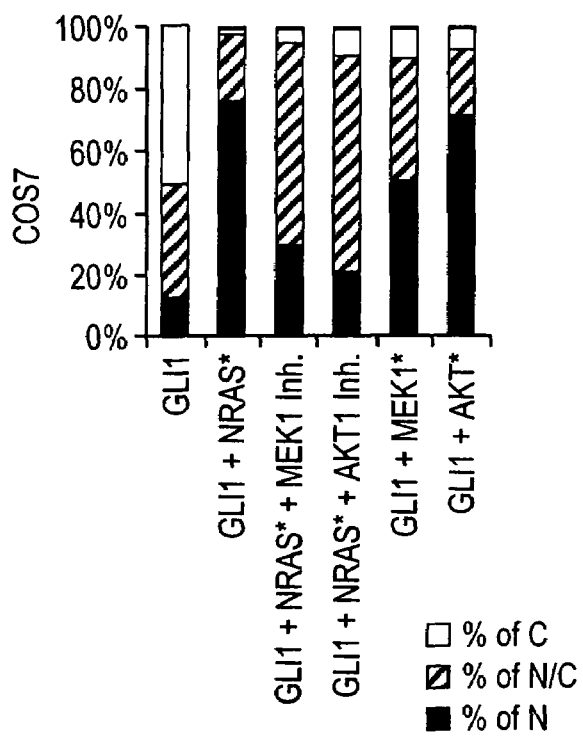
FIG. 11D
FIG. 11E
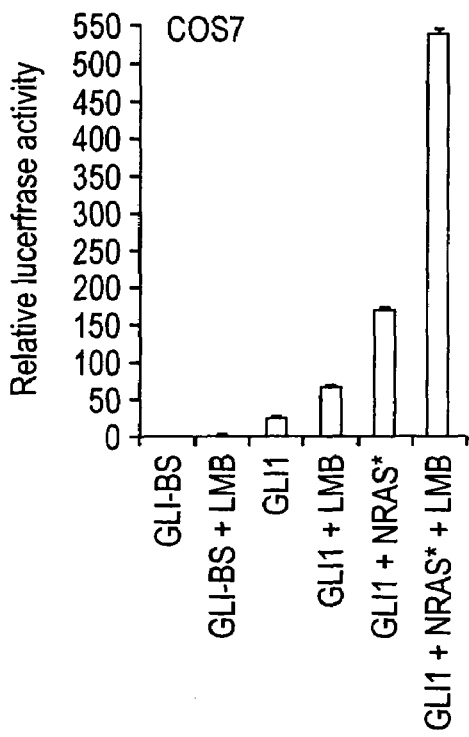
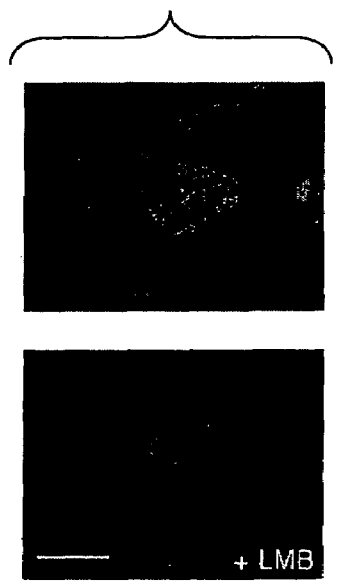
FIG. 11F
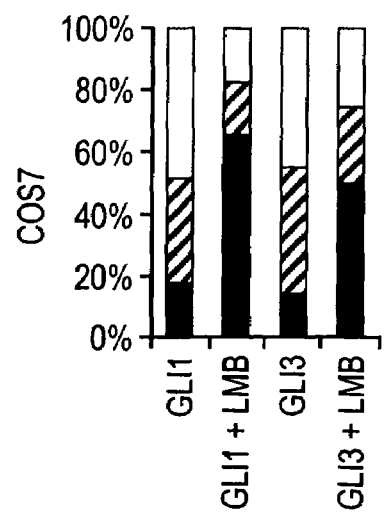
FIG. 11G

- cyc 5um
- sh6 20um
- sh6 20um + cyc 5um

- cyc 5um
- MEKi 1um
- MEKi 1um + cyc 5um

PPMTI

FPP-based FTI

SCH44342

SCH66336

$R_1$=H     $R_3$=CH$_3$ $R_2$=⌬     $R_4$=⌬⌬

R$_1$ & R$_2$ GGTI-287     R$_3$ & R$_4$ GGTI-298

R$_2$ & R$_3$ GGTI-286     R$_1$ & R$_4$ GGTI-297

METHODS AND COMPOSITIONS FOR INHIBITING TUMORIGENESIS

CROSS-REFERENCE TO RELATED APPLICATIONS

The present application is a Continuation-in-Part of U.S. Ser. No. 10/930,723, filed Aug. 31, 2004 and of U.S. Ser. No. 10/927,951, filed Aug. 29, 2004 now abandoned, both of which are a Continuation-in-Part of U.S. Ser. No. 10/456,954, filed Jun. 6, 2003 now abandoned, which is a Continuation-in-Part of non-provisional application U.S. Ser. No. 09/825,155, filed Apr. 3, 2001 now abandoned, which is a Continuation of U.S. Ser. No. 09/102,491, filed Jun. 22, 1998, now U.S. Pat. No. 6,238,876, which claims benefit of priority to provisional application 60/050,286, filed Jun. 20, 1997; and is also a Continuation-in-Part of non-provisional application U.S. Ser. No. 10/414,267, filed Apr. 15, 2003 now abandoned, which claims the benefit of priority to provisional application U.S. Ser. No. 60/372,508, filed Apr. 15, 2002. Applicants claim the benefit of all of the above applications under 35 U.S.C. §119(e) and 35 U.S.C. §120, and the disclosures of all of the above applications are incorporated herein by reference in their entireties.

FIELD OF THE INVENTION

The present invention relates generally to the diagnosis and treatment of pathologies involving tumor formation, cancer and neoplasia, and more particularly to compositions and methods of inhibiting tumorigenesis, tumor growth and tumor survival using agents that inhibit the sonic hedgehog (SHH or HH) and GLI signaling pathway. The present invention also relates to particular biomarkers that can be used in the diagnosis and prognosis of cancer. Methods of treating cancer, including but not limited to melanoma, are also provided through the use of relevant therapeutic agents based on their effect on the level of expression and/or activity of GLI genes. Small organic compounds, siRNAs and blocking antibodies that inhibit or block the SHH/GLI pathway are contemplated for the preparation of therapeutic compositions and methods of use. Furthermore, combination therapy with an agent that inhibits the GLI pathway and an agent that inhibits the RAS-RAF-MEK and AKT pathways, for treating melanomas, prostate cancer and other cancers and tumorous growths, is also contemplated.

BACKGROUND OF THE INVENTION

Inductive signaling plays a critical role in both normal and disease development as developmental pathways that become unregulated in the adult can lead to abnormal patterning, overproliferation and neoplasia. One signaling pathway that is involved in several patterning events during embryogenesis is that triggered by secreted sonic hedgehog (Shh) (Echelard, Y., Epstein, D. J., St-Jacques, B., Shen, L., Mohler, J., McMahon, J. A. & McMahon, A. P., Cell 75, 1417-1430 (1993); Riddle, R., Johnson, R. L., Laufer, E. & Tabin, C., Cell 75, 1401-1418 (1993); Krauss, S., Concordet, J.-P. & Ingham, P. W, Cell 75, 1431-1444 (1993); Roelink, H., Augsburger, A., Heemskerk, J., Korzh, V., Norlin, S., Ruiz i Altaba, A., Tanabe, Y., Placzek, M., Edlund, T., Jessell, T. M. & Dodd, J., Cell 76, 761-775 (1994)). Shh binding to the membrane patched (ptc)-smoothened (smo) receptor complex elicits a cascade of cytoplasmic signal transduction events, including the inhibition of protein kinase A (PKA) (Fan, C.-M., Porter, J. A., Chiang, C., Chang, D. T., Beachy, P. A. & Tessier-Lavigne, M., Cell 81, 457-465 (1995); Hynes, M., Porter, J. A., Chiang, C., Chang, D., Tessier-Lavigne, M., Beachy, P. A. & Rosenthal, A., Neuron 15, 35-34 (1995); Concordet, J.-P., Lewis, K. E., Moore, J., Goodrich, L. V., Johnson, R. L., Scott, M. P. & Ingham, P. W., Development 122, 2835-2846 (1996); Epstein, D. J., Martí, E., Scott, M. P. & McMahon, A. P., Development 122, 2885-2894 (1996); Goodrich, L. V., Johnson, R. L., Milenkovic, L., McMahon, J. A. & Scott, M. P., Genes Dev. 10, 301-312 (1996); Hammerschmidt, M., Bitgood, M. J. & McMahon, A. P., Genes and Dev. 10, 647-658 (1996); Marigo, V., Johnson, R. L., Vortkamp, A. & Tabin, C. J., Dev. Biol. 180, 273-283 (1996); Stone, D. M., Hynes, M., Armanini, M., Swanson, T. A., Gu, Q., Johnson, R. L., Scott, M. P., Pennica, D., Goddard, A., Phillips, H., Noll, M., Hooper, J. E., de Sauvage, F. & Rosenthal, A., Nature 384, 129-134 (1996)) that leads to the transcription of the zinc finger transcription factor gene Gli1 (Marigo, V., Johnson, R. L., Vortkamp, A. & Tabin, C. J., Dev. Biol. 180, 273-283 (1996); Lee, J., Platt, K. A., Censullo, P. & Ruiz i Altaba, A., Development (1997)). Gli1 is a proto-oncogene first isolated as an amplified gene in a glioma that can transform fibroblasts in cooperation with E1A (Kinzler, K. W., Bigner, S. H., Bigner, D. D., Trent, J. M., Law, M. L., O'Brien, S. J., Wong, A. J. & Vogelstin, B., Science 236, 70-73 (1987); Ruppert, J. M., Vogelstein, B. & Kinzler, K. W., Molecular and Cellular Biology 11, 1724-1728 (1991)). Gli1 is a member of a family comprising two other related genes: Gli2 and Gli3 (Ruppert, J. M., Vogelstein, B., Arheden, K. & Kinzler, K. W., Mol. Cell Biol. 10, 5408-5415 (1990); Hui, C.-C., Slusarski, D., Platt, K. A., Holmgren, R. & Joyner, A. L., Developmental Biology 162, 402-413 (1994)). However, only Gli1 has been shown to be a target of Shh and mimic its effects (Lee, J., Platt, K. A., Censullo, P. & Ruiz i Altaba, A., Development (1997)). In Drosophila, hedgehog signaling (Forbes, A. J., Nakano, Y., Taylor, A. M. & Ingham, P. W., Development Supplement 115-124 (1993)) similarly leads to the action of cubitus interruptus (ci), a Gli homolog that activates transcription of hedgehog-target genes (Dominguez, M., Brunner, M., Hafen, E. & Basler, K., Science 272, 1621-1625 (1996); Alexandre, C., Jacinto, A. & Ingham, P. W., Genes and Dev. 10, 2003-2013 (1996); Hepker, J., Wang, Q.-T., Motzny, C. K., Holmgren, R. & Orenic, T. V., Development 124, 549-558 (1997); von Ohnen, T., Lessing, D., Nusse, R. & Hooper, J. E., Proc. Natl. Acad. Sci. USA. 94, 2404-2409 (1997); Mullor, J. L., Calleja, M., Capdevila, J. & Guerrero, I., Development 124, 1227-1237 (1997)).

One of the processes in which Shh signaling is involved is the differentiation of ventral neural tube cell types acting as a notochord and floor plate-derived signal (Echelard, Y., Epstein, D. J., St-Jacques, B., Shen, L., Mohler, J., McMahon, J. A. & McMahon, A. P., Cell 75, 1417-1430 (1993); Roelink, H., Augsburger, A., Heemskerk, J., Korzh, V., Norlin, S., Ruiz i Altaba, A., Tanabe, Y., Placzek, M., Edlund, T., Jessell, T. M. & Dodd, J., Cell 76, 761-775 (1994); Martí, E., Bumcrot, D. A., Takada, R. & McMahon, A. P., Nature 375, 322-325 (1995); Ruiz i Altaba, A., Roelink, H. & Jessell, T. M., Mol. Cell. Neurosci. 6, 106-121 (1995); Chiang, C., Litingtung, Y., Lee, E., Young, K. E., Corden, J. L., Westphal, H. & Beachy, P. A., Nature 383, 407-413 (1996); Ericson, J., Morton, S., Kawakami, A., Roelink, H. & Jessell, T. M., Cell 87, 661-673 (1996)).

In addition to effects on neural tissue, it has been found that ectopic expression of Shh and Gli1 also leads to the activation of Shh signaling target genes in epidermal non-neural ectoderm. Injected Shh induced the ectopic expression of Gli1, HNF-3β and Shh (Ruiz i Altaba, A., Roelink, H. & Jessell, T. M., Mol. Cell. Neurosci. 6, 106-121 (1995)), and ectopic expression of Gli1 induced the ectopic expression of HNF-3β and Shh (Lee, J., Platt, K. A., Censullo, P. & Ruiz i Altaba, A. Gli1 is a target of sonic hedgehog that induces ventral neural tube development. *Development* (1997)). Together, these results indicated that both neural and epidermal cells have functional reception and transduction mechanisms for Shh and can respond by activating the expression of Shh/Gli1 target genes even though epidermal cells do not normally receive the Shh signal at this stage.

Furthermore, SHH signaling has been implicated in many aspects of animal development, acting through the transmembrane proteins PATCHED1 (PTCH1) and SMOH to activate the GLI zinc-finger transcription factors (Ingham, P. & McMahon, A., *Genes Dev.* 15, 3059-87 (2001); Ruiz i Altaba, A., Sanchez, P. & Dahmane, N., *Nat. Rev. Cancer* 2, 361-372 (2002).

A different signaling pathway is triggered by HEDGEHOG (HH) proteins, acting through the transmembrane proteins PATCHED1 (PTCH1) and SMOOTHENED (SMOH), to regulate the three GLI zinc finger transcription factors. SHH-GLI signaling is required for the growth of certain sporadic cancers, including basal cell carcinomas (BCCs) (Dahmane, N., et al., (1997). Activation of the transcription factor Gli1 and the Sonic hedgehog signalling pathway in skin tumours. Nature 389, 876-881; Williams et al., (2003) Identification of a small molecule inhibitor of the hedgehog signaling pathway: effects on basal cell carcinoma-like lesions. Proc Natl Acad Sci USA. 100, 4616-4621; Athar et al., (2004) Inhibition of smoothened signaling prevents ultraviolet B-induced basal cell carcinomas through regulation of Fas expression and apoptosis. Cancer Res. 64, 7545-7552, medulloblastomas (Dahmane et al., (2001) The Sonic Hedgehog-Gli pathway regulates dorsal brain growth and tumorigenesis. Development 128, 5201-5212; Berman et al., (2002) Medulloblastoma growth inhibition by hedgehog pathway blockade. Science 297, 1559-1561, gliomas (Dahmane et al., (2001) The Sonic Hedgehog-Gli pathway regulates dorsal brain growth and tumorigenesis. Development 128, 5201-5212, pancreatic (Thayer et al., (2003) Hedgehog is an early and late mediator of pancreatic cancer tumorigenesis. Nature 425, 851-856, stomach (Berman et al., (2003) Widespread requirement for Hedgehog ligand stimulation in growth of digestive tract tumours. Nature 425, 846-851 and prostate cancers (Sanchez et al., (2004) Inhibition of prostate cancer proliferation by interference with SONIC HEDGEHOG-GLI1 signaling. Proc. Natl. Acad. Sci. USA. 101, 12561-12566; Karhadkar et al., (2004) Hedgehog signalling in prostate regeneration, neoplasia and metastasis. Nature 431, 707-712; Sheng et al., (2004) Sheng, T., Li, C., Zhang, X., Chi, S., He, N., Chen, K., McCormick, F., Gatalica, Z., Xie, J. (2004) Activation of the hedgehog pathway in advanced prostate cancer. Mol Cancer. 3, 29).

Alterations in several different oncogenic signaling pathways are found in many cancer types, begging the question of how such different events converge to produce reproducible and diagnosable tumors. An exception appears to be cutaneous melanomas in which activation of the RAS-RAF-MEK/AKT signaling is ubiquitous (Chin, (2003) The genetics of malignant melanoma: lessons from mouse and man. Nat Rev Cancer. 3, 559-570; Chudnovsky et al., (2005) Melanoma genetics and the development of rational therapeutics. J. Clin. Invest. 115, 813-824; Meier et al., (2005), The RAS/RAF/MEK/ERK and PI3K/AKT signaling pathways present molecular targets for the effective treatment of advanced melanoma. Front Biosci. 10, 2986-3001). Melanomas originate from melanocytes and/or from their neural crest-derived pluripotent precursors, and can develop, directly or from skin moles or nevi, into incurable distant metastasis in viscera, bone and brain.

These findings contrast with the fact that such tumors commonly harbor mutations in various oncogenes and tumor suppressors, including EGFR, RAS and PTEN (Vogelstein and Kinzler, (2004) Cancer genes and the pathways they control. Nat Med. 10, 789-799. It is not known whether the effects of such oncogenic mutations could affect the function of the GLI proteins. More particularly, it has yet to be determined whether SHH-GLI signaling could have a role in melanocytes and cutaneous melanoma. The findings of an association between the oncogenic mutations noted above and the function of the GLI proteins could address the need for novel therapeutics for the treatment of melanomas and other tumor types in which oncogenic mutations and the presence of GLI potentiates the tumorigenic process. The work presented herein addresses this need.

The molecular mechanisms underlying cancer development and metastases are beginning to be understood and with this the hope that rational and targeted cures can be developed. The incidence of cutaneous melanoma is increasing and it remains one of the deadliest cancers after metastasis. A large body of evidence gathered over many years shows that cutaneous human melanomas and their metastases routinely involve oncogenic activation of the RAS-RAF-MEK and AKT signaling pathways (Meier, F. et al. The RAS/RAF/MEK/ERK and PI3K/AKT signaling pathways present molecular targets for the effective treatment of advanced melanoma. *Front Biosci.* 10, 2986-3001 (2005)). Common alterations include those activating NRAS—which activates both the BRAF-MEK and AKT cascades—and BRAF; as well as increases in the level of AKT3, with AKT signaling being critical for melanomagenesis (Davies, H. et al. Mutations of the BRAF gene in human cancer. *Nature* 417, 949-954 (2002); Stahl, J. M. et al. Deregulated Akt3 activity promotes development of malignant melanoma. *Cancer Res.* 64, 7002-7010 (2004); Chudnovsky, Y., Khavari, P. A. & Adams, A. E. Melanoma genetics and the development of rational therapeutics. *J. Clin. Invest.* 115, 813-824 (2005)). In addition, we have recently shown that cutaneous melanomas depend on sustained SHH-GLI signaling—a cellular communication pathway involved in patterned growth and in stem cell/progenitor lineages—and on GLI1 function for growth, recurrence and metastasis (Stecca, B. et al. Melanocyte proliferation and melanoma growth, recurrence and metastasis require sustained SONIC HEDGEHOG-GLI signaling. *Submitted*. (2006)). These results raise the question of how signaling pathways involved in critical aspects of embryonic development, adult homeostasis and human cancers interact. Here we show that RAS-MEK/AKT and SHH signaling converge to regulate the behavior of GLI1, the function of which is required in human cancers, including prostate cancer and melanoma (Stecca, B. et al. Melanocyte proliferation and melanoma growth, recurrence and metastasis require sustained SONIC HEDGEHOG-GLI signaling. *Submitted*. (2006); Sanchez, P. et al. Inhibition of prostate cancer proliferation by interference with SONIC HEDGEHOG-GLI1 signaling. *Proc. Natl. Acad. Sci. USA.* 101, 12561-12566 (2004)). Moreover, we show that SUPPRESSOR OF FUSED (SUFUH) provides a critical counterbalance to oncogenic RAS-MEK/AKT and SHH pathway inputs.

The citation of any reference herein should not be construed as an admission that such reference is available as "Prior Art" to the instant application.

SUMMARY OF THE INVENTION

The human zinc finger transcription factors GLI1, GLI2 and GLI3 encode downstream effectors of the Sonic hedgehog pathway, which play critical roles during early development, organogenesis and in the adult, particularly in development of the nervous system. GLI1 has also been implicated in a number of cancers, including basal cell carcinoma, rhabdomyosarcoma, medulloblastoma, gliomas and small cell lung tumors. The studies presented herein provide further evidence for GLI1, GLI2 and GLI3 in tumorigenesis, particularly in melanomas. Since cancer may be a disease of stem cell lineages and SHH-GLI signaling controls the behavior of precursors and of cells with stem cell properties in the mammalian brain (Lai K, Kaspar B K, Gage F H & Schaffer D V, *Nat Neurosci* 6, 21-7 (2003); Machold R, et al., *Neuron* 39, 937-50 (2003); Palma, V & Ruiz i Altaba, A., *Development* 131, 337-345 (2004)), as well as in other organs and species (Zhang Y & Kalderon D., *Nature.* 410, 599-604 (2001); Park Y, et al., *Dev Biol.* 253, 247-57 (2003)), the inventors propose that many cancers, including those disclosed herein, in particular, melanomas, derive from inappropriate expansion of stem cell lineages due to abnormal SHH-GLI function. That is, while the SHH/GLI pathway plays a positive role in terms of promoting the generation of adult neuronal cells from stem cells, thus providing a means for generation of populations of neuronal cells useful for treatment of various neurodegenerative diseases, this signaling pathway also has a deleterious effect on cells in terms of promotion of tumorigenesis. Moreover, the present invention relates to the unexpected finding that the SHH/GLI pathway interacts with other oncogenic pathways, such as the PGF-RTK-RAS-RAF-MEK and AKT signaling pathways. That is, it was determined that the activity of RAS-RAF-MEK and AKT signaling in melanomas depends on an active SHH-GLI pathway, and that GLI activity and expression requires RAS-RAF-MEK or AKT signaling. Furthermore, the invention relates to the finding of a requirement of EGFR for GLI activity. In addition, it was determined that GLI1 induces the expression of Mitf and Wnt genes. Accordingly, since MITF is a critical regulator of melanocyte and melanoma development, these findings show that the interaction of the SHH-GLI pathway with these other pathways may result in enhanced tumorigenesis, in particular, with the progression, recurrence and metastasis of melanomas. In addition, the unexpected finding that the SHH-GLI pathway interacts with these other melanomagenic pathways may lead to the development of other tumor therapies that can act in synergy to eliminate both primary and metastatic tumor growth and proliferation. Therefore, the present invention describes novel strategies to prevent the tumorigenic effects of the SHH/GLI pathway, through the use of stand-alone therapies that target the SHH-GLI pathway only or combination therapy using agents that have an effect on the SHH-GLI pathway in conjunction with at least one agent that is targeted to at least one of the other oncogenic pathways noted above (eg. PGF-RTK-RAS-RAF-MEK or AKT).

Accordingly, methods and compositions are described herein for treating cancers and hyperproliferative conditions, in particular, melanomas, by using agents that prevent signaling through the SHH/GLI pathway, either alone or in combination with at least one other agent that prevents signaling through at least one other oncogenic signaling pathway, such as but not limited to, the PGF-RTK-RAS-MEK and AKT pathways. Furthermore, as shown herein, it would be advantageous to develop a means of determining whether a subject is suffering from a hyperproliferative condition or a cancerous condition, in particular, melanoma, by measurement of GLI in tumor samples or other body tissues, cells or body fluids as a means of assessing the presence of various cancers, which could then aid in developing the most effective treatment regimen. Thus, a GLI protein or a nucleic acid encoding a GLI protein may be used as a biomarker for the presence of a cancerous or hyperproliferative condition, for example, a melanoma.

A first aspect of the invention provides a method for inhibiting the synthesis or expression or activity of a GLI protein in a cell in vitro or in vivo comprising, contacting the cell with, or introducing into the cell an inhibitor or antagonist of GLI synthesis or expression or activity.

In one particular embodiment, the inhibitor or antagonist is selected from the group consisting of a small molecule inhibitor or antagonist of GLI synthesis or expression or activity, an antisense molecule or a siRNA molecule that is essentially complementary to at least a part of the sequence of a nucleic acid encoding the GLI protein, antibodies to GLI, and agents that exhibit mimicry to GLI or antagonism to it or control over its production. In another particular embodiment, the contacting of the cell or the introducing the inhibitor or antagonist into the cell results in inhibition of synthesis or expression or activity of the GLI protein in the cell. In another particular embodiment, the cell is a melanocyte, or the cell is found in a benign or atypical nevus, in a primary melanoma or in a metastatic melanoma.

In another particular embodiment, the contacting of the cell or the introducing the inhibitor or antagonist into the cell results in inhibition of cellular proliferation, inhibition of cancer/tumor cell growth or survival, or inhibition of tumorigenesis. Thus, another particular embodiment provides for inhibition or antagonism of the SHH/GLI pathway or for inhibition or antagonism of at least one other oncogenic pathway by the agents of the present invention in a tumor cell. In yet another particular embodiment, the invention provides for combination therapy for inhibiting cellular proliferation, or for inhibiting tumor cell growth, or tumor cell metastasis by inhibiting or antagonizing the SHH/GLI pathway and at least one other oncogenic pathway described above, by the agents of the present invention. In yet another particular embodiment, the tumor cells in which said agents may be effective are tumor cells obtained from tumors selected from the group consisting of primitive neuroectodermal tumors (PNETS), and tumors of the skin including basal or squamous cell carcinomas, and primary or metastatic melanomas. In yet another particular embodiment, the GLI protein is selected from the group consisting of GLI1, GLI2 and GLI3.

In another particular embodiment, the antagonist comprises an antisense compound comprising an oligonucleotide of about 10 to 50 nucleobases in length targeted to a nucleic acid encoding a GLI protein, wherein said antisense compound inhibits the expression and/or activity of said GLI protein. In yet another particular embodiment, the antagonist comprises an antisense compound comprising an oligonucleotide of about 10 to 30 nucleobases in length targeted to a nucleic acid encoding a GLI protein, wherein said antisense compound inhibits the expression and/or activity of said GLI protein. In yet another particular embodiment, the antagonist comprises an antisense compound comprising an oligonucleotide of about 17 to 25 nucleobases in length targeted to a nucleic acid encoding a GLI protein, wherein said antisense compound inhibits the expression and/or activity of said GLI protein. In another particular embodiment, the antagonist is an antisense molecule specific for at least one of the oncogenic signaling molecules noted herein, which may inhibit their expression or synthesis or activity.

In another particular embodiment, the antagonist comprises a siRNA molecule, the siRNA molecule comprising a double stranded structure having a nucleotide sequence which is substantially identical to or complementary to at least a part of the gli gene in an amount sufficient to inhibit the synthesis or expression or activity of a gli gene. In yet another particular embodiment, the gli gene may be selected from the group consisting of gli1, gli2 and gli3. In yet another particular embodiment, the siRNA hybridizes under standard conditions to the gli gene. In yet another particular embodiment, the siRNA molecule is about 10 to 50 nucleotides in length. In yet another particular embodiment, the siRNA molecule is about 10 to 30 nucleotides in length. In yet another particular embodiment, the siRNA molecule is about 17 to 25 nucleotides in length. In yet another particular embodiment, the siRNA molecule is selected from the group consisting of the nucleic acid sequences set forth in SEQ ID NO: 1, SEQ ID NO: 2, SEQ ID NO: 3 and SEQ ID NO: 57. In another particular embodiment, the antagonist is a siRNA specific for at least one of the oncogenic signaling molecules noted herein, which may inhibit their expression or synthesis or activity.

In another particular embodiment, the antagonist is a small molecule inhibitor of GLI expression or synthesis or activity. In yet another particular embodiment, the small molecule inhibitor is a plant alkaloid or its analogs or derivatives thereof. In yet another particular embodiment, the plant alkaloid is selected from cyclopamine, jervine and their analogs or derivatives thereof. In another particular embodiment, the antagonist is a small molecule inhibitor of at least one of the oncogenic signaling molecules including inhibition of their expression or synthesis or activity.

In another particular embodiment, the antagonist is an antibody specific for at least one of the GLI proteins or one of the other signaling molecules, including but not limited to PGF-RTK-RAS-MEK and AKT. In yet another particular embodiment, the antibody may be a polyclonal antibody or a monoclonal antibody. The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397). The antibody may be a human or a humanized antibody. The antibody may be a single chain antibody. (See, e.g., Curiel et al., U.S. Pat. No. 5,910,486 and U.S. Pat. No. 6,028,059). The antibody may be prepared in, but not limited to, mice, rats, guinea pigs, rabbits, goats, sheep, swine, dogs, cats, or horses. It may be may be an Fab fragment or a soluble component thereof. In yet another particular embodiment, the invention provides for an immortal cell line that produces the antagonistic monoclonal antibody. In yet another particular embodiment, the antibody is a blocking antibody and is effective as a therapeutic agent to prevent the proliferation of tumor cells in vivo. In yet another particular embodiment, the antibody may be coupled to an anti-tumor drug or radioisotope for use in treating tumor cells in situ. The antibody may be effective as a diagnostic agent to aid in identification of tumor cells in situ or in vivo. The antibody may be coupled to an imaging reagent and is used for imaging of tumor cells in situ or in vivo.

A second aspect of the invention provides a method of preventing or treating cellular debilitations, derangements, dysfunctions or hyperplastic/hyperproliferative or cancerous disease states, or metastasis of tumor cells, in a mammal characterized by the presence or expression of a gli gene or gene product, such as a GLI protein, comprising administering to a mammal a therapeutically effective amount of an agent that inhibits or antagonizes the synthesis or expression or activity of a GLI molecule, alone or in combination with at least one inhibitor of at least one other signaling molecule, including but not limited to, PGF-RTK-RAS-MEK and AKT.

In one particular embodiment, the inhibitors/antagonists are selected from the group consisting of small molecule antagonists, antisense compounds, siRNA nucleic acids, antibodies, and agents that exhibit mimicry to GLI or antagonism to it or control over its production. In another particular embodiment, the antagonist comprises agents that increase negative, or decrease positive acting elements affecting SHH-GLI signaling, said agents selected from the group consisting of small molecules that alter PKA kinase activity, small molecules that alter GSK3 kinase activity, small molecules that alter CK1 kinase activity and small molecules or siRNAs/antisense RNAs that alter DYRK1 kinase activity. In yet another particular embodiment, the inhibitors/antagonists are specific for the PGF-RTK-RAS-MEK and AKT pathways. In yet another particular embodiment the GLI molecule is selected from the group consisting of GLI1, GLI2 and GLI3.

In another particular embodiment, the hyperproliferative or cancerous disease states are selected from the group consisting of, primitive neuroectodermal tumors (PNETS), basal or squamous cell carcinomas, and melanomas.

In another particular embodiment, the antagonist comprises an antisense compound comprising an oligonucleotide of about 10 to 50 nucleobases in length targeted to a nucleic acid encoding a GLI protein, wherein said antisense compound inhibits the expression and/or activity of said GLI protein. In yet another particular embodiment, the antagonist comprises an antisense compound comprising an oligonucleotide of about 10 to 30 nucleobases in length targeted to a nucleic acid encoding a GLI protein, wherein said antisense compound inhibits the expression and/or activity of said GLI protein. In another particular embodiment, the antagonist comprises an antisense compound comprising an oligonucleotide of about 17 to 25 nucleobases in length targeted to a nucleic acid encoding a GLI protein, wherein said antisense compound inhibits the expression or activity of said GLI protein. In another particular embodiment, the antisense compound, upon administering to said mammal, results in the inhibition of expression or activity of said GLI protein in the cells of said mammal. In another particular embodiment, the delivery of said antisense compound to said mammal further results in inhibition of cellular proliferation in said mammal.

In another particular embodiment, the antagonist comprises a siRNA molecule, said siRNA molecule comprising a double stranded structure having a nucleotide sequence which is substantially identical to at least a part of the gli gene in an amount sufficient to inhibit the synthesis and/or expression and/or activity of a gli gene. In another particular embodiment, the gli gene may be selected from the group consisting of gli1, gli2 and gli3. In another particular embodiment, the siRNA hybridizes under stringent conditions to the gli gene. In another particular embodiment, the siRNA molecule is about 10-50 nucleotides in length. In another particular embodiment, the siRNA molecule is about 10-30 nucleotides in length. In yet another particular embodiment, the siRNA molecule is about 17-25 nucleotides in length. In yet another particular embodiment, the siRNA molecule may be selected from the group consisting of the nucleic acid sequences set forth in SEQ ID NO: 1, SEQ ID NO: 2, SEQ ID NO: 3 and SEQ ID NO: 57.

In another particular embodiment, the antagonist is a small molecule inhibitor of GLI expression, synthesis or activity. In another particular embodiment, the small molecule inhibitor is a plant alkaloid or its analogs or derivatives thereof. In another particular embodiment, the plant alkaloid is selected from cyclopamine, jervine or their analogs or derivatives thereof.

In another particular embodiment, the antagonist is an antibody specific for at least one of the GLI proteins. In yet another particular embodiment, the antibody may be a polyclonal antibody or a monoclonal antibody. The antibody may be a single chain antibody. It may be a chimeric antibody. It may be may be an Fab fragment or a soluble component thereof. It may be a human or humanized antibody. It may be produced in other animals, including but not limited to horses, goats, sheep, mice, rats, rabbits and guinea pigs. In yet another particular embodiment, the invention provides for an immortal cell line that produces the antagonistic monoclonal antibody. In yet another particular embodiment, the antibody is a blocking antibody and is effective as a therapeutic agent to prevent the proliferation of tumor cells in vivo. In yet another particular embodiment, the antibody may be coupled to an anti-tumor drug or radioisotope for use in treating tumor cells in situ. The antibody may be effective as a diagnostic agent to aid in identification of tumor cells in situ or in vivo. The antibody may be coupled to an imaging reagent and is used for imaging of tumor cells in situ or in vivo.

A third aspect of the invention provides a method of treating apoptotic resistant tumor cells comprising administering an antagonist of the SHH/GLI signaling pathway to said tumor cell in vitro or in vivo. In one embodiment, the method comprises the use of an antagonist or inhibitor of the SHH/GLI pathway as a means of inducing a tumor cell to undergo senescence, apoptosis, or necrosis. In another embodiment, said administering results in tumor cell death and prevention from metastasis. In another particular embodiment, the antagonist comprises agents that increase negative, or decrease positive acting elements affecting SHH-GLI signaling, said agents selected from the group consisting of small molecules that alter PKA kinase activity, small molecules that alter GSK3 kinase activity and small molecules that alter CK1 kinase activity, and small molecules or siRNAs/antisense RNAs that alter DYRK1 kinase activity. In yet another particular embodiment, the tumor cell is selected from the group consisting of primitive neuroectodermal tumors (PNETS); skin tumors, e.g. basal cell carcinoma or squamous cell carcinoma, and melanomas A fourth aspect of the invention provides a double stranded siRNA for inhibiting expression of a gli gene, or for inhibiting cellular proliferation or tumorigenesis or tumor metastasis. In one embodiment, the siRNA comprises a first nucleotide sequence that hybridizes under stringent conditions to a nucleotide sequence of a gli gene and/or its mRNA and a second nucleotide sequence that is complementary to said first nucleotide sequence. In a particular embodiment, the siRNA is about 10-50 nucleotides long. In another particular embodiment, the siRNA is about 10-50 nucleotides long. In another particular embodiment, the siRNA is about 10-30 nucleotides long. In yet another particular embodiment, the siRNA is about 17-25 nucleotides long. In another particular embodiment, the siRNA is selected from the group consisting of the nucleic acid sequences as set forth in SEQ ID NO: 1, SEQ ID NO: 2, SEQ ID NO: 3 and SEQ ID NO: 57. In yet another particular embodiment, the siRNA, upon delivery to a cell containing the gli gene for which said siRNA molecules are specific, inhibits the proliferation of said cell. In yet another particular embodiment, the double stranded siRNA is a short hairpin RNA (shRNA) comprising a first nucleotide sequence that hybridizes under stringent conditions to a nucleotide sequence of a gli gene, and a second nucleotide sequence which is a complementary inverted repeat of said first nucleotide sequence and hybridizes to said first nucleotide sequence to form a hairpin structure. In another particular embodiment, the shRNA may have a foreign hairpin from another gene and the stem of the hairpin is formed by the gli sequences.

A fifth aspect of the invention provides a pharmaceutical composition comprising at least one inhibitor or antagonist of GLI synthesis, expression or activity, and a pharmaceutically acceptable carrier. In one particular embodiment, the inhibitor or antagonist is selected from the group consisting of a small molecule inhibitor or antagonist of GLI synthesis, expression or activity, an antisense molecule or a siRNA molecule that is essentially complementary to at least a part of the sequence of a nucleic acid encoding the GLI protein, antibodies to GLI, and agents that exhibit mimicry to GLI or antagonism to it or control over its production, said contacting or introducing resulting in inhibition of synthesis and/or expression and/or activity of the GLI protein in said cell. In a yet further embodiment, the pharmaceutical composition comprises a siRNA molecule that comprises the nucleic acid sequence as set forth in SEQ ID NOs: 1, 2, 3 and 57. In a yet further embodiment, the pharmaceutical composition comprises a small molecule inhibitor comprising a plant alkaloid, such as, but not limited to cyclopamine, jervine and/or analogs or derivatives thereof. In another particular embodiment, the composition comprises at least one inhibitor or antagonist of GLI combined with at least one inhibitor or antagonist of at least one other signaling pathway associated with tumorigenesis.

A sixth aspect of the invention provides a method of screening for necrotic, senescent, or apoptotic resistant tumor cells, comprising measuring the level of expression of GLI in said tumor cells, wherein enhanced expression of GLI correlates with apoptosis resistance in said tumor cells. In a particular embodiment, the tumor cells are selected from the group consisting of primitive neuroectodermal tumors (PNETS), basal or squamous cell carcinomas, and melanomas. In another particular embodiment, the screening may be done by immunological methods, such as western blotting techniques, immunofluorescence or radioimmunoassays using an antibody specific for GLI. Alternatively, standard molecular biological approaches may be used, including PCR techniques using primers or probes specific for GLI.

A seventh aspect of the invention provides for detection of GLI in skin tumor samples, or in/from metastatic cells present in bodily fluids from a subject as a means of correlating the presence of a gli gene or gene product, such as a GLI protein, with the presence of a skin cancer, for example, a melanoma. If GLI is present in a skin sample from the subject, using the procedures outlined below which are known to one skilled in the art, then there is an increased risk of the presence of a tumor. GLI, if present in low amounts, can be detected by PCR, Western blot and/or Northern blot and/or as provided for herein. When GLI is not measurable at all in the sample from the animal subject, the animal subject is identified as being unlikely to have a cancer. In one embodiment, the sample is obtained by biopsy. In yet another embodiment, the level of GLI is determined in another bodily sample selected from whole blood, plasma, serum, urine or cerebrospinal fluid.

In one embodiment the determination of the level of GLI is performed in situ. In another embodiment the determination of the level of GLI is performed in vitro. In still another embodiment, the determination of the level of GLI is performed in vivo. In a particular embodiment the determination of the level of GLI is performed with an antibody specific for GLI. In another such embodiment the determination of the level of GLI is performed by PCR with a primer specific for an mRNA encoding GLI. In still another embodiment the determination of the level of GLI is performed with a nucleotide probe specific for an mRNA encoding GLI. In still another embodiment the determination of the level of GLI is performed by a Northern blot. In yet another embodiment the determination of the level of GLI is performed by a ribonuclease protection assay. In still another embodiment the determination of the level of GLI is performed by immunohistochemistry. In still another embodiment the determination of the level of GLI is performed by RT-PCR.

An eighth aspect of the invention provides for the use of GLI as a biomarker for skin cancer, such as a melanoma, as well as other cancers which utilize the SHH/GLI pathway for cell signaling, and in which GLI is present. In one embodiment, the presence of increasing levels of the gli gene or gene product, such as a GLI protein, is indicative of an increased risk for the presence of a cancer. In a preferred embodiment, the metastasis is to bone and to other organs.

A ninth aspect of the invention provides an isolated nucleic acid probe specific for GLI. In a particular embodiment, the probe is used to identify GLI in a tumor sample. In another particular embodiment, the probe can differentiate between the presence and absence of tumors, such as, but not limited to, melanomas and benign tumors in a patient sample. In another particular embodiment, the GLI is a mammalian GLI. In yet another particular embodiment, the mammalian GLI is human GLI. In yet another particular embodiment, the GLI is GLI1, GLI2 or GLI3.

A tenth aspect of the invention provides for a method of regulating the activity of Gli-1 or its cellular localization comprising administering a modulator of the RAS-MEK and/or AKT signaling pathways.

In one particular embodiment, the modulator is an inhibitor of the RAS-MEK and/or AKT signaling pathways. In another particular embodiment, the modulator affects SUFUH. In another particular embodiment, the inhibitor of the RAS-MEK and/or AKT signaling pathways also or independently inhibits the activity of Gli-1 or its cellular localization. In another particular embodiment, RAS-MEK and/or AKT signaling does not directly act on Gli, but acts by preventing the inhibition of Gli by SUFUH. Accordingly, another aspect of the invention provides a method of inhibiting cellular proliferation or tumor formation by preventing the activity of RAS on SUFUH. In yet another particular embodiment, the inhibitor of the RAS-MEK and/or AKT signaling pathways is selected from a small organic molecule, a protein, a nucleic acid, an antibody and any combination thereof. In yet another particular embodiment, the administering of an inhibitor of RAS-MEK and/or AKT signaling results in inhibition of Gli-1 induced or Gli-1 augmented benign growth or malignant tumor or cancer cell proliferation.

An eleventh aspect of the invention provides a method of regulating the activity of RAS-MEK and/or AKT signaling comprising administering a modulator of the SHH-GLI signaling pathway.

In one particular embodiment, the modulator is an inhibitor of the SHH-GLI signaling pathway. In another particular embodiment, the inhibitor of the SHH-GLI signaling pathway also inhibits the oncogenic or other activity of RAS-MEK and/or AKT signaling. In another particular embodiment the inhibitor of the SHH-GLI signaling pathway is selected from a small organic molecule (synthetic or naturally derived), a protein, a nucleic acid, an antibody and any combination thereof. In another particular embodiment the administering of an inhibitor of the SHH-GLI pathway results in inhibition of RAS-MEK and/or AKT induced benign growth or malignant tumor or cancer cell proliferation. In another particular embodiment the modulator of the SHH-GLI pathway exhibits its effect downstream of ligand binding and/or the action of membrane-bound signaling components. In another particular embodiment the nucleic acid is an RNA or a DNA molecule. In another particular embodiment the RNA is an antisense molecule or a shRNA or a siRNA molecule. In another particular embodiment the siRNA is selected from SEQ ID NOS.: 1, 2, 3 and 57.

Other aspects and advantages will become apparent from a review of the ensuing detailed description taken in conjunction with the following illustrative drawings.

Figure 1K:
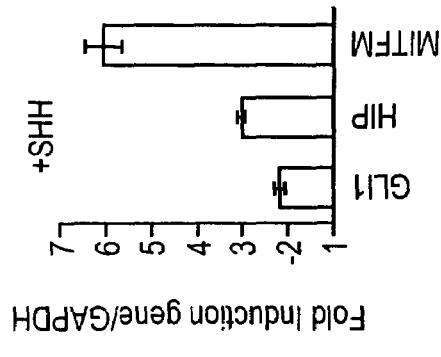
FIG. 1 Localization of SHH-GLI signaling in human hair follicle melanocytes and effects on proliferation and MITF expression.

A-J) H&E (A,F), in situ hybridization (B-D, G-I) and immunofluorescence (E,J) of sections of human scalp hair follicles showing the expression of SHH (B,G), GLI1 (C,H), PTCH1 (D,I) and MITF (E,J). Arrows in (E) point to melanocytes in the outer root sheath. K) Diagram of a human hair follicle showing the different components and the localization of the images in (A-J).

(L,M) Effects of SHH over PBS and cyclopamine over tomatidine on BrdU incorporation in proliferating melanocytes (L), and of SHH on gene expression 8 h after treatment (M) determined by qPCR normalized to GAPDH levels. N) Stage ±32 tadpole phenotype of injection of GLI1 RNA targeting epidermis/neural crest (bottom two embryos). LacZ-injected tadpoles are normal (top). Arrows point to pigmented tumors. O) qPCR analyses of gene expression in dissected GLI1-induced tumors as compared with lacZ-injected epidermis, normalized to the level of EF1α expression. Error bars in all figures are s.e.m. Scale bar=100 μm (A-J), 0.8 mm (N).

FIG. 2 Quantitative analyses of gene expression and localization of SHH-GLI expressing cells in human nevi and melanomas A) qPCR histograms of the various samples, including proliferating melanocytes (m, black), benign nevi (white), atypical nevi (gray), primary melanomas (light blue), metastatic melanomas (dark blue), melanoma cell lines (yellow) and basal cell carcinomas (BCCs, green), showing expression of different genes as indicated. Values shown are normalized to GAPDH and EEF1A levels. m: proliferating melanocytes. Asterisks denote samples not tested. B-E) H&E staining (left column) and in situ hybridization for SHH, PTCH1, GLI1, GLI2 and GLI3 (5 center columns) and immunolocalization of MITF and MLAN-A (two right columns) in a benign nevus (A), skin metastases (C,D) and a lymph node metastasis (E). Clinical data are supplied in Suppl. Materials. Scale bar=100 μm (B-E).

FIG. 3 Effects of SHH and SHH antagonists in human melanomas.

A) Representative phase contrast image of a live Me-3 melanoma cell in culture.

B) RT-PCR of the five primary cultures used (Me-1 through Me-5) for the genes indicated.

C) Decrease in the levels of gene expression as indicated 4 h after cyclopamine treatment.

D-I) Histograms of changes in BrdU incorporation in primary cultures (D,F,H) and cell lines (E,G,I) 48 h after addition of SHH, anti-SHH Ab (5E1) or cyclopamine as indicated. J) Reduction in BrdU incorporation during long-term treatment for 2, 5 or 10 days with cyclopamine. K) Recovery of viable cells following 10 or 20 days treatments and 10 days recovery (rec) without cycloapmine. Arrows point to lack of recovery. L,M) Histogram of the increase in activated Caspase3 immunoreactivity after treatment of primary cultures (L) or cell lines (M) with cyclopamine. N,O) Representative images of BrdU labeling (red) after treatment as described. Nuclei are counterstained blue with DAPI. All values for SHH and anti-SHH Ab treatments are compared to PBS and cyclopamine to tomatidine. Scale bar=15 µm (A), 45 µm (N,O).

FIG. 4 RNA interference analyses of GLI gene function in human melanoma

A,B) Histograms of the reduction in BrdU incorporation in primary melanomas (A) or cell lines (B) 48 h after lipofection with siRNAs as indicated. All values are given over the effects of an unrelated control siRNA. C,D) Reduction in BrdU incorporation (C) of the number of viable cells (D) after long term treatment with siRNA against GLI1 lipofecting anew every 2 days.

E) Rescue of the inhibition of BrdU incorporation by cyclopamine by interference with GLI3.

F) Examples of lipofected cells with an FITC-labeled control siRNA. G,H) Decrease in target RNA levels 4 h after lipofection with GLI1 (1), GLI2 (2) or GLI3 (3) siRNAs in WM-115 cells.

H) Comparison of reduction in GLI1 levels by cyclopamine and siRNA against GLI1 in WM-115 cells 4 hr after lipofection or treatment. Scale bar=100 µm (F).

FIG. 5 Inhibition of human melanoma growth, recurrence and metastasis in mice.

A) Effects of cyclopamine treatment on subcutaneous MeWo/LacZ melanomas in nude mice as compared with tumors treated with cyclodextrin carrier alone. Arrow points to the disappearance of cyclopamine-treated tumors. B) Recurrence of melanomas after cessation of treatment and prevention of recurrences after sustained treatment for 20 (thick arrow) but not 3 or 10 days after tumor disappearance. C-H) Representative images of nude mice with carrier only treated MeWo/LacZ black melanomas (C,F), or treated with cyclopamine until partial (B,G) or complete (E,H) disappearance. I-K). Histological analyses after X-Gal stained MeWo/LacZ cells in tumors similar to those shown above each image in (C-H). L-N). Histogram (L) and images of dissected lungs after X-Gal staining (insets in L, M,N) showing the inhibition of intravenously injected MeWo/LacZ lung metastases by systemic cyclopamine treatment as compared with treatment with cyclodextrin carrier control only. The size of metastatic colonies was scored (L) accounting also for macro and micrometastases (arrows, M). Inset in (M) shows a histological section of a MeWo/LacZ metastasis in the lung. Scale bar=1 cm (C-D), 0.3 cm (F-H), 70 µm (I-K), 0.75 cm (L inset), 150 µm (M,N).

FIG. 6 Integration of oncogenic RAS and SHH-GLI signaling and effects on nuclear accumulation of GLI proteins.

A) Histogram of the reduction of BrdU incorporation in a primary culture (Me-3) and cell lines 48 h after treatment with inhibitors as indicated. Values are given over DMSO treatment.

B, C) Reduction in the expression of GLI1 and PTCH1 4 h after addition of MEK1 (B) or AKT (C) inhibitors assessed by qPCR and normalized to GAPDH levels. D) Increase in the number of BrdU incorporation 48 h after transfection of plasmids driving the expression of GLI1 or oncogenic HRAS (RAS*), together with GFP-expressing plasmid. Only GFP+/BrdU+ cells were counted. Values are over GFP-transfection alone. E, F) Inhibition of GLI1 (E) or oncogenic RAS (F) mediated BrdU enhancement by 48 h treatment with inhibitors as indicated. Cyclopamine values are over tomatidine, and forskolin (FK) values over the inactive derivative 1,9-dideoxyforskolin. G) Number of colonies selected in Geneticin 3 weeks after transfection of different plasmids as shown. GLI3R: GLI3 repressor. H) Representative examples of stained colonies (G). I) Representative immunofluorescence images of the localization of myc-tagged GLI proteins in transfected COS-7 cells as indicated, 48 h after transfection and 1 hr after inhibitor (inh.) addition. Results in percentages for nuclear (n), nuclear and cytoplasmic (n/c) and cytoplasmic (c) localization were: Frog Gli1: 10n, 48n/c, 42c; Gli1+RAS*: 32n, 54n/c, 13c; Gli1+RAS*+MEK1 inh: 27n, 51n/c, 21c; Gli1+RAS*+AKT inh: 18n, 53n/c, 29c. Frog Gli2: 12n, 39n/c, 49c; Gli2+RAS*: 48n, 43n/c, 9c; Gli2+RAS*+MEK1 inh: 14n, 56n/c, 30c; Gli2+RAS*+AKT inh: 19n, 57n/c, 24c. Human GLI3: 17n, 30n/c, 53c; GLI3+RAS*: 41n, 50n/c, 9c; GLI3+RAS*+MEK1 inh: 24n, 37n/c, 38c; GLI3+RAS*+AKT inh: 12n, 47n/c, 41c. Human GLI3Rep (GLI3C'ΔCla1): 85n, 9n/c, 6c; GLI3rep+RAS*: 84n, 15n/c, 1c; GLI3Rep+RAS*+MEK inh: 77n, 22n/c, 1c; GLI3Rep+RAS*+AKT inh: 81n, 18n/c, 1c.

Scale bar=30 mm (H), 20 µm (I).

Figure 7:
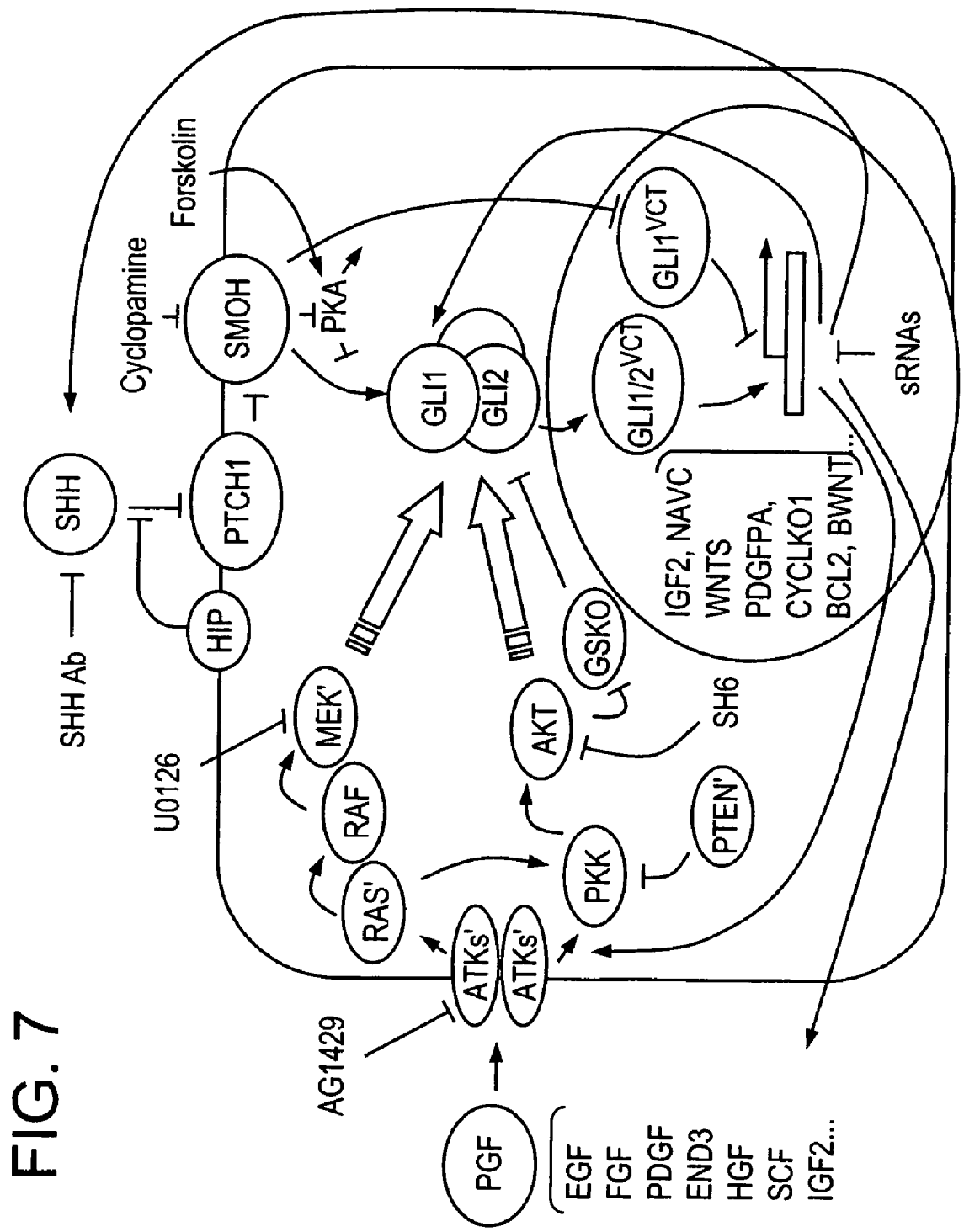

FIG. 7 SHH-GLI and oncogenic RAS pathway integration

Diagram of the flow of SHH-GLI and RAS-MEK/AKT pathways and integration at the level of GLI function (large yellow arrows). The site of action of inhibitors used is shown.

FIG. 8. Interdependence of SHH-GLI and RAS-MEK/AKT signaling in human melanoma cells a) Histogram of the change in BrdU incorporation in a melanoma primary culture derived from a cutaneous metastasis (Me-3) and two human melanoma cell lines 48 h after treatment with inhibitors as indicated.

b, c) Reduction in the expression of GLI1 and PTCH1 4 h after addition of MEK-1 (b) or AKT (c) inhibitors assessed by qPCR and normalized to GAPDH levels.

d, e) Change in BrdU incorporation 48 h after transfection of plasmids driving the expression of GLI1 (d) or NRAS$^{Q61K}$ (RAS*; e) together with lacZ-expressing plasmids. Only □gal++BrdU+ cells were counted. Values are over lacZ-transfection alone as indicated.

f, g) Number of colonies on p60 plates selected in geneticin, 3 weeks after transfection of different plasmids as shown including HRAS$^{V12G}$ (RAS*) and GLI repressors (GLI3R, Gli2R).

Asterisks (*) in histograms denote significative (p<0.05) changes as compared to controls. ns: change not significative between samples depicted by the connected arrows.

FIG. 9. Mouse melanomas from transgenic mice expressing oncogenic RAS harbor an active SHH-GLI pathway and require its function for growth.

a,b) Appearance of skin melanomas (a) and superficial cervical lymph node metastases in the ventral neck (b) in Tyr-NRAS$^{Q61K}$; Ink4a$^{-/-}$ mice.

c) qPCR analyses of the expression of the NRAS$^{Q61K}$ transgene and Tyrosinase (top), and Gli1 and Ptch1 (bottom) in mouse melanomas normalized to Gapdh expression. As control, normal lymph nodes were dissected and used to quantify normal gene expression without metastases: ax: axillary; cer:

superficial cervical; ing: inguinal. Names of tumors: the first number denotes the mouse and the last number the melanoma sample. PM; primary skin melanoma; LNM: lymph node metastasis.

d, e) In situ hybridization of frozen sections of a skin (dermal) melanoma for the probes and control sense probes described. Specific hybridization for Gli1 and Ptch1 in cells is shown in blue. High magnification images of single melanoma cells (g) show the presence of pigment granules (brown) and mRNA expression (blue) for Gli1 and Ptch1, and no signal in a Gli1 sense control. Pigment largely interferes with the in situ hydridization procedure explaining the segregation of pigment granules and blue signal revealing the presence of the specific mRNA being tested. There is partial inhibition of the colorimetric reaction by pigment.

f,g) High-magnification (f) and low-magnification (g) micrographs. f) a live cell from the 1-LNM5 primary culture displaying pigment granules and prominent nucleoli with an overall elongated morphology. The amount of pigment granules decrease over time in culture. g) 1-PM2 culture 4 days after tumor dissociation. Note the elongated form of confluent cells and abundant pigment (arrows).

h) Immunolabeling of 1-LNM5 culture with S100 and Nestin antibodies. Note the widespread staining with S100 (recognizing mostly S100beta) and the presence of ±30% of cells expressing Nestin, as expected[13].

i) Histogram of the effects of tomatidine, cyclopamine and GLI1 on a mouse skin primary melanoma (1-PM2; left set) and a lymph node melanoma metastasis (1-LNM5; right set). All transfections included equal amounts of a plasmid driving the expression of GFP. The numbers are per 1000 cells and reflect low transfection efficiencies in these primary cultures and the fact that only doubly BrdU+ and GFP+ cells were counted. *=significative change as compared with tomatidine treatment p<0.01; ns=not significative change between samples under the horizontal bars.

j) Histogram of the change in proliferation as measured by BrdU incorporation of one primary skin melanomas and 11 lymph node metastases from 2 mice after treatment with 10 µM tomatidine as control and 5 and 10 µM cyclopamine for 48 h.

Scale bar=3 mm (a), 2 mm (b), 60 µm (d,g,h), 20 µm (e) 10 µm (f).

FIG. 10. RAS-MEK/AK signaling enhances the transcriptional activity of GLI1.

a-d) Histograms of the results of luciferase reporter assays with the 7GLI binding site reporter (blue; GLI-BS series), a reporter without Gli binding sites (white; pcontrol series in a) or the PTCH1 reporter (gray series in a, d) in SK-MEL2 melanoma (a-c) or COS7 (d) cells. Cotransfections were done at equimolar amounts except for GLI3R in (b), which was at 1:1, 1:2 and 1:3.

Figure 11A:
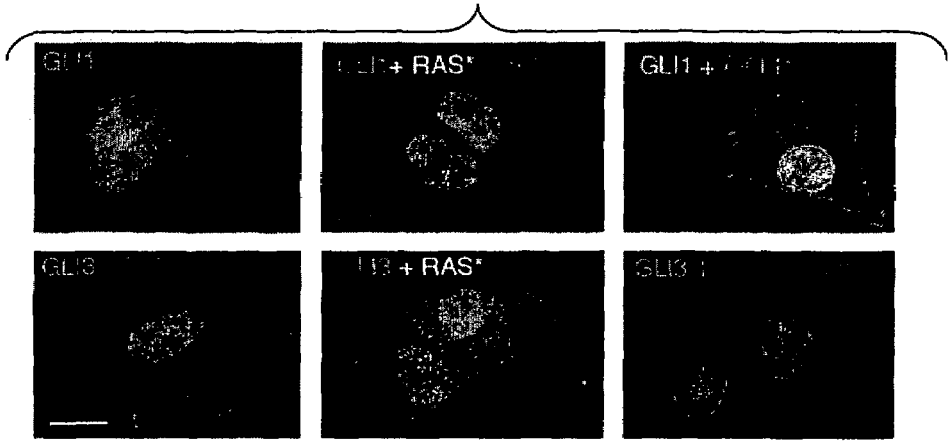
Figure 11B:
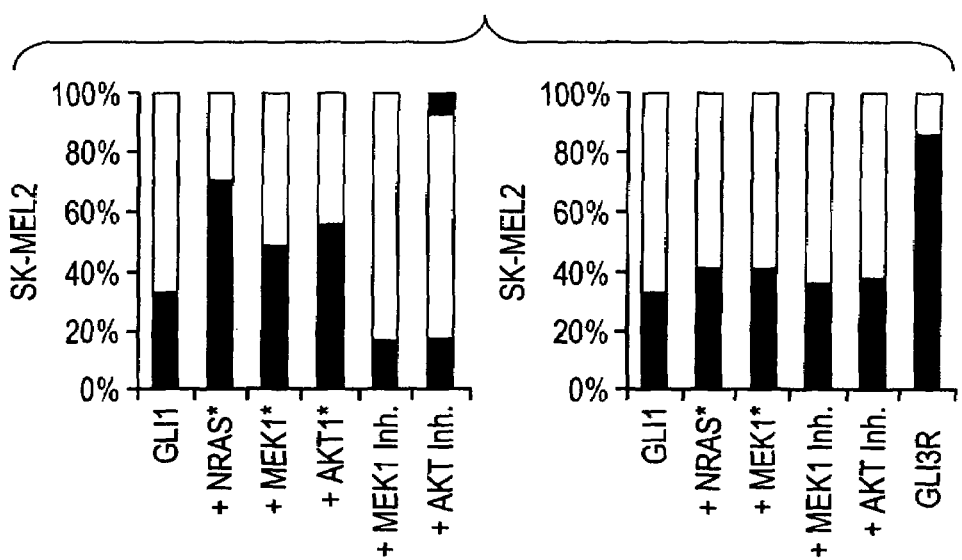

FIG. 11. RAS-MEK/AKT signaling induces the nuclear accumulation of GLI1.

a-d) Localization of GLI1 in SK-MEL2 (a, b) or COS7 (c,d) cells after transfection as indicated. a,c) show examples of representative cells and (b,d) histograms of the quantification of results. In each case over 500 cells were counted. Myc-tagged GLI1 and AKT1 were detected with anti-myc antibodies except in the upper right panel in (a) and the lower three panels of (c) which used a rabbit polyclonal anti-human GLI antibody that only recognizes overexpressed protein.

e) GLI luciferase reporter activity using a 7 GLI binding site reporter (GLI-BS) with GLI1 or GLI1+NRAS* (NRAS$^{Q61K}$) in the presence or absence of 5 nM leptomycin B (LMB) for 6 h following 48 h post-transfection.

f,g) Nuclear localization of GLI1 induced by LMB treatment. f) Shows representative examples without (top) and with (bottom) LMB treatment. Quantification of the localization of transfected GLI1 and GLI3 after LMB treatments is shown in (g). Nuclei were counterstained with DAPI (blue). Scale bar=20 µm (a,c,f)

FIG. 12. SUPPRESSOR OF FUSED reverses oncogenic RAS-induced nuclear accumulation and transcriptional activity of GLI1 and modulates melanoma growth.

a) qPCR analyses of the expression of SUFUH in human melanocytes in culture (mel), a human melanoma primary culture (Me-3) and two human melanoma cell lines (WM-115 and SK-Mel2). The histogram shows expression normalized to the housekeeping gene GAPDH.

b,c) Localization of GLI1 in SK-Mel2 and COS7 cells alone or after co-expression with oncogenic NRAS$^{Q61K}$ (RAS*) and/or SUFUH shown in representative microphotographs after fluorescence immunocytochemistry (b) and histograms after quantification (c). Over 500 cells were counted in each case.

e,f) Luciferase reporter analyses from a 7 GLI binding site construct (GLI-BS) in SK-MEL2 (e) and COS7 (f) cells showing its activation by GLI1, hyperactivation by GLI1 plus NRAS$^{Q61K}$ (RAS*) and concentration dependent inhibition by SUFUH. Coexpression was at equimolar amounts except for GLI1 and SUFUH (1:1, 1:2, 1:3) and GLI1+RAS*+SUFUH (1:1, 1:2; 1:4, 1:6) in SK-MEL2 cells (e) and for GLI1+RAS*+SUFUH (1:1:1/12, 1:1:1/6, 1:1:1/3, 1:1:2/3, 1:1:1, 1:1:2) in COS7 cells (f). Each transfection had the same amount of total DNA. g) qPCR analysis of the decrease of SUFUH mRNA after lipofection of SUFUH siRNA after 4, 8, 12 and 24 h in SK-Mel2 cells. Untreated cells are used as control and their level set at 1.

h) qPCR analysis of the upregulation of GLI1 in cells transfected with SUFUH following the decrease of SUFUH levels (g).

i) Change in BrdU incorporation in WM-115 and SK-MEL2 human melanoma cells after lipofection of SUFUH siRNA or a control siRNA.

j) Decrease in the number of doubly BrdU+ and GFP+ SK-MEL2 cells cotransfected with plasmids driving the expression of SUFUH and GFP as compared with the number of double BrdU+/GFP+ cells cotransfected with empty vector and a plasmid driving the expression of GFP.

Scale bar=15 µm (b)

Figure 13:
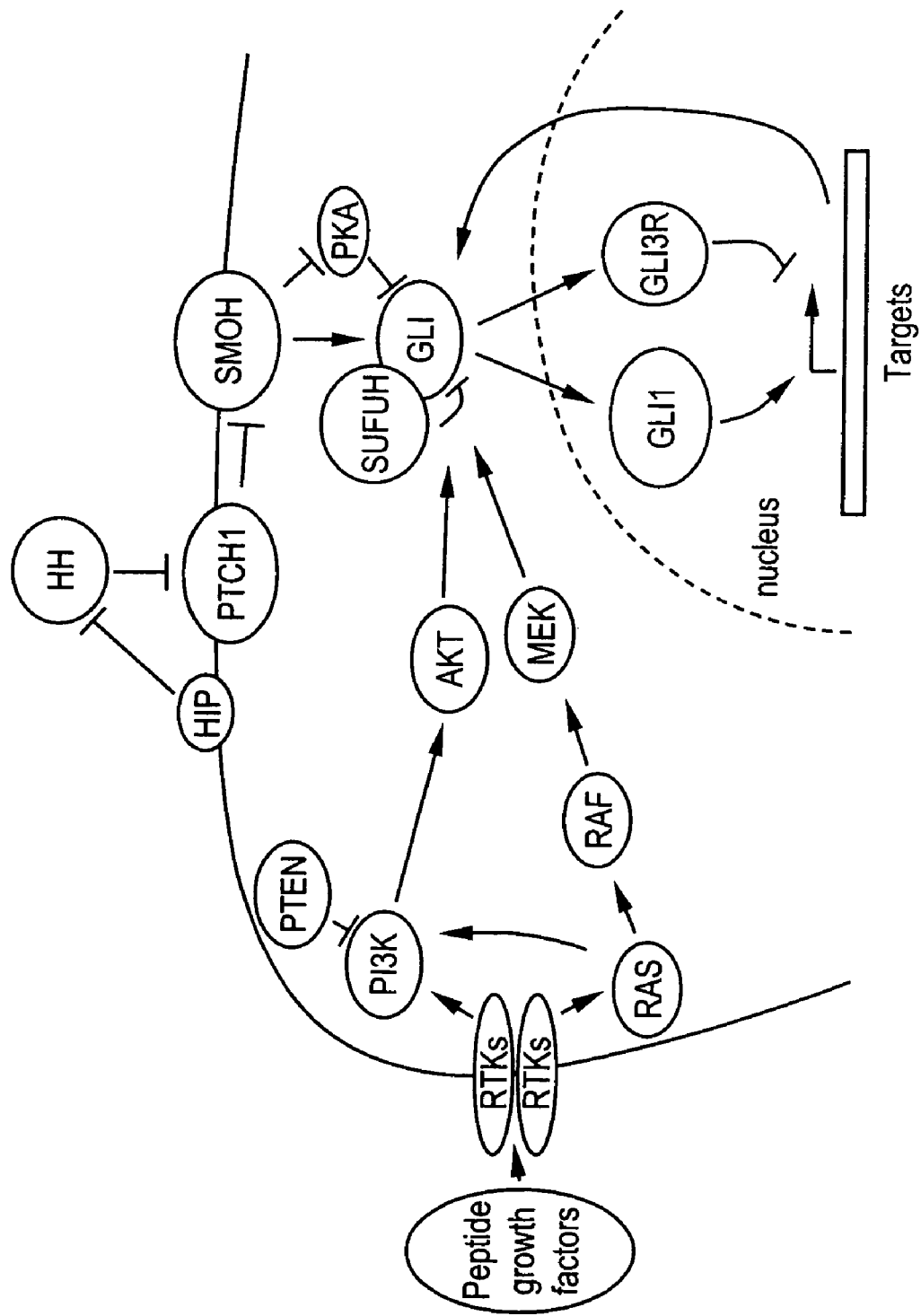

FIG. 13. Convergence of oncogenic RAS-MEK/AKT, SHH and SUFUH on GLI function.

Diagram of the flow of SHH-GLI (green) and RAS-MEK/AKT (blue) pathways and convergence on GLI function. The site of action of activators (green) inhibitors (red) used is shown. Filled ovals in orange denote components with tumor suppressor activity (e.g. PTEN, GLI3R) and in green and blue oncogenes or tumor promoters (e.g. RAS, SMOH). GLI1 can autoregulate (green curved arrow from Targets to GLI).

Figure 14:
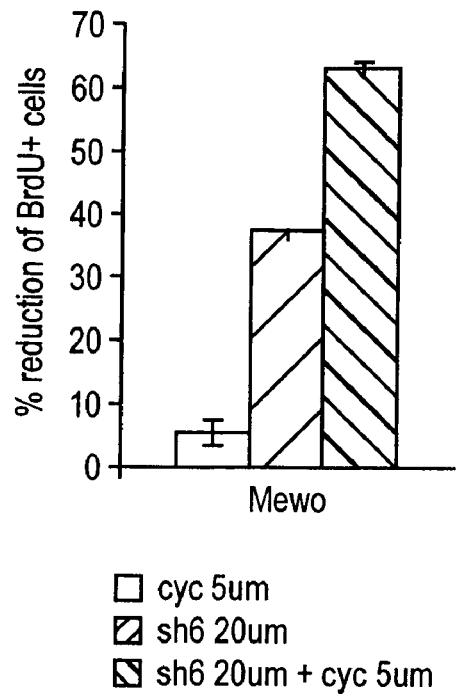

FIG. 14. Synergistic Effect of an AKT inhibitor plus cyclopamine on Proliferation of Mewo Cells. Histogram of the change in BrdU incorporation in Mewo Cells in the presence of suboptimal concentrations of an AKT inhibitor SH6 plus cyclopamine. Mewo cells were treated for 48 hours with either 5 µM of cyclopamine alone, or 20 µM of SH6 alone, or a combination of each at the given concentrations. Cell proliferation was assessed after incubation with BrdU as described.

Figure 15:
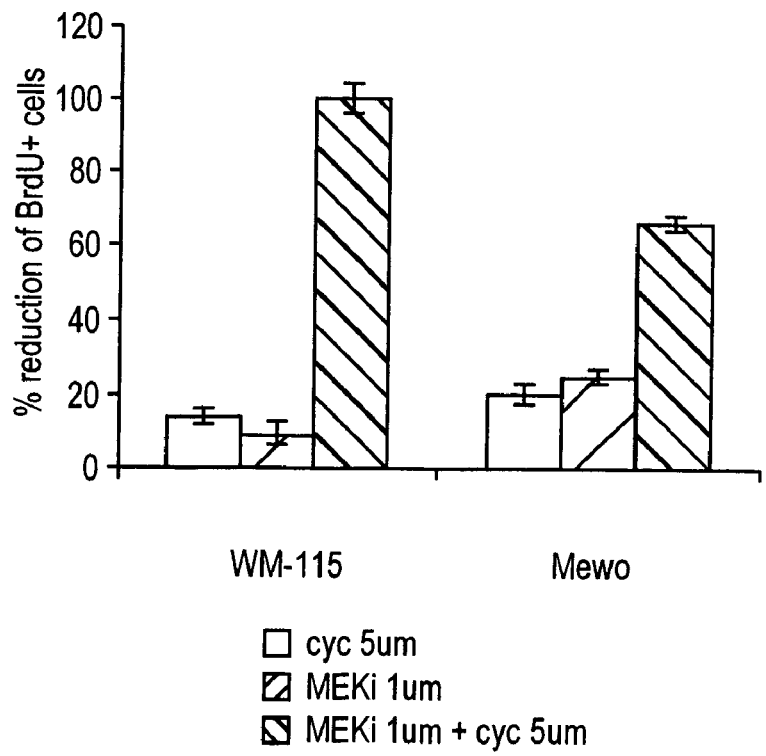

FIG. 15. Synergistic Effect of an MEK inhibitor plus cyclopamine on Proliferation of WM115 Cells. Histogram of the change in BrdU incorporation in WM115 Cells in the presence of an MEK inhibitor U0126 plus cyclopamine. WM115 cells were treated for 48 hours with either 5 µM of cyclopamine alone, or 1 µM of U0126 alone, or a combination of each at the given concentrations. Cell proliferation was assessed after incubation with BrdU as described.

Figure 16:
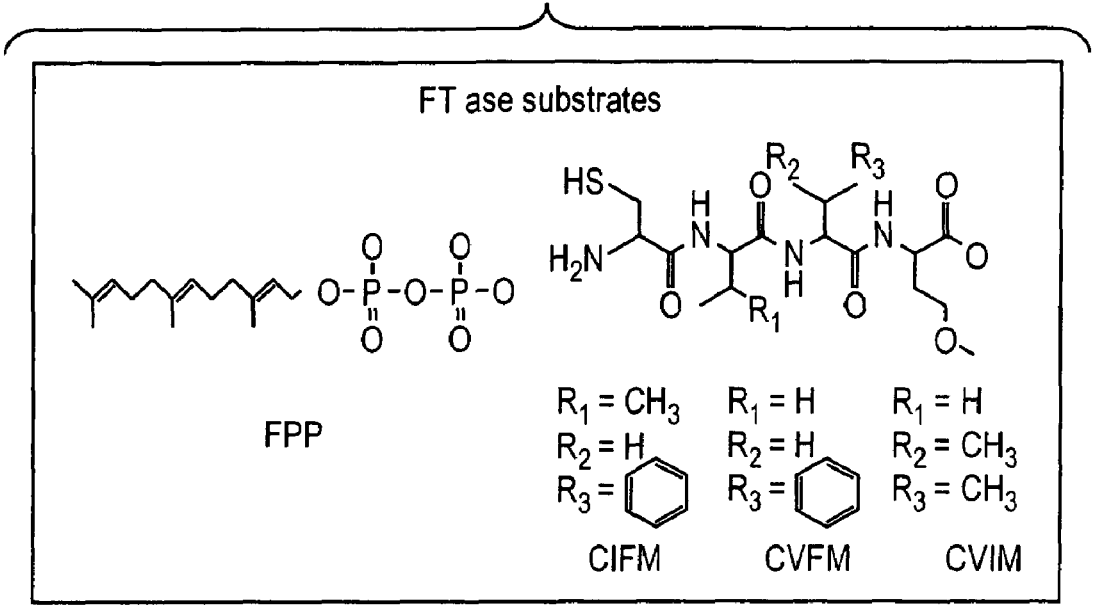
Figure 16:
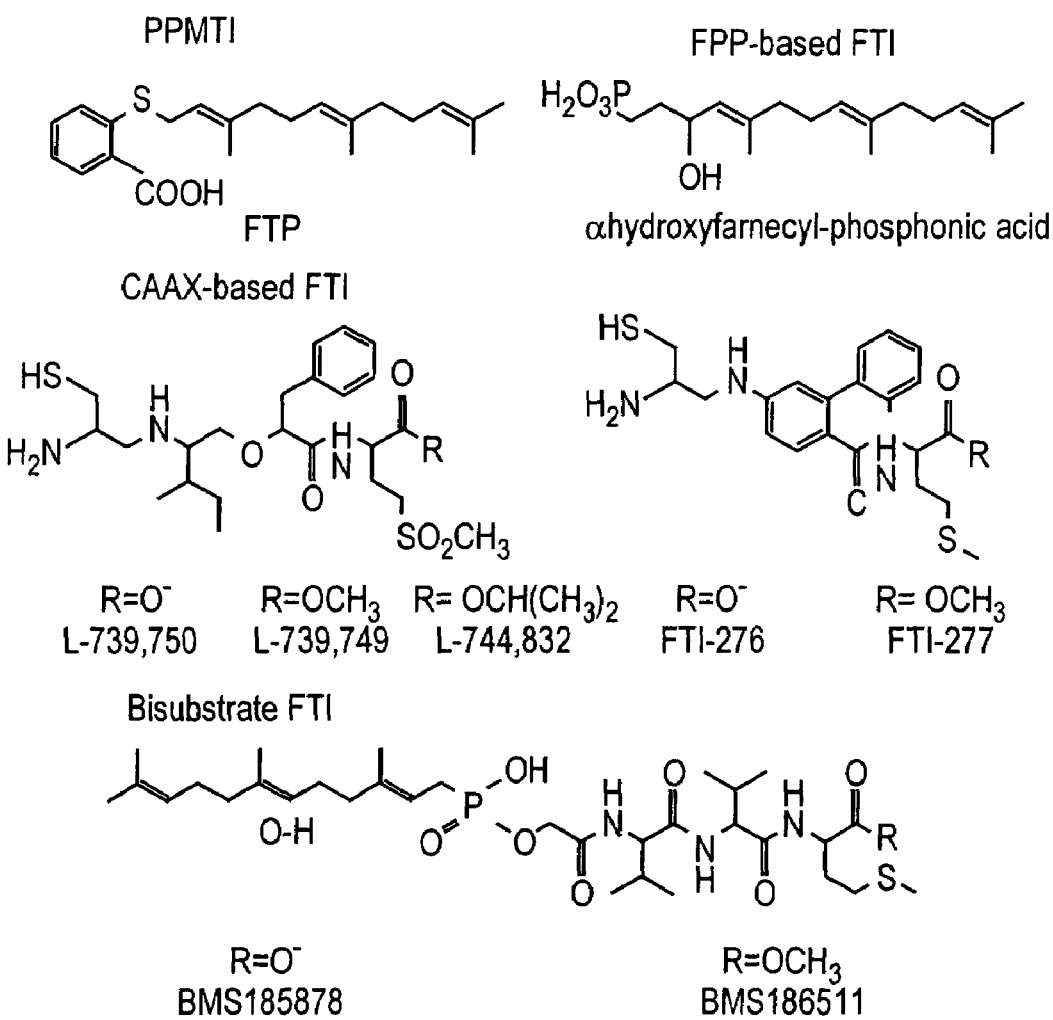

FIG. 16. Exemplary Structures of FPP-, CAAX-based, and bisubstrate inhibitors of Farnesyl Transferase (FTase). A. Chemical structures of FTase inhibitors are composed of a hydrophobic farnesyl group and a highly charged pyrophosphate moiety and a linker. B. CAAX-based FTase inhibitors. In FTI-276 and 277, the amino acid residues of the CAAX motif have been replaced by a hydrophobic linker. C. In bisubstrate FTase inhibitors, the farnesyl group of FPP and the tripeptide group of the CAAX motif are connected via a linker.

Figure 17:
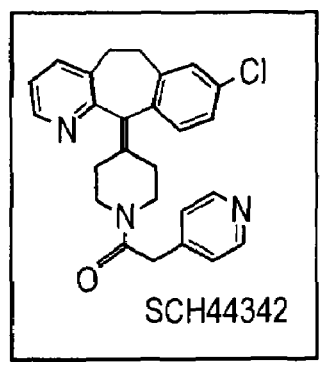
Figure 17:
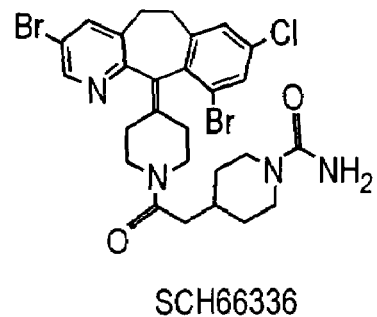

FIG. 17. Exemplary Non-peptidic, tricyclic FTase Inhibitors.

Figure 18:
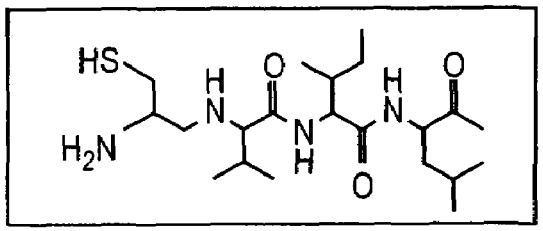
Figure 18:
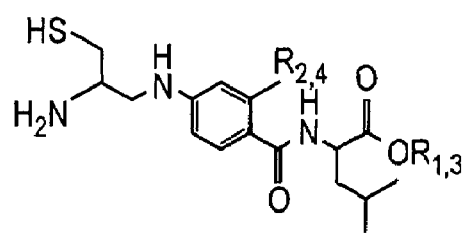

FIG. 18. Exemplary CAAL-based Inhibitors of geranylgeranylation (GGTase I inhibitors)

GGTase I catalyzes the geranylgeranylation of proteins terminating with CAAX sequences where X is restricted to leucine, isoleucine, or phenylalanine. Proteins modified by GGTase I include Rap1, Rap1B, Rac1, Rac2, G25K and RhoA.

DETAILED DESCRIPTION OF THE INVENTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated by reference in their entireties.

DEFINITIONS

As noted above, the terms used herein have the meanings recognized and known to those of skill in the art. However, for convenience and completeness, particular terms and their meanings are set forth below.

As used herein the "SHH/GLI pathway" or "HH/GLI pathway" or "GLI-pathway" or "GLI signaling pathway" is used interchangeably with the "Sonic hedgehog (SHH) signaling pathway" and is the signaling pathway initiated by a hedgehog protein binding to its receptor(s) leading to the expression and/or function of a GLI protein. "GLI" as used herein refers to any one of the GLI 1, GLI 2 or GLI 3 proteins. "gli" refers to the gene encoding the GLI proteins, and gli1, gli2 and gli3 are the genes encoding the GLI1, GLI2 and GLI3 proteins. The nucleic acids encoding the human GLI1, GLI2, and GLI3 proteins are found in SEQ ID NOS: 73, 74 and 75, respectively. The amino acid sequences for human GLI1, GLI2 and GLI3 are found in SEQ ID NOS: 76, 77 and 78, respectively. Factors involved and/or can function in the SHH-GLI pathway include any hedgehog protein such as sonic hedgehog, Indian hedgehog, and desert hedgehog, patched 1 and 2, smoothened, agonists and antagonists of such proteins, PKA, fused, suppressor of fused, costal-2, and modifiers and/or partners of any of the GLI 1, 2, or 3 proteins e.g., the Zic gene products.

As used herein the term "hedgehog" is used interchangeably with the term "HH" and is a cytokine that binds to the HH receptor to stimulate the beginning of the SHH-GLI pathway. The human SHH protein is encoded by the nucleotide sequence of SEQ ID NO: 59 and has the amino acid sequence of SEQ ID NO:60. The murine SHH protein is encoded by the nucleotide sequence of SEQ ID NO:61 and has the amino acid sequence of SEQ ID NO:62. The rat SHH protein is encoded by the nucleotide sequence of SEQ ID NO:63 and has the amino acid sequence of SEQ ID NO:64. *Xenopus* HH protein is encoded by the nucleotide sequence of SEQ ID NO:65 and has the amino acid sequence of SEQ ID NO:66. The human Indian hedgehog (IHH) protein is encoded by the nucleotide sequences of SEQ ID NO:67 and/or 69 and has the amino acid sequence of SEQ ID NO:68 and/or 70. The murine desert hedgehog (DHH) protein is encoded by the nucleotide sequence of SEQ ID NO:71 and has the amino acid sequence of SEQ ID NO:72. Hedgehog proteins from species as different as humans and insects appear to play this same role and can be used interchangeably (see e.g., Pathi et al., (2001) Mech Dev. 106:107-117).

As used herein an "active fragment" of a hedgehog is a fragment of a hedgehog protein that can comprises the first 174 amino acids of the protein (not counting the signal sequence) and can stimulate both the in vitro proliferation and in vitro differentiation of a mouse subventricular stem cell such that the number of neuronal cells obtained in the presence of 100 µM or less active fragment of the HH is at least 2-fold greater than that obtained in its absence.

As used herein a "small organic molecule" is an organic compound (or organic compound complexed with an inorganic compound (e.g., metal)) that has a molecular weight of less than 3 kilodaltons, and preferably less than 1.5 kilodaltons.

As used herein a "reporter" gene is used interchangeably with the term "marker gene" and is a nucleic acid that is readily detectable and/or encodes a gene product that is readily detectable such as green fluorescent protein (as described in U.S. Pat. No. 5,625,048 issued Apr. 29, 1997, and WO 97/26333, published Jul. 24, 1997, the disclosures of each are hereby incorporated by reference herein in their entireties) or luciferase.

A "vector" is a replicon, such as plasmid, phage, virus, or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "homologue" is used interchangeably with the term "ortholog" and refers to the relationship between proteins that have a common evolutionary origin and differ because they originate from different species. For example, mouse SHH is a homologue of human SHH.

As used herein the term "heterologous nucleotide sequence" is a nucleotide sequence that is added to a nucleotide sequence of the present invention by recombinant molecular biological methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by a nucleotide sequence of the present invention after the recombinant nucleic acid is expressed. In still another embodiment the heterologous nucleotide can function as a means of detecting a nucleotide sequence of the present invention. A heterologous nucleotide sequence can comprise non-coding sequences including restriction sites, regulatory sites, promoters and the like. Thus, the nucleic acids that encode the proteins being used and/or detected in the present invention can comprise a heterologous nucleotide sequence.

As used herein the terms "fusion protein" and "fusion peptide" are used interchangeably and encompass "chimeric proteins and/or chimeric peptides" and fusion "intein proteins/peptides". A fusion protein of the present invention can comprise at least a portion of a HH protein of the present invention, for example, joined via a peptide bond to at least a portion of another protein or peptide including a second HH protein in a chimeric fusion protein.

As used herein a polypeptide or peptide "consisting essentially of" or that "consists essentially of" a specified amino acid sequence is a polypeptide or peptide that retains the general characteristics, e.g., activity of the polypeptide or peptide having the specified amino acid sequence and is otherwise identical to that protein in amino acid sequence except it consists of plus or minus 10% or fewer, preferably plus or minus 5% or fewer, and more preferably plus or minus 2.5% or fewer amino acid residues.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

In a specific embodiment, the term "about" means within 20%, preferably within 10%, and more preferably within 5%.

RNA interference (RNAi) is an evolutionarily conserved mechanism in plant and animal cells that directs the degradation of messenger RNAs homologous to short double-stranded RNAs termed "small interfering RNA" or "siRNA". The ability of siRNA to direct gene silencing in mammalian cells has raised the possibility that siRNA might be used to investigate gene function in a high throughput fashion or to modulate gene expression in human diseases. Methods of preparing siRNAs are known to those skilled in the art. The following references are incorporated herein by reference in their entirety: Reich et al., *Mol Vis.* 9:210-6 (2003); Gonzalez-Alegre P et al., *Ann Neurol.* 53:781-7 (2003); Miller et al., *Proc Natl Acad Sci USA.* (2003); Bidere et al., *J Biol Chem.*, published as manuscript M301911200 (Jun. 2, 2003); Van De Wetering et al., EMBO Rep. 4:609-15 (2003); Miller and Grollman, *DNA Repair (Amst)* 2:759-63 (2003); Kawakami et al., *Nat Cell Biol.* 5:513-9 (2003); Abdelrahim et al., *Mol Pharmacol.* 63:1373-81 (2003); Williams et al., *J Immunol.* 170:5354-8 (2003); Daude et al., *J Cell Sci.* 116:2775-9 (2003); Jackson et al., *Nat Biotechnol.* 21:635-7 (2003); Dillin, *Proc Natl Acad Sci USA.* 100:6289-91 (2003); Matta et al., *Cancer Biol Ther.* 2:206-10 (2003); Wohlbold et al., Blood. (2003); Julien and Herr, *EMBO J.* 22:2360-9 (2003); Scherr et al., *Cell Cycle.* 2:251-7 (2003); Giri et al., *J Immunol.* 170:5281-94 (2003); Liu and Erikson, *Proc Natl Acad Sci USA.* 100:5789-94 (2003); Chi et al., *Proc Natl Acad Sci USA.* 100:6343-6 (2003); Hall and Alexander, *J Virol.* 77:6066-9 (2003).

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present invention.

"Analog" as used herein, refers to a small organic compound, a nucleotide, a protein, or a polypeptide that possesses similar or identical activity or function(s) as the compound, nucleotide, protein or polypeptide or compound having the desired activity and therapeutic effect of the present invention. (eg. inhibition of tumor growth), but need not necessarily comprise a sequence or structure that is similar or identical to the sequence or structure of the preferred embodiment As used herein, a nucleic acid or nucleotide sequence, or an amino acid sequence of a protein or polypeptide is "similar" to that of a nucleic acid, nucleotide or protein or polypeptide having the desired activity if it satisfies at least one of the following criteria: (a) the nucleic acid, nucleotide, protein or polypeptide has a sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleic acid, nucleotide, protein or polypeptide sequences having the desired activity as described herein (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of the AAPI; or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the polypeptides of the present invention having the desired therapeutic effect. As used herein, a polypeptide with "similar structure" to that of the preferred embodiments of the invention refers to a polypeptide that has a similar secondary, tertiary or quarternary structure as that of the preferred embodiment. The structure of a polypeptide can determined by methods known to those skilled in the art, including but not limited to, X-ray crystallography, nuclear magnetic resonance, and crystallographic electron microscopy.

The term "antibody" as used herein includes intact molecules as well as fragments thereof, such as Fab and F(ab')$_2$, which are capable of binding the epitopic determinant. Antibodies that bind the genes or gene products of the present invention can be prepared using intact polynucleotides or polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g, a mouse, rat or rabbit). The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397). The antibody may be a single chain antibody. The antibody may be a human or a humanized antibody. The antibody may be prepared in mice, rats, goats, sheep, swine, dogs, cats, or horses. A "blocking antibody" refers to an antibody that interferes with the function, activity or expression of a particular molecule, in the matter of the present invention, an antibody to SHH or GLI.

The term "apoptosis" and "programmed cell death" (PCD) are used as synonymous terms and describe the molecular and morphological processes leading to controlled cellular self-destruction (see, e.g., Kerr J. F. R. et al., 1972, Br J Cancer. 26:239-257). Apoptotic cell death can be induced by a variety of stimuli, such as ligation of cell surface receptors, starvation, growth factor/survival factor deprivation, heat shock, hypoxia, DNA damage, viral infection, and cytotoxic/chemotherapeutic agents. Apoptotic cells can be recognized by stereotypical morphological changes: the cell shrinks, shows deformation and looses contact to its neighboring cells. Its chromatin condenses, and finally the cell is fragmented into compact membrane-enclosed structures, called "apoptotic bodies" which contain cytosol, the condensed chromatin, and organelles. The apoptotic bodies are engulfed by macrophages and thus are removed from the tissue without causing an inflammatory response. This is in contrast to the necrotic mode of cell death in which case the cells suffer a major insult, resulting in loss of membrane integrity, swelling and disrupture of the cells. During necrosis, the cell contents are released uncontrolled into the cell's environment what results in damage of surrounding cells and a strong inflammatory response in the corresponding tissue. See, e.g., Tomei L. D. and Cope F. O., eds., 1991, Apoptosis: The Molecular Basis of Cell Death, Plainville, N.Y.: Cold Spring Harbor Laboratory Press; Isaacs J. T., 1993, Environ Health Perspect. 101 (suppl 5):27-33; each of which is herein incorporated by reference in its entirety for all purposes. "Apoptosis" is characterized by certain cellular characteristics such as membrane blebbing, chromatin condensation and fragmentation, formation of apoptotic bodies and a positive "TUNEL" staining pattern. Degradation of genomic DNA during apoptosis results in formation of characteristic, nucleosome sized DNA fragments; this degradation produces a diagnostic (about) 180 bp laddering pattern when analyzed by gel electrophoresis. A later step in the apoptotic process is degradation of the plasma membrane, rendering apoptotic cells leaky to various dyes (e.g., trypan blue and propidium iodide). Accordingly, a variety of apoptosis assays are well known to one of skill in the art (e.g., DNA fragmentation assays, radioactive proliferation assays, DNA laddering assays for treated cells, Fluorescence microscopy of 4'-6-Diamidino-2-phenylindole (DAPI) stained cells assays, and the like).

"Surrogate biomarker" or "biomarker" as used herein, refers to a highly specific molecule, the existence and levels of which are causally connected to a complex biological process, and reliably captures the state of said process. Furthermore, a surrogate biomarker, to be of practical importance, must be present in samples that can be obtained from individuals without endangering their physical integrity or well-being, preferentially from biological fluids such as blood, urine, saliva or tears.

"Derivative" refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

"Treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

"Subject" or "patient" refers to a mammal, preferably a human, in need of treatment for a condition, disorder or disease.

"Modulators" or "regulators" of RAS-MEK and/or AKT or SHH-GLI signaling pathways refer to inhibitory or activating molecules identified using in vitro and in vivo assays for these particular pathways. "Inhibitors," or "antagonists" refer to inhibitory molecules identified using in vitro and in vivo assays for pathway function. In particular, inhibitors and antagonists refer to compounds or agents that decrease signaling that occurs via the SHH-GLI pathway or through one of the other noted oncogenic pathways, such as, but not limited to, PGF-RTK-RAS-RAF-MEK and AKT. Inhibitors may be compounds that decrease, block, or prevent, signaling via these pathways. Such assays for inhibitors or antagonists may include assaying for the effect of such compounds on tumor cell proliferation or inhibition thereof.

"Antisense" nucleic acids are DNA or RNA molecules that are complementary to at least a portion of a specific mRNA molecule (See Weintraub, *Sci. Amer.* 262:40-46 (1990); Marcus-Sekura, *Nucl. Acid Res,* 15: 5749-5763 (1987); Marcus-Sekura *Anal. Biochem.,* 172:289-295 (1988); Brysch et al., *Cell Mol. Neurobiol.,* 14:557-568 (1994)). In the cell, the single stranded antisense molecule hybridizes to that mRNA, forming a double stranded molecule. The cell does not translate an mRNA in this double-stranded form. Therefore, antisense nucleic acids interfere with the expression of mRNA into protein. Oligomers of greater than about fifteen nucleotides and molecules that hybridize to the AUG initiation codon will be particularly efficient. Antisense methods have been used to inhibit the expression of many genes in vitro (Marcus-Sekura, *Anal. Biochem.,* 172:289-295 (1988); Hambor et al., *Proc. Natl. Acad. Sci. U.S.A.* 85:4010-4014 (1988)) and in situ (Arima et al., *Antisense Nucl. Acid Drug Dev.* 8:319-327 (1998); Hou et al., *Antisense Nucl. Acid Drug Dev.* 8:295-308 (1998)).

The term "oligonucleotide," as used herein is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Agents that "increase negative, or decrease positive acting elements affecting SHH-GLI signaling", as used herein, refers to agents that potentiate positive or transactivating function of the Gli proteins, for example, increasing their transcriptional activity on target genes, or agents that decrease their negative or repressive transcription function on target genes.

Tumors that are "apoptotic resistant" are tumors that are inhibited from undergoing apoptosis. This inhibition of apoptosis may be due in part to the expression of at least one of the GLI proteins or gene products.

"Combination therapy", as used herein, refers to the use of a "second agent" or a "third agent" in combination with a either a GLI inhibitor or antagonist or an antagonist of the RAS-MEK signaling pathway and/or AKT signaling pathway. The "second agent" may have similar activity to the GLI inhibitor or antagonist (eg. it may also inhibit or antagonize GLI expression or activity), or it may act on a different oncogenic signaling pathway (such as RAS-RAF-MEK/AKT), and may act synergistically with the GLI inhibitor or antagonist. Other second agents of the invention include inhibitors of EGF, IGF, FGF, PDGF, and HGF, that is, inhibitors of peptide growth factor signaling that lead to RAS action known to those skilled in the art. The "third agent" may be a standard chemotherapeutic agent or irradiation therapy used to treat the cancers described herein, in particular, melanomas. The second agent or third agent may be capable of negatively affecting cancer in a patient, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, aiding to overcome resistance of a tumor to standard therapies, or increasing the lifespan of a subject with cancer. More generally, these other agents would be provided in a combined amount effective to kill or inhibit proliferation of the cell. This process may involve contacting or exposing the cells to the GLI inhibitor and the second or third agent(s) at the same time, or sequentially. This may be achieved by contacting the cell with a single composition or pharmacological formulation that includes one, two or three agents, or by contacting the cell with two or three distinct compositions or formulations, at the same time, wherein one composition includes the GLI inhibitor or antagonist and the other includes the second and third agent(s) together, or each of the second and third agents in their own compositions.

An agent that "exhibits antagonism to" a GLI protein may be any type of molecule that prevents, retards, inhibits, or antagonizes the activity of the GLI protein, one such activity being its tumorigenic activity, and this agent may be a protein, a peptide, an antibody, a synthetic or naturally derived small organic molecule, a nucleic acid (including DNA, RNA, antisense nucleic acids, small interfering RNAs), a carbohydrate, a lipid or a lipoprotein.

The term "has control over its production" refers to an agent that may prevent or enhance the biosynthesis of the GLI proteins. The control may be by way of modifying the level of transcription of the GLI nucleic acid or by modifying the level of translation of the GLI protein. In the present invention, the agent that "has control over the production of a GLI protein" generally refers to an inhibitor or antagonist that prevents the synthesis or expression of the GLI molecule, thereby inhibiting the tumorigenic properties associated with the SHH-GLI pathway.

"Antagonist" refers to an agent that down-regulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that down-regulates expression of a gene or which reduces the amount of expressed protein present.

The terms "contacting" and "exposing," are used herein to describe the process by which a therapeutic agent is delivered to a target cell or is placed in direct juxtaposition with the target cell. To achieve cell killing or stasis, the agent is delivered to a cell in an amount effective to kill the cell or prevent it from dividing.

General Description

The Hedgehog-Gli signaling pathway, or SHH/GLI signaling pathway, regulates numerous events during the normal development of many cell types and organs, including the brain, bone, skin, gonads, lung, prostate, gastrointestinal tract and blood. The hedgehog (hh) gene—like many of the components of the signaling pathway triggered by Hedgehog (Hh) protein—was first identified in *Drosophila*, where it affects pattern formation very early in embryonic development. The binding of Hh to cell membranes triggers a signaling cascade that results in the regulation of transcription by zinc-finger transcription factors of the Gli family.

Of the three hh-family genes in mammals—Sonic hedgehog (Shh), Indian hedgehog (Ihh) and Desert hedgehog (Dhh)—Shh has been the most studied, mainly because it is expressed in various tissues but also because experiments with Shh protein are generally also applicable to other members of the family. The correct regulation of the HH-GLI signaling pathway is essential not only for normal development but also to prevent a number of human diseases associated with abnormally increased or decreased signaling. Here, we discuss the potential use of small-molecule modulators of the HH-GLI-signaling system.

Hedgehogs are secreted glycoproteins that act through the transmembrane proteins Patched1 (Ptc1) and Smoothened (Smo) to activate an intricate intracellular signal-transduction pathway. Hh binds Ptc1, a protein with 12 trans-membrane domains, and this releases the basal repression that Ptc1 exerts on Smo, a 7-transmembrane-domain protein that has homology to G-protein-coupled receptors. Inside the cell, a multimolecular complex, including Costal2 (Cos2), Fused (Fu) and suppressor of Fused (Su(Fu)), responds to the activation of Smo in such a way as to modify the activity of the Gli proteins. There are three Gli transcription factors in vertebrates: Gli1 appears to act as a transcriptional activator and is universally induced in Hh-responding cells, whereas Gli2 and Gli3 can act as activators or repressors of transcription depending on the particular cellular context. The fate of Gli proteins, which appear to reside in the cytoplasm in their inactive state, depends on the state of Hh signaling. In the absence of Hh, Gli 3 is processed into a smaller, nuclear transcriptional repressor that lacks the carboxy-terminal domain of full-length Gli3. Upon activation of Smo (and Hh signaling), Gli3 protein cleavage is prevented and an apparent full-length form with transcription-activating function is generated. Gli2 also encodes a repressor function in its carboxy-terminally truncated form, but its formation does not appear to be regulated by Hh signaling.

Mutations in components of the HH-GLI pathway in humans (human gene and protein names are given in capitals) lead to several diseases that result from either loss of function or ectopic activation of the pathway. For example, haploinsufficiency of SHH or mutation in the human PTCH1 gene are associated with holoprosencephaly, a common syndrome affecting development of the forebrain and mid-face. Moreover, ectopic expression of Shh, Gli1 or Gli2 in model systems leads to the formation of tumors that resemble basal cell carcinomas (BCCs), and sporadic human BCCs consistently express GLI, suggesting that all sporadic BCCs have this pathway active. Similarly, human mutations in the Suppressor of Fused—SU(FU)—gene predispose the carrier to medulloblastoma; sporadic medulloblastomas can carry PTCH1 mutations and express GLI1—again suggesting that they harbor an active pathway—and Ptc+/− mice can develop medulloblastomas. Furthermore, a number of sporadic prostate tumors express GLI1 (Dahmane N, et al. The Sonic Hedgehog-Gli pathway regulates dorsal brain growth and tumorigenesis. *Development* 128, 5201-5212 (2001)), a reliable marker of HH signaling (Lee J, Platt K A, Censullo P, & Ruiz i Altaba A. Gli1 is a target of Sonic hedgehog that induces ventral neural tube development. *Development* 124, 2537-2552 (1997), raising the possibility that this pathway participates in prostate cancer (PC). Moreover, genetic mapping data reveals that at least two of the genes present in the SHH-GLI pathway (SMOH and Suppressor of Fused (SU-FUH)) are located in chromosomal regions implicated in familial human PC by genetic mapping studies Easton, D. F., Schaid, D. J., Whittemore, A. S. & Isaacs, W. J., *Prostate* 57, 261-269 (2003); Xu, J. et al., *Prostate* 57, 320-325 (2003).

From an examination of the different mutations that cause aberrant suppression or activation of the HH-GLI pathway in humans, it seems clear that the development of small molecules that could act as agonists or antagonists of the function of proteins such as PTCH1, SMO or GLI might provide an effective therapeutic approach. One such drug could be SHH protein itself, a natural agonist. For example, it has been reported that injection of Shh into the striatum reduces behavioral deficits in a rat model of Parkinson's disease, that Shh can induce dopaminergic neuronal differentiation and that Shh is a neuroprotective agent. But Shh has a relatively short half-life in serum and its therapeutic effects have been difficult to evaluate in vivo. The use of synthetic Hh agonists could therefore provide a viable alternative to Shh protein. Frank-Kamenetsky et al. have now identified a synthetic nonpeptidyl small molecule that faithfully activates the Hh-Gli pathway, triggering the known biological effects of Hh signaling. They have shown that this agonist promotes proliferation and differentiation in a cell-type-specific manner in vitro, while in vivo it rescues developmental defects of Shh-null mouse embryos. But this agonist, unlike Shh protein, appears to bypass the Ptc1-regulatory step, by interacting directly with Smo (*Journal of Biology* 2002, Volume 1, Issue 2, Article 9; Stecca and Ruiz i Altaba, *Journal of Biology* 2002, 1:9. From a therapeutic point of view, the fact that the molecule retains its activity after oral administration is a great advantage and, if its ability to cross the blood-brain and placental barriers occurs in humans, it could be a very valuable therapeutic agent. Nevertheless, systemic side effects are to be expected, as there are many HH-responsive cell populations in the body.

Treatment of human diseases resulting from ectopic HH-GLI pathway activation, such as those caused by oncogenic mutations in SMOH and PTCH1 or in any element of the pathway that results in activation of GLI function, requires the use of pathway antagonists. Up to now, inhibition of ectopic activity has been achieved by treatment with signaling antagonists that block the pathway at different levels: first, blocking anti-Shh antibodies that act extracellularly, second, cyclopamine, a plant alkaloid that acts at the level of Smo in the cell membrane, third, forskolin, an intracellular activator of protein kinase A (PKA) that is a cytoplasmic inhibitor of the pathway; and fourth, Gli-repressor proteins that act within the nucleus to inhibit positive GLI function from mediating the HH signal. Use of forskolin is likely to lead to numerous side effects, given the wide-spread activity of PKA. In contrast, the use of the small molecule cyclopamine or analogs thereof, holds great promise. A number of studies suggest that cyclopamine specifically inhibits Smo activity and that it can affect disease states caused by activation of the HH-GLI pathway. For example, the proliferation of a number of human brain-tumor cell lines and primary tumor cultures, including those from medulloblastomas and some gliomas as well as medulloblastoma allografts, are inhibited by treatment with cyclopamine. This suggests that pathway activation is required for tumor maintenance. The activity of Gli proteins, the terminal elements of the pathway, is sufficient to induce tumor development. Thus, HH-pathway activity may be involved in the initiation as well as the maintenance of different tumors. This provides an additional opportunity to inhibit the growth of a number of tumors in different organs and tissues, including basal cell carcinoma in the skin, lung cancer (small cell and non small cell lung cancer), prostate cancer, medulloblastoma, glioblastoma and PNETs, and other brian tumors, cancer of the stomach, GI tract, pancreas, rhabdomyosarcomas, and soft tissue sarcomas, all with the same agent. Cyclopamine could be such an agent if the diseases to be treated arise from activation of the HH-signaling pathway at the level of SMOH or above. But cyclopamine is currently very expensive, and alternative HH-pathway antagonists might be economically more attractive. Frank-Kamenetsky et al. (Frank-Kamenetsky et al *J. Biol.* 2002, 1:10) report the use of a new, synthetic, small-molecule inhibitor, Cur61414, which has inhibitory properties similar to those of cyclopamine and also acts at the level of Smo (Williams et al, PNAS, (2003), 100(8):4616-21). Whether Cur61414, or four additional small-molecule antagonists (SANT1-4) that also act on Smo and were recently identified (Chen et al, (2002), PNAS, 99:14071-14076), will prove to be better and easier to use than cyclopamine remains to be determined, but testing them against skin (Williams et al supra) and brain tumors is warranted from a biological point of view.

Finally, given that carboxy-terminally truncated repressor forms of GLI3 are potent inhibitors of the activating output of the HH-signaling pathway, these could be used as antagonists for the treatment of tumors. The difficulty of delivering them into cells might require the development of in vivo transducing strategies, taking advantage, for example, of the ability of the Penetratin, TAT or VP22 peptides to cross cell membranes while loaded with cargo. It also suggests that it would be useful to search for and design small molecules that inhibit GLI's transcription-activating function, perhaps by promoting endogenous GLI-repressor formation. This may be very difficult, but such drugs would be very specific and would be usable in cases where the cancer is due to mutation in the pathway at any level, from the extracellular ligand, the HH proteins, to the final mediators, the GLI proteins. Agents that inhibit HH signaling may induce the regression of tumors that are dependent on a deregulated HH-GLI pathway, but these agents are likely also to affect the behavior of other normal pathway-dependent cells in the patient. This may, however, be a small price to pay in order to combat cancer, and the agents may have fewer side effects than current non-specific cytotoxic anti-cancer chemotherapies.

Patients with metastatic malignant melanoma, who have a median survival of approximately one year, are treated generally with a combination of chemotherapy agents such as cisplatin, DTIC, and BCNU, with or without cytokines such as interleukin-2 (IL-2) or interferon-α (IFN-α) (Balch et al., 1993; Koh, 1991; Legha and Buzaid, 1993). Response rates to chemotherapy have been reported to be as high as 60%, yet only approximately 5% of patients experience long-term survival, regardless of the therapeutic regimen employed. The conventional forms of chemotherapy aim to control the growth of cancer by targeting rapidly growing cells. Unfortunately, this form of therapy is not specific, since many normal cells, such as those of the bone marrow and the intestinal epithelium, also have a basal level of proliferation. Thus, many of these normal cells in the body are susceptible to the toxic effects of chemotherapy, and as such, conventional chemotherapy can impart a substantial degree of morbidity to the patient. Clearly, new approaches to the treatment of melanoma are needed.

Ras-Raf-MEK and AKT Signaling Pathways and Tumorigenesis

Cell signaling through growth factor receptors and protein kinases is an important regulator of cell growth, proliferation and differentiation. In normal cell growth, growth factors, through receptor activation (i.e. PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., Methods in Enzymology, 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., Methods in Enzymology, 2001, 332, 417-431). Phosphorylated ERK dimerizes and then translocates to the nucleus where it accumulates (Khokhlatchev et al., Cell, 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., Molecular Cell, 2000, 6, 1343-1354). Overall, treatment of cells with growth factors leads to the activation of ERK1 and 2 which results in proliferation and, in some cases, differentiation (Lewis et al., Adv. Cancer Res., 1998, 74, 49-139).

In proliferative diseases, genetic mutations and/or overexpression of the growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., Science, 1993, 260, 1834-1837). Recently, bRaf mutations have been identified in more than 60% of malignant melanoma (Davies, H. et al., Nature, 2002, 417, 949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R. et al., Oncogene, 1999, 18, 813-822). Hence, there is a strong correlation between cancers and an overactive MAP kinase pathway resulting from genetic mutations.

AKT Protein Kinases

The Akt protein kinase family consists of three members, Akt1/PKBα Akt2/PKBβ and Akt3/PKBγ, which share a high degree of structural similarity (Brazil et al., Cell 111:293-303 (2002); and Nicholson et al., Cell Signal 14:381-395 (2002)). Family members share extensive structural similarity with one another, exhibiting greater than 80% homology at the amino acid level (Nicholson K M, Anderson N G. Cell Signal. 14(5):381-95 (2002), Datta S R et al. Genes Dev. 13(22): 2905-27 (1999)). All Akt isoforms share major structural features, having three distinct functional domains (Testa J R, Bellacosa. A. Proc Natl Acad Sci USA. 98(20): 10983-5 (2001), Nicholson K M, Anderson N G. Cell Signal. 14(5): 381-95 (2002), Scheid M P, Woodgett J R. Nat Rev Mol Cell Biol. 2(10):760-8 (2001), Scheid M P, Woodgett J R. FEBS Lett. 546(1): 108-12 (2003), Bellacosa A et al. Cancer Biol Ther. 3(3):268-75. Epub 2004 (2004), Brazil D P et al. Trends Biochem Sci. 29(5):233-42 (2004), Brazil, D. P. et al. Cell 111:293-303 (2002), Brazil D P, Hemmings B A. Trends Biochem Sci. 26(11):657-64 (2001), Datta S R et al. Genes Dev. 13(22):2905-27 (1999)). One is an amino-terminal pleckstrin homology domain (PH) domain that mediates protein-protein and protein-lipid interactions. This domain consists of approximately one hundred amino acids, resembles the three phosphoinsitides binding domains in other signaling molecules (Lietzke S E et al. Mol Cell. 6(2):385-94 (2000), Ferguson K M et al. Mol Cell. 6(2):373-84 (2000)). The second domain is a carboxy-terminal kinase catalytic region that mediates phosphorylation of substrate proteins. It shows a high degree of similarity to those in protein kinase A (PKA) and protein kinase C (PKC) (Jones P F et al. Cell Regul. 2(12):1001-9 (1991), Andjelkovic M, Jones P F, Grossniklaus U, Cron P, Schier A F, Dick M, Bilbe G, Hemmings B A. Developmental regulation of expression and activity of multiple forms of the *Drosophila* RAC protein kinase. J Biol Chem. 270(8):4066-75 (1995)). The third domain is a tail region with an important regulatory role. This region is sometimes referred to as the tail or regulatory domain. Within the latter two regions are serine and threonine residues whose phosphorylation is required for Akt activation. The sites vary slightly dependent of the particular Akt isoform. The first site on all three isoforms is a threonine at amino acid position 308/309/305 and on Akt1/2/3 respectively. The second site is a serine occurring within the hydrophobic C-terminal tail at amino acid positions 473/474/472 on Akt 1/2/3 respectively. Phosphorylation on both sites occurring in response to growth factors or other extracellular stimuli is essential for maximum Akt activation (Alessi D R, Andjelkovic M, Caudwell B, Cron P, Morrice N, Cohen P, Hemmings B A. Mechanism of activation of protein kinase B by insulin and IGF-1. EMBO J. 15(23):6541-51 (1996)). Akt may also be phosphorylated on other residues; however, the functional significance of this phosphorylation is an area of continuing investigation (Alessi D R, Andjelkovic M, Caudwell B, Cron P, Morrice N, Cohen P, Hemmings B A. Mechanism of activation of protein kinase B by insulin and IGF-1. EMBO J. 15(23):6541-51 (1996)). Also, although splice variants of Akt3 lacking the serine 472 phosphorylation site have been identified, the cellular role of this variant remains uncertain (Brodbeck D, Hill M M, Hemmings B A. J Biol Chem. 276 (31):29550-8. Epub 2001 (2001)). It is also unknown whether this variant is present or performs any role in the melanoma cells.

While all isoforms may be expressed in a particular cell type, only certain isoforms may be active. It also appears that each isoform can perform unique as well as common functions in cells (Brazil et al., Cell 111:293-303 (2002); and Nicholson et al., Cell Signal 14:381-395 (2002); Chen et al., Genes Dev 15:2203-2208 (2001); and Cho et al., Science 292:1728-1731 (2001)). Knockout mice lacking Akt1 are growth retarded and have increased rates of spontaneous apoptosis in the testis and thymus (Chen et al., Genes Dev 15:2203-2208 (2001); Cho et al., J Biol Chem 276:38349-38352 (2001); Peng et al., Genes Dev 17:1352-1365 (2003)). In contrast, Akt2 knockout mice have impaired insulin regulation and consequently a defective capability of lowering blood glucose levels due to defects in the action of insulin on liver and skeletal muscle (Cho et al., Science 292:1728-1731 (2001); Peng et al., Genes Dev 17:1352-1365 (2003)). Currently, there is no published report describing the phenotype associated with an Akt3 knockout mouse; thus, there is very little known about the specific functions of Akt3 or its role in human cancer.

Genetic amplification that increases the expression of Akt1 or Akt2 have been reported in cancers of the stomach, ovary, pancreas and breast (Staal, S. P., Proc Nat Acad Sciences ISA 84:5034-5037 (1987); Cheng et al., Proc Nat Acad Sciences USA 89:9267-9271 (1992); Cheng et al., Proc Nat Acad Sciences USA 93:3636-3641 (1996); Lu et al., Chung-Hua I Hsuch Tsa Chih [Chinese Medical Journal] 75:679-682 (1995); Bellacosa et al., Int J Cancer 64:280-285 (1995); and van Dekken et al., Cancer Res 59:749-752 (1999)). Total Akt activity has also been measured in melanomas using immunohistochemistry to demonstrate increased levels of total phosphorylated Akt in severely dysplastic nevi and metastatic melanomas compared to normal or mildly dysplastic nevi (Dhawan et al., Cancer Res 62:7335-7342 (2002)). Recently, the phosphoinositide 3-kinase (PI3K)/Akt signaling pathway was found to play a critical role in melanoma tumorigenesis (Stahl et al., Cancer Res 63:2891-2897 (2003)). Deregulated Akt activity through loss of the PTEN phosphatase, a negative regulator of PI3K/Akt signaling, was found to decrease the apoptotic capacity of melanoma cells and thereby regulate melanoma tumorigenesis (Stahl et al., Cancer Res 63:2891-2897 (2003)).

RAF Protein Kinases

The Raf protein serine/threonine kinase family consists of three members, A-Raf, B-Raf, and C-Raf. (Mercer et al., Biochim Biophys Acta 1653:2540 (2003)). Raf family members are intermediate molecules in the MAPK (Ras/Raf/MAPK kinase (MEK)/extracellular signal-regulated kinase (ERK) pathway, which is a signal transduction pathway that relays extracellular signals from cell membrane to nucleus via an ordered series of consecutive phosphorylation events (Mercer et al., Biochim Biophys Acta 1653:2540 (2003), Smalley. Int J Cancer 104: 527-32 (2003)). Typically, an extracellular ligand binds to its tyrosine kinase receptor, leading to Ras activation and initiation of a cascade of phosphorylation events (Mercer et al., Biochim Biophys Acta 1653: 2540 (2003), Smalley. Int J Cancer 104: 527-32 (2003)). Activated Ras causes phosphorylation and activation of Raf, which in turn phosphorylates and activaters MEK1 MEK2. MEK kinases in turn phosphorylate and activate ERK1 and ERK2 (Chong et al, Cell Signal 15:163-69 (2003)), which phosphorylates several cytoplasmic and nuclear targets that ultimately lead to expression of proteins playing important roles in cell growth and survival (Chang et al., Int J Oncol 22:469-80 (2003)).

Mutations that lead to activation of B-Raf have been found in the majority of sporadic melanomas, mainly B-RAF the most mutated gene in melanomas with a mutation rate ranging from 60 to 90% (Davies et al., Nature 417:949-54 (2002); Pollock et al., Nat Genet 33:19-20 (2003); Brose et al., Cancer Res 62:6997-7000 (2002); and Yazdi et al., J Invest Dermatol 121:1160-62 (2003)). The majority of B-RAF mutations occur as a result of a single base missense substitution that converts T to A at nucleotide 1796 which substitutes a Valine for a Glutamic Acid at codon 599 (V599E) in exon 15 (Davies et al., Nature 417:949-54 (2002)). This mutation increases basal kinase activity of B-Raf, resulting in hyperactivity of the MAPK pathway evidenced by constitutively elevated levels of downstream kinases MEK and ERK (Davies et al., Nature 417:949-54 (2002)). B-RAF mutations are acquired, somatic, post-zygotic events that have not been identified in familial melanomas (Lang et al. Hum Mutat 21:327-30 (2003); Laud et al, Cancer Res 63:3061-65 (2003); and Meyer et al, Int J Cancer 106:78-80 (2003)).

EGFR Kinases

The ErbB family of receptor tyrosine kinases are important mediators of cell growth, differentiation and survival. The receptor family includes four distinct members including epidermal growth factor receptor (EGFR or ErbB1), HER2 (ErbB2 or p185$^{neu}$), HER3 (ErbB3) and HER4 (ErbB4 or tyro2).

EGFR, encoded by the erbB1 gene, has been causally implicated in human malignancy. Increased EGFR receptor expression is often associated with increased production of the EGFR ligand, transforming growth factor alpha (TGFα) by the same tumor cells resulting in receptor activation by an autocrine stimulatory pathway (Baselga and Mendelsohn Pharmac. Ther. 64:127-154 (1994)). Monoclonal antibodies directed against the EGFR or its ligands, TGFα and EGF, have been evaluated as therapeutic agents in the treatment of such malignancies. See, e.g., Baselga and Mendelsohn., supra; Masui et al. Cancer Research 44:1002-1007 (1984); and Wu et al. J. Clin. Invest. 95:1897-1905 (1995).

The second member of the ErbB family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., Science, 235:177-182 (1987); Slamon et al., Science, 244:707-712 (1989); and U.S. Pat. No. 4,968,603). To date, no point mutation analogous to that in the neu proto-oncogene has been reported for human tumors. Overexpression of ErbB2 (frequently but not uniformly due to gene amplification) has also been observed in other carcinomas including carcinomas of the stomach, endometrium, salivary gland, lung, kidney, colon, thyroid, pancreas and bladder. See, among others, King et al., Science, 229:974 (1985); Yokota et al., Lancet: 1:765-767 (1986); Fukushigi et al., Mol Cell Biol., 6:955-958 (1986); Geurin et al, Oncogene Res., 3:21-31 (1988); Cohen et al., Oncogene, 4:81-88 (1989); Yonemura et al., Cancer Res., 51:1034 (1991); Borst et al., Gynecol. Oncol., 38:364 (1990); Weiner et al., Cancer Res., 50:421-425 (1990); Kern et al., Cancer Res., 50:5184 (1990); Park et al., Cancer Res., 49:6605 (1989); Zhau et al, Mol. Carcinog., 3:354-357 (1990); Aasland et al. Br. J. Cancer 57:358-363 (1988); Williams et al. Pathiobiology 59:46-52 (1991); and McCann et al., Cancer, 65:88-92 (1990). ErbB2 may be overexpressed in prostate cancer (Gu et al. Cancer Lett. 99:185-9 (1996); Ross et al. Hum. Pathol. 28:827-33 (1997); Ross et al. Cancer 79:2162-70 (1997); and Sadasivan et al. J. Urol. 150:126-31 (1993)).

Antibodies directed against the rat p185$^{neu}$ and human ErbB2 protein products have been described. Drebin and colleagues have raised antibodies against the rat neu gene product, p185.sup.neu See, for example, Drebin et al., Cell 41:695-706 (1985); Myers et al., Meth. Enzym. 198:277-290 (1991); and WO94/22478. Drebin et al. Oncogene 2:273-277 (1988) report that mixtures of antibodies reactive with two distinct regions of p185.sup.neu result in synergistic antitumor effects on neu-transformed NIH-3T3 cells implanted into nude mice. See also U.S. Pat. No. 5,824,311 issued Oct. 20, 1998.

Hudziak et al., Mol. Cell. Biol. 9(3):1165-1172 (1989) describe the generation of a panel of anti-ErbB2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-.alpha. See also U.S. Pat. No. 5,677,171 issued Oct. 14, 1997. The anti-ErbB2 antibodies discussed in Hudziak et al. are further characterized in Fendly et al. Cancer Research 50:1550-1558 (1990); Kotts et al. In Vitro 26(3):59A (1990); Sarup et al. Growth Regulation 1:72-82 (1991); Shepard et al. J. Clin. Immunol. 11(3): 117-127 (1991); Kumar et al. Mol. Cell. Biol. 11(2): 979-986 (1991); Lewis et al. Cancer Immunol. Immunother. 37:255-263 (1993); Pietras et al., Oncogene 9:1829-1838 (1994); Vitetta et al. Cancer Research 54:5301-5309 (1994); Sliwkowski et al. J. Biol. Chem. 269(20):14661-14665 (1994); Scott et al. J. Biol. Chem. 266:14300-5 (1991); D'souza et al. Proc. Natl. Acad. Sci. 91:7202-7206 (1994); Lewis et al. Cancer Research 56:1457-1465 (1996); and Schaefer et al. Oncogene 15:1385-1394 (1997).

A recombinant humanized version of the murine anti-ErbB2 antibody 4D5 (huMAb4D5-8, rhuMAb HER2 or HERCEPTIN®; U.S. Pat. No. 5,821,337) is clinically active in patients with ErbB2-overexpressing metastatic breast cancers that have received extensive prior anti-cancer therapy (Baselga et al., J. Clin. Oncol. 14:737-744 (1996)). HERCEPTIN® received marketing approval from the Food and Drug Administration Sep. 25, 1998 for the treatment of patients with metastatic breast cancer whose tumors overexpress the ErbB2 protein.

Other anti-ErbB2 antibodies with various properties have been described in Tagliabue et al. Int. J. Cancer 47:933-937 (1991); McKenzie et al. Oncogene 4:543-548 (1989); Maier et al. Cancer Res. 51:5361-5369 (1991); Bacus et al. Molecular Carcinogenesis 3:350-362 (1990); Stancovski et al. PNAS (USA) 88:8691-8695 (1991); Bacus et al. Cancer Research 52:2580-2589 (1992); Xu et al. Int. J. Cancer 53:401-408 (1993); WO94/00136; Kasprzyk et al. Cancer Research 52:2771-2776 (1992); Hancock et al. Cancer Res. 51:4575-4580 (1991); Shawver et al. Cancer Res. 54:1367-1373 (1994); Arteaga et al. Cancer Res. 54:3758-3765 (1994); Harwerth et al. J. Biol. Chem. 267:15160-15167 (1992); U.S. Pat. No. 5,783,186; and Klapper et al. Oncogene 14:2099-2109 (1997).

Homology screening has resulted in the identification of two other ErbB receptor family members; ErbB3 (U.S. Pat. Nos. 5,183,884 and 5,480,968 as well as Kraus et al. PNAS (USA) 86:9193-9197 (1989)) and ErbB4 (EP Pat Appln No 599,274; Plowman et al., Proc. Natl. Acad. Sci. USA, 90:1746-1750 (1993); and Plowman et al., Nature, 366:473-475 (1993)). Both of these receptors display increased expression on at least some breast cancer cell lines.

The ErbB receptors are generally found in various combinations in cells and heterodimerization is thought to increase the diversity of cellular responses to a variety of ErbB ligands (Earp et al. Breast Cancer Research and Treatment 35: 115-132 (1995)). EGFR is bound by six different ligands; epidermal growth factor (EGF), transforming growth factor alpha (TGFα.), amphiregulin, heparin binding epidermal growth factor (HB-EGF), betacellulin and epiregulin (Groenen et al. Growth Factors 11:235-257 (1994)). A family of heregulin proteins resulting from alternative splicing of a single gene are ligands for ErbB3 and ErbB4. The heregulin family includes alpha, beta and gamma heregulins (Holmes et al., Science, 256:1205-1210 (1992); U.S. Pat. No. 5,641,869; and Schaefer et al. Oncogene 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. Growth Factors 11:235-257 (1994); Lemke, G. Molec. & Cell. Neurosci. 7:247-262 (1996) and Lee et al. Pharm. Rev. 47:51-85 (1995). Recently three additional ErbB ligands were identified; neuregulin-2 (NRG-2) which is reported to bind either ErbB3 or ErbB4 (Chang et al. Nature 387 509-512 (1997); and Carraway et al Nature 387:512-516 (1997)); neuregulin-3 which binds ErbB4 (Zhang et al. PNAS (USA) 94(18):9562-7 (1997)); and neuregulin-4 which binds ErbB4 (Harari et al. Oncogene 18:2681-89 (1999)) HB-EGF, betacellulin and epiregulin also bind to ErbB4.

While EGF and TGFα do not bind ErbB2, EGF stimulates EGFR and ErbB2 to form a heterodimer, which activates EGFR and results in transphosphorylation of ErbB2 in the heterodimer. Dimerization and/or transphosphorylation appears to activate the ErbB2 tyrosine kinase. See Earp et al., supra. Likewise, when ErbB3 is co-expressed with ErbB2, an active signaling complex is formed and antibodies directed against ErbB2 are capable of disrupting this complex (Sliwkowski et al., J. Biol. Chem., 269(20): 14661-14665 (1994)). Additionally, the affinity of ErbB3 for heregulin (HRG) is increased to a higher affinity state when co-expressed with ErbB2. See also, Levi et al., Journal of Neuroscience 15: 1329-1340 (1995); Morrissey et al., Proc. Natl. Acad. Sci. USA 92: 1431-1435 (1995); and Lewis et al, Cancer Res., 56:1457-1465 (1996) with respect to the ErbB2-ErbB3 protein complex. ErbB4, like ErbB3, forms an active signaling complex with ErbB2 (Carraway and Cantley, Cell 78:5-8 (1994)).

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR (see WO98/50433, Abgenix). The anti-EGFR antibody may be conjugated with a cytotoxic agent, thus generating an immunoconjugate (see, e.g., EP659, 439A2, Merck Patent GmbH). Examples of small molecules that bind to EGFR include ZD1839 (Astra Zeneca), CP-358774 (OSI/Pfizer) and AG1478.

Inhibitors of the Ras-MAPK Pathway

Ras is a 21,000 molecular weight protein, which is important in the signal transduction pathway for normal cell growth. The protein is produced in the ribosome, released into the cytosol, and post-translationally modified. The first step in the series of post-translational modifications is the alkylation of $Cys^{168}$ with farnesyl pyrophosphate in a reaction catalyzed by the enzyme farnesyl transferase (Hancock, J F, et al., Cell 57:1167-1177 (1989)). Subsequently, the three C-terminal amino acids are cleaved (Gutierrez, L, et al., EMBO J. 8:1093-1098 (1989)), and the terminal Cys[168] is methyl esterified (Clark, S, et al., Proc. Nat'l Acad. Sci. (USA) 85:4643-4647 (1988)). Some forms of Ras are also reversibly palmitoylated on cysteine residues immediately N-terminal to Cys[168] (Buss, J E, et al., Mol. Cell. Biol. 6:116-122 (1986)). These modifications increase the hydrophobicity of the C-terminal region of Ras, causing it to localize at the surface of the cell membrane. Localization of Ras to the cell membrane is necessary for normal function (Willumsen, B M, et al., Science 310:583-586 (1984)).

Oncogenic forms of Ras are observed in a relatively large number of cancers (Bos, J L, Cancer Research 49:4682-4689 (1989)). These observations suggest that intervention in the function of Ras mediated signal transduction may be useful in the treatment of cancer, more particularly, Ras-induced tumors. Support for this can further be found in studies whereby the elimination of Ras function by homologous gene recombination or antisense RNA has demonstrated that expression of activated Ras is necessary for maintaining the transformed phenotype of tumor cells. One strategy to impede oncogenic Ras function in vivo is the inhibition of Ras posttranslational modification.

It has been shown that the C-terminal tetrapeptide of Ras has the "CAAX" motif (wherein C is cysteine, A is an aliphatic amino acid, and X is any amino acid). Tetrapeptides having this structure have been shown to be inhibitors of farnesyl transferase (Reiss, et al., Cell 62:81-88 (1990)). Other farnesyl transferase inhibitors have been identified that have more favorable pharmacokinetic behavior (James, G L, et al., Science 260:1937-1942 (1993); Kohl, N E, et al., Proc. Nat'l Acad. Sci. (USA) 91:9141-9145 (1994); deSolms, S J, et al., J. Med. Chem. 38:3967-3971 (1995); Nagasu, T, et al., Cancer Research 55:5310-5314 (1995); Lerner, E C, et al., J. Biol. Chem. 270:26802-26806 (1995)).

Furthermore, it has been shown that a farnesyl transferase inhibitor will block growth of Ras-dependent tumors in nude mice (Kohl, N E, et al., Proc. Nat'l Acad. Sci. (USA) 91:9141-9145 (1994)). In addition, it has been shown that over 70 percent of a large sampling of tumor cell lines are inhibited by farnesyl transferase inhibitors with selectivity over non-transformed epithelial cells (Sepp-Lorenzino, I, et al., Cancer Research, 55:5302-5309 (1995)).

Inhibitors of Ras Farnesyltransferase (Ftase)

Farnesyltransferase (Ftase) has become a very attractive target for the development of anticancer agents because it appears that control of Ras farnesylation can control the function of oncogenic Ras. Many inhibitors of Ras Ftase have been identified, and these can be grouped into 3 classes: (1) FPP analogues such as (α-hydroxfarnesyl)phosphonic acid, β-ketophosphonic and β-hydroxyphosphonic acid derivatives, and J-10487 (FIG. 15A); (2) CAAX peptide analogues such as BZA-5B, BZA-2B, L-731,734, L-731,735, L-739-749, L-739,787, L-739, 750, L-744,832, B581, Cys-4-ABA-Met and Cys-AMBA-Met, FTI-276, FTI-277, B956, and its methyl ester B1096 (FIG. 15B); in addition, nonpeptidic, tricyclic Ftase inhibitors have been developed such as SCH44342, SCH54429, SCH59228, and SCH66336, (FIG. 16) and (3) bisubstrate inhibitors such as phosphonic acid analogues, the phosphinate inhibitors BMS-185878, phosphinyl acid-based derivatives, and the hydroxamine acid analogues (FIG. 15C).

In addition to chemically synthesized compounds, several natural products have been identified as Ftase inhibitors. These include limonene, manumycin (UCFI-C) and its related compounds UCFI-A and UCFI-B, chaetomellic acid A and B, zaragozic acids, pepticinnamins, gliotoxin, barceloneic acid A, RPR113228, actinoplanic acids A and B, oreganic acid, lupane derivatives, saquayamycins, valinoctin A and its analogues, and gandoeric acid A and C.

Effects of Ftase Inhibitors in Animal Models.

Ftase inhibitors have also been shown to inhibit the growth of Ras-induced tumors in mouse xenograft models and more dramatically, in transgenic mouse models (Tables 4 and 5). Manumycin was reported to inhibit the growth of K-Ras-transformed fibrosarcoma transplanted into nude mice by approximately 70% compared with untreated controls. The CAAX peptide analogue L-739,749 specifically suppressed the tumor growth of H-Ras-, N-Ras-, and K-Ras-induced Rat-1 cell tumors in nude mice by 51% to 66%. The peptidomimetic Ftase inhibitors B956 and B1086 were shown to inhibit tumor growth of EJ-1 human bladder carcinoma.

Analogues of the tetrapeptide CVFM, the compound Nos. 46 and 51, showed inhibition of anchorage-independent growth of stably H-Ras-transformed HIH3T3 fibroblasts as well as antitumor activity in an athymic mouse model implanted with H-Ras-transformed Rat-1 cells. J-104871, an FPP-competitive Ftase inhibitor, suppressed tumor growth in nude mice transplanted with activated H-Ras-transformed HIG3T3 cells.

In addition to the mouse xenograft models, Ftase inhibitors have been tested in transgenic mouse models. The CAAX-based Ftase inhibitor L-744,832 induced regression of mammary and salivary carcinomas in MMTV-v-Ha-Ras mice.

Other inhibitors of Farnesyl transferase can be found in U.S. Pat. Nos. 6,943,183; 6,936,431; 6,790,633; 6,673,927; 6,528,535; 6,528,523; 6,228,856; 6,214,828; 6,159,984; 6,143,766; 6,124,295 and 6,124,465, all of which are incorporated by reference in their entireties.

Inhibitors of Geranylgeranyl Transferase 1

The resistance of K-Ras to Ftase inhibitors, the lack of potency of Ftase inhibitors against K-Ras transformed cells, and the observation that K-Ras becomes geranylgeranylated in the presence of Ftase inhibitors led to the development of GGTase 1 inhibitors (FIG. 17). GGTI-279, GGTI-287, GGTI-297 and GGTI-298 are CAAL-based peptidomimetics that are selective for GGTase 1 over Ftase. In contrast, FTI-276 and FTI-277 are CAAM-based peptidomimetics that are potent and selective inhibitors of Ftase over GGTase 1.

Inhibitors of the Prenylated Protein Methyltransferase

The C-terminal prenylated protein methyltransferase (PP-Mtase) is another potential therapeutically relevant target in the development of inhibitors against the posttranslational processing of Ras. N-acetyl-trans, trans-farnesyl-L-cycstein (AFC) is a substrate for PPMTase and acts as a competitive inhibitor.

Five-chloro- and 4- or 5-flouro-derivatives of FTS and a C20S-geranylgeranyl derivative of thiosalicyclic acid also cause inhibition of Ras-dependent MAPK activity, DNA synthesis, and EJ-1 cell growth. However, several other derivatives were inactive, suggesting stringent structural requirements for the anti-Ras activity of S-prenylanalgues. Recently, FTS was shown (1) to reduce the amount of activated N-Ras and wild-type Ras isoforms in human melanoma cells and Rat-1 fibroblasts, (2) to disrupt ERK signaling, (3) to revert their transformed phenotype, and (4) to cause a significant reduction in the growth of human melanoma in SCID mice.

The dorrigocins are novel antifungal antibiotics that were found to reverse the morphology of Ras-transformed HIG3T3 fibroblasts. Dorrigocin A did not inhibit protein prenylation or protein synthesis but was instead found to inhibit the C-terminal methylation in K-Ras-transformed cells.

Selective Inhibitors of Ras C-Terminal Sequence-Specific Endoprotease

UM96001, TPCK and BFCCMK are Ras C-terminal sequence specific endoprotease inhibitors (REPI) and potently inhibit ras-transformed rat kidney cell growth as well as growth of human cancer cells. These compounds have been reported to almost completely block the anchorage-independent clonogenic growth of these cancer cells. REPIs may selectively induce apoptosis in these cells.

MEK Inhibitors

As constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., Nature-Medicine, 1999, 5 (7), 810-816; Trachet et al., AACR Apr. 6-10, 2002, Poster #5426; Tecle, H., IBC 2.sup.nd International Conference of Protein Kinases, Sep. 9-10, 2002), block static allodynia in animals (WO 01/05390) and inhibit growth of acute myeloid leukemia cells (Milella et al., J. Clin. Invest., 2001, 108 (6), 851-859).

Small molecule inhibitors of MEK have been disclosed, including in U.S. Patent Publication Nos. 2005/0256123; 2005/0143438; 2005/0130976; 2005/0059710; 2005/0049419; 2005/0004186; 2003/0232869, 2004/0116710, and 2003/0216460, and U.S. patent application Ser. Nos. 10/654,580 and 10/929,295, each of which is hereby incorporated by reference. At least fifteen additional patent applications have appeared in the last several years. See, for example: U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077914; and WO 03/077855.

Selective Inhibitors of MAPKKs or MEK

PD098059 is a synthetic inhibitor of the Ras-MAPK pathway that selectively blocks the activation of MEK-1 and to a lesser extent the activation of MEK-2 (Alessi D R, Cuenda A, Cohen P, Dudley D T, Saltiel A R. J Biol Chem. 1995; 270: 27489-27494). The inhibition of MEK-1 activation was demonstrated to prevent activation of MAPKs ERK-12 and subsequent phosphorylation of MAPK substrates both in vitro and in intact cells. In contrast to Ftase inhibitors, PD098059 inhibited stimulation of cell growth by several growth factors. Furthermore, PD098059 reversed the transformed phenotype of Ras-transformed BALB3T3 mouse fibroblasts and rat kidney cells. PD098059 failed to inhibit the stress, and IL-1 stimulated JNK/SAPK and the p38 pathways, demonstrating its specificity for the ERK pathway. PD098059 has subsequently been used as a tool to study MAPK signaling in various cell types and in carcinogenesis.

Recently, 2 novel inhibitors of MEK-1 and MEK-2 have been identified: U0126 and Ro 09-2210. U0126 and PD098059 are noncompetitive inhibitors with respect to both MEK substrates (ATP and ERK) and bind to free MEK as well as MEK*ERK and MEK*ATP complexes. U0126 is an organic compound (1,4-diamino-2,3-dicyano-1,4-bis[2-aminophenylthio]butadiene) that has been identified as an inhibitor of AP-1 transactivation in cell-based reporter assays (Favata, M. et al. (1998) J. Biol. Chem. 273, 18623). It specifically inhibits MEK1 and MEK2 (Favata, M. et al. (1998) J. Biol. Chem. 273, 18623) and thus inhibits activation of ERK1 and ERK2. U0126 displays significantly higher affinity for all forms of MEK (44- to 357-fold) than does PD 098059. U0126 and Ro 09-2210 have an inhibitory concentration of 50% ($IC_{50}$) of 50 to 50 nmol/L, whereas PD098059 has an $IC_{50}$ of 5 pmol/L. In contrast to U0126 and PD098059, Ro 09-2210 is also able to inhibit other dual-specificity kinases such as MKK-4, MKK-6, and MKK-7, albeit at 4- to 10-fold higher $IC_{50}$ concentrations compared with its effect on MEK-1.

The present invention provides methodologies for treating tumors, e.g., treating melanomas and other hyperproliferative conditions wherein the condition is characterized as having increased levels of expression of one or more members of the family of GLI proteins. In a preferred embodiment, the invention provides for methods of treating tumors using inhibitors of the sonic hedgehog (SHH) and/or GLI pathways. In another preferred embodiment, the invention provides for treating tumors with antisense RNAs, small interfering RNAs (siRNAs) or a small molecule such as cyclopamine. In a yet further embodiment, the tumors are melanomas, both primary as well as metastatic or other tumors derived from melanocytes. In yet another particular embodiment, the tumors are inhibited from undergoing apoptosis (they are apoptotic resistant) due in part to the expression of at least one of the GLI proteins or gene products. Accordingly, it is an object of the invention to provide for a combination of targeted therapies, in order to address the need for treating such a devastating disease for which limited therapies are available. Moreover, it is a further object of the invention to target two different signaling pathways in order to provide a means for synergy between two different therapeutic modalities used to treat melanomas. In addition, the current approach further addresses the potential of targeting two oncogenic signaling pathways with inhibitors or antagonists for each of the pathways (the SHH-GLI pathway and the RAS-RAF-MEK and AKT pathways), and combining these two treatment modalities with standard chemotherapy or radiation therapy known to those skilled in the art for treating melanomas. As noted above, since standard chemotherapy and radiation therapy may have deleterious side effects due to their effects on normal, non-cancerous, highly proliferative cells, such as those in the bone marrow, it would be advantageous to be able to lower the dose of such treatments to non-toxic levels, to alleviate the morbidity associated with such therapies. This may be accomplished by combining such standard therapies with the therapies disclosed in the present invention. It may be possible to lower the dose of the standard chemotherapeutic agents or the dose of irradiation to non-toxic levels by combining either or both of them with the targeting strategies disclosed herein.

A yet further aspect of the invention provides for pharmaceutical compositions comprising the agents that inhibit tumors whose growth is regulated via the SHH and/or GLI pathway and a pharmaceutically acceptable carrier. In particular, the agents that inhibit tumors are selected from the group consisting of a siRNA, antisense nucleic acid, cyclopamine or analogs or derivatives thereof and is formulated in a composition that allows for topical delivery or for delivery via an intravenous, intraperitoneal, subcutaneous, intramuscular, intracerebral, intraventricular, or intrathecal route with a pharmaceutically acceptable carrier.

The inventors of the present application provide evidence that the gli genes are expressed in melanocytes and that cyclopamine and siRNAs specific for gli inhibit the proliferation of such cells. It is thus a further object of the invention to provide for compounds, short or small interfering RNAs (siRNAs) or short hairpin RNAs (shRNAs), and compositions and methods that target the SHH-GLI pathway, for inhibiting tumorigenesis in a subject in need of such therapy. Moreover, it is a further object of the invention to combine such GLI inhibitors or antagonists with agents that target other oncogenic signaling pathways, such as but not limited to RAS-RAF-MEK and AKT, or to combine the GLI inhibitors with standard chemotherapy or irradiation therapy. Alternatively, the three types of agents may be used in combination, that is, an agent that targets SHH-GLI plus an agent that targets a different oncogenic signaling pathway, such as RAS-RAF-MEK and AKT, plus a third agent such as a standard chemotherapeutic agent or irradiation therapy. Such combinations would allow for the lowering of possibly toxic levels of drugs, which when used alone at higher doses, result in significant morbidity to the patient undergoing such therapy.

Nucleic Acids Encoding SHH and GLI

The present invention contemplates use of nucleic acids encoding a Hedgehog family member such as sonic hedgehog (e.g., genomic or cDNA) and nucleic acids encoding active fragments thereof, or nucleic acids encoding the GLI family of proteins, including GLI1, GLI2 and GLI3 or active fragments thereof. HH or GLI can be used from any animal species, including insects, but preferably a mammalian source, and more preferably a human source. In accordance with the present invention there may be employed conventional molecular biology, microbiology, and recombinant DNA techniques within the skill of the art. Such techniques are explained fully in the literature. (See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); Sambrook and Russell, *Molecular Cloning: A Laboratory Manual*, Third Edition (2001) Cold Spring Harbor Laboratory Press, Cold Spring Harbor, N.Y.; *DNA Cloning: A Practical Approach*, Volumes I and II D. N. Glover ed. 1985; *Oligonucleotide Synthesis*, M. J. Gait ed. (1984); *Nucleic Acid Hybridization*, B. D. Hames & S. J. Higgins eds. (1985); *Transcription And Translation*, B. D. Hames & S. J. Higgins, eds. (1984); *Animal Cell Culture*. R. I. Freshney, ed. (1986); *Immobilized Cells And Enzymes*, IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994)).

Accordingly, any animal cell potentially can serve as the nucleic acid source for the molecular cloning of an hh gene or a gli gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The nucleotide sequence of the human SHH, SEQ ID NO: 59, or of the human GLI 1, 2, and 3, SEQ ID NOs: 73 (PubMed accession number NM_005269), 74 (PubMed accession number AB007296) and 75 (PubMed accession number NM_000168), respectively, can also be used to search for highly homologous genes from other species, or for proteins having at least one homologous domain, using computer data bases containing either partial or full length nucleic acid sequences. Human ESTs, for example, can be searched. The human Shh sequence can be compared with other human sequences, e.g., in GenBank, using GCG software and the blast search program for example. Matches with highly homologous sequences or portions thereof can then be obtained.

If the sequence identified is an EST, the insert containing the EST can be obtained and then fully sequenced. The resulting sequence can then be used in place of, and/or in conjunction with SEQ ID NO: 59 or SEQ ID NOs: 73, 74 and 75, to identify other ESTs which contain coding regions of the SHH homologue (or SHH domain homologue) or GLI homologue. Plasmids containing the matched EST for example can be digested with restriction enzymes in order to release the cDNA inserts. If the plasmid does not contain the full length homologue the digests can be purified, e.g., run on an agarose gel and the bands corresponding to the inserts can be cut from the gel and purified. Such purified inserts are likely to contain overlapping regions which can be combined as templates of a PCR reaction using primers which are preferably located outside of the SHH open reading frame. Amplification should yield the expected product which can be ligated into a vector and used to transform an *E. coli* derivative e.g., via TA cloning (Invitrogen) for example. A resulting full-length SHH or GLI homologue can be placed into an expression vector and the expressed recombinant SHH or GLI can then be assayed for its ability to stimulate the proliferation and differentiation of brain stem cells. Alternatively, the expressed proteins can be used to prepare antibodies, which can then be used to inhibit the unwanted (tumorigenic) effects of the SHH/GLI pathway.

A modified HH or GLI can be made by altering nucleic acid sequences encoding the HH or GLI by making substitutions, additions or deletions that provide for functionally equivalent molecules. Preferably, such derivatives are made that have enhanced or increased effect on the proliferation and differentiation of adult brain stem cells.

Due to the degeneracy of nucleotide coding sequences, other DNA sequences which encode substantially the same amino acid sequence as an hh gene may be used in the practice of the present invention including those comprising conservative substitutions thereof. These include but are not limited to modified allelic genes, modified homologous genes from other species, and nucleotide sequences comprising all or portions of hh genes which are altered by the substitution of different codons that encode the same amino acid residue within the sequence, thus producing a silent change. Likewise, the HH derivative of the invention can include, but is not limited to, those containing, as a primary amino acid sequence, all or part of the amino acid sequence of an HH protein including altered sequences in which functionally equivalent amino acid residues are substituted for residues within the sequence resulting in a conservative amino acid substitution. And thus, such substitutions are defined as a conservative substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces— turns in the protein's structure.

When comparing a particular full-length SHH for example, with human SHH having the amino acid sequence of SEQ ID NO: 60, or human GLI 1, 2 or 3, having the amino sequence of SEQ ID NOs: 76, 77 and 78, respectively, deletions or insertions that could otherwise alter the correspondence between the two amino acid sequences are taken into account. Preferably standard computer analysis is employed for the determination that is comparable, (or identical) to that determined with an Advanced Blast search at www.ncbi.nlm.nih.gov under the default filter conditions (e.g., using the GCG (Genetics Computer Group, Program Manual for the GCG Package, Version 7, Madison, Wis.) pileup program using the default parameters).

The genes encoding HH or GLI derivatives and analogs of the invention can be produced by various methods known in the art. The manipulations which result in their production can occur at the gene or protein level. For example, an hh or gli gene sequence can be produced from a native hh or gli clone by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of a nucleic acid encoding an HH, care should be taken to ensure that the modified gene remains within the same translational reading frame as the hh gene, uninterrupted by translational stop signals, in the gene region where the desired activity is encoded.

Additionally, the HH or GLI-encoding nucleic acid sequence can be produced by in vitro or in vivo mutations, to create and/or destroy translation, initiation, and/or termination sequences, or to create variations in coding regions and/ or form new restriction endonuclease sites or destroy preexisting ones, to facilitate further in vitro modification. Preferably such mutations will further enhance the specific properties of the gene products identified to have the capabilities disclosed by the present invention. Any technique for mutagenesis known in the art can be used, including but not limited to, in vitro site-directed mutagenesis (Hutchinson, C., et al., *J. Biol. Chem.*, 253:6551 (1978); Zoller and Smith, *DNA*, 3:479-488 (1984); Oliphant et al., *Gene*, 44:177 (1986); Hutchinson et al., *Proc. Natl. Acad. Sci. U.S.A.*, 83:710 (1986)), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70). A general method for site-specific incorporation of unnatural amino acids into proteins is described in Noren et al., (*Science*, 244:182-188 (1989)). This method may be used to create analogs with unnatural amino acids.

Expression of HH and GLI Polypeptides and Active Fragments Thereof

The nucleotide sequence coding for an HH, or GLI or a functionally equivalent derivative including a chimeric protein thereof, can be inserted into an appropriate expression vector, i.e., a vector which contains the necessary elements for the transcription and translation of the inserted protein-coding sequence. Such elements are termed herein a "promoter." Thus, the nucleic acid encoding an HH or GLI is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the corresponding HH or GLI and/or its flanking regions. Any person with skill in the art of molecular biology or protein chemistry, in view of the present disclosure, would readily know how to assay the HH or GLI expressed as described herein, to determine whether such a modified protein can indeed perform the functions of an HH or GLI taught by the present invention. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. Expression of an SHH may be controlled by any promoter/ enhancer element known in the art, e.g., a Simian Virus 40 (SV40) promoter, a cytomegalus virus promoter (CMV) promoter, or a tissue specific promoter such as the human glial fibrillary acidic protein promoter (GFAP) promoter, as long as these regulatory elements are functional in the host selected for expression. The resulting SHH or GLI protein or fragment thereof can be purified, if desired, by any methodology such as one that is well known in the art.

Production of Cells from Tissue

Cells that can be used in the methods of the present invention can be obtained from tissue specimens, including tumor biopsies by methods known to those skilled in the art.

Once the cells are isolated they can be proliferated and grown in the presence of specific growth medium and any other factor (or molecule) that can maintain cell viability. Thus the cells can be cultured in vitro as described below, in the presence of any other factor (or molecule) that can maintain cell viability until cellular testing for the presence of GLI can be done.

Antisense Therapy

The relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state. In the present invention, the targets are nucleic acids encoding GLI; in other words, a gene encoding GLI, or mRNA expressed from the gli gene. mRNA which encodes GLI (GLI1, GLI2 or GLI3) is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention, which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding GLI, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a particular target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a particular target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of GLI. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

The antisense oligonucleotides of this invention can be used in diagnostics, therapeutics, prophylaxis, and as research reagents and in kits. Since the oligonucleotides of this invention hybridize to nucleic acids encoding GLI, sandwich, calorimetric and other assays can easily be constructed to exploit this fact. Provision of means for detecting hybridization of oligonucleotide with the gli gene or mRNA can routinely be accomplished. Such provision may include enzyme conjugation, radiolabelling or any other suitable detection systems. Kits for detecting the presence or absence of GLI may also be prepared.

The present invention is also suitable for diagnosing certain cancers in tissue or other samples from patients suspected of having hyperproliferative condition or cancer such as, but not limited to a skin cancer, including basal or squamous cell carcinomas, and melanomas, both primary and metastatic. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 10 to about 50 nucleobases. Particularly preferred are antisense oligonucleotides comprising from about 10 to about 30 nucleobases (i.e. from about 10 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2=, 3= or 5=hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3= to 5=phosphodiester linkage.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering 1990, pages 858-859, Kroschwitz, J. I., ed. John Wiley & Sons, those disclosed by Englisch et al. (Angewandte Chemie, International Edition 1991, 30, 613-722), and those disclosed by Sanghvi, Y. S., Chapter 15, Antisense Research and Applications 1993, pages 289-302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications 1993, CRC Press, Boca Raton, pages 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA 1989, 86, 6553-6556), cholic acid (Manoharan et al., Bioorg. Med. Chem. Lett. 1994, 4, 1053-1059), a thioether, e.g., hexyl-5-tritylthiol (Manoharan et al., Ann. N.Y. Acad. Sci. 1992, 660, 306-309; Manoharan et al., Bioorg. Med. Chem. Let. 1993, 3, 2765-2770), a thiocholesterol (Oberhauser et al., Nucl. Acids Res. 1992, 20, 533-538), an aliphatic chain, e.g., dodecandiol or undecyl residues (Saison-Behmoaras et al., EMBO J. 1991, 10, 1111-1118; Kabanov et al., FEBS Lett. 1990, 259, 327-330; Svinarchuk et al., Biochimie 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett. 1995, 36, 3651-3654; Shea et al., Nucl. Acids Res. 1990, 18, 3777-3783), a polyamine or a polyethylene glycol chain (Manoharan et al., Nucleosides & Nucleotides 1995, 14, 969-973), or adamantane acetic acid (Manoharan et al., Tetrahedron Lett. 1995, 36, 3651-3654), a palmityl moiety (Mishra et al., Biochim. Biophys. Acta 1995, 1264, 229-237), or an octadecylamine or hexylamino-carbonyl-oxycholesterol moiety (Crooke et al., J. Pharmacol. Exp. Ther. 1996, 277, 923-937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also contemplated.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the skilled artisan. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta 1995, 78, 486-504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. Pharmaceutically acceptable salts are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," J. of Pharma Sci. 1977, 66, 1-19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention may be prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention (the antisense oligonucleotides and the siRNA molecules described below) may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems 1991, 8, 91-192; Muranishi, Critical Reviews in Therapeutic Drug Carrier Systems 1990, 7, 1-33). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., Critical Reviews in Therapeutic Drug Carrier Systems 1991, page 92; Muranishi, Critical Reviews in Therapeutic Drug Carrier Systems 1990, 7, 1; El-Hariri et al., J. Pharm. Pharmacol. 1992 44, 651-654).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems 1991, page 92; Muranishi, Critical Reviews in Therapeutic Drug Carrier Systems 1990, 7, 1-33; Buur et al., J. Control Rel. 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems 1991, page 92); and perfluorochemical emulsions, such as FC43 (Takahashi et al., J. Pharm. Phamacol. 1988, 40, 252-257).

Non-surfactants include, for example, unsaturated cyclic ureas, 1-alkyl- and 1-alkenylazacyclo-alkanone derivatives (Lee et al., Critical Reviews in Therapeutic Drug Carrier Systems 1991, page 92); and non-steroidal anti-inflammatory agents such as diclofenac sodium, indomethacin and phenylbutazone (Yamashita et al., J. Pharm. Pharmacol. 1987, 39, 621-626).

As used herein, "carrier compound" as used in the context of the oligonucleotides of the present invention, refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved.

Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ found to be effective in vitro and in in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

siRNA Therapy

In general terms, RNA interference (RNAi) is the process whereby the introduction of double stranded RNA into a cell inhibits the expression of a gene corresponding to its own sequence. RNAi is usually described as a post-transcriptional gene-silencing (PTGS) mechanism in which dsRNA triggers degradation of homologous messenger RNA in the cytoplasm. The mediators of RNA interference are 21- and 23-nucleotide small interfering RNAs (siRNA) (Elbashir, S. M. et al., (2001), Genes Dev. 15, 188-200; Elbashir, S. M. et al. (2001), Nature 411: 494-498; Hutvagner, G. et al., (2001), Science 293:834-838). In a second step, siRNAs bind to a ribonuclease complex called RNA-induced silencing complex (RISC) that guides the small dsRNAs to its homologous mRNA target. Consequently, RISC cuts the mRNA approximately in the middle of the region paired with the antisense siRNA, after which the mRNA is further degraded. A ribonuclease III enzyme, dicer, is required for processing of long dsRNA into siRNA duplexes (Bernstein, E. et al. ((2001), Nature 409: 363-366).

Mechanism of RNAi

The only RNA molecules normally found in the cytoplasm of a cell are molecules of single-stranded mRNA. If the cell finds molecules of double-stranded RNA (dsRNA), it uses a ribonuclease III enzyme, dicer, for processing of long dsRNA into siRNA duplexes (Bernstein, E. et al. ((2001), Nature 409: 363-366) containing ~22 base pairs (~2 turns of a double helix). Dicer is a bidentate RNase III, which also contains an ATP-dependent RNA helicase domain and a PAZ domain, presumably important for dsRNA unwinding and mediation of protein-protein interactions, respectively ((Bernstein, E. et al. ((2001), Nature 409: 363-366). Dicer is evolutionarily conserved in worms, flies, plants, fungi and mammals, and has a second cellular function important for the development of these organisms (Grishok, A. (2001), Cell 106:23-34; Knight, S. W. et al. (2001), Science 293:2269-2271; Hutvagner, G. et al., (2001), Science 293:834-838). At present, it is uncertain whether dicer activity in species other than D. melanogaster produces siRNAs of predominantly 21 nt in length. The estimates of siRNA size vary in the literature between 21 and 25 nt (Hamilton, A. J. et al. (1999), Science 286: 950-952; Zamore, P. D. et al. (2000), Cell 101: 25-33; Elbashir, S. M. et al., (2001), Genes Dev. 15, 188-200; Elbashir, S. M. et al. (2001), Nature 411: 494-498; Hammond, S. M. et al. (2000), Nature 404: 293-296; Hutvagner, G. et al., (2001), Science 293:834-838

The two strands of each fragment then separate enough to expose the antisense strand so that it can bind to the complementary sense sequence on a molecule of mRNA. In RNAi, a siRNA-containing endonuclease complex cleaves a single-stranded target RNA in the middle of the region complementary to the 21 nt guide siRNA of the siRNA duplex (Elbashir, S. M. et al., (2001), Genes Dev. 15, 188-200; Elbashir, S. M. et al. (2001), Nature 411: 494-498). This cleavage site is one helical turn displaced from the cleavage site that produced the siRNA from long dsRNA, suggesting dramatic conformational and/or compositional changes after processing of long dsRNA to 21 nt siRNA duplexes. The target RNA cleavage products are rapidly degraded because they either lack the stabilizing cap or poly(A) tail. A protein component of the ~500 kDa endonuclease or RNA-induced silencing complex (RISC) was recently identified and is a member of the argonaute family of proteins (Hammond, S. M. et al. (2001) Science 293: 1146-1150), however, it is currently unclear whether dicer is required for RISC activity. Thus, the cleavage of the mRNA destroys its ability to be translated into a polypeptide. Because of their action, these fragments of RNA have been named "short (or small) interfering RNA" (siRNA).

Introducing dsRNA corresponding to a particular gene will knock out the cell's own expression of that gene. This can be done in particular tissues at a chosen time. This often provides an advantage over conventional gene "knockouts" where the missing gene is carried in the germline and thus whose absence may kill the embryo before it can be studied.

Although it has been suggested that the one disadvantage of simply introducing dsRNA fragments into a cell is that gene expression is only temporarily reduced, it has recently been shown that the system can be manipulated using a DNA vector such that the siRNA molecule can be continuously synthesized for prolonged periods of time in order to continue in suppression of the desired gene (Brummelkamp et. al. 19 Apr. 2002, Science). After two months, the cells still failed to manufacture the protein whose gene had been turned off by RNAi. Effective siRNA molecules may be designed using the following guidelines:

a) In general, siRNA oligonucleotides should be about 21 nucleotides in length with 2 nucleotide overhangs, usually 3' TT.

b) Sequences located in the 5' or 3' UTR of the mRNA target and nearby the start codon should be avoided, as they may be richer in regulatory protein binding sites.

c) Search for a sequence AA(N19)TT or AA(N21) with approximately 50% G/C content.

d) Compare the selected siRNA nucleotide sequence against databases to ensure that only one gene will be targeted.

Target recognition is a highly sequence specific process, mediated by the siRNA complementary to the target. One or two base pair mismatches between the siRNA and the target gene will greatly reduce the silencing effect. It might be necessary to test several sequences since positional effects of siRNAs have been reported.

The 3'-most nucleotide of the guide siRNA does not contribute to the specificity of target recognition, while the penultimate nucleotide of the 3' overhang affects target RNA cleavage and a mismatch reduces RNAi 2- to 4-fold. The 5' end of the guide siRNA also appears more permissive for mismatched target RNA recognition when compared with the 3' end. Nucleotides in the center of the siRNA, located opposite to the target RNA cleavage site, are important specificity determinants and even single nucleotide changes reduce RNAi to undetectable levels. This suggests that siRNA duplexes may be able to discriminate mutant or polymorphic alleles in gene targeting experiments, which may become an important feature for future therapeutic developments.

Double-stranded RNA has been shown to attenuate specific gene expression in C. elegans, Drosophila and Trypanosoma brucei (M. Montgomery, et al., Proc. Natl. Acad. Sci. U.S.A. 95, 15502-15507 (1998); J. Kennerdell et al., Cell 95, 1017-1026 (1998); H. Ngo et al., Proc. Natl. Acad. Sci. U.S.A. 95, 14687-14692 (1998)). The types of genes attenuated in these invertebrates include some encoding transcription factors and others that encode growth factor receptors. There is also evidence that double-stranded RNA may effectively silence gene expression in plants (M. Wassenegger et al., Plant. Mol. Biol. 37, 349-362 (1998); P. Watergiyse et al., Proc. Natl. Acad. Sci. U.S.A. 95, 13959-13964 (1998)).

A definitive mechanism through which double-stranded RNA effects gene silencing remains has not been identified (M. Montgomery et al., Trends Genet. 14, 255-258 (1998)). Recently, Montgomery et al. reported that double-stranded RNA induces specific RNA degradation in nematodes (Proc. Natl. Acad. Sci. U.S.A. 95, 15502-15507 (1998)). This conclusion was based upon the fact that DNA sequences in the targeted regions of the gene were not altered and that 100% of the F2 generation reverted to the wild type phenotype. In addition, C. elegans has a unique genetic organization. Genes in this animal are organized in operons in which a single promoter controls expression of a number of genes. They showed that the double-stranded RNA affects only expression of the targeted gene. In contrast, however, others have observed heritable effects of double-stranded RNA on the expression of a number of genes in C. elegans, suggesting that more than one mechanism may be involved in double-stranded RNA-mediated inhibition of gene activity (H. Tahara, Science 28, 431-432 (1998)).

The present invention provides a method for attenuating gene expression in a cell using gene-targeted double-stranded RNA (dsRNA). The dsRNA contains a nucleotide sequence that is essentially identical to the nucleotide sequence of at least a portion of the target gene, in the matter of the present invention, the shh or gli genes. The cell into which the dsRNA is introduced is preferably a tumor cell containing at least one gli gene to which the dsRNA is targeted. Gene expression can be attenuated in a whole organism, an organ or tissue of an organism, including a tissue explant, or in cell culture. Preferably, the cell is a mammalian cell, but the invention is not limited to mammals. Double-stranded RNA is introduced directly into the cell or, alternatively, into the extracellular environment from which it is taken up by the cell. Inhibition is specific for the targeted gene. Depending on the particular target gene and the dose of dsRNA delivered, the method may partially or completely inhibit expression of the gene in the cell. The expression of two or more genes can be attenuated concurrently by introducing two or more double stranded RNAs into the cell in amounts sufficient to attenuate expression of their respective target genes. Double stranded RNAs that are administered "concurrenty" are administered, together or separately, so as to be effective at generally the same time.

In yet another aspect, the invention provides a method for attenuating the expression of a gli gene in a cell that includes annealing two complementary single stranded RNAs in the presence of potassium chloride to yield double stranded RNA; contacting the double stranded RNA with RNAse to purify the double stranded RNA by removing single stranded RNA; and introducing the purified double stranded RNA into the cell in an amount sufficient to attenuate expression of the target gene, e.g. at least one of the gli genes.

The invention further provides a method for treating or preventing a hyperproliferative condition or a cancerous condition in a mammal. Double stranded RNA is administered to the mammal in an amount sufficient to attenuate expression of the gli gene, the expression of which is associated with the cancerous condition. Concurrent inhibition of multiple genes is advantageous to treat diseases associated with multiple genes, or to treat two or more diseases or infections concurrently.

The present invention provides a method for gene silencing in organisms and cells, especially mammals, using gene-specific double-stranded RNA. The ability to use double-stranded RNA to specifically block expression of particular genes in a multicellular setting both in vivo and in vitro has broad implications for the study of numerous diseases, in the matter of the present invention, cancerous consitions.

The method of the present invention allows for attenuation of gene expression in a cell. "Attentuation of gene expression" can take the form of partial or complete inhibition of gene function. Mechanistically, gene function can be partially or completely inhibited by blocking transcription from the gene to mRNA, or by blocking translation of the mRNA to yield the protein encoded by the gene, although it should be understood that the invention is not limited to any particular mechanism of attenuation of gene expression. Inhibition of gene function is evidenced by a reduction or elimination, in the cell, of the activity associated with the protein encoded by the gene. Whether and to what extent gene function is inhibited can be determined using methods known in the art For example, in many cases inhibition of gene function leads to a change in phenotype which is revealed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Attenuation of gene expression can be quantified, and the amount of attenuation of gene expression in a treated cell compared to a cell not treated according to the present invention can be determined. Lower doses dsRNA may result in inhibition in a smaller fraction of cells, or in partial inhibition in cells. In addition, attenuation of gene expression can be time-dependent; the longer the period of time since the administration of the dsRNA, the less gene expression may be attenuated. Attenuation of gene expression can occur at the level of transcription (i.e., accumulation of mRNA of the targeted gene), or translation (i.e., production of the protein encoded by the targeted gene). For example, mRNA from the targeted gene can be detected using a hybridization probe having a nucleotide sequence outside the region selected for the inhibitory double-stranded RNA, and translated polypeptide encoded by the target gene can be detected via Western blotting using an antibody raised against the polypeptide. It should be noted that the method of the invention is not limited to any particular mechanism for reducing or eliminating cellular protein activity; indeed, as noted above, it is not yet fully understood how the introduction of dsRNA into a cell causes attenuation of expression of the targeted gene, nor is it known whether single or multiple mechanisms are at work.

The attenuation of gene expression achieved by the method of the invention is specific for the gli genes, that is, gli1, gli2 or gli3. In other words, the dsRNA inhibits at least one of the target genes without manifest effects on other genes of the cell.

Double-Stranded RNA

The dsRNA is formed from one or more strands of polymerized ribonucleotide. When formed from only one strand, it takes the form of a self-complementary hairpin-type molecule that doubles back on itself to form a duplex. When formed from two strands, the two strands are complementary RNA strands. The dsRNA can include modifications to either the phosphate-sugar backbone or the nucleoside. For example, the phosphodiester linkages of natural RNA may be modified to include at least one of a nitrogen or sulfur heteroatom. Likewise, bases may be modified to block the activity of adenosine deaminase.

The nucleotide sequence of the dsRNA is defined by the nucleotide sequence of its targeted gene, ie. gli1, gli2 or gli3 (Seq ID NOs: 73, 74, and 75, respectively). The dsRNA contains a nucleotide sequence that is essentially identical to at least a portion of the target gene; preferably the dsRNA contains a nucleotide sequence that is completely identical to at least a portion of the target gene. It should be understood that in comparing an RNA sequence to a DNA sequence, an "identical" RNA sequence will contain ribonucleotides where the DNA sequence contains deoxyribonucleotides, and further that the RNA sequence will contain a uracil at positions where the DNA sequence contains thymidine. More preferably, the dsRNA that is completely identical to at least a portion of the target gene does not contain any additional nucleotides.

A dsRNA that is "essentially identical" to a least a portion of the target gene, e.g. gli, is a dsRNA wherein one of the two complementary stands (or, in the case of a self-complementary RNA, one of the two self-complementary portions) is either identical to the sequence of that portion of the target gene or contains one or more insertions, deletions or single point mutations relative to the nucleotide sequence of that portion of the target gene. The invention thus has the advantage of being able to tolerate sequence variations that might be expected due to genetic mutation, strain polymorphism, or evolutionary divergence. Alternatively, a dsRNA that is "essentially identical" to at least a portion of the target gene can be functionally as a dsRNA wherein one of the two complementary strands (or, in the case of a self-complementary RNA, one of the two self-complementary portions) is capable of hybridizing with a portion of the target gene transcript (e.g., under conditions including 400 mM NaCl, 40 mM PIPES pH 6.4, 1 mM EDTA, 50° C. or 70° C. hybridization for 12-16 hours; followed by washing).

The dsRNA nucleotide sequence that is essentially or completely identical to at least a portion of the target gene has a length of preferably at least about 5-10 bases, more preferably 10-25 bases, more preferably at least about 50 bases, and most preferably at least about 100 bases. The dsRNA nucleotide sequence has a length of preferably less than about 400 bases, more preferably less than about 300 base, more preferably less than about 200 bases and most preferably less than about 100 bases. It will be understood that the length of the dsRNA, the degree of homology necessary to affect gene expression, and the most effective dosages can be optimized for each particular application using routine methods.

Synthesis of dsRNA

Single strands of RNA are synthesized in vitro. Preferably, single stranded RNA is enzymatically synthesized from the PCR products of a DNA template, preferably a cloned a cDNA template. Provided the sequence of the target gene is known, e.g. gli, a cloned cDNA template can be readily made from target cell RNA using reverse-transcriptase polymerase chain reaction (RT-PCR) to generate a cDNA fragment, following by cloning the cDNA fragment into a suitable vector. Preferably, the vector is designed to allow the generation of complementary forward and reverse PCR products. The vector pGEM-T (Promega, Madison Wis.) is well-suited for use in the method because it contains a cloning site positioned between oppositely oriented promoters (i.e., T7 and SP6 promoters; T3 promoter could also be used). After purification of the PCR products, complementary single stranded RNAs are synthesized, in separate reactions, from the DNA templates via RT-PCR using two different RNA polymerases (e.g., in the case of pGEM-T, T7 polymerase and SP6 polymerase). RNAse-free DNAse is added to remove the DNA template, then the single-stranded RNA is purified. Single strands of RNA can also be produced enzymatically or by partial/total organic synthesis. The use of in vitro enzymatic or organic synthesis allows the introduction of any desired modified ribonucleotide. The RNA strands may or may not be polyadenylated; and the RNA strands may or may not be capable of being translated into a polypeptide by a cell's translational apparatus. Preferably, purification of RNA is performed without the use of phenol or chloroform.

Double stranded RNA is formed in vitro by mixing complementary single stranded RNAs, preferably in a molar ratio of at least about 3:7, more preferably in a molar ratio of about 4:6, and most preferably in essentially equal molar amounts (i.e., a molar ratio of about 5:5). Preferably, the single stranded RNAs are denatured prior to annealing, and the buffer in which the annealing reaction takes place contains a salt, preferably potassium chloride. Prior to administration, the mixture containing the annealed (i.e., double stranded) RNA is preferably treated with an enzyme that is specific for single stranded RNA (for example, RNAse A or RNAse T) to confirm annealing and to degrade any remaining single stranded RNAs. Addition of the RNAse also serves to excise any overhanging ends on the dsRNA duplexes.

Delivery of dsRNA to a Cell

Double stranded RNA can be introduced into the cell in a number of different ways. For example, the dsRNA is conveniently administered by microinjection; other methods of introducing nucleic acids into a cell include bombardment by particles covered by the dsRNA, soaking the cell or organism in a solution of the dsRNA, electroporation of cell membranes in the presence of the dsRNA, liposome-mediated delivery of dsRNA and transfection mediated by chemicals such as calcium phosphate, viral infection, transformation, and the like. The dsRNA may be introduced along with components that enhance RNA uptake by the cell, stabilize the annealed strands, or otherwise increase inhibition of the target gene. In the case of a cell culture or tissue explant, the cells are conveniently incubated in a solution containing the dsRNA or lipid-mediated transfection; in the case of a whole animal or plant, the dsRNA is conveniently introduced by injection or perfusion into a cavity or interstitial space of an organism, or systemically via oral, topical, parenteral (including subcutaneous, intramuscular and intravenous administration), vaginal, rectal, intranasal, ophthalmic, or intraperitoneal administration. In addition, the dsRNA can be administered via and implantable extended release device. Methods for oral introduction include direct mixing of RNA with food of the organism, as well as engineered approaches in which a species that is used as food is engineered to express an RNA, then fed to the organism to be affected. The dsRNA may be sprayed onto a plant or a plant may be genetically engineered to express the RNA in an amount sufficient to kill some or all of a pathogen known to infect the plant.

Alternatively, dsRNA can be supplied to a cell indirectly by introducing one or more vectors that encode both single strands of a dsRNA (or, in the case of a self-complementary RNA, the single self-complementary strand) into the cell. Preferably, the vector contains 5' and 3' regulatory elements that facilitate transcription of the coding sequence. Single stranded RNA is transcribed inside the cell, and, presumably, double stranded RNA forms and attenuates expression of the target gene. Methods for supplying a cell with dsRNA by introducing a vector from which it can be transcribed are set forth in WO 99/32619 (Fire et al., published 1 Jul. 1999). A transgenic animal that expresses RNA from such a recombinant construct may be produced by introducing the construct into a zygote, an embryonic stem cell, or another multipotent cell derived from the appropriate organism. A viral construct packaged into a viral particle would accomplish both efficient introduction of an expression construct into the cell and transcription of RNA encoded by the expression construct.

The dsRNA is typically administered in an amount that allows delivery of at least one copy per cell. The amount of dsRNA administered to a cell, tissue, or organism depends on the nature of the cell, tissue, or organism, the nature of the target gene, and the nature of the dsRNA, and can readily be optimized to obtain the desired level of gene inhibition. To attenuate gene expression in a single cell embryo, for example, at least about $0.8 \times 10^6$ molecules of dsRNA are injected; more preferably, at least about $20 \times 10^6$ molecules of dsRNA are injected; most preferably, at least about $50 \times 10^6$ molecules of dsRNA are injected. The amount of dsRNA injected into a single cell embryo is, however, preferably at most about $1000 \times 10^6$ molecules; more preferably, it is at most about $500 \times 10^6$ molecules, most preferably, at most about $100 \times 10^6$ molecules. In the case of administration of dsRNA to a cell culture or to cells in tissue, by methods other than injection, for example by soaking, electroporation, or lipid-mediated transfection, the cells are preferably exposed to similar levels of dsRNA in the medium. For example, 8-10 μL of cell culture or tissue can be contacted with about $20 \times 10^6$ to about $2000 \times 10^6$ molecules of dsRNA, more preferably about $100 \times 10^6$ to about $500 \times 10^6$ molecules of dsRNA, for effective attenuation of gene expression.

Once the minimum effective length of the dsRNA has been determined, it is routine to determine the effects of dsRNA agents that are produced using synthesized oligoribonucleotides. The administration of the dsRNA can be by microinjection or by other means used to deliver nucleic acids to cells and tissues, including culturing the tissue in medium containing the dsRNA.

The siRNA molecules of the present invention may be used to introduce dsRNA into a cell for the treatment or prevention of disease. To treat or prevent a disease or other pathology, a target gene is selected which is required for initiation or maintenance of the disease/pathology. The dsRNA can be introduced into the organism using in vitro, ex vivo or by in vivo methods. In an in vitro method, the dsRNA is introduced into a cell, which may or may not be a cell of the organism, and the dsRNA-containing cell is then introduced into the organism. In an ex vivo method, cells of the organism are explanted, the dsRNA is introduced into the explanted cells, and the dsRNA-containing cells are implanted back into the host. In an in vivo method, dsRNA is administered directly to the organism. As noted above, the dsRNA can also be delivered to a cell using one or more vectors that encode the complementary RNAs (or self-complementary RNA), which are then transcribed inside the cell and annealed to yield the desired dsRNA.

In medical applications, the dsRNA may be introduced into a cancerous cell or tumor, and thereby inhibit expression of a gene required for maintenance of the carcinogenic/tumorigenic phenotype.

Assessment of Melanoma Tumor Cell Growth and Metastasis

The incidence of melanoma has risen greatly in recent times. This is thought to be due in part to increased detection as a result of screening. Certain traits are associated with an increased risk of developing melanoma, and these include multiple typical moles, atypical moles, freckling, history of severe sunburn, ease of burning, inability to tan, and light hair/blue eyes. Other factors include the presence of familial atypical mole and melanoma syndrome, disorders of DNA repair, and excessive sun exposure. Cutaneous melanoma is a distinct clinical and histologic entity. Clinical features of de novo pigmented lesions suggestive of melanoma include Asymmetry, Border irregularity, Color variegation, and Diameter greater than 6 millimeters (the ABCD's of melanoma). An asymmetric lesion is one that is not regularly round or oval. Border irregularity refers to notching, scalloping, or poorly defined lesion margins. Color variegation refers to a lesion with shades of brown, tan, red, white, or blue/black, or combinations thereof. Although a high level of suspicion exists for a lesion greater than 6 millimeters in diameter, early melanomas may be diagnosed at a smaller size. Earliest lesions are flat or macular and may have altered skin markings. However, a palpable lesion with uniform or irregular surface features or benign-appearing pigmented and non-pigmented lesions that change rapidly can represent early melanoma.

Melanoma has classically been divided into subtypes:

Superficial spreading melanoma (SSM) is the most common subtype, located on any anatomic site, and with the above typical clinical features described for melanoma.

Nodular melanoma (NM) presents as an elevated or polypoid lesion on any anatomic site. It may be uniform in pigmentation and frequently shows ulceration when advanced.

Lentigo maligna melanoma (LMM) occurs as a macular lesion on sun-exposed skin (head, neck), often in elderly patients.

Acral lentiginous melanoma (ALM) presents as a darkly pigmented, flat to nodular lesion on palms, soles, and subungually.

Pharmaceutical Compositions

In yet another aspect of the present invention, provided are pharmaceutical compositions of the inhibitors or antagonists of GLI, including the nucleic acids described above, but also the small molecule inhibitors and antibodies that block SHH/GLI signaling and a pharmaceutically acceptable carrier. Pharmaceutical compositions may be formulated for topical, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Carriers suitable for use with the present invention will be known to those of skill in the art. Such carriers include but are not limited to a liposome, a nanoliposome, a ceramide-containing nanoliposome, a proteoliposome, a nanoparticulate, a calcium phosphor-silicate nanoparticulate, a calcium phosphate nanoparticulate, a silicon dioxide nanoparticulate, a nanocrystaline particulate, a semiconductor nanoparticulate, poly(D-arginine), a nano-dendrimer, a virus, and calcium phosphate nucleotide-mediated nucleotide delivery. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990), Mack Publishing Co., Easton, Pa. 18042 pages 1435-1712 which are herein incorporated by reference. The compositions may be prepared in liquid form, or may be in dried powder, such as lyophilized form.

Nasal Delivery

Nasal delivery of an HH protein or derivative thereof is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Liquid Aerosol Formulations

The present invention provides aerosol formulations and dosage forms. In general such dosage forms contain a pharmaceutical composition of the present invention in a pharmaceutically acceptable diluent. Pharmaceutically acceptable diluents include but are not limited to sterile water, saline, buffered saline, dextrose solution, and the like.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure.

Aerosol Dry Powder Formulations

It is also contemplated that the present aerosol formulation can be prepared as a dry powder formulation comprising a finely divided powder form of pharmaceutical composition of the present invention and a dispersant. Formulations for dispensing from a powder inhaler device will comprise a finely divided dry powder containing pharmaceutical composition of the present invention (or derivative) and may also include a bulking agent, such as lactose, sorbitol, sucrose, or mannitol in amounts which facilitate dispersal of the powder from the device, e.g., 50 to 90% by weight of the formulation. The pharmaceutical composition of the present invention (or derivative) should most advantageously be prepared in particulate form with an average particle size of less than 10 mm (or microns), most preferably 0.5 to 5 mm, for most effective delivery to the distal lung.

In a further aspect, recombinant cells that have been transformed with an hh gene, e.g., sonic hedgehog gene and that express high levels of the polypeptide can be transplanted in a subject in need of the HH protein. Preferably autologous cells transformed with HH protein are transplanted to avoid rejection; alternatively, technology is available to shield non-autologous cells that produce soluble factors within a polymer matrix that prevents immune recognition and rejection.

Methods of Treatment, Methods of Preparing a Medicament

In yet another aspect of the present invention, methods of treatment and manufacture of a medicament are provided. Conditions alleviated or modulated by the administration of the present derivatives are those indicated above.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing.

A subject in whom administration of HH is an effective therapeutic regiment is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Antibodies to GLI for Therapeutic or Diagnostic Use

According to the present invention, GLI, as produced by a recombinant source, or through chemical synthesis, or isolated from natural sources; and derivatives or analogs thereof, including fusion proteins, may be used as an immunogen to generate antibodies that recognize the GLI, as exemplified below. Such antibodies include but are not limited to polyclonal, monoclonal, chimeric including humanized chimeric, single chain, Fab fragments, and a Fab expression library. The anti-GLI antibodies, for example, of the invention may be cross reactive, that is, they may recognize a GLI derived from a different source. Polyclonal antibodies have greater likelihood of cross reactivity. Alternatively, an antibody of the invention may be specific for a single form of GLI, such as the human GLI proteins GLI! 1, 2 or 3, having the amino acid sequences of SEQ ID NOs: 16, 18 or 20, respectively, or a fragment of a human GLI protein.

Various procedures known in the art may be used for the production of polyclonal antibodies to GLI or derivatives or analogs thereof. For the production of an antibody, various host animals can be immunized by injection with GLI, or a derivative (e.g., or fusion protein) thereof, including but not limited to rabbits, mice, rats, sheep, goats, etc. In one embodiment, GLI or a fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward GLI, or analog, or derivative thereof, any technique that provides for the production of antibody molecules by continuous cell lines in culture may be used. These include but are not limited to the hybridoma technique originally developed by Kohler and Milstein [*Nature,* 256:495-497 (1975)], as well as the trioma technique, the human B-cell hybridoma technique [Kozbor et al., *Immunology Today,* 4:72 (1983); Cote et al., *Proc. Natl. Acad. Sci. U.S.A.,* 80:2026-2030 (1983)], and the EBV-hybridoma technique to produce human monoclonal antibodies [Cole et al., in *Monoclonal Antibodies and Cancer Therapy,* Alan R. Liss, Inc., pp. 77-96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.,* 159:870 (1984); Neuberger et al., *Nature,* 312:604-608 (1984); Takeda et al., *Nature,* 314:452-454 (1985)] by splicing the genes from a mouse antibody molecule specific for GLI together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce e.g., GLI-specific single chain antibodies. An additional embodiment of the invention utilizes the techniques described for the construction of Fab expression libraries [Huse et al., Science, 246:1275-1281 (1989)] to allow rapid and easy identification of monoclonal Fab fragments with the desired specificity for a GLI, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of GLI, one may assay generated hybridomas for a product which binds to the GLI fragment containing such epitope and choose those which do not cross-react with GLI. For selection of an antibody specific to GLI from a particular source, one can select on the basis of positive binding with GLI expressed by or isolated from that specific source.

The foregoing antibodies can be used in methods known in the art relating to the localization and activity of the GLI, e.g., for Western blotting, imaging GLI in situ, measuring levels thereof in appropriate physiological samples, etc. using any of the detection techniques mentioned herein or known in the art. The standard techniques known in the art for immunoassays are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) J. Clin. Chem. Clin. Biochem. 22:895-904.

In a specific embodiment, antibodies that agonize or antagonize the activity of GLI can be generated. Such antibodies can be tested using the assays described infra for identifying ligands.

One aspect of the invention provides a method of using an antibody against GLI to diagnose a melanoma in a subject. As GLI levels correlate with the presence of a melanoma it provides a general biomarker for highly invasive or malignant tumors, and may be predictive of the invasiveness of other tumors that utilize the SHH-GLI signaling pathway. Thus, the antibody compositions and methods provided herein are particularly deemed useful for the diagnosis of invasive tumors including solid tumors such as melanomas, as well as other tumors that utilize the SHH-GLI signaling pathway. More particularly, cancers that may be treated by the compositions and methods of the invention include, but are not limited to, Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma [squamous cell, undifferentiated small cell, undifferentiated large cell, adenocarcinoma], alveolar [bronchiolar] carcinoma, bronchial adenoma, sarcoma, lymphoma, chondromatous hamartoma, mesothelioma; Gastrointestinal: esophagus [squamous cell carcinoma, adenocarcinoma, leiomyosarcoma, lymphoma], stomach [carcinoma, lymphoma, leiomyosarcoma], pancreas [ductal adenocarcinoma, insulinoma, glucagonoma, gastrinoma, carcinoid tumors, VIPoma], small bowel [adenocarcinoma, lymphoma, carcinoid tumors, Kaposi's sarcoma, leiomyoma, hemangioma, lipoma, neurofibroma, fibroma], large bowel [adenocarcinoma, tubular adenoma, villous adenoma, hamartoma, leiomyoma]; Genitourinary tract: kidney [adenocarcinoma, Wilms tumor (nephroblastoma), lymphoma, leukemia], bladder and urethra [squamous cell carcinoma, transitional cell carcinoma, adenocarcinoma], prostate [adenocarcinoma, sarcoma], testis [seminoma, teratoma, embryonal carcinoma, teratocarcinoma, choriocarcinoma, sarcoma, Leydig cell tumor, fibroma, fibroadenoma, adenomatoid tumors, lipoma]; Liver: hepatocellular carcinoma, cholangiocarcinoma, hepatoblastoma, angiosarcoma, hepatocellular adenoma, hemangioma; Bone: osteogenic sarcoma [osteosarcoma], fibrosarcoma, malignant fibrous histiocytoma, chondrosarcoma, Ewing's sarcoma, malignant lymphoma [reticulum cell sarcoma], multiple myeloma, malignant giant cell tumor, chordoma, osteochondroma [osteocartilaginous exostoses], benign chondroma, chondroblastoma, chondromyxoid fibroma, osteoid osteoma and giant cell tumors; Nervous system: skull [osteoma, hemangioma, granuloma, xanthoma, Paget's disease of bone], meninges [meningioma, meningiosarcoma, gliomatosis], brain [astrocytoma, medulloblastoma, glioma, ependymoma, germinoma (pinealoma), glioblastoma multiforme, oligodendroglioma, schwannoma, retinoblastoma, congenital tumors], spinal cord [neurofibroma, meningioma, glioma, sarcoma]; Gynecological: uterus [endometrial carcinoma], cervix [cervical carcinoma, pre-invasive cervical dysplasia], ovaries [ovarian carcinoma (serous cystadenocarcinoma, mucinous cystadenocarcinoma, endometrioid carcinoma, clear cell adenocarcinoma, unclassified carcinoma), granulosa-theca cell tumors, Sertoli-Leydig cell tumors, dysgerminoma, malignant teratoma and other germ cell tumors], vulva [squamous cell carcinoma, intraepithelial carcinoma, adenocarcinoma, fibrosarcoma, melanoma], vagina [clear cell carcinoma, squamous cell carcinoma, sarcoma botryoides (embryonal rhabdomyosarcoma), fallopian tubes [carcinoma]; Hematologic: blood [myeloid leukemia (acute and chronic), acute lymphoblastic leukemia, chronic lymphocytic leukemia, myeloproliferative diseases, multiple myeloma, myelodysplastic syndrome], Hodgkin's disease, non-Hodgkin's lymphoma (malignant lymphoma); Skin: malignant melanoma, basal cell carcinoma, squamous cell carcinoma, Kaposi's sarcoma, nevi, dysplastic nevi, lipoma, angioma, dermatofibroma, keloids, psoriasis; and Adrenal glands: neuroblastoma.

The diagnostic method of the invention provides contacting a biological sample such as a biopsy sample, tissue, cell or fluid (e.g., whole blood, plasma, serum, or urine) isolated from a subject with an antibody which binds GLI. The antibody is allowed to bind to the antigen to form an antibody-antigen complex. The conditions and time required to form the antibody-antigen complex may vary and are dependent on the biological sample being tested and the method of detection being used. Once non-specific interactions are removed by, for example, washing the sample, the antibody-antigen complex is detected using any one of the immunoassays described above as well a number of well-known immunoassays used to detect and/or quantitate antigens [see, for example, Harlow and Lane, Antibodies: A Laboratory Manual, Cold Spring Harbor Laboratory, New York (1988) 555-612]. Such well-known immunoassays include antibody capture assays, antigen capture assays, and two-antibody sandwich assays. In an antibody capture assay, the antigen is attached to solid support, and labeled antibody is allowed to bind. After washing, the assay is quantitated by measuring the amount of antibody retained on the solid support. In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that binds to the antigen.

These immunoassays typically rely on labeled antigens, antibodies, or secondary reagents for detection. These proteins may be labeled with radioactive compounds, enzymes, biotin, or fluorochromes. Of these, radioactive labeling may be used for almost all types of assays. Enzyme-conjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof may be accomplished using standard techniques such as those described by Kennedy, et al. [(1976) Clin. Chim. Acta 70:1-31], and Schurs, et al. [(1977) Clin. Chim Acta 81:1-40].

In accordance with the diagnostic method of the invention, the presence or absence of the antibody-antigen complex is correlated with the presence or absence in the biological sample of the antigen, or a peptide fragment thereof. A biological sample containing elevated levels of said antigen is indicative of an invasive cancer in a subject from which the biological sample was obtained. Accordingly, the diagnostic method of the invention may be used as part of a routine screen in subjects suspected of having an invasive cancer or for subjects who may be predisposed to having an invasive cancer. Moreover, the diagnostic method of the invention may be used alone or in combination with other well-known diagnostic methods to confirm the presence of an invasive cancer.

The diagnostic method of the invention further provides that an antibody of the invention may be used to monitor the levels of GLI antigen in patient samples at various intervals of drug treatment to identify whether and to which degree the drug treatment is effective in reducing or inhibiting hyperproliferation of cells. Furthermore, antigen levels may be monitored using an antibody of the invention in studies evaluating efficacy of drug candidates in model systems and in clinical trials. The antigens provide for surrogate biomarkers in biological fluids to non-invasively assess the global status of tumor cell proliferation. For example, using an antibody of this invention, antigen levels may be monitored in biological samples of individuals treated with known or unknown therapeutic agents or toxins. This may be accomplished with cell lines in vitro or in model systems and clinical trials, depending on the cancer being investigated. Persistently increased total levels of GLI antigen in biological samples during or immediately after treatment with a drug candidate indicates that the drug candidate has little or no effect on cell proliferation. Likewise, the reduction in total levels of GLI antigen indicates that the drug candidate is effective in reducing or inhibiting tumor cell proliferation. This may provide valuable information at all stages of pre-clinical drug development, clinical drug trials as well as subsequent monitoring of patients undergoing drug treatment.

Antibody Labels

The GLI proteins of the present invention, antibodies to GLI proteins, and nucleic acids that hybridize to gli genes (e.g. probes) etc. can all be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. Such labels may also be appropriate for the nucleic acid probes used in binding studies with GLI. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419-439 (1980) and in U.S. Pat. No. 4,857, 453.

Suitable enzymes include, but are not limited to, alkaline phosphatase and horseradish peroxidase.

In addition, GLI, a fragment thereof can be modified to contain a marker protein such as green fluorescent protein as described in U.S. Pat. No. 5,625,048 filed Apr. 29, 1997, WO 97/26333, published Jul. 24, 1997 and WO 99/64592 all of which are hereby incorporated by reference in their entireties.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^{3}H]$-amino acids (with the tritium substituted at non-labile positions).

Therapeutic Uses of an Antibody that Blocks the SHH-GLI Pathway

Another aspect of the invention provides that an antibody, or a fragment thereof, which blocks signaling via the SHH-GLI pathway, may be administered to a human or other animal in an amount to decrease or inhibit cell proliferation, and tumorigenesis. As one may appreciate, any hyperproliferative disorder such as cancer, which may be diagnosed by an antibody of the invention, may also be treated using an antibody of the invention. A skilled clinician or physician would be able, by routine experimentation, to determine what an effective, non-toxic amount of antibody would be for the purpose of decreasing or inhibiting cell proliferation. Generally, however, an effective dosage will be in the range of about 0.05 to 100 milligrams per kilogram body weight per day.

Furthermore, an antibody of the invention may be administered to a human or other animal in a conventional dosage form prepared by combining an antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The antibodies of the present invention may also be used to target other chemotherapeutic agents to the site where needed. Alternatively, the antibodies can be used to target radioisotopes to the site where inhibition of cellular proliferation is desirable. The antibodies may also be employed for diagnostic purposes to identify sites within the patient where the tumor burden is greatest. Furthermore, the antibodies may be used to assess the effectiveness of anti-tumor therapy for prognostic value.

The route of administration of an antibody, or fragment thereof, may be oral, parenteral, by inhalation or topical. The antibody may be delivered locally to the site of the cancer. The term parenteral as used herein includes intravenous, intramuscular, subcutaneous, rectal, vaginal or intraperitoneal administration. The subcutaneous and intramuscular forms of parenteral administration are generally preferred. The antibody may be delivered using a slow release formulation. It may be delivered in a liposome or a similar device.

The daily parenteral and oral dosage regimens for employing antibodies of the invention to therapeutically decrease cell proliferation will generally be in the range of about 0.05 to 100, but preferably about 0.5 to 10, milligrams per kilogram body weight per day.

An antibody of the invention may also be administered by inhalation. Inhalation, as used herein, includes intranasal and oral inhalation administration. Appropriate dosage forms for such administration, such as an aerosol formulation or a metered dose inhaler, may be prepared by conventional techniques. The preferred dosage amount of an antibody of the invention to be employed is generally within the range of about 10 to 100 milligrams.

An antibody of the invention may also be administered topically. By topical administration is meant non-systemic administration and includes the application of an antibody, or fragments thereof, externally to the epidermis, to the buccal cavity and instillation of such an antibody into the ear, eye and nose, and where it does not significantly enter the blood stream. In a particular topical formulation, the antibody may be effective in treatment of a hyperproliferative condition such as cancer. By systemic administration is meant oral, intravenous, intraperitoneal and intramuscular administration. The amount of an antibody required for therapeutic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

An alternate therapeutic approach for use of the antibodies of the present invention is via insertion of the gene encoding the antibody into a tumor cell whereby the intracellular expression of the antibody gene allows for modulation of the function of the protein for which the antibody is specific. Accordingly, this invention provides for methods and compositions for modulating SHH-GLI function in a cell involving intracellular expression of the antibody described herein. The invention is particularly applicable to inhibiting the SHH-GLI signaling in a cancer cell, thus inhibiting proliferation and survival of the cell.

To express an antibody homologue within a cell, a nucleic acid molecule encoding the antibody homologue, such as a recombinant expression vector encoding the antibody homologue, is introduced into the cell. Preferably, the antibody homologue used to modulate SHH-GLI signaling is a single chain Fv (scFv) fragment, although whole antibodies, or antigen binding fragments thereof (e.g., Fab fragments) may also be useful.

In a particularly preferred embodiment of the invention, an antibody homologue is expressed intracellularly in a cancerous mammalian cell to inhibit the cell proliferation function of SHH-GLI. The target cells of interest may be selected from any cell in which SHH-GLI plays a role in proliferation, such as cancer cells. A nucleic acid molecule encoding the antibody homologue can be introduced in vivo into cells of interest, by, for example, use of a recombinant viral vector or other vector system suitable for delivery of genes to cells in vivo.

To express an antibody homologue within a cell, a nucleic acid molecule(s) encoding the antibody homologue is prepared and introduced into the cell. An isolated nucleic acid molecule encoding an antibody homologue can be prepared according to standard molecular biology methods using nucleic acid sequences obtained from antibody genes. Isolated nucleic acid molecules encoding antibody chains (or relevant antigen binding portions thereof, such as $V_H$ or $V_L$ regions), specific for many different particular proteins have been described, and/or are available, in the art. Additionally, such nucleic acids can be isolated by standard techniques, for example, from a hybridoma that expresses a monoclonal antibody specific for a protein of interest, or by screening an immunoglobulin expression library (e.g., an immunoglobulin phage display library) with the protein of interest.

Monoclonal antibodies specific for an antigenic polypeptide of interest may be prepared, for example, using the technique of Kohler and Milstein, Eur. J. Immunol. 6:511-519, 1976, and improvements thereto. Briefly, these methods involve the preparation of immortal cell lines capable of producing antibodies having the desired specificity. Such cell lines may be produced, for example, from spleen cells obtained from an immunized animal. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Alternatively, monoclonal antibodies can be prepared by constructing a recombinant immunoglobulin library, such as a scFv or Fab phage display library and nucleic acid encoding an antibody chain (or portion thereof) can be isolated therefrom. Immunoglobulin light chain and heavy chain first strand cDNAs can be prepared from mRNA derived from lymphocytes of a subject immunized with a protein of interest using primers specific for a constant region of the heavy chain and the constant region of each of the kappa and lambda light chains. Using primers specific for the variable and constant regions, the heavy and light chain cDNAs can then by amplified by PCR. The amplified DNA is then ligated into appropriate vectors for further manipulation in generating a library of display packages. Restriction endonuclease recognition sequences may also be incorporated into the primers to allow for the cloning of the amplified fragment into a vector in a predetermined reading frame for expression on the surface of the display package.

The immunoglobulin library is expressed by a population of display packages, preferably derived from filamentous phage, to form an antibody display library. In addition to commercially available kits for generating phage display libraries (e.g., the Pharmacia Recombinant Phage Antibody System, Catalog No. 27-9400-01; and the Stratagene SurfZAP™ Phage Display Kit, Catalog No. 240612), examples of methods and reagents particularly amenable for use in generating antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffiths et al. (1993) EMBO J 12:725-734; Hawkins et al. (1992) J Mol Biol 226:889-896; Clackson et al. (1991) Nature 352:624-628; Gram et al. (1992) Proc. Natl. Acad. Sci. USA 89:3576-3580; Garrad et al. (1991) Bio/Technology 2:1373-1377; Hoogenboom et al. (1991) Nuc Acid Res 19:4133-4137; and Barbas et al. (1991) Proc. Natl. Acad. Sci. USA 88:7978-7982. As generally described in McCafferty et al. Nature (1990) 348:552-554, complete VH and VL domains of an antibody, joined by a flexible ($Gly_4$-$Ser)_3$ linker, can be used to produce a single chain antibody expressed on the surface of a display package, such as a filamentous phage.

Once displayed on the surface of a display package (e.g., filamentous phage), the antibody library is screened with a protein of interest to identify and isolate packages that express an antibody that binds the protein of interest. Display packages expressing antibodies that bind immobilized protein can then be selected. Following screening and identification of a monoclonal antibody (e.g., a monoclonal scFv) specific for the protein of interest, nucleic acid encoding the selected antibody can be recovered from the display package (e.g., from the phage genome) by standard techniques. The nucleic acid so isolated can be further manipulated if desired (e.g., linked to other nucleic acid sequences) and subcloned into other expression vectors by standard recombinant DNA techniques.

Once isolated, nucleic acid molecules encoding antibody chains, or portions thereof, can be further manipulated using standard recombinant DNA techniques. For example, a single chain antibody gene can also be created by linking a VL coding region to a VH coding region via a nucleotide sequence encoding a flexible linker (e.g., ($Gly_4$-$Ser)_3$). Single chain antibodies can be engineered in accordance with the teachings of Bird et al. (1988) Science 242:423-426; Huston et al. (1988) Proc. Natl. Acad. Sci USA 85:5879-5883; Ladner, et al. International Publication Number WO 88/06630; and McCafferty, et al. International Publication No. WO 92/10147. A preferred single chain antibody for use in the invention blocks SHH-GLI signaling. A plasmid encoding a scFv antibody would be prepared using standard molecular biological techniques.

Another manipulation that can be performed on isolated antibody genes is to link the antibody gene to a nucleotide sequence encoding an amino acid sequence that directs the antibody homologue to a particular intracellular compartment. A preferred nucleotide sequence to which an antibody gene is linked encodes a signal sequence (also referred to as a leader peptide). Signal sequences are art-recognized amino acid sequences that direct a protein containing the signal sequence at its amino-terminal end to the endoplasmic reticulum (ER). Typically, signal sequences comprise a number hydrophobic amino acid residues. Alternatively, an antibody homologue can be linked to an amino acid sequence that directs the antibody homologue to a different compartment of the cell. For example, a nuclear localization sequence (NLS) can be linked to the antibody homologue to direct the antibody homologue to the cell nucleus. Nuclear localization sequences are art-recognized targeting sequences. Typically, an NLS is composed of a number of basic amino acid residues.

Following isolation of antibody genes, as described above, and, if desired, further manipulation of the sequences, DNA encoding the antibody homologue can be inserted into an expression vector to facilitate transcription and translation of the antibody coding sequences in a host cell. Within the expression vector, the sequences encoding the antibody homologue are operatively linked to transcriptional and translational control sequences. These control sequences include promoters, enhancers and other expression control elements (e.g., polyadenylation signals). Such regulatory sequences are known to those skilled in the art and are described in Goeddel, Gene Expression Technology: Methods in Enzymology 185, Academic Press, San Diego, Calif. (1990). The expression vector and expression control sequences are chosen to be compatible with the host cell used. Expression vectors can be used to express one antibody chain (e.g., a single chain antibody) or two antibody chains (e.g., a Fab fragment). To express two antibody chains, typically the genes for both chains are inserted into the same expression vector but linked to separate control elements.

Expression of a nucleic acid in mammalian cells is accomplished using a mammalian expression vector. When used in mammalian cells, the expression vector's control functions are often provided by viral material. For example, commonly used promoters are derived from polyoma, Adenovirus 2, cytomegalovirus (CMV) and Simian Virus 40. An example of a suitable mammalian expression vector is pCDNA3 (commercially available from Invitrogen), which drives transcription via the CMV early intermediate promoter/enhancer and contains a neomycin resistance gene as a selective marker. Other examples of mammalian expression vectors include pCDM8 (Seed, B., (1987) Nature 329:840) and pMT2PC (Kaufman et al. (1987), EMBO J 6:187-195). Alternative to the use of constitutively active viral regulatory sequences, expression of an antibody homologue gene can be controlled by a tissue-specific regulatory element that directs expression of the nucleic acid preferentially in a particular cell type. Tissue-specific regulatory elements are known in the art.

In one embodiment, a recombinant expression vector of the invention is a plasmid vector. Plasmid DNA can be introduced into cells by a variety of techniques either as naked DNA or, more commonly, as DNA complexed with or combined with another substance. Alternatively, in another embodiment, the recombinant expression vector of the invention is a virus, or portion thereof, which allows for expression of a nucleic acid introduced into the viral nucleic acid. For example, replication defective retroviruses, adenoviruses and adeno-associated viruses can be used for recombinant expression of antibody homologue genes. Virally-mediated gene transfer into cells can be accomplished by infecting the target cell with the viral vector.

Non-limiting examples of techniques which can be used to introduce an expression vector encoding an antibody homologue into a host cell include:

Adenovirus-Polylysine DNA Complexes: Naked DNA can be introduced into cells by complexing the DNA to a cation, such as polylysine, which is then coupled to the exterior of an adenovirus virion (e.g., through an antibody bridge, wherein the antibody is specific for the adenovirus molecule and the polylysine is covalently coupled to the antibody) (see Curiel, D. T., et al. (1992) Human Gene Therapy 3:147-154). Entry of the DNA into cells exploits the viral entry function, including natural disruption of endosomes to allow release of the DNA intracellularly. A particularly advantageous feature of this approach is the flexibility in the size and design of heterologous DNA that can be transferred to cells.

Receptor-Mediated DNA Uptake: Naked DNA can also be introduced into cells by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J Biol. Chem. 267:963-967; and U.S. Pat. No. 5,166,320). Binding of the DNA-ligand complex to the receptor facilitates uptake of the DNA by receptor-mediated endocytosis. Receptors to which a DNA-ligand complex have targeted include the transferrin receptor and the asialoglycoprotein receptor. Additionally, a DNA-ligand complex can be linked to adenovirus capsids which naturally disrupt endosomes, thereby promoting release of the DNA material into the cytoplasm and avoiding degradation of the complex by intracellular lysosomes (see for example Curiel et al. (1991) Proc. Natl. Acad. Sci. USA 88:8850; and Cotten, M. et al. (1992) Proc. Natl. Acad. Sci. USA 89:6094-6098; Wagner, E. et al. (1992) Proc. Natl. Acad. Sci. USA 89:6099-6103). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Liposome-Mediated transfection ("lipofection"): Naked DNA can be introduced into cells by mixing the DNA with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel, F. M. et al. (eds.) Greene Publishing Associates, (1989), Section 9.4 and other standard laboratory manuals. Additionally, gene delivery in vivo has been accomplished using liposomes. See for example Nicolau et al. (1987) Meth. Enz. 149:157-176; Wang and Huang (1987) Proc. Natl. Acad. Sci. USA 84:7851-7855; Brigham et al. (1989) Am. J Med. Sci. 298:278; and Gould-Fogerite et al. (1989) Gene 84:429-438.

Direct Injection: Naked DNA can be introduced into cells by directly injecting the DNA into the cells. For an in vitro culture of cells, DNA can be introduced by microinjection, although this not practical for large numbers of cells. Direct injection has also been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo can be used. Such an apparatus is commercially available (e.g., from BioRad).

Retroviral Mediated Gene Transfer: Defective retroviruses are well characterized for use in gene transfer for gene therapy purposes (for a review see Miller, A. D. (1990) Blood 76:271). A recombinant retrovirus can be constructed having a nucleic acid encoding a gene of interest (e.g., an antibody homologue) inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art.

Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). While any retrovirus may be utilized, the lentivirus approach allows for delivery to a broad variety of cellular targets, both ex vivo (cell lines, primary cells including stem cells, fertilized oocytes, and blastocysts) and in vivo (e.g., brain, lung, liver). The lentivirus vector-mediated delivery of siRNAs allows for the controllable suppression of cellular genes both with a high degree of efficacy and without significant leakiness.

Adenoviral Mediated Gene Transfer: The genome of an adenovirus can be manipulated such that it encodes and expresses a gene product of interest (e.g., an antibody homologue) but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to many other gene delivery vectors (Berkner et al. cited supra; Haj-Ahmand and Graham (1986) J Virol. 57:267). Most replication-defective adenoviral vectors currently in use are deleted for all or parts of the viral E1 and E3 genes but retain as much as 80% of the adenoviral genetic material.

Adeno-Associated Viral Mediated Gene Transfer: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). It is also one of the few viruses that may integrate its DNA into non-dividing cells, and exhibits a high frequency of stable integration (see for example Flotte et al. (1992) Am. J Respir. Cell. Mol. Biol. 7:349-356; Samulski et al. (1989) J Virol. 63:3822-3828; and McLaughlin et al. (1989) J Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J Virol. 51:611-619; and Flotte et al. (1993) J Biol. Chem. 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of the introduced DNA can be detected, for example, by Northern blotting, RNase protection or reverse transcriptase-polymerase chain reaction (RT-PCR). Expression of the introduced gene product (e.g., the antibody homologue) in the cell can be detected by an appropriate assay for detecting proteins, for example by immunohistochemistry.

As will be appreciated by those skilled in the art, the choice of expression vector system will depend, at least in part, on the host cell targeted for introduction of the nucleic acid. For example, nucleic acid encoding an antibody homologue which blocks SHH-GLI signaling is preferably introduced into tumor cells showing enhanced proliferative capacity and highly invasive characteristics. Tumor cells that are responsive to treatment with the blocking antibodies of the present invention include prostate cancer, lung cancer (small cell and non small cell lung cancer), basal cell carcinoma, melanoma, glioblastoma, medulloblastoma, PNETs, other brian tumors, stomach, GI tract including colon, pancreas, rhabdomyosarcomas, and soft tissue sarcomas. Preferred expression vectors and delivery systems for introducing nucleic acid into malignant cells include transfection with adenoviral-polylysine DNA complexes and adenoviral vector-mediated gene transfer. These delivery systems are suitable for introduction of nucleic acid into cells in vitro, or more preferably for tumor cells, in vivo.

The functional outcome of intracellular antibody expression, on the subsequent expression and/or function of the protein targeted for antibody binding (referred to as the target protein) can be assessed by suitable assays that monitor the expression and/or function of the target protein, including standard immunohistochemistry or immunoelectron microscopy techniques.

Alternatively, cell proliferation can be measured using commercially available cell proliferation assays. The functional outcome of intracellular antibody homologue expression targeting SHH-GLI on tumor cell growth and survival, or on the expansion of immunocompetent cells with unwanted specificity in a mammal can be assessed in vivo using animal model systems that may be predictive of therapeutic efficacy in humans. For example, the antibody genes may be inserted into a human cancer cell known to have the SHH-GLI signaling pathway. These cells may be implanted into athymic nude mice, and tumor growth may be monitored visually over time.

Other Diagnostic Means of Determining Levels of Gli

Cell-Based Reporters and Instrumentation

Cellular screening techniques can be broadly classified into two groups: semi-biochemical approaches that involve the analysis of cell lysates, or live cell assays. Whole cell assay methodologies vary with respect to assay principle, but have largely in common a form of luminescence or fluorescence for detection. Luminescence is a phenomenon in which energy is specifically channeled to a molecule to produce an excited state. Luminescence includes fluorescence, phosphorescence, chemiluminescence and bioluminescence.

An ever-increasing list of fluorescent proteins include the widely-used GFP derived from Aequorea Victoria and spectral variants thereof. The list includes a variety of fluorescent proteins derived from other marine organisms; bacteria; fungi; algae; dinoflagellates; and certain terrestrial species. These reporters have the advantage of not requiring any exogenous substrates or co-factors for the generation of a signal but do require an external source of radiation for excitation of the intrinsic fluorophore. In addition, the increasing availability of genes encoding a broad spectrum of fluorescent reporter proteins enables the construction of assays tailored for specific applications, cell types, and detection systems.

Different classes of luminescent proteins, luciferases, have been have been discovered in bacteria and eukaryotes. Luciferases are proteins that catalyze the conversion of a natural substrate into a product that emits light in the visible spectrum and thus require no external radiation source. Monomeric forms of luciferase have been cloned from firefly, *Renilla*, and other organisms. Firefly luciferase is the most common of the bioluminescent reporters and is a 61 kDa monomeric enzyme that catalyzes a two-step oxidation reaction to yield light. *Renilla* luciferase is a 31 kDa monomeric enzyme that catalyzes the oxidation of coelenterazine to yield coelenteramide and blue light of 480 nm. Substrates for luciferase are widely available from commercial suppliers such as Promega Corporation and Invitrogen Molecular Probes.

A variety of useful enzymatic reporters are enzymes that either generate a fluorescent signal or are capable of binding small molecules that can be tagged with a fluorescent moiety to serve as a fluorescent probe. For example, dihydrofolate reductase (DHFR) is capable of binding methotrexate with high affinity; a methotrexate-fluorophore conjugate can serve as a quantitative fluorescent reagent for the measurement of the amount of DHFR within a cell. By tagging methotrexate with any of a number of fluorescent molecules such as fluorescein, rhodamine, Texas Red, BODIPY and other commercially available molecules (such as those available from Molecular Probes/Invitrogen and other suppliers) a range variety of fluorescent readouts can be generated. The wide range of techniques of immunohistochemistry and immunocytochemistry can be applied to whole cells. For example, ligands and other probes can be tagged directly with fluorescein or another fluorophore for detection of binding to cellular proteins; or can be tagged with enzymes such as alkaline phosphatase or horseradish peroxidase to enable indirect detection and localization of signal.

Many other enzymes can be used to generate a fluorescent signal in live cells by using specific, cell-permeable substrate that either becomes fluorescent or shifts its fluorescence spectrum upon enzymatic cleavage. For example, substrates for beta-lactamase exist whose fluorescence emission properties change in a measurable way upon cleavage of a beta-lactam core moiety to which fluorophores are attached. Changes include, shifts in fluorophore absorption or emission wavelengths, or cleavage of a covalent assembly of emmision-absorption-mathched fluorophore pairs that in the covalently-assembled form sustain resonance energy transfer between the two fluorophores that is lost when the two are separated. Membrane-permeant, fluorescent BLA substrates such as the widely-used CCF2/AM allow the measurement of gene expression in live mammalian cells in the absence or presence of compounds from a biologically active chemical library.

Luminescent, fluorescent or bioluminescent signals are easily detected and quantified with any one of a variety of automated and/or high-throughput instrumentation systems including fluorescence multi-well plate readers, fluorescence activated cell sorters (FACS) and automated cell-based imaging systems that provide spatial resolution of the signal. A variety of instrumentation systems have been developed to automate HCS including the automated fluorescence imaging and automated microscopy systems developed by Cellomics, Amersham, TTP, Q3DM, Evotec, Universal Imaging and Zeiss. Fluorescence recovery after photobleaching (FRAP) and time lapse fluorescence microscopy have also been used to study protein mobility in living cells. Although the optical instrumentation and hardware have advanced to the point that any bioluminescent signal can be detected with high sensitivity and high throughput, the existing assay choices are limited either with respect to their range of application, format, biological relevance, or ease of use.

Transcriptional Reporter Assays

Cell-based reporters are often used to construct transcriptional reporter assays, which allow monitoring of the cellular events associated with signal transduction and gene expression. Reporter gene assays couple the biological activity of a target to the expression of a readily detected enzyme or protein reporter. Based upon the fusion of transcriptional control elements to a variety of reporter genes, these systems "report" the effects of a cascade of signaling events on gene expression inside cells. Synthetic repeats of a particular response element can be inserted upstream of the reporter gene to regulate its expression in response to signaling molecules generated by activation of a specific pathway in a live cell. The variety of transcriptional reporter genes and their application is very broad and includes drug screening systems based on beta-galactosidase (beta-gal), luciferase, alkaline phosphatase (luminescent assay), GFP, aequorin, and a variety of newer bioluminescent or fluorescent reporters.

In general, transcription reporter assays have the capacity to provide information on the response of a pathway to natural or synthetic chemical agents on one or more biochemical pathways, however they only indirectly measure the effect of an agent on a pathway by measuring the consequence of pathway activation or inhibition, and not the site of action of the compound. For this reason, mammalian cell-based methods have been sought to directly quantitate protein-protein interactions that comprise the functional elements of cellular biochemical pathways and to develop assays for drug discovery based on these pathways.

Cellular Assays for Individual Proteins Tagged with Fluorophores or Luminophores.

Subcellular compartmentalization of signaling proteins is an important phenomenon not only in defining how a biochemical pathway is activated but also in influencing the desired physiological consequence of pathway activation. This aspect of drug discovery has seen a major advance as a result of the cloning and availability of a variety of intrinsically fluorescent proteins with distinct molecular properties.

High-content (also known as high-context) screening (HCS) is a live cell assay approach that relies upon image-based analysis of cells to detect the subcellular location and redistribution of proteins in response to stimuli or inhibitors of cellular processes. Fluorescent probes can be used in HCS; for example, receptor internalization can be measured using a fluorescently-labeled ligand that binds to the transferrin receptor. Often, individual proteins are either expressed as fusion proteins, where the protein of interest is fused to a detectable moiety such as GFP, or are detected by immunocytochemistry after fixation, such as by the use of an antibody conjugated to Cy3 or another suitable dye. In this way, the subcellular location of a protein can be imaged and tracked in real time. One of the largest areas of development is in applications of GFP color-shifted mutants and other more recently isolated new fluorescent proteins, which allow the development of increasingly advanced live cell assays such as multi-color assays. A range of GFP assays have been developed to analyze key intracellular signaling pathways by following the redistribution of GFP fusion proteins in live cells. For drug screening by HCS the objective is to identify therapeutic compounds that block disease pathways by inhibiting the movement of key signaling proteins to their site of action within the cell.

Tagging a protein with a fluorophore or a luminophore enables tracking of that particular protein in response to cell stimuli or inhibitors. For example, the activation of cell signaling by TNF can be detected by expressing the p65 subunit of the NFkB transcription complex as a GFP fusion and then following the redistribution of fluorescence from the cytosolic compartment to the nuclear compartment of the cell within minutes after TNF stimulation of live cells (J A Schmid et al., 2000, Dynamics of NFkB and IkBa studied with green fluorescent protein (GFP) fusion proteins, J. Biol. Chem. 275: 17035-17042). What has been unique about these approaches is the ability to allow monitoring of the dynamics of individual protein movements in living cells, thus addressing both the spatial and temporal aspects of signaling.

Gene Therapy and Transgenic Vectors

A gene encoding a hedgehog protein or a GLI protein, e.g., SHH or GLI1, GLI2 or GLI3, an active fragment thereof, derivative thereof, or structural/functional domain thereof, can be introduced either in vivo, ex vivo, or in vitro in a viral vector as noted previously.

In a particular embodiment, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon, or anti-CD4 antibody, can be administered to block humoral or cellular immune responses to the viral vectors (see, e.g., Wilson, *Nature Medicine*, (1995)). In addition, it is advantageous to employ a viral vector that is engineered to express a minimal number of antigens.

In another embodiment, and as noted above, the Shh or gli gene can be introduced in a retroviral vector, e.g., as described in U.S. Pat. No. 5,399,346; Mann et al., (1983) *Cell*, 33:153; U.S. Pat. No. 4,650,764; U.S. Pat. No. 4,980,289; Markowitz et al., (1988) *J. Virol.*, 62:1120; U.S. Pat. No. 5,124,263; International Patent Publication No. WO 95/07358, published Mar. 16, 1995; and Kuo et al., (1993) *Blood*, 82:845.

Targeted gene delivery is described in International Patent Publication WO 95/28494, published October 1995.

Alternatively, the vector can be introduced by lipofection. Liposomes may be used for encapsulation and transfection of nucleic acids in vitro. Synthetic cationic lipids designed to limit the difficulties and dangers encountered with liposome mediated transfection can be used to prepare liposomes for in vivo transfection of a gene encoding SHH (Felgner, et. al., *Proc. Natl. Acad. Sci. U.S.A.*, 84:7413-7417 (1987); see Mackey, et al., *Proc. Natl. Acad. Sci. U.S.A.*, 85:8027-8031 (1988)). The use of cationic lipids may promote encapsulation of negatively charged nucleic acids, and also promote fusion with negatively charged cell membranes (Felgner and Ringold, *Science*, 337:387-388 (1989)). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as the brain. Lipids may be chemically coupled to other molecules for the purpose of targeting (see Mackey et. al., *Proc. Natl. Acad. Sci. U.S.A.*, 85:8027-8031 (1988)).

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., (1992) *J. Biol. Chem.*, 267:963-967; Wu and Wu, (1988) *J. Biol. Chem.*, 263:14621-14624; Hartmut et al., Canadian Patent Application No. 2,012,311, filed Mar. 15, 1990).

In a preferred embodiment of the present invention, a gene therapy vector as described above employs a transcription control sequence operably associated with the nucleotide sequence encoding the SHH inserted in the vector. That is, a specific expression vector of the present invention can be used in gene therapy.

Such an expression vector is particularly useful to regulate expression of a therapeutic hh gene, e.g., sonic hedgehog gene. In one embodiment, the present invention contemplates constitutive expression of the hh gene, even if at low levels. Alternatively, a regulatable promoter may be used.

Administration

According to the present invention, a therapeutic composition, e.g., an SHH or GLI protein or active fragment thereof and a pharmaceutically acceptable carrier of the invention or an agent such as a small organic molecule that stimulates the SHH-GLI pathway and/or increases expression of SHH, or alternatively, a small organic molecule or an siRNA or blocking antibody to block or inhibit the SHH-GLI pathway to prevent tumorigenesis, may be introduced parenterally, transmucosally, e.g., nasally. Preferably, administration is by intracranial, intrathecal or intraventricular administration. Alternatively, the therapeutic composition can be placed (e.g., injected) into the bloodstream after coupling the SHH or GLI protein or active fragment thereof to a carrier that will allow the SHH or GLI protein or active fragment thereof— carrier complex to cross the blood-brain barrier.

In a preferred aspect, an HH or GLI protein of the present invention can cross cellular or nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to an HH or GLI protein. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. (On the other hand SHH may itself be considered a targeting molecule since it binds its own receptor). In a specific embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the SHH protein via a reduced sulfhydryl.

Antibodies for use as targeting molecule are specific for cell surface antigen. In one embodiment, the antigen is a receptor. For example, an antibody specific for a receptor on a brain stem cell can be used. This invention further provides for the use of other targeting molecules, such as lectins, carbohydrates, proteins and steroids.

In another embodiment, the therapeutic compound can be delivered in a vesicle, in particular a liposome (see Langer, (1990) *Science,* 249:1527-1533; Treat et al., (1989) in *Liposomes in the Therapy of Infectious Disease and Cancer,* Lopez-Berestein and Fidler (eds.), Liss: New York, pp. 353-365; Lopez-Berestein, ibid., pp. 317-327; see generally ibid.).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer (1990) supra; Sefton, (1987) *CRC Crit. Ref. Biomed. Eng.,* 14:201; Buchwald et al., (1980) *Surgery,* 88:507; Saudek et al., (1989) *N. Engl. J. Med.,* 321: 574). In another embodiment, polymeric materials can be used (see *Medical Applications of Controlled Release,* Langer and Wise (eds.), CRC Press: Boca Raton, Fla. (1974); *Controlled Drug Bioavailability, Drug Product Design and Performance,* Smolen and Ball (eds.), Wiley: New York (1984); Ranger and Peppas, (1983) *J. Macromol. Sci. Rev. Macromol. Chem.,* 23:61; see also Levy et al., (1985) *Science,* 228:190; During et al., (1989) *Ann. Neurol.,* 25:351; Howard et al., (1989) *J. Neurosurg.,* 71:105). In yet another embodiment, a controlled release system can be placed in proximity of the therapeutic target, i.e., the brain, thus requiring only a fraction of the systemic dose (see, e.g., Goodson, in *Medical Applications of Controlled Release,* supra, vol. 2, pp. 115-138 (1984)). Preferably, a controlled release device is introduced into a subject in proximity of the adult brain stem cells, e.g., the striatal subventricular zone (SVZ). Other controlled release systems are discussed in the review by Langer (1990) supra.

Specific Embodiments

As shown below the inventors have not only examined the role of GLI proteins in carcinogenesis, in particular melanomas, but have explored the effects of Gli1 on apoptosis induced by various chemotherapeutic agents. The inventors have provided evidence to support a role for GLI in tumorigenesis and tumor cell proliferation and more importantly from a clinical point of view, in skin cancers, in particular, melanoma.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

SHH-GLI Signaling and Tumorigenesis

Experimental Procedures

Cell Lines and Patient Samples

Human foreskin melanocytes (Promocell) were grown in serum-free M2 medium (Promocell). WM-115, SK-MEL-2, SK-MEL-5, MeWo and COS7 cell lines (ATCC) were grown as specified. Tumors were chopped, incubated in E-MEM (Sigma) containing collagenase A (300 U/ml, Worthington) and hyaluronidase (100 U/ml, Sigma), mechanically dissociated and plated in E-MEM with 10% FBS, 1 mM sodium pyruvate (GIBCO) and 1 ng/ml EGF (GIBCO). A small slice of human scalp from a 30-year-old Caucasian was used for in situ hybridization. All melanoma samples and BCC were obtained following approved protocols. (See Tables 1-3) (Dahmane et al., (1997), Activation of the transcription factor Gli1 and the Sonic hedgehog signalling pathway in skin tumours. Nature 389, 876-881)

In Situ Hybridization and Immunocytochemistry

Immunohistochemistry on cryostat sections with mouse anti-BrdU (Beckton Dickinson), rabbit anti-Caspase3 (Cell Signaling), mouse anti-MlanA (Dako), mouse anti-MITF (Vector Laboratories). Mouse anti-Myc (9E10; Santa Cruz) and rabbit anti-β-galactosidase (Cappel) used FITC- or RITC-conjugated secondary antibodies (Boehringer Mannheim). In situ hybridization on frozen sections with digoxygenin-labeled probes was as described (Dahmane et al, (1997), Activation of the transcription factor Gli1 and the Sonic hedgehog signalling pathway in skin tumours. Nature 389, 876-881; Dahmane. Et al., (2001), The Sonic Hedgehog-Gli pathway regulates dorsal brain growth and tumorigenesis. Development 128, 5201-5212).

RT-PCR and qRT-PCR

Real-time quantitative PCR amplifications with different primers (Suppl. Materials) were carried out at 60° C. on an Opticon machine (MJ Research) using iQ™ SYBR Green supermix (Biorad) and values calculated using the standard curve method.

Drugs, Treatments and Proliferation Assays

Commercial N-SHH (R&D Systems) was used at 100 nM. 5E1 anti-SHH blocking antibody (Hybridoma Bank, University of Iowa) was used at 10 µg/ml. Forskolin (FK) and 1,9-dideoxyforskolin (ddFK; Sigma) were used at 50 µM. Cyclopamine (TRC) and Tomatidine (Sigma) were used at 5 and 10 µM unless otherwise noted. MEK-1 (U0126; Promega), EGFR (AG1478; Biosource) and AKT (SH6; Alexis corporation) inhibitors were used at 1, 10, and 40 µM, respectively, dissolved in DMSO. Drug treatments were for 48 h in 2.5% serum. BrdU (Sigma) was pulsed at 4 µg/ml for 2 h before fixation followed by immunodetection with anti-BrdU antibodies (BD Biosciences). The number of viable cells was assessed by Trypan blue exclusion (Promega).

RNA Interference 21 nt-long double stranded siRNAs purified and desalted (Dharmacon Inc) were: GLI1: AACUCCACAGGCAUA-CAGGAU (SEQ ID NO: 1); GLI2: AAGAUCUGGACAGG-GAUGACU (SEQ ID NO: 2); GLI3: AAUGAG-GAUGAAAGUCCUGGA (SEQ ID NO: 3). Control siRNA with or without an FITC tag: AACGUACGCGGAAUA-CAACGA (SEQ ID NO: 4) (Sanchez et al, (2004), Inhibition of prostate cancer proliferation by interference with SONIC HEDGEHOG-GLI1 signaling. Proc. Natl. Acad. Sci. USA. 101, 12561-12566). siRNA transfections (0.2 µM) were performed with Oligofectamine (Invitrogen) for 48 h.

Cell Transfections and Colony Formation Assay

Cells were transfected (3 µg/p35 plate) with myc-tagged full-length CMV expression vectors for human GLI1 (Lee, J., Platt, K. A., Censullo, P. & Ruiz i Altaba, A. Gli1 is a target of Sonic hedgehog that induces ventral neural tube development. *Development* 124, 2537-2552 (1997)), HRAS-V12

(kindly provided by Dr. A. Pellicer, NYU) and LacZ with FUGENE (Roche). For selection, SK-MEL-2 and MeWo cells were transfected (4 μg/p60 plate) with PGK-neo and CMV-eGFP alone or in a 1/1/8 ratio with HRAS-12G, GLI3C'ΔClaI (Ruiz i Altaba 1999) or (frog) fGli2C'Δ (Ruiz i Altaba 1999), or in a 1/1/4/4 ratio with HRAS-12G/ GLI3C'ΔClaI or HRAS-12G/fGli2C'Δ. After Geneticin (400 μg/ml, Gibco) selection for 20 days, colonies were stained with 0.5% crystal violet. Colony size was measured in duplicate dishes in three independent experiments. For subcellular localization, pCS2-Myc frog Gli2, frog Gli2, human GLI3 and human GLI3C'ΔCla1 (Ruiz i Altaba, 1999) were transfected into COS-7 (ATCC) cells with our without HRAS (V12).

Synthetic RNA Microinjection into Frog Embryos and Tumor Collection

Microinjection of synthetic RNA into pigmented *Xenopus laevis* embryos was performed as described (Dahmane et al, (1997), Activation of the transcription factor Gli1 and the Sonic hedgehog signalling pathway in skin tumours. Nature 389, 876-881; Dahmane. Et al., (2001), The Sonic Hedgehog-Gli pathway regulates dorsal brain growth and tumorigenesis. Development 128, 5201-5212), targeting the animal region of ventral cells at the 4-cell stage as determined by asymmetrical pigment distribution. The tumors of GLI1-injected embryos were dissected without contaminating tissues at stage ±32. The epidermis of LacZ-injected embryos was used as control.

Nude Mouse Xenografts, Metastases and Tumor Treatment

MeWo cells were infected with a LacZ expressing lentivirus at high MOI. $5 \times 10^5$ MeWo/LacZ, WM-115 or $10^6$ primary Me-3 melanoma cells were inoculated subcutaneously (s.c.) at two sides per adult male (NMRI-nu) nude mouse and the tumors were measured daily. Mewo/LacZ melanomas were treated i.p. with cyclopamine (10 mg/kg/twice day) complexed with 45% 2-hydroxypropyl-β-cyclodextrin (HBC, Sigma) or HBC alone. Alternatively, MeWo/LacZ or WM-115 melanomas were treated by direct injection into the tumor of HBC-coupled cyclopamine (200 μg/tumor/twice day) or HBC alone. For metastasis studies, $1 \times 10^6$ Mewo/LacZ cells were injected into the tail vein (i.v.) of adult male nude mice. Two weeks later, HBC-coupled cyclopamine (10 mg/kg/twice day) or HBC alone were injected i.p. for 45 days. At the end of the treatment the lungs were dissected and stained with XGal.

Supplementary Experimental Procedures

Human primer sequences were 5'→3': GLI1-F: GGGAT-GATCCCACATCCTCAGTC (SEQ ID NO: 5) and GLI1-R: CTGGAGCAGCCCCCCCAGT (SEQ ID NO: 6); GLI2-F: CACCGCTGCTCAAAGAGAA (SEQ ID NO: 7) and GLI2-R: TCTCCACGCCACTGTCATT (SEQ ID NO: 8); GLI3-F: CGAACAGATGTGAGCGAGAA (SEQ ID NO: 9) and GLI3-R: TTGATCAATGAGGCCCTCTC (SEQ ID NO: 10); PTCH1-F: CCACAGAAGCGCTCCTACA (SEQ ID NO: 11) and PTCH1-R: CTGTAATTTCGCCCCTTCC (SEQ ID NO: 12); SHH-2F: TCCAAGGCACATATCCACTG (SEQ ID NO: 13) and SHH-2R: CCAGGAAAGTGAGGAAGTCG (SEQ ID NO: 14); HIP-F: CCCACACTTCAACAGCACCA (SEQ ID NO: 15) and HIP-R: GCTTTGTCACAG-GACTTTGC (SEQ ID NO: 16); FOXM1-F: GCGACTCTC-GAGCATGGAGAATTGTCACCTG (SEQ ID NO: 17) and FOXM1-R: GCGCTACTCGAGTTCGGTTTTGATGGT (SEQ ID NO: 18); PDGFRα-F: AGATGTAGCCCTTGTAC-CTCA (SEQ ID NO: 19) and PDGFRα-R: TTTAAGAGCT-TCCATTTCTA (SEQ ID NO: 20); MITF-F: CTTGCCAT-GTCCAAACCAG (SEQ ID NO: 21) and MITF-R: ACTCGCTCTCTGCCCTGTT (SEQ ID NO: 22); SOX10-F: CTTCATGGTGTGGGGCTAG (SEQ ID NO: 23) and SOX10-R: TGTAGTCCGGGTGGTCTTTC (SEQ ID NO: 24); PAX3-F: GATTCCTTCCAACCCAGACA (SEQ ID NO: 25) and PAX3-R: GACACCGTGGTGGTAGGTTC (SEQ ID NO: 26); GP100-F: GCTACCTATCCCTGAGCCT-GAA (SEQ ID NO: 27) and GP100-R: GGGCCCAGG-GAACCTGTA (SEQ ID NO: 28); MLANA-F: GAT-CATCGGGACAGCAAAGTG (SEQ ID NO: 29) and MLANA-R: TTT CTCATAAGCAGGTGGAGCAT (SEQ ID NO: 30); BMI1-F: TTCATTGATGCCACAACA (SEQ ID NO: 31); BMI1-R: CCATTGGCAGCATCAGC (SEQ ID NO: 32); EEF1A1-F: AGCAAAAATGACCCACCAATG (SEQ ID NO: 33) and EEF1A1-R: GGCCTGGATGGT-TCAGGATA (SEQ ID NO: 34). Primers for GAPDH were as described (Sanchez et al., (2004) Inhibition of prostate cancer proliferation by interference with SONIC HEDGEHOG-GLI1 signaling. Proc. Natl. Acad. Sci. USA. 101, 12561-12566).

*Xenopus laevis* primer sequences were: fPax3F: ACCCTAT-GAACCCAGCCATT (SEQ ID NO: 35) and fPax3R: TGCT-GTAACCTGAGGTGCTG (SEQ ID NO: 36); fSox10F: CTCTGAAGCTGAGGGTGGAG (SEQ ID NO: 37) and fSox10R: TTCTCCCAATGAACGAGACC (SEQ ID NO: 38); fMitfF: GAGCAGATGCAACAGCAAGA (SEQ ID NO: 39) and fMitfR: GTGTTTGGCCGTAGTCAGGT (SEQ ID NO: 40). Other primers were as in Mullor et al. (2001) (Mullor, J. L., Dahmane, N., Sun, T., Ruiz i Altaba, A. (2001). Wnt signals are targets and mediators of Gli function. Curr. Biol. 11, 769-7730) and Dahmane et al. (2001) (Dahmane, N., Sanchez, P., Gitton, Y., Palma, V., Sun, T., Beyna, M., Weiner, H., Ruiz i Altaba, A. (2001). The Sonic Hedgehog-Gli pathway regulates dorsal brain growth and tumorigenesis. Development 128, 5201-5212).

Results

Melanocytes in the Human Hair Follicle Express SHH-GLI Signaling Components

RNA in situ hybridization demonstrated expression of SHH, PTCH1 and GLI1, the best marker of an active pathway (Lee, J., Platt, K. A., Censullo, P. & Ruiz i Altaba, A. Gli1 is a target of Sonic hedgehog that induces ventral neural tube development. *Development* 124, 2537-2552 (1997)), in the bulb of anagen-stage, human scalp hair follicles (FIG. 1A-J). Homogeneous expression in the matrix surrounded the dermal papilla, including pigmented melanocytes (FIG. 1F, K) and those expressing the melanocyte lineage regulator MITF (FIG. 1J; Widlund and Fisher, 2003). Expression of SHH, PTCH1 or GLI1 was not detected with this method in the upper hair follicle, where MITF+ melanocytes are detected (arrows, FIG. 1E) or in differentiated melanocytes in the epidermal basal layer (FIG. 1B-D, K and not shown), demonstrating specificity and similarity with their expression in mice (e.g St. Jacques et al., 1998). Sense probes gave no signal (insets in FIG. 2C,E and not shown).

Proliferating Melanocytes Respond to and Require SHH Signaling

Figure 1L:
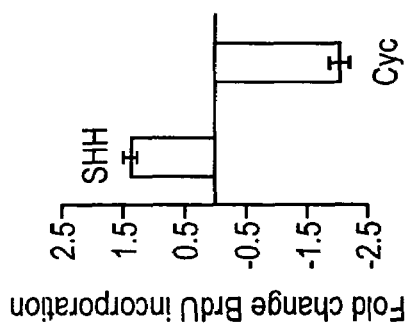
Figure 2A:
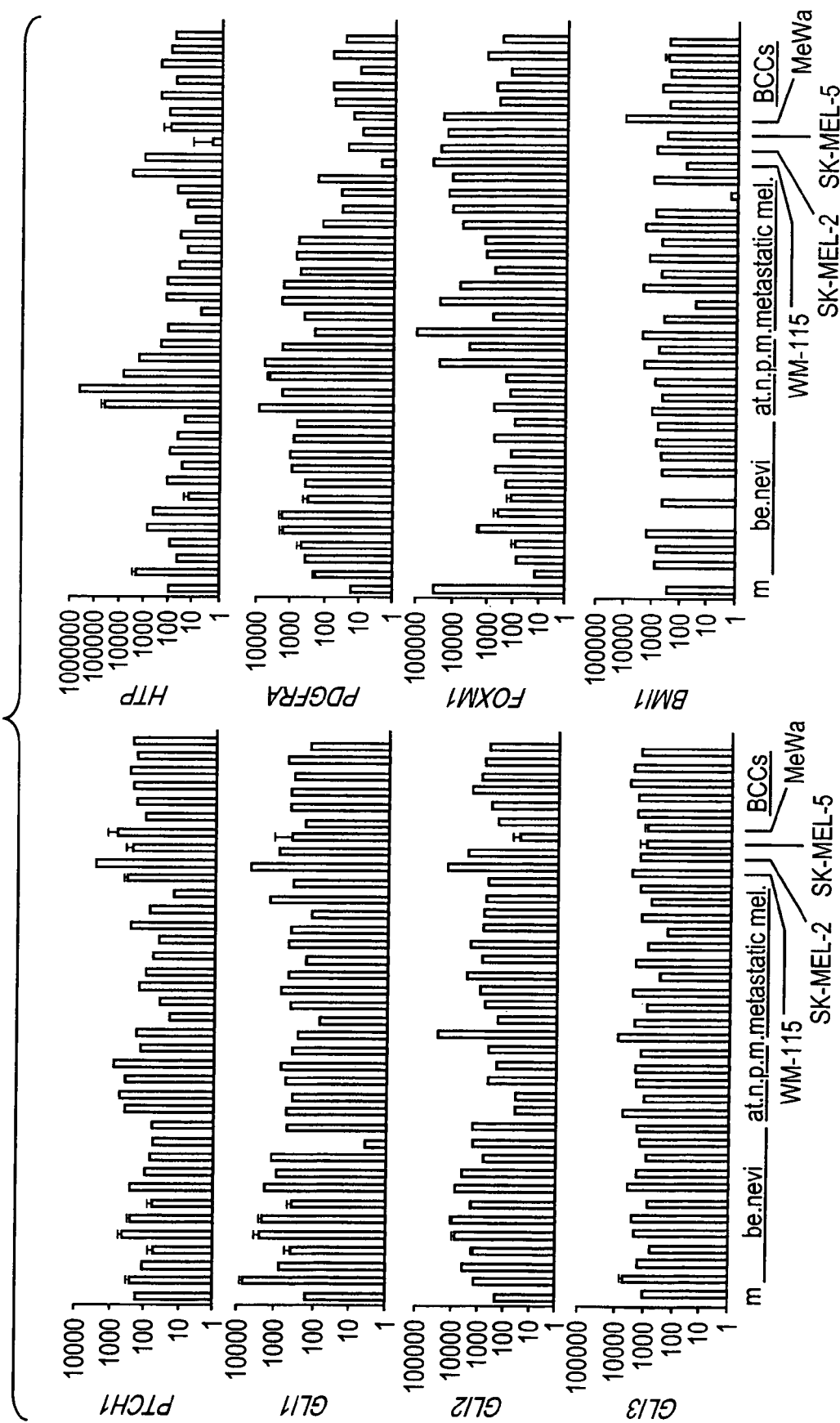
Figure 2B:
Figure 2C:
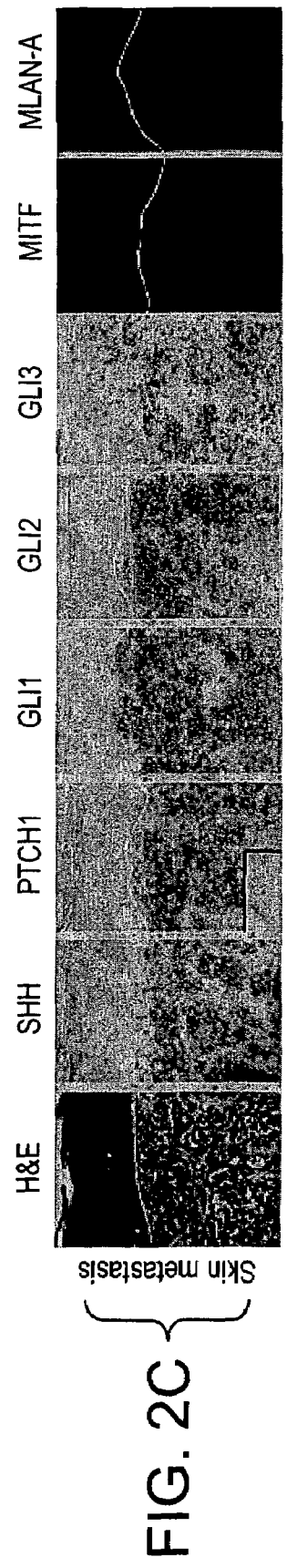
Figure 2D:
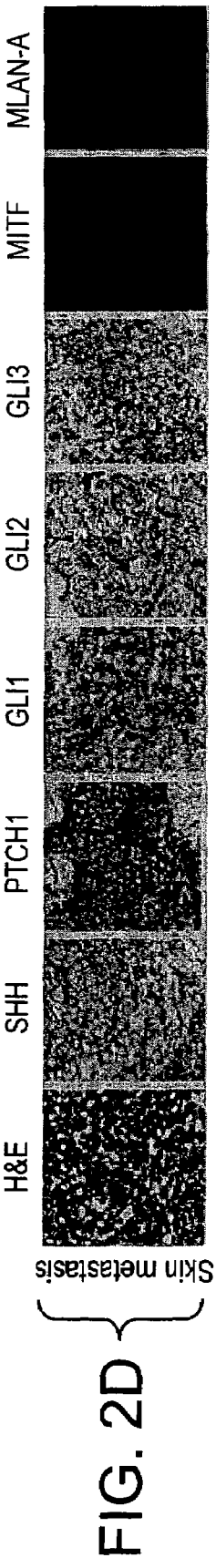
Figure 2E:
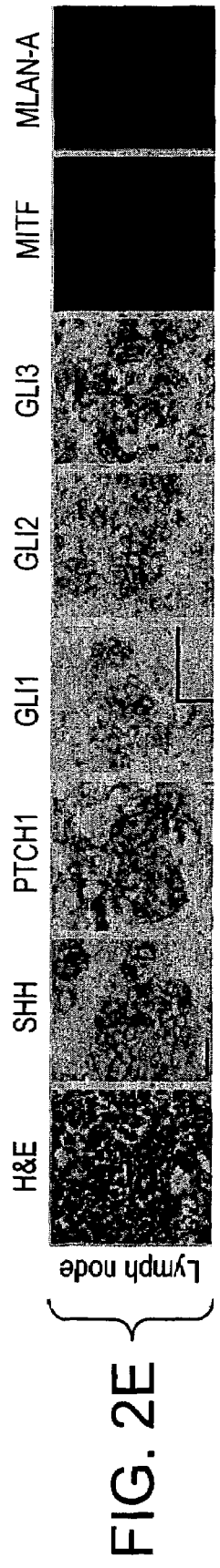

Proliferating melanocytes from human foreskin expressed GLI1 and other pathway components (m in FIG. 2A). Addition of recombinant SHH ligand for 48 h increased their proliferation by ±⅓ (FIG. 1L). Treatment with cyclopamine, a selective inhibitor of SMOOTHENED (SMOH), decreased their proliferation by 2 fold (FIG. 1L), but did not induce the senescence marker SA-β-gal (not shown).

Figure 1M:
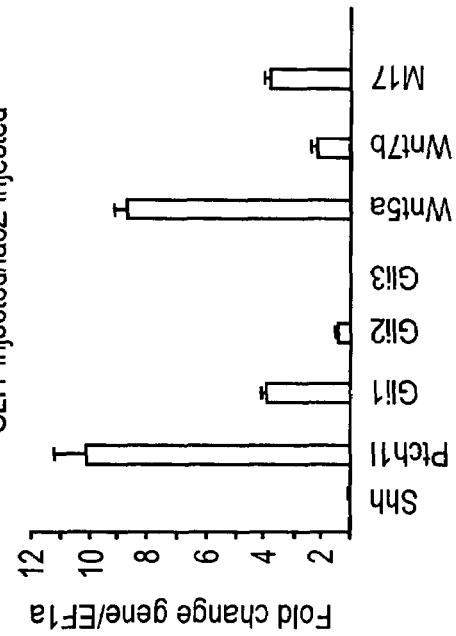
Figure 1N:
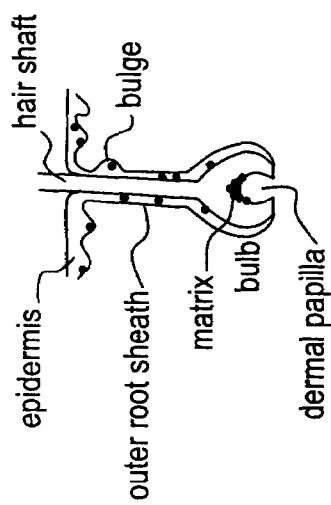
Figure 1O:
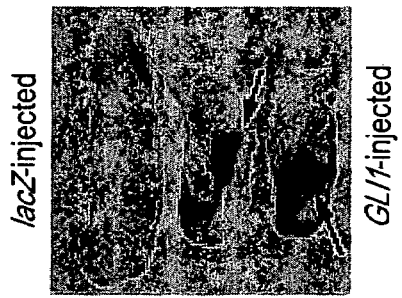

SHH-GLI Regulates the Expression of the Master Melanocyte-Melanoma Lineage Regulator MITF SHH treatment of proliferating melanocytes induced the expression of GLI1 and HIP by 2-3 fold, as expected, and that of MITFM by 6 fold (FIG. 1M), the melanocyte-specific transcript of a master melanocyte/melanoma regulator MITF (Widlund, H. R. & Fisher, D. E. Microphthalamia-associated transcription factor: a critical regulator of pigment cell development and survival. *Oncogene* 22, 3035-3041 (2003)). As an additional assay we misexpressed human GLI1 in developing frog embryos (Dahmane et al., (1997), Activation of the transcription factor Gli1 and the Sonic hedgehog signalling pathway in skin tumours. Nature 389, 876-881) targeting the animal-ventral area of 4-8-cell embryos that includes the prospective melanogenic neural crest. Injection of GLI1 RNA, but not lacZ RNA used as control, resulted in the formation of large, pigmented tumors in the skin (n=30 embryos; 100% with tumors; FIG. 1N). As expected for epidermal tumors (Dahmane et al., (1997), Activation of the transcription factor Gli1 and the Sonic hedgehog signalling pathway in skin tumours. Nature 389, 876-881), GLI1-induced tumors overexpressed Ptc1 and Gli1, but not Shh, Gli2 or Gli3, all measured by qPCR, as compared to unaffected lacZ-injected control epidermis (n=30 embryos; 100% normal; FIG. 1N,O). GLI1, however, also induced the expression of Mitf (FIG. 1O; Kumasaka et al., (2003) Isolation and developmental expression of tyrosinase family genes in *Xenopus laevis*. Pigment Cell Res. 16, 455-462) and that of Wnt5a and Wnt7b (Mullor et al., (2001), Wnt signals are targets and mediators of Gli function. Curr. Biol. 11, 769-773), two genes expressed in human melanomas (Pham et al., (2004), Wnt ligand expression in malignant melanoma: pilot study indicating correlation with histopathological features. Mol. Pathol. 56, 280-285) (FIG. 1O). The finding of several GLI binding sites located within the human MITF regulatory region (not shown) that are identical to those shown to bind GLI1 in HNF3β and CYCLIND2 (Yoon et al., (2002), Gene expression profiling leads to identification of GLI1-binding elements in target genes and a role for multiple downstream pathways in GLI1-induced cell transformation. J Biol Chem. 277, 5548-5555), suggests direct regulation.

Human Nevi and Melanomas Express SHH-GLI Pathway Components qPCR analyses of proliferating melanocytes, benign and atypical nevi, primary and metastatic melanoma and melanoma cell lines showed the consistent yet varied expression of PTCH1, GLI1, GLI2 and GLI3 (FIG. 2A). Expression of GLI1 and other pathway components was also prominent in BCCs (FIG. 2A) included as controls (Dahmane et al., (1997), Activation of the transcription factor Gli1 and the Sonic hedgehog signalling pathway in skin tumours. Nature 389, 876-881).

RNA in situ hybridization localized the expression of SHH-GLI pathway components in tumor or nevus cells (FIG. 2B-E; Suppl. Materials), coincident with the expression of MITF and MLANA, two specific markers of melanocytic-melanoma lineages (FIG. 2B-E). Adjacent normal tissue did not express these genes with the exception of hair follicles (Dahmane et al., (1997), Activation of the transcription factor Gli1 and the Sonic hedgehog signalling pathway in skin tumours. Nature 389, 876-881; St. Jacques et al., (1998), Sonic hedgehog signaling is essential for hair development. Curr Biol. 8, 1058-1068).

Partial Overlap of SHH-GLI Targets in Melanomas and Other Tumors qPCR analyses showed that two GLI targets in BCCs, PDGFRα and FOXM1 (Xie et al., (2001), A role of PDGFRalpha in basal cell carcinoma proliferation., Proc. Natl. Acad. Sci. USA. 98, 9255-9259; Teh et al., (2002), FOXM1 is a downstream target of Gli1 in basal cell carcinomas. Cancer Res. 62, 4773-4780), are also expressed in melanomas (FIG. 2A). PDGFRα expression in nevi and metastatic melanoma samples showed higher expression than BCCs (FIG. 2A) and expression of FOXM1 was low in nevi, at levels comparable to those of BCCs, and high in metastatic melanomas (FIG. 2A; p=0.01 anova test). The polycomb gene BMI1 is regulated by SHH signaling in the cerebellum and medulloblastoma (Leung et al. (2004), Bmi1 is essential for cerebellar development and is overexpressed in human medulloblastomas. Nature 428, 337-341; Bruggerman et al., (2005), Ink4a and Arf differentially affect cell proliferation and neural stem cell self-renewal in Bmi1-deficient mice. Genes Dev. 19, 1438-1443) and was uniformly expressed in nevi and melanomas, much like the GLI genes (FIG. 2A).

A Subset of Melanomas Respond to and Require SHH Ligand

Figure 3A:
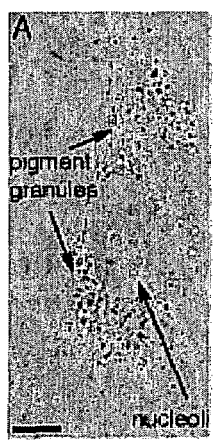
Figure 3B:
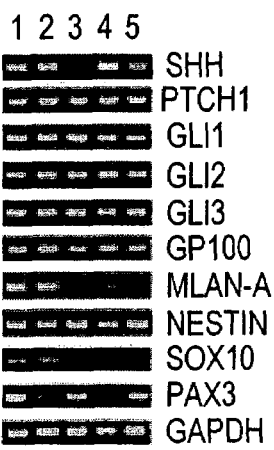
Figure 3C:
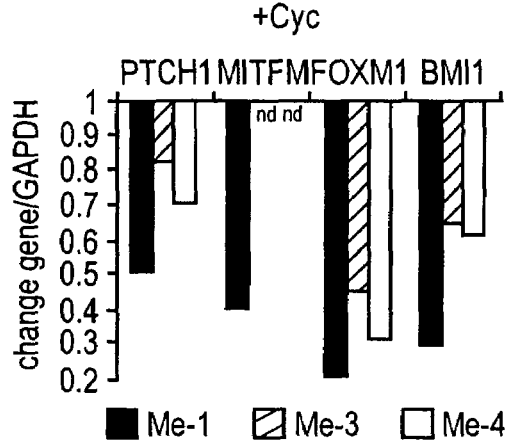

Four skin metastases (Me-1,3-5) and one lymph node metastasis (Me-2) grown as primary cultures had elongated cells with pigment granules and prominent nucleoli (Me-3; FIG. 3A) and all expressed SHH-GLI pathway components (FIG. 3B). Me-3 was tumorigenic in nude mice with a tumor latency period of 75 days (not shown). All of these cultures expressed the melanoma markers GP100 and NESTIN (Florenes et al. (1994), Expression of the neuroectodermal intermediate filament nestin in human melanomas. Cancer Res. 54, 354-356; Du et al., (2003), MLANA/MART1 and SILV/PMEL17/GP100 are transcriptionally regulated by MITF in melanocytes and melanoma. Am. J. Pathol. 163, 333-343), with MLAN-A and the melanoma stem/precursor markers SOX10 and PAX3 (Lang et al., (2005), Pax3 functions at a nodal point in melanocyte stem cell differentiation. Nature 433, 884-887) being expressed heterogeneously (FIG. 3B).

Figure 3D:
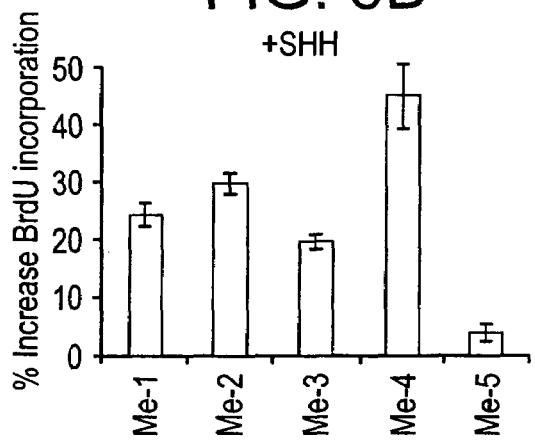
Figure 3E:
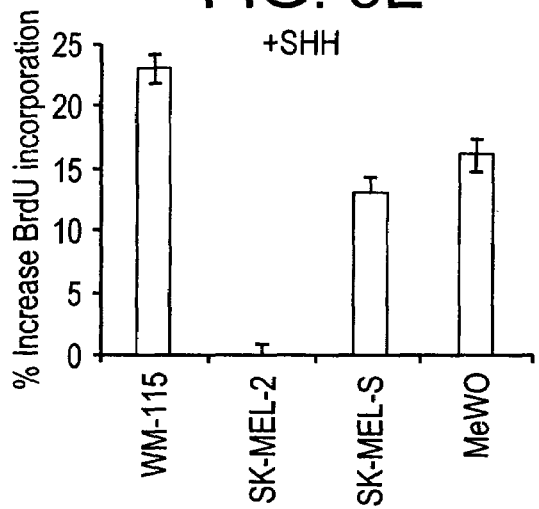
Figure 3F:
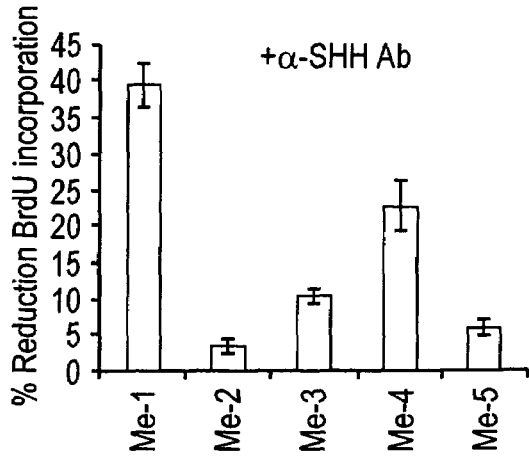
Figure 3G:
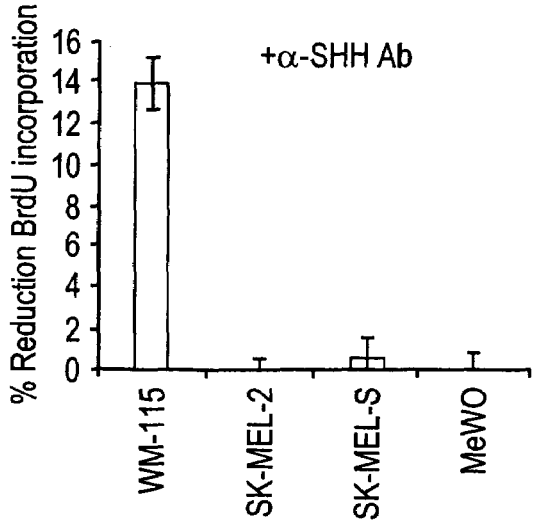

The ability of melanomas to respond to exogenous SHH ligand was tested on the five primary cultures and on four cell lines in which we confirmed the mutation status of NRAS and BRAF: WM115, derived from a primary cutaneous melanoma harboring an activating mutation in BRAF (V599D); SK-MEL-2, derived from a skin metastasis harboring an activating mutation in NRAS (Q61R); SK-MEL-5, derived from a axillary lymph node metastasis with an activating mutation in BRAF (V599E); and MeWo, derived from a lymph node metastasis with wild type NRAS and BRAF (e.g. Davies, H. et al. Mutations of the BRAF gene in human cancer. *Nature* 417, 949-954 (2002)). Addition of exogenous recombinant SHH ligand for 48 h increased BrdU incorporation in 4/5 primary cultures and in 3/4 cell lines above a basal level (10%) (FIG. 3D,E). Conversely, addition of anti-SHH blocking antibody for 48 h reduced proliferation in 2/5 primary melanomas and 1/4 cell lines (FIG. 3F,G). Cells that respond to both treatments, such as Me-1 and WM-115 (FIG. 3D-G), appear to have active autocrine signaling; those that respond to ligand but are not inhibited by the blocking antibody, such as Me-2, SK-Mel-5 and MeWo, may harbor an inducible pathway that is activated downstream of ligand action; and those not responding to these treatments, such as SK-MEL-2, may have activation of HH-GLI signaling downstream of ligand action.

Figure 3H:
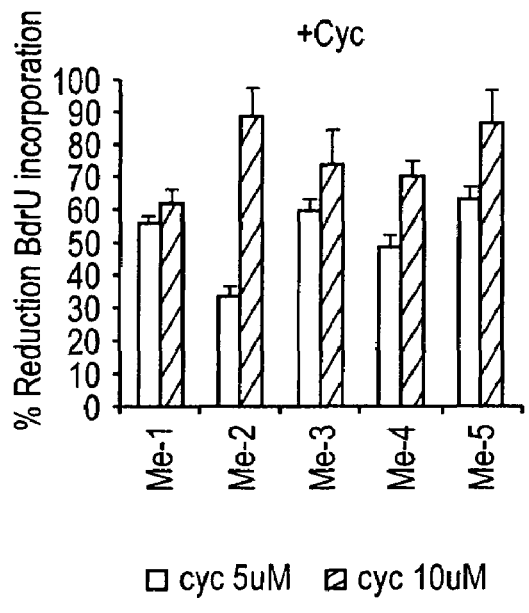
Figure 3I:
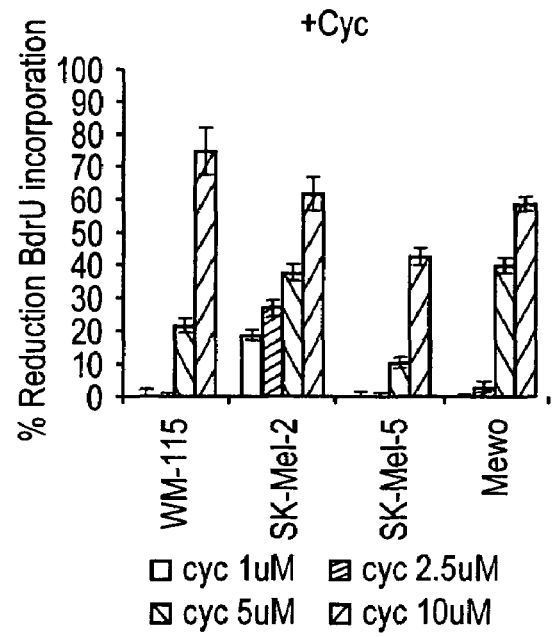
Figure 3J:
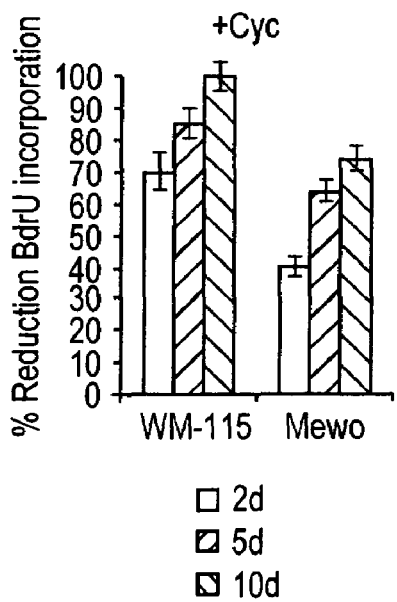
Figure 3K:
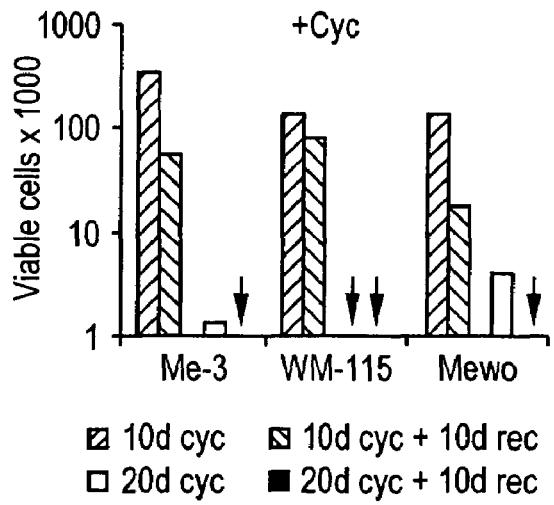
Figure 3L:
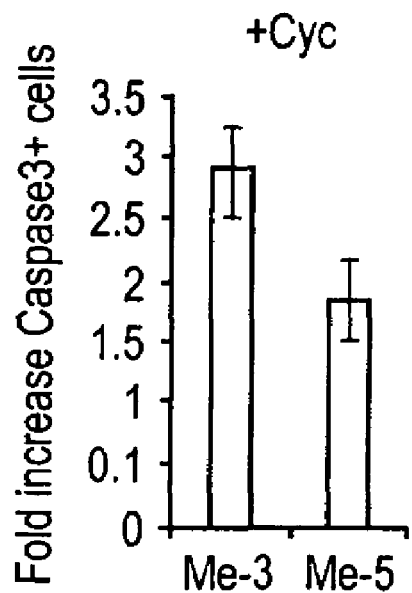
Figure 3M:
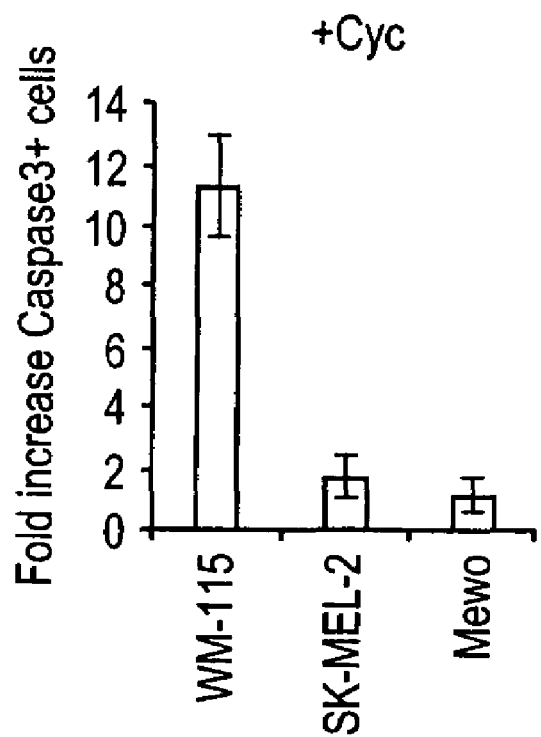
Figure 3N:
Figure 3O:

Cyclopamine-Mediated Interference with SMOOTHENED Function Induces Widespread Inhibition of Melanoma Cell Proliferation and Enhances Apoptosis All cultures require SMOH function as all responded to 24-48 h cyclopamine treatment in a dose-dependent manner and decreased GLI1 expression (FIG. 4H and not shown), as compared to control sibling cultures treated with the inactive compound tomatidine (FIG. 3H,I,N,O). Long-term testing of cyclopamine effects on two cells lines showed cumulative effects (FIG. 3J) on the inhibition of BrdU incorporation. Ten days of treatment, changing the drug-containing media anew every 2 days, was sufficient to inhibit all BrdU incorporation in WM-115 cells, but the culture recovered as assayed 10 days after drug removal (FIG. 3K). A similar recovery was also observed for Me-3 and MeWo (FIG. 3K). 20 days of treatment, however, were sufficient to kill all cells and prevent the recovery of the culture (FIG. 3K; arrows). Apoptotic cell death was revealed by an increase in activated Caspase-3 immunoreactivity after 48 h cyclopamine treatment in 3/5 cultures tested (FIG. 3L, M) although all cultures showed cell death (not shown).

SHH-GLI Signaling Regulates the Expression of MITFM, FOXM1 and BMI1 in Melanoma

Cyclopamine treatment for 8 h inhibited PTCH1 expression in 3 primary cultures tested (FIG. 3C and not shown) as expected. Expression of BMI1, FOXM1 and MITFM was also repressed although MITFM was not detected in Me-3 or Me-4 (FIG. 3C), consistent with its induction by SHH (FIG. 1) and its common repression in metastatic melanomas (Selzer et al., (2002), The melanocyte-specific isoform of the microphthalmia transcription factor affects the phenotype of human melanoma. Cancer Res. 62:2098-103).

Figure 4A:
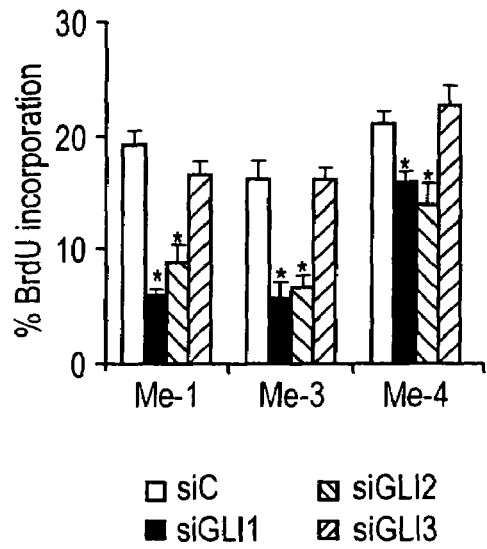
Figure 4B:
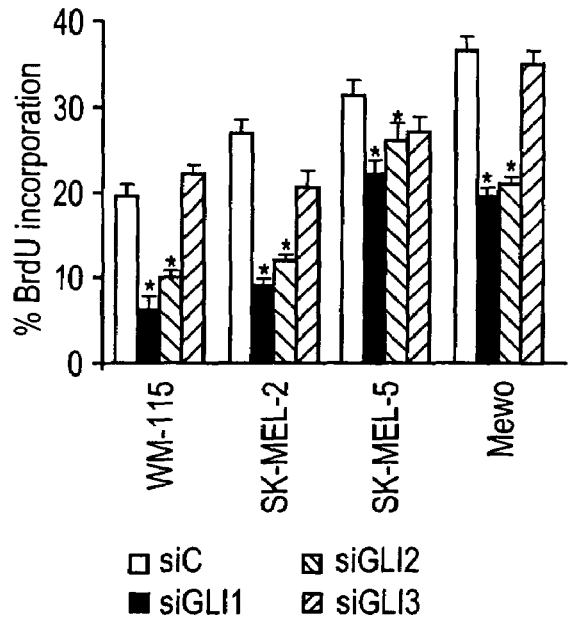

GLI1 and to a Lesser Extent GLI2, but not GLI3, are Required for Melanoma Growth and Survival To directly investigate the role of each of the three GLI genes in melanoma, specific 21-nt siRNAs that specifically target the appropriate transcripts were used (Sanchez et al., (2004), Inhibition of prostate cancer proliferation by interference with SONIC HEDGEHOG-GLI1 signaling. Proc. Natl. Acad. Sci. USA. 101, 12561-12566; P. Sanchez and Ariel Ruiz I Altaba, not shown; FIG. 4G, H). As control, an unrelated siRNA (siC) was used in all assays and the effects are shown as ratios of the specific siGLI over siC. All primary cultures and all cell lines used in this study were sensitive to interference of GLI1 reducing BrdU incorporation after 48 h (FIG. 4A,B). GLI2 had similar effects although it was generally less potent and was not required in Me-5 (FIG. 4A,B). GLI3, in contrast, had very minor effects only in 3/5 cases (FIG. 4A,B). The varying effects of siRNAs within a sample reflects the differential roles of the GLI proteins, but comparison among samples is complicated by varying lipofection efficiencies revealed with an FITC-labeled control siRNA: ±70-80% for Me-1 and Me-3, WM115, SK-MEL-2 and MeWo but <50% for Me-2,4,5 and SK-Mel-5 (FIG. 4F and not shown).

Figure 4C:
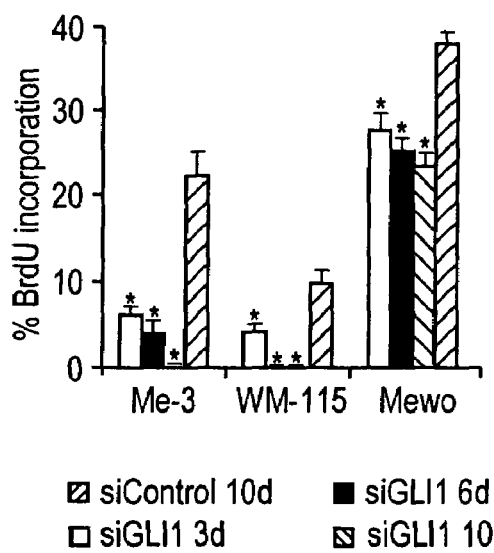
Figure 4D:
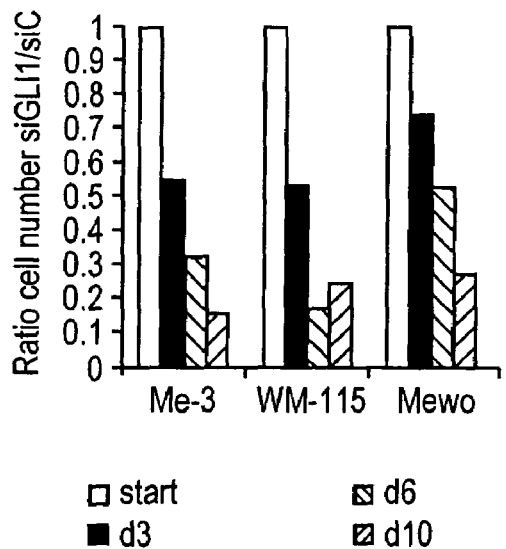

Long-term siGLI1 treatment lipofecting the siRNA anew every 2 days showed increased growth inhibition, with complete arrest after 6 days for Me-3 and WM-115 (FIG. 4C). MeWo cells (FIG. 4B) was more refractory (FIG. 4C) although the number of viable cells was gradually decreased in all cases (FIG. 4D).

GLI3 Mediates SHH-GLI Pathway Suppression by Cyclopamine

Figure 4E:
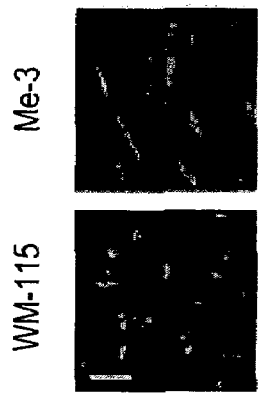
Figure 4F:
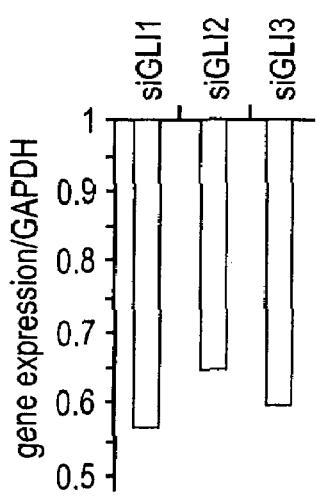
Figure 4G:
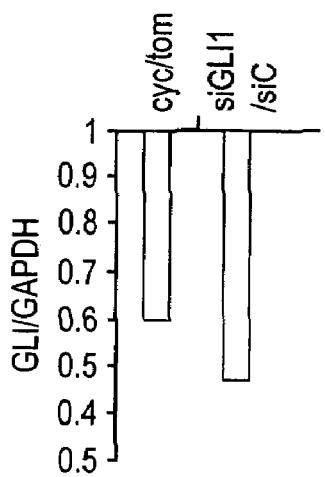
Figure 4H:
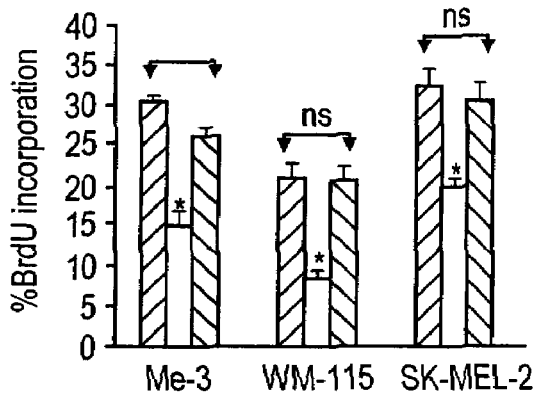
Figure 4I:
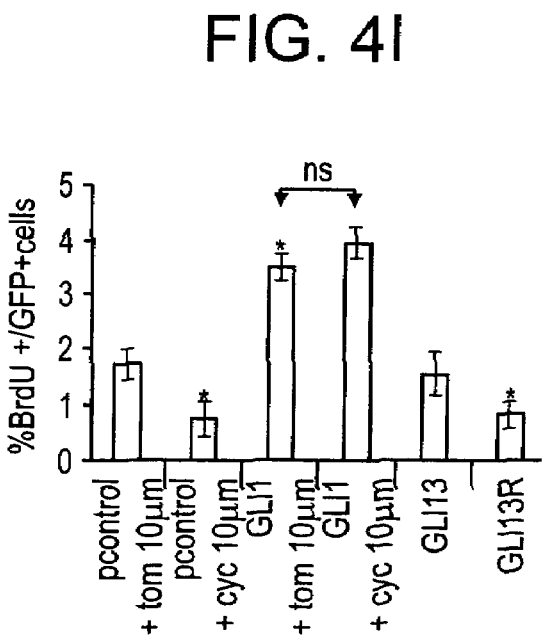

Given that GLI3 function has a minor positive contribution in only a subset of melanomas (FIG. 4A,B), we tested if GLI3 could have an opposite role that is suppressed by SHH signaling. Three cultures showing a high degree of inhibition of BrdU by cyclopamine (Me-3; WM-115 and SK-MEL-2; FIG. 3F,G) were transfected with siGLI3 or siC and then treated with cyclopamine for 48 h. Whereas siC had no effect on the inhibitory action of cyclopamine, siGLI3 reversed or eliminated the effects of the drug (FIG. 4E).

Figure 5A:
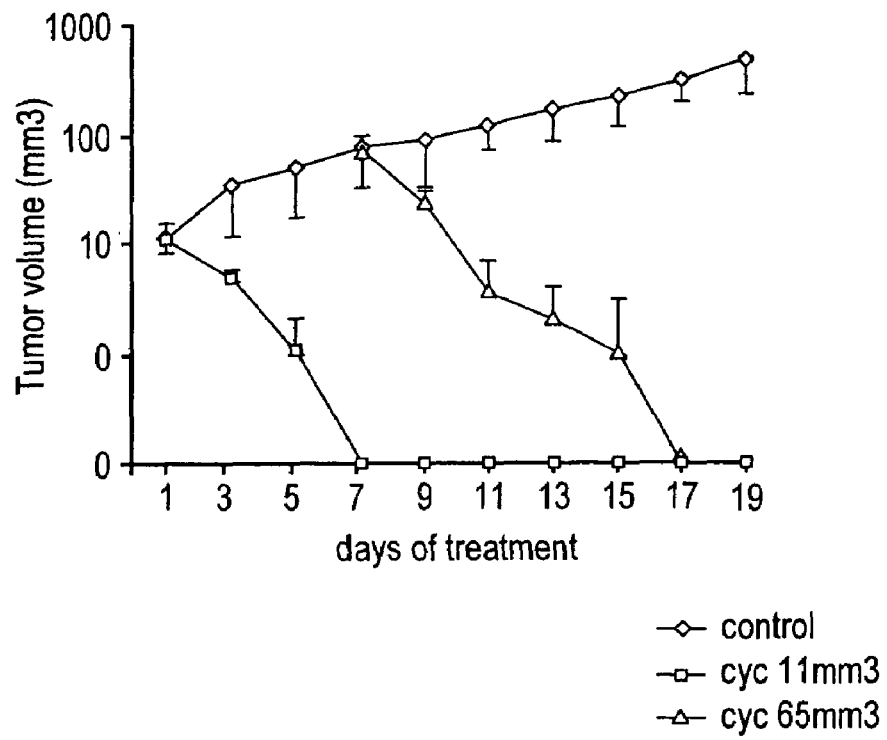
Figure 5B:
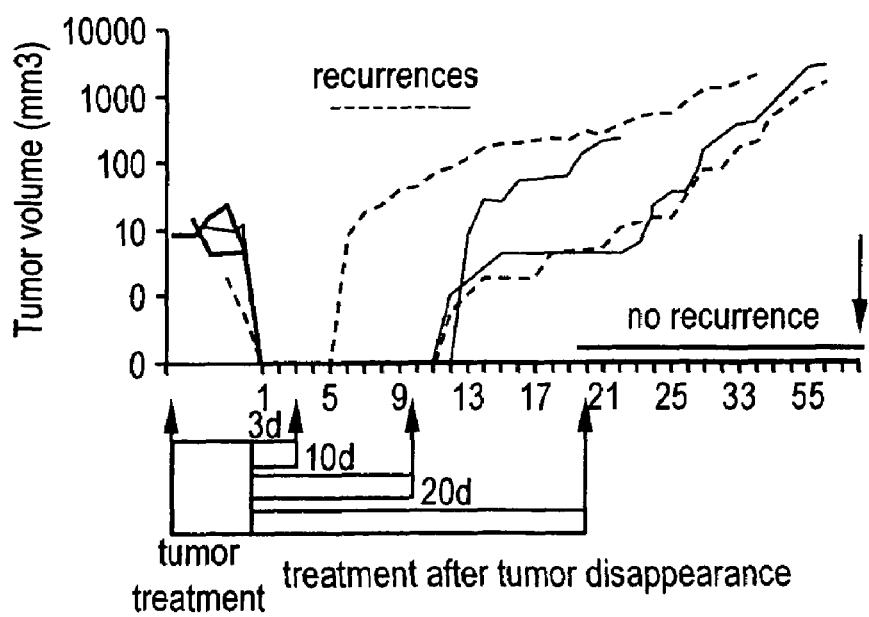
Figure 5C:
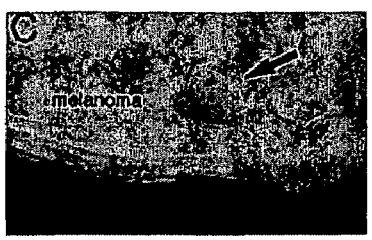
Figure 5D:
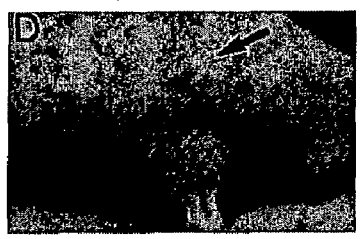
Figure 5E:
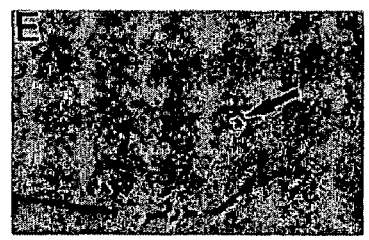
Figure 5F:
Figure 5G:
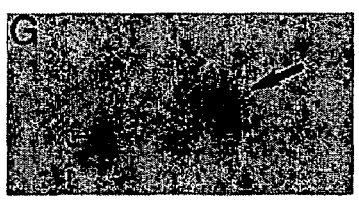
Figure 5H:
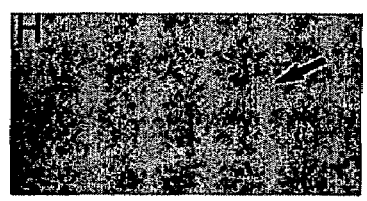
Figure 5I:
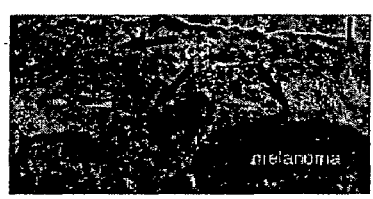
Figure 5J:
Figure 5K:
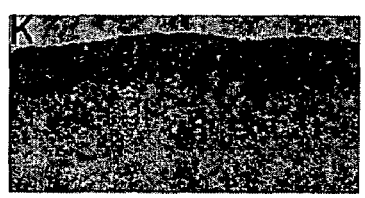

Inhibition of Human Melanoma Xenograft Growth In Vivo by Interference with SHH-GLI Signaling Subcutaneous injection of metastatic melanoma MeWo cell into nude mice resulted in the rapid growth (within 1 week) of heavily pigmented black tumors in or under the skin (FIG. 5A,C,F; n=6). MeWo cells were infected with a lacZ expressing lentivirus to allow for the tracing of melanoma cells through β-galactosidase activity and were blue after X-Gal staining tissue sections (FIG. 5I). Injection of cyclo-dextrin-complexed cyclopamine (Sanchez and Ruiz i Altaba, (2005), In vivo inhibition of endogenous brain tumors through systemic interference of Hedgehog signaling in mice. Mech Dev. 122, 223-230), but not cyclodextrin alone as carrier, into the tumor resulted in the rapid regression and disappearance of the tumors (FIG. 5A), whether the tumors were small (±10 mm$^3$; n=5) or larger (±65 mm$^3$; n=2) (FIG. 5A,C-K). The length of treatment to achieve macroscopically loss of tumor varied depending on the initial size of the tumors (FIG. 5A). Before and after complete tumor disappearance, a white scar zone developed (FIG. 5D,E,G,H,J,K). The primary melanoma cell line WM-115 was also used to generate subcutaneous tumors in nude mice with a latency of ±90 days and cyclopamine treatment also lead to their disappearance (n=2 control carrier treated with tumors and n=2 cyclopamine treated without tumors; not shown).

Systemic treatment of large subcutaneous tumors (±65 mm$^3$) was less effective than direct intratumoral injection, showing a 33% decrease in tumor volume after 16 days of cyclopamine treatment (n=20) as compared with carrier-only treated tumors (n=20; not shown). The incomplete effects are likely due to low levels of cyclopamine reaching the growing tumor instead of the selection of resistant mutant cells as in vitro culture showed that tumor-derived MeWo/lacZ cells exhibited the same sensitivity to cyclopamine in vitro than parental cells (not shown). X-Gal staining of serial histological sections of five cured tumors taken 1-2 days after macroscopic disappearance showed that 4/5 tumors contained small pockets of β-gal$^+$ tumor cells or groups of single cells (FIG. 5J and not shown), posing the threat of recurrence.

Prevention of Subcutaneous Melanoma Recurrence In Vivo

MeWo/lacZ-melanoma bearing mice were treated with cyclopamine until tumor disappearance, split into three groups (FIG. 5B), treated for an additional 3, 10 or 20 days injecting into the site where the tumor has been and then left untreated. Tumors reappeared within 2-7 d from the end of 3 d (n=2 mice) and 10 d (n=2) cyclopamine treatments. However, there were no recurrences after 42 additional days following 20 d treatment after tumor disappearance (n=3).

Figure 5L:
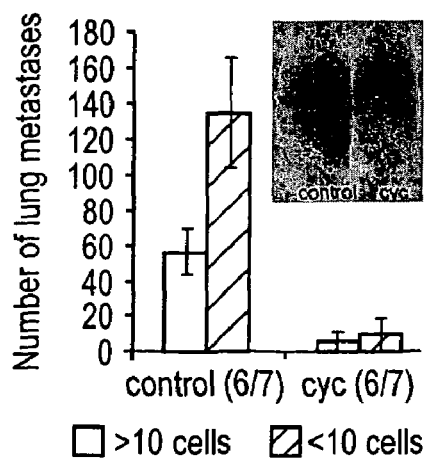
Figure 5M:
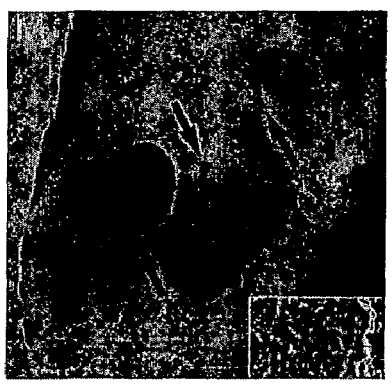
Figure 5N:
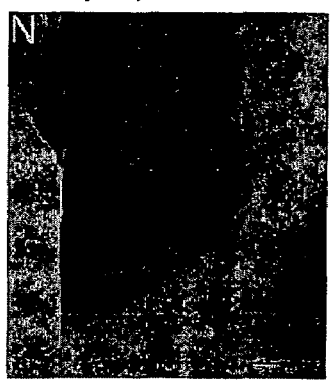

Inhibition of Melanoma Metastasis to the Lungs by Systemic Interference with SHH Signaling In Vivo Systemic cyclopamine treatment is effective to reduce medulloblastoma size (Sanchez and Ruiz i Altaba, (2005), In vivo inhibition of endogenous brain tumors through systemic interference of Hedgehog signaling in mice. Mech Dev. 122, 223-230), inhibit brain stem cell proliferation (Palma et al., (2005), Sonic hedgehog controls stem cell behavior in the postnatal and adult brain. Development 132, 335-344), and prevent metastasis of a prostate cell line (Kardahkar et al., (2004), Hedgehog signalling in prostate regeneration, neoplasia and metastasis. Nature 431, 707-712). To mimic as much as possible the human condition, $10^6$ MeWo/LacZ melanoma cells were injected into the tail vein of adult nude mice and the animals allowed to rest for 2 weeks before starting treatment. Intraperitoneal (IP) injections of cyclodextrin-coupled cyclopamine were at 10 mg/kg/twice a day or of cyclodextrin alone at an equivalent dose for 45 days. 6/7 injected, vehicle-treated mice had metastases in all lung lobes, with numerous large and small melanoma cell clusters (FIG. 5L,M). In contrast, the lungs of only one cyclopamine-treated mouse showed a very limited number of metastasis and these were all small (FIG. 5L). The other cyclopamine-treated mice (6/7) did not have a single blue cell in their lungs (FIG. 5L,N).

Blockage of EGF, MEK or AKT Signaling Inhibits Melanoma Growth and Decreases the Expression of GLI1 and PTCH1

Figure 6A:
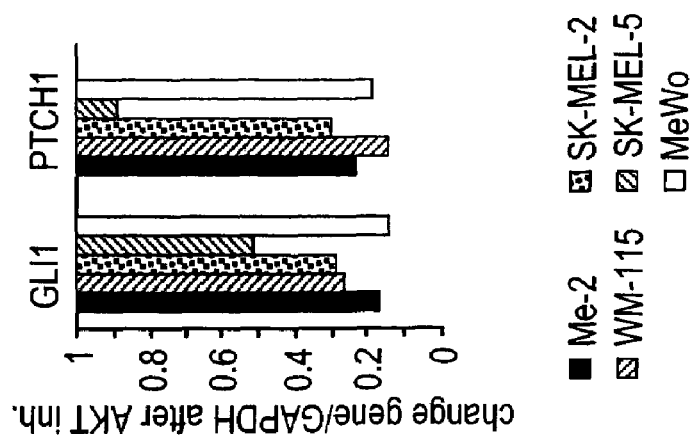
Figure 6B:
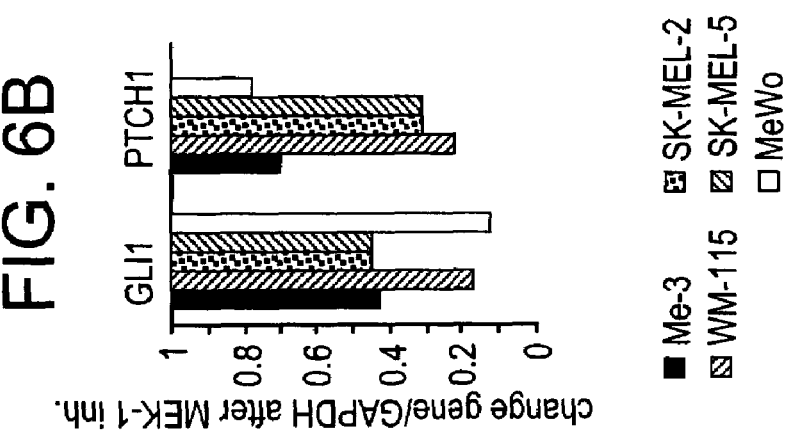
Figure 6C:
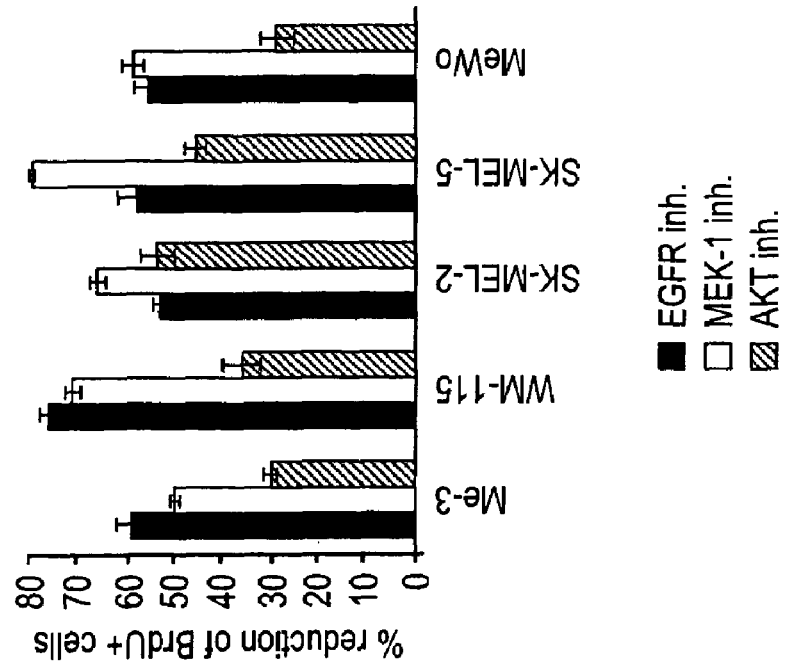

Treatment of melanoma cells with specific inhibitors of EGFR (AG1428), MEK-1 (U0126) or AKT (SH6) function decreased BrdU incorporation after 48 h in all four melanoma cell lines tested and Me-3 (FIG. 6A). Treatment with U0126 or SH6, blocking signaling downstream of EGF-RAS, also resulted in the reduction of GLI1 and PTCH1 levels after 4 h in all cultures (FIG. 6B,C), similar to those seen with cyclopamine (FIG. 4H), indicating an effect on SHH-GLI signaling.

Figure 6F:
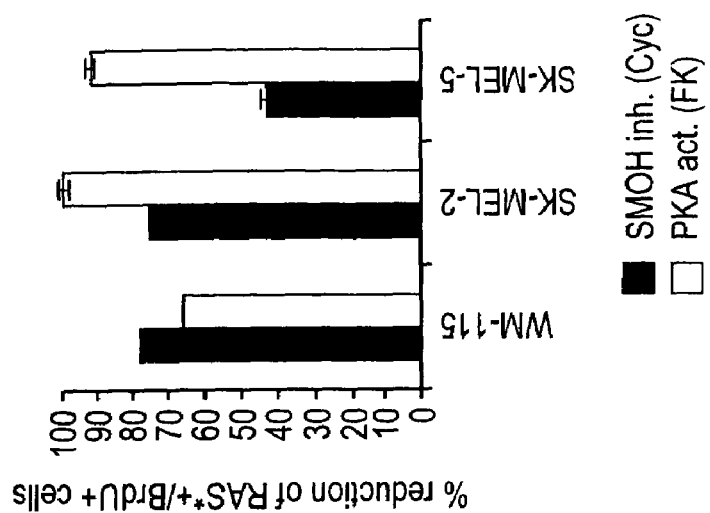
Figure 6E:
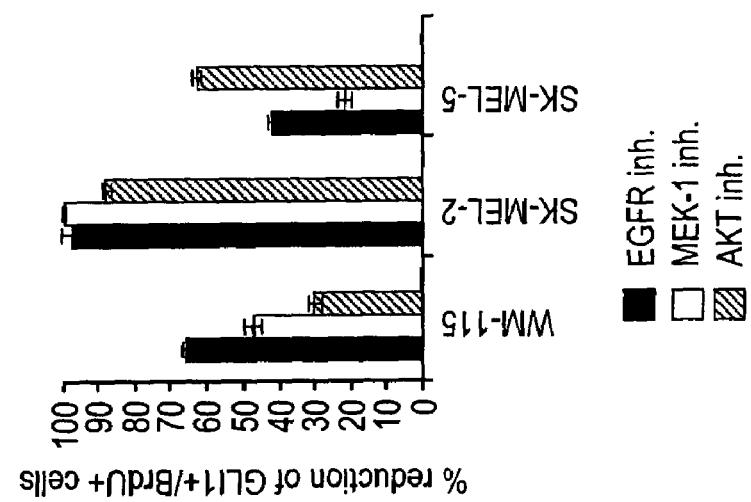
Figure 6D:
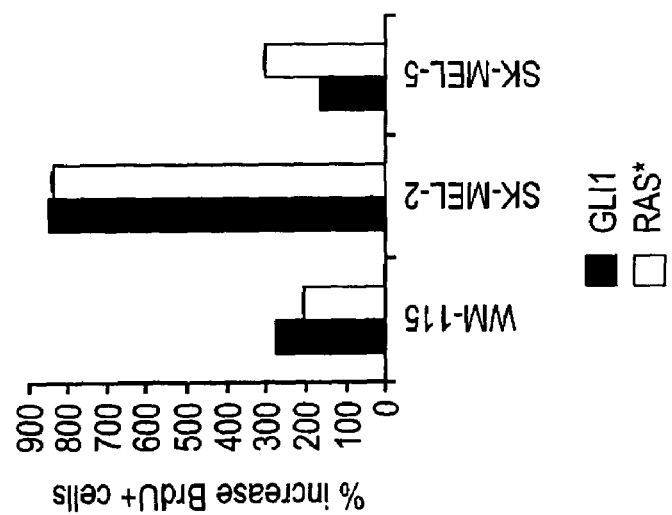

Enhanced Levels of GLI1 or Oncogenic Ras Boost Melanoma Cell Proliferation but Their Effects are Mutually Dependent Transfection with vectors expressing full-length human GLI1 or a mutant HRAS (V12), previously shown to induce melanoma (Chin et al., (1999), Essential role for oncogenic Ras in tumour maintenance. Nature 400, 468-472), resulted in enhanced proliferation 1.5-8 fold (FIG. 6D) of transfected WM-115, SK-MEL-2 and SK-MEL-5. Primary cultures and MeWo cells transfected poorly. The effects of GLI1 were reversed by treatment with the EGFR, MEK1 or AKT inhibitors (FIG. 6E), whereas the effects of oncogenic RAS were reversed by treatment with cyclopamine, or with Forskolin, which activates the GLI antagonist Protein Kinase A (PKA) (FIGS. 6F,7).

GLI3 Repressors Antagonize Oncogenic RAS Activity

Figure 6I:
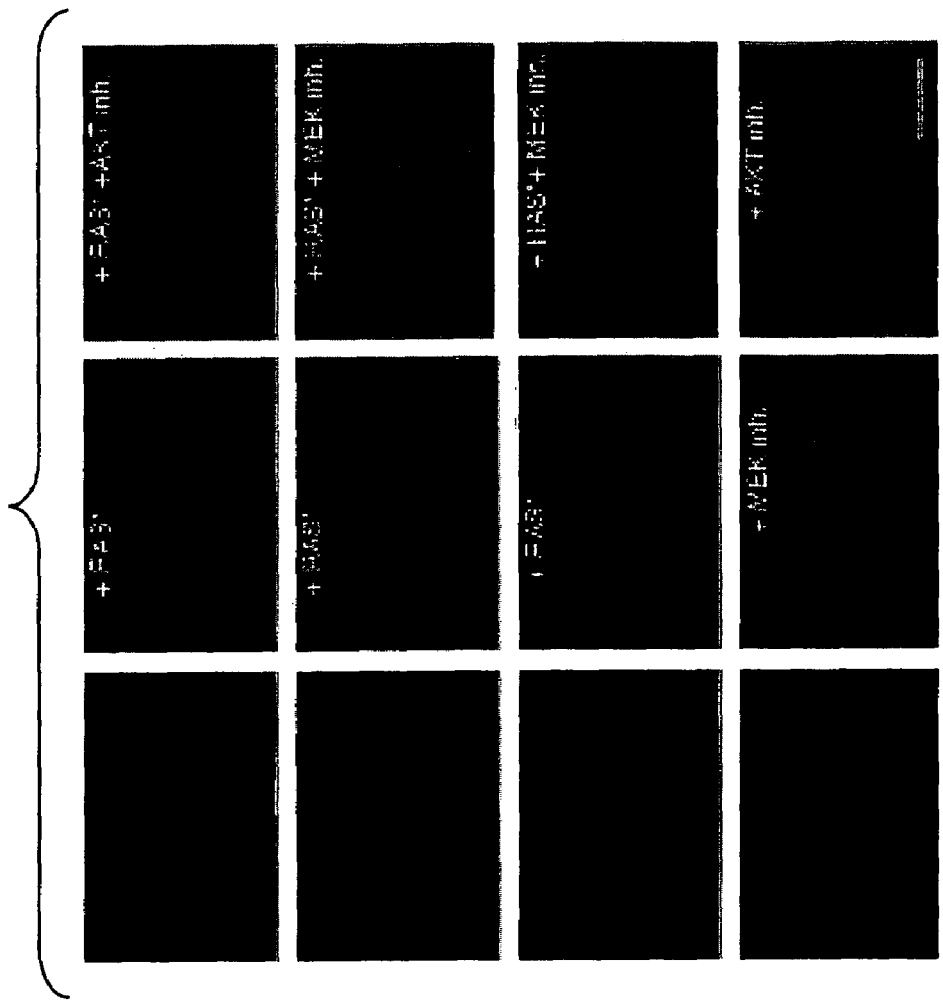
Figure 6G:
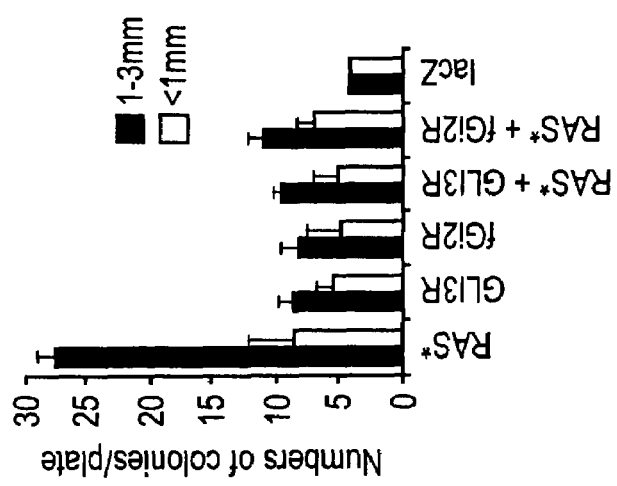
Figure 6H:

Inhibition of SMOH function with cyclopamine leads to the formation and activity of GLI3 repressors (FIG. 4E). SK-MEL-2 melanoma cells were stably transfected with a vector expressing oncogenic HRAS (G12V), thus increasing overall RAS activity along with a vector expressing the neo resistance gene. After selection in geneticin for 20 days, exogenous RAS-expressing SK-MEL-2 cells formed ±5-fold more colonies than the same cells transfected with the neo resistant vector alone (FIG. 6G,H). This effect was fully inhibited by the stable co-transfection of a vector driving the expression of human GLI3C'ΔCla1 (Ruiz i Altaba, (1999), Gli proteins encode context-dependent positive and negative functions: implications for development and disease. Development 126, 3205-3216), encoding a potent GLI3 repressor (FIG. 6G,H). A similar effect was observed with a C-terminally truncated frog Gli2 (Gli2C'Δ), which acts like the human GLI3 repressor (Ruiz i Altaba, (1999), Gli proteins encode context-dependent positive and negative functions: implications for development and disease. Development 126, 3205-3216; Brewster et al., (2000), Gli2 functions in FGF signaling during antero-posterior patterning. Development 127, 4395-4405). Expression of the GLI3 or Gli2 repressors alone had little effect, yielding a background number of colonies (FIG. 6G).

Oncogenic RAS Induces the Nuclear Accumulation of GLI Proteins

To test if oncogenic RAS signaling could modify GLI function through modification of their nucleocytoplasmic distribution and in the absence of reliable anti-GLI antibodies, mammalian COS7 cells were transfected with Myc epitope-tagged, full length or C-terminally truncated GLI constructs with or without activated HRAS (G12V). COS7 cells were used previously to characterize the localization of GLI proteins (Ruiz i Altaba, (1999), Gli proteins encode context-dependent positive and negative functions: implications for development and disease. Development 126, 3205-3216; Nguyen et al., (2005), Cooperative requirement of the Gli proteins in neurogenesis. Development 132, 3267-3279). Co-transfected oncogenic RAS enhanced the nuclear accumulation of cytoplasmic full-length frog GLI1, frog Gli2 or human GLI3 proteins (FIG. 6I), with the effects on Gli2 and GLI3 being stronger than on Gli1 (FIG. 6I legend). The effect of RAS was reversed by treatment for 1 h with the AKT inhibitor SH6 or the MEK-1 inhibitor U0126 (FIG. 6I) 24 h after transfection. MEK inhibition, however, had little effect on Gli1 (FIG. 6I legend), suggesting differential effects. Oncogenic RAS or the inhibitors had no effect on the already nuclear GLI3 repressor (GLI3C'ΔCla1; Ruiz i Altaba, (1999) Gli proteins encode context-dependent positive and negative functions: implications for development and disease. Development 126, 3205-3216; FIG. 6I). AKT or MEK inhibitors also did not change the localization of transfected GLI proteins without co-transfected RAS.

Discussion

SHH-GLI Signaling in the Melanocyte Lineage

The finding that SHH and GLI1 are expressed in the matrix of the human follicle and that SHH-GLI signaling regulates melanocyte proliferation in vitro indicates that this pathway contributes to the control of melanocyte number. Since HH-GLI signaling also affects the keratinocyte (e.g. Dahmane et al., (1997), Activation of the transcription factor Gli1 and the Sonic hedgehog signalling pathway in skin tumours. Nature 389, 876-881; St. Jacques et al., (1998), Sonic hedgehog signaling is essential for hair development. Curr Biol. 8, 1058-1068; Silva-Vargas et al., (2005), Beta-catenin and Hedgehog signal strength can specify number and location of hair follicles in adult epidermis without recruitment of bulge stem cells. Dev Cell. 9, 121-31) and sebaceous (Niemann et al., (2003), Indian hedgehog and beta-catenin signaling: role in the sebaceous lineage of normal and neoplastic mammalian epidermis. Proc Natl Acad Sci USA. 100 Suppl 1, 11873-11880) lineages, HH-GLI signaling orchestrates multiple aspects of skin development and homeostasis. A parallel between the effects of SHH-GLI on melanocytes and keratinocytes is also suggested by its general presence and requirement in sporadic human tumors derived from both of these cell types and by the coexpression of a number of SHH-GLI targets (this work, Dahmane et al., (1997), Activation of the transcription factor Gli1 and the Sonic hedgehog signalling pathway in skin tumours. Nature 389, 876-881; Williams et al., (2003), Identification of a small molecule inhibitor of the hedgehog signaling pathway: effects on basal cell carcinoma-like lesions. Proc Natl Acad Sci USA. 100, 4616-4621; Athar et al., (2004), Inhibition of smoothened signaling prevents ultraviolet B-induced basal cell carcinomas through regulation of Fas expression and apoptosis. Cancer Res. 64, 7545-7552).

Interaction of the SHH-GLI and PGF-RTK-RAS-MEK/AKT Signaling Pathways

We show that the activity of required RAS-RAF/AKT signaling in human melanomas depends on an active SHH-GLI pathway, and that GLI1 activity and expression requires RAS-RAF-MEK/AKT signaling. We also demonstrate the requirement of EGFR for GLI activity. Since FGF, IGF, HGF, Endothelin3, and other PGFs that are critical for melanoma, activate RTKs that trigger RAS signaling (Meier et al., (2005), The RAS/RAF/MEK/ERK and PI3K/AKT signaling pathways present molecular targets for the effective treatment of advanced melanoma. Front Biosci. 10, 2986-3001), their actions may funnel into positive GLI function like in the case of EGF. Moreover, and even though there are SHH-GLI-only and RAS-only targets (Yoon et al., (2002), Gene expression profiling leads to identification of GLI 1-binding elements in target genes and a role for multiple downstream pathways in GLI 1-induced cell transformation J Biol Chem. 277, 5548-5555; Louro et al., (2002), Comparative gene expression profile analysis of GLI and c-MYC in an epithelial model of malignant transformation. Cancer Res. 62, 5867-5873) and each signaling component has multiple effects, the ability of GLI3 repressors to inhibit oncogenic RAS action further indicates that the balance of positive (activating) and negative (repressive) GLI functions, the GLI code (Ruiz i Altaba et al., (2003), The emergent design of the neural tube: prepattern, SHH morphogen and GLI code. Curr Opin Genet Dev 13, 513-521), is a critical node for the convergence of SHH and RAS-MEK/AKT signaling in melanoma. Such convergence supports the funnel hypothesis (Ruiz i Altaba et al., (2004), Hedgehog—Gli signaling in brain tumors: stem cells and paradevelopmental programs in cancer. Cancer Lett. 204, 145-157).

We propose a general model in which parallel PGF-RTK-RAS-RAF-MEK/AKT and SHH-GLI signaling pathways converge to regulate the GLI code in melanomas and other SHH-GLI dependent tumors (FIG. 7). Here, RAS-MEK/AKT signaling leads to enhanced positive GLI function, with SHH signaling being required to initiate and enhance the expression of full-length GLI proteins providing the substrate for RAS-MEK/AKT action. SHH signaling is also required to block the formation of C-terminally truncated GLI3 repressors, which act as epigenetic tumor suppressors that negate full positive GLI function. Thus, whereas combined PGF-RAS-MEK/AKT and SHH signaling effectively shift the GLI code towards an activating state by inducing positive GLI1-3 function and by inhibiting GLI3 repressor formation, oncogenic RTK-RAS-RAF/AKT and SHH signaling lock the GLI code in a hyperactivating state.

RAS-MEK/AKT action could enhance positive GLI function and nuclear accumulation by directly affecting the GLI proteins, their levels or interactions (Nguyen et al., (2005) Cooperative requirement of the Gli proteins in neurogenesis. Development 132, 3267-3279), or by affecting GLI modulators (e.g. Kogerman et al., (1999), Mammalian suppressor-of-fused modulates nuclear-cytoplasmic shuttling of Gli-1. Nat Cell Biol. 1, 312-319; Nguyen et al., (2005), Cooperative requirement of the Gli proteins in neurogenesis. Development 132, 3267-3279). Increased nuclear GLI accumulation parallels the effect of RAS on SMAD2 (Oft et al., (2002), Metastasis is driven by sequential elevation of H-ras and Smad2 levels. Nat Cell Biol. 4, 487-494). Since full-length GLI1-3, but not C'Δ GLI3 repressors are rendered cytoplasmic by AKT or MEK1 inhibition, RAS signaling may therefore induce nuclear accumulation of full-length activating GLI proteins, enhancing their function and preventing cytoplasmic degradation and processing into repressor forms. RAS-AKT may also enhance positive activity by inhibiting GSK3 (FIG. 7; Jope and Johnson, (2004), The glamour and gloom of glycogen synthase kinase-3. Trends Biochem Sci. 29, 95-102), which phosphorylates the GLI proteins, targeting them for degradation (Jia et al., (2002), Shaggy/GSK3 antagonizes Hedgehog signalling by regulating Cubitus interruptus. Nature 416, 548-552. Price and Kalderon, (2002), Proteolysis of the Hedgehog signaling effector Cubitus interruptus requires phosphorylation by Glycogen Synthase Kinase 3 and Casein Kinase 1. Cell 108, 823-835). In some cases PGF-RTK-RAS signaling may induce GLI gene expression directly, as in the embryonic mesoderm (Brewster et al., (2000), Gli2 functions in FGF signaling during antero-posterior patterning. Development 127, 4395-4405). In addition, positive autocrine same-pathway and cross-pathway feedback loops contribute to tumor maintenance (FIG. 7; Sibilia et al., (2000), The EGF receptor provides an essential survival signal for SOS-dependent skin tumor development. Cell 102, 211-220; Satyamoorthy et al., (2003), Constitutive mitogen-activated protein kinase activation in melanoma is mediated by both BRAF mutations and autocrine growth factor stimulation. Cancer Res. 63, 756-759; Berman et al., (2003), Widespread requirement for Hedgehog ligand stimulation in growth of digestive tract tumours. Nature 425, 846-851; Sanchez et al., (2004), Inhibition of prostate cancer proliferation by interference with SONIC HEDGEHOG-GLI1 signaling. Proc. Natl. Acad. Sci. USA. 101, 12561-12566; Karhadkar et al., (2004), Hedgehog signalling in prostate regeneration, neoplasia and metastasis. Nature 431, 707-712; Bardeesy et al., (2005), Role of epidermal growth factor receptor signaling in RAS-driven melanoma. Mol Cell Biol. 25, 4176-88; Stepan et al., (2005), Regulation and function of the sonic hedgehog signal transduction pathway in isolated gastric parietal cells. J. Biol. Chem. 280, 15700-15708). Finally, regulation of BMI1 by SHH-GLI signaling could facilitate positive GLI function through its inhibition of $p16^{IKN4a}$ and $p14^{ARF}$ (Bruggerman et al., (2005), Ink4a and Arf differentially affect cell proliferation and neural stem cell self-renewal in Bmi1-deficient mice. Genes Dev. 19, 1438-1443; Molofsky et al., (2005), Bmi-1 promotes neural stem cell self-renewal and neural development but not mouse growth and survival by repressing the p16Ink4a and p19Arf senescence pathways. Genes Dev. 19, 1432-1437), which is complete upon the common loss of CDKN2A detected during melanoma progression (Sharpless and Chin, (2003), The INK4α/ARF locus and melanoma. Oncogene 22, 3092-3098).

Our model has important implications for development and disease as PGF-RAS-MEK/AKT and SHH-GLI signaling are involved in numerous aspects of embryogenesis and homeostasis, can act morphogenetically and underlie a major part of human cancers. Indeed, our model can account for previously unexplained observations in development and cancer: i) FGF signaling requires the function of Gli2 and Gli3 for ventro-posterior development in frog embryos (Brewster et al., (2000), Gli2 functions in FGF signaling during antero-posterior patterning. Development 127, 4395-4405). ii) EGF and SHH signaling synergize in the control of neurosphere proliferation in mice (Palma and Ruiz i Altaba, (2004) Hedgehog-Gli signaling regulates the behavior of cells with stem cell properties in the developing neocortex. Development 131, 337-345; Palma et al., (2005), Sonic hedgehog controls stem cell behavior in the postnatal and adult brain. Development 132, 335-344). iii) SHH signaling in capillary morphogenesis induces and requires the activation of PI3K, which induces AKT (Kanda et al., (2003), Sonic hedgehog induces capillary morphogenesis by endothelial cells through phosphoinositide 3-kinase. J. Biol. Chem. 278, 8244-8249). iv) The oligodendrocyte-inducing activity of SHH in vitro depends on FGFR and MEK function (Kessaris et al., (2004), Cooperation between sonic hedgehog and fibroblast growth factor/MAPK signalling pathways in neo-cortical precursors. Development 131, 1289-1298). v) BCC cell proliferation and survival requires both SHH-GLI and MEK signaling (Dahmane et al., (1997), Activation of the transcription factor Gli1 and the Sonic hedgehog signalling pathway in skin tumours. Nature 389, 876-881; Xie et al. (1998), Activating Smoothened mutations in sporadic basal-cell carcinoma. Nature. 391, 90-92; Xie et al. (2001). A role of PDGFR alpha in basal cell carcinoma proliferation, Proc. Natl. Acad. Sci. USA. 98, 9255-9259; Williams et al., (2003), Identification of a small molecule inhibitor of the hedgehog signaling pathway: effects on basal cell carcinoma-like lesions. Proc Natl Acad Sci USA. 100, 4616-4621; Athar et al., (2004), Inhibition of smoothened signaling prevents ultraviolet B-induced basal cell carcinomas through regulation of Fas expression and apoptosis. Cancer Res. 64, 7545-7552; Tas and Avci, (2004), Induction of the differentiation and apoptosis of tumor cells in vivo with efficiency and selectivity. Eur. J. Dermatol. 14, 96-102; Li et al., (2004), IFNalpha induces Fas expression and apoptosis in hedgehog pathway activated BCC cells through inhibiting Ras-Erk signaling. Oncogene 23, 1608-1617), and SHH signaling induces RAS-MEK function through its activation of PDGFRA (Xie et al., (2001), A role of PDGFRalpha in basal cell carcinoma proliferation, Proc. Natl. Acad. Sci. USA. 98, 9255-9259). vi) Medulloblastomas require SHH-GLI (Dahmane et al., (2001) The Sonic Hedgehog-Gli pathway regulates dorsal brain growth and tumorigenesis. Development 128, 5201-5212; Berman et al., (2002), Medulloblastoma growth inhibition by hedgehog pathway blockade. Science 297, 1559-1561) and PDGF-MEK (MacDonald et al., (2001), Expression profiling of medulloblastoma: PDGFRA and the RAS/MAPK pathway as therapeutic targets for metastatic disease. Nat Genet. 29, 143-152) signaling, and SHH synergizes with IGF2-AKT in the induction of medulloblastoma in mice (Rao et al., (2004), Sonic hedgehog and insulin-like growth factor signaling synergize to induce medulloblastoma formation from nestin-expressing neural progenitors in mice. Oncogene 23, 6156-6162; Hartmann et al., (2005), Insulin-like growth factor II is involved in the proliferation control of medulloblastoma and its cerebellar precursor cells. Am. J. Pathol. 166, 1153-1162). vii) Gliomas have been proposed to depend on SHH-GLI signaling (Dahmane et al., (2001), The Sonic Hedgehog-Gli pathway regulates dorsal brain growth and tumorigenesis. Development 128, 5201-5212) and commonly harbor mutations activating EGFR and/or inactivating PTEN, leading to RAS/MEK/AKT function (Maher et al., (2001), Malignant glioma: genetics and biology of a grave matter. Genes Dev. 15, 1311-1333). viii) The induction of rhabdomyosarcomas by SHH in mice requires IGF2-AKT activity (Kappler et al., (2003), Molecular characterization of Patched-associated rhabdomyosarcoma. J Pathol. 200, 348-356).

Interactions of SHH-GLI Signaling with Other Melanomagenic Pathways

The requirement of SHH-GLI signaling in human melanomas that we demonstrate also suggests its integration with other signaling pathways. WNT signaling is required in human melanomas (Widlund et al., (2002), Beta-catenin-induced melanoma growth requires the downstream target Microphthalmia-associated transcription factor. J. Cell Biol. 158, 1079-1087; You et al., (2004), An anti-Wnt-2 monoclonal antibody induces apoptosis in malignant melanoma cells and inhibits tumor growth. Cancer Res. 64, 5385-5389), it can regulate MITF (Takeda et al., (2000), Induction of melanocyte-specific microphthalmia-associated transcription factor by Wnt-3a. J. Biol. Chem. 275, 14013-14016) and WNTs may in turn regulate the HH-GLI pathway (Watt, (2004), Unexpected Hedgehog-Wnt interactions in epithelial differentiation. Trends Mol. Med. 10, 577-580). Since, GLI1 induces the expression of Mitf and Wnt genes (this work; Mullor et al., (2001). Wnt signals are targets and mediators of Gli function. Curr. Biol. 11, 769-773), the SHH-GLI and WNT pathways may thus also interact through cross-regulatory loops, resulting in increased function of MITF, a critical regulator of melanocyte and melanoma development (Widlund and Fisher, (2003), Microphthalamia-associated transcription factor: a critical regulator of pigment cell development and survival. Oncogene 22, 3035-3041).

Signaling Integration, Strength and Melanoma Progression

The homogeneity in the expression and requirement of SHH-GLI signaling in all melanomas tested suggests a general and critical role. Nevertheless, benign nevi also appear to have an active pathway even though their growth is largely arrested by senescence (Michalogou et al., (2005), BRAFE600-associated senescence-like cell cycle arrest of human naevi. Nature 436, 720-724). SHH-GLI activity could thus be a basal requirement for nevi and melanoma with other events driving disease progression. However, signaling integration also raises the possibility that the acquisition of oncogenic mutations that progressively activate the RAS-RAF-MEK and AKT pathways during melanomagenesis (e.g. Tsao et al., (2000), Relative reciprocity of NRAS and PTEN/MMAC1 alterations in cutaneous melanoma cell lines. Cancer Res. 60, 1800-1804; Davies et al., (2002), Mutations of the BRAF gene in human cancer. Nature 417, 949-954; Stahl et al., (2004), Deregulated Akt3 activity promotes development of malignant melanoma. Cancer Res. 64, 7002-7010; Patton et al., (2005), BRAF mutations are sufficient to promote nevi formation and cooperate with p53 in the genesis of melanoma. Curr Biol. 15, 249-254; Meier et al., (2005), The RAS/RAF/MEK/ERK and PI3K/AKT signaling pathways present molecular targets for the effective treatment of advanced melanoma. Front Biosci. 10, 2986-3001) results in increasing levels of positive GLI function, as revealed by the enhanced expression of a restricted number of SHH-GLI targets such, as FOXM1 and WNT5A (this work, Mullor et al., (2001), Wnt signals are targets and mediators of Gli function. Curr. Biol. 11, 769-773; Weeraratna et al., (2002), Wnt5a signaling directly affects cell motility and invasion of metastatic melanoma. Cancer Cell 1, 279-288), in metastatic melanoma. Sequential oncogene-driven increases in the levels of nuclear, positive GLI function could similarly underlie the progression prostate (Sanchez et al., (2004), Inhibition of prostate cancer proliferation by interference with SONIC HEDGEHOG-GLI1 signaling. Proc. Natl. Acad. Sci. USA. 101, 12561-12566; Karhadkar et al., (2004), Hedgehog signalling in prostate regeneration, neoplasia and metastasis. Nature 431, 707-712; Sheng et al., (2004), Activation of the hedgehog pathway in advanced prostate cancer. Mol Cancer. 3, 29) and other SHH-GLI-dependent cancers.

The GLI Code in the Treatment of Melanoma and Other SHH-GLI-Dependent Sporadic Human Cancers Melanoma incidence and mortality are on the rise and there are no treatments for advanced metastatic disease (Meier et al., (2005), The RAS/RAF/MEK/ERK and PI3K/AKT signaling pathways present molecular targets for the effective treatment of advanced melanoma. Front Biosci. 10, 2986-3001). Our data provide the basis for a novel therapeutic approach for human melanoma through topical and systemic interference of SHH-GLI signaling to inhibit tumor growth, prevent recurrence and eradicate metastases. Since the human cancers that we and others have shown to depend on sustained SHH-GLI function, including melanoma, BCCs, glioma, medulloblastoma, prostate, pancreas, stomach and muscle cancers (reviewed in Ruiz i Altaba et al., (2004), Hedgehog—Gli signaling in brain tumors: stem cells and paradevelopmental programs in cancer. Cancer Lett. 204, 145-157) also require PGF-RAS-MEK activity (e.g MacDonald et al., (2001), Expression profiling of medulloblastoma: PDGFRA and the RAS/MAPK pathway as therapeutic targets for metastatic disease. Nat Genet. 29, 143-152; Xie et al., (2001), A role of PDGFRalpha in basal cell carcinoma proliferation. Proc. Natl. Acad. Sci. USA. 98, 9255-9259; Maher et al., (2001), Malignant glioma: genetics and biology of a grave matter. Genes Dev. 15, 1311-1333; Weber and Giolei, (2004), Ras signaling in prostate cancer progression J. Cell. Biochem. 91, 13-25), modulating the GLI code towards a repressing state directly or through a combined strategy with anti-RTK-RAS-RAF-MEK/AKT plus anti-SHH-GLI agents are attractive, wide-spectrum anti-cancer goals.

Summary of Results

The data presented here demonstrate that the Sonic Hedgehog (SHH)-GLI pathway regulates the proliferation of human melanocytes and melanomas. Growth, recurrence and metastasis of human melanoma xenografts in mice are prevented by interference with SHH-GLI function. The data also shows that the GLI code integrates RAS-RAF-MEK/AKT and SHH-GLI signaling, that oncogenic RAS-MEK/AKT induces the nuclear accumulation of GLI1, GLI2 and GLI3 proteins and that positive GLI function can regulate, in turn, other melanomagenic pathways and factors, including MITF. The results presented here suggest a novel therapeutic approach and provide the framework to understand the requirement of SHH-GLI function in melanomas, which may be extended to other SHH-GLI dependent human cancers harboring oncogenic activation of PGF-RTK-RAS-MEK/AKT signaling.

Furthermore, the data presented here shows that the Sonic Hedgehog (SHH)-GLI pathway regulates the proliferation of human melanocytes and melanomas. Growth, recurrence and metastasis of human melanoma xenografts in mice are prevented by interference with SHH-GLI function. We also show that the GLI code integrates RAS-RAF-MEK/AKT and SHH-GLI signaling, that oncogenic RAS-MEK/AKT induces the nuclear accumulation of GLI1, GLI2 and GLI3 proteins and that positive GLI function can regulate, in turn, other melanomagenic pathways and factors, including MITF. The results presented here suggest a novel therapeutic approach and provide the framework to understand the requirement of SHH-GLI function in melanomas, which may be extended to other SHH-GLI dependent human cancers harboring oncogenic activation of PGF-RTK-RAS-MEK/AKT signaling.

Example 2

GLI1 is a Critical Node Integrating Mutually Dependent Hedgehog and Oncogenic RAS-MEK/AKT Signaling in Melanoma Methods Cells and Mice WM-115, SK-MEL-2 and COS7 cell lines (ATCC) were grown according to the specifications of the provider. The primary Me-3 melanoma (Stecca, B. et al. Melanocyte proliferation and melanoma growth, recurrence and metastasis require sustained SONIC HEDGEHOG-GLI signaling. *Submitted*. (2006)) was grown in E-MEM with 10% FBS (Hyclone), 1 mM sodium pyruvate (GIBCO) and 1 ng/ml EGF (GIBCO). Proliferating human melanocytes from foreskin (Promocell) were grown in M2 media (Promocell). Melanomas from ±6 month-old Tyr→NRAS$^{Q61K}$; Ink4a$^{-/-}$ mice on a light coat color Dct$^{-/-}$ background[13] were collected from the skin and lymph nodes. Tumors were dissociated and grown in E-MEM with 10% FBS, 1 mM sodium pyruvate (GIBCO) and 1 ng/ml EGF (GIBCO). Mouse embryonic fibroblasts (MEFs) were prepared from E14.5 Swiss Webster mouse embryos and grown in DMEM with 10% FBS.

Immunocytochemistry

Immunohistochemistry on cells or cryostat sections with mouse anti-BrdU (Beckton Dickinson), mouse anti-Myc (9E10; Santa Cruz), rabbit anti-GFP (Molecular Probes), rabbit anti-β-gal (Cappel, ICN, clone 55976), rabbit anti-S100 (Dako), mouse anti-Nestin (Becton-Dickinson) and an affinity purified rabbit anti-human GLI1 that we raised and is specific but detects only overexpressed protein, used FITC- or PE-conjugated secondary antibodies (Molecular Probes).

RT-PCR and qRT-PCR

Real-time quantitative PCR amplifications with different primers were carried out at 60° C. on an Opticon machine (MJ Research) using iQ™ SYBR Green supermix (Biorad) and values calculated using the standard curve method. Human primer sequences were 5'→3': GLI1-F: GGGATGATCCCA-CATCCTCAGTC (SEQ ID NO: 5) and GLI1-R: CTGGAG-CAGCCCCCCCAGT (SEQ ID NO: 6); PTCH1-F: CCACA-GAAGCGCTCCTACA (SEQ ID NO: 11) and PTCH1-R: CTGTAATTTCGCCCCTTCC (SEQ ID NO: 12); NRAS-F: TTTGCCAACAAGGACAGTTG (SEQ ID NO: 41) and NRAS-R: CCCTGAGTCCCATCATCACT (SEQ ID NO: 42); si-SUFUH-F2: ACCTGTCCTTCCACCAATCA (SEQ ID NO: 43) and si-SUFUH-R2: CCCCTTAGGCAGAGAG-GAAT (SEQ ID NO: 44); EEF1A1-F: AGCAAAAATGAC-CCACCAATG (SEQ ID NO: 33) and EEF1A1-R: GGC-CTGGATGGTTCAGGATA (SEQ ID NO: 34). For mice: Gli1-F: GCTGCCTATAGCCAGTGTC (SEQ ID NO: 45) and Gli1-R: GAAGCAGGTGCAAAGCCAG (SEQ ID NO: 46); Sufu-F: CTCCAGGTTACCGCTATCGTC (SEQ ID NO: 47) and Sufu-R: CACTTGGTCCGTCTGTTCCTG (SEQ ID NO: 48); Shh-F: GCAGGTTTCGACTGGGTCTA (SEQ ID NO: 49) and Shh-R: GAAGGTGAG-GAAGTCGCTGT (SEQ ID NO: 50); Tyrosinase-F:5' CCA-GAAGCCAATGCACCTAT (SEQ ID NO: 51) and Tyrosinase-R: ATAACAGCTCCCACCAGTGC (SEQ ID NO: 52); Gapdh-3: AGTATGATGACATCAAGAAGG (SEQ ID NO: 53) and Gapdh-4: ATGGTATTCAAGAGAGTAGGG (SEQ ID NO: 54); Ptch1-F: ATGGTCCTGGCTCTGATGAC (SEQ ID NO: 55) and Ptch1-R: TAGCCCTGTGGTTCTTGTCC (SEQ ID NO: 56).

Drugs, Treatments, Proliferation Assays and RNA Interference

Cyclopamine (Toronto Research Chemicals (TRC), catalog No. C988400) and Tomatidine (Sigma) were used in all cells at 10 μM or 5 μM for 48 h in 2.5% FBS. Forskolin (FK) and 1,9-dideoxyforskolin (ddFK; Sigma) were used at 50 μM. MEK-1 (U0126; Promega), and AKT (SH6; Alexis corporation) inhibitors were used at 1 and 40 μM, respectively, dissolved in DMSO. U0126 and SH6 were used for 1 h, 48 h post-transfection. Leptomycin B (LMB; Sigma) was used at 5 nM for 6 h, 48 h post-transfection. BrdU (Sigma) was pulsed at 4 µg/ml for 2 h before fixation followed by immunodetection with anti-BrdU antibodies (BD Biosciences). The number of viable cells was assessed by Trypan blue exclusion (Promega). SUFUH siRNA: GCUUGAGAGCGUACAUCUG (SEQ ID NO: 57) (target-validated from Ambion). Control siRNA: AACGUACGCGGAAUACAACGA SEQ ID NO: 58) (Sanchez, P. et al. Inhibition of prostate cancer proliferation by interference with SONIC HEDGEHOG-GLI1 signaling. *Proc. Natl. Acad. Sci. USA.* 101, 12561-12566 (2004)). siRNA transfections (0.2 µM) were performed with Oligofectamine (Invitrogen) for 48 h.

Plasmids, Cell Transfections and Colony Formation Assay

Cells were transfected (3 µg/p35 plate) with myc-tagged full-length CMV expression vectors with FUGENE (Roche). Transfections were at equimolar amounts unless otherwise specified with combinations of pCS2-Myc-tagged human GLI1, GLI3, GLI3R (GLI3C'ΔClaI), frog Gli2R (Gli2C') (Ruiz i Altaba, A. Gli proteins encode context-dependent positive and negative functions: implications for development and disease. *Development* 126, 3205-3216 (1999), pCMV-HA-tagged GLI1 (ref. 20), HRAS$^{V12G}$ (from A. Pellicer), NRAS$^{Q61K}$ (Ackermann, J. et al. Metastasizing melanoma formation caused by expression of activated N-RasQ61K on an INK4a-deficient background. *Cancer Res.* 65, 4005-4011 (2005)), activated (myristoylated) myc-tagged AKT1 (Upstate), activated MEK1 (p45MAPKK$^{S222D}$; from J. Pouyssegur), Myc-tagged SUFUH (Kogerman, P. et al. Mammalian suppressor-of-fused modulates nuclear-cytoplasmic shuttling of Gli-1. *Nat Cell Biol.* 1, 312-319 (1999)), and pCMV-eGFP or pCMV-lacZ. For selection, SK-MEL2 and MeWo cells were transfected (4 µg/p60 plate) with PGK-neo and CMV-eGFP alone or in a 1/1/8 ratio with oncogenic RAS, GLI3R or (frog) Gli2R, or in a 1/1/4/4 ratio with RAS/GLI3R or RAS/Gli2R. After Geneticin (400 µg/ml, Gibco) selection for 20 days, colonies were stained with 0.5% crystal violet. Colony size was measured in duplicate dishes in three independent experiments.

Luciferase Assay p7 GBS-Luc (Sasaki, H., Hui, C., Nakafuku, M. & Kondoh, H. A binding site for Gli proteins is essential for HNF-3beta floor plate enhancer activity in transgenics and can respond to Shh in vitro. *Development* 124, 1313-1322 (1997)), pcontrol (without GLI binding sites, pBT-Luc; Promega), and pPTCH1-Luc (Agren, M., Kogerman, P., Kleman, M. I., Wessling, M. & Toftgard, R. Expression of the PTCH1 tumor suppressor gene is regulated by alternative promoters and a single functional Gli-binding site. *Gene.* 330, 101-114 (2004)) were used in combination with plasmids driving the expression of GLI proteins (i Altaba, A. Gli proteins encode context-dependent positive and negative functions: implications for development and disease. *Development* 126, 3205-3216 (1999)). Cells were plated in 12-well plates, grown to 60% confluence in 10% FCS (Hyclone) and transfected with FuGene 6 (Roche) with 1 µg of DNA total, at a reagent:DNA ratio of 3:1 in Optimem medium (Invitrogen), containing a constant 300 ng of GLI1 plasmid in COS7 cells and 100 ng in SK-Mel2 cells. Cells were then incubated for 48 h with the transfected DNA and harvested with 200 ul of the passive lysis buffer (Promega). Luciferase activities normalized with *Renilla* pRL-TK vector were measured in triplicate with 20 ul of protein lysate for SK-Mel2 and 6 µl for COS7 by using the dual-luciferase reporter assay system (Promega) and a Turner TD-20/20 luminometer.

Results

RAS-MEK/AKT and SHH-GLI Signaling Show Mutual Dependence in Human Melanomas

Figure 8A:
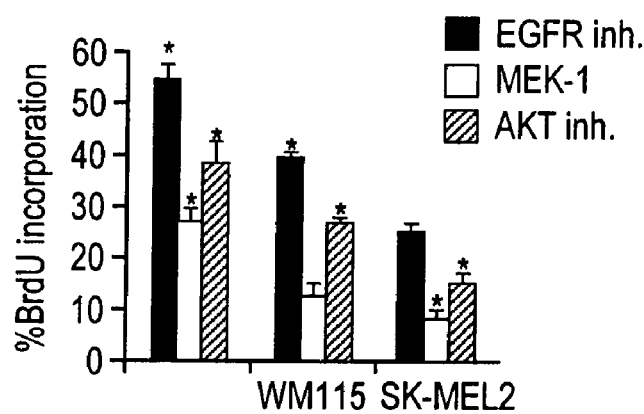
Figure 8B:
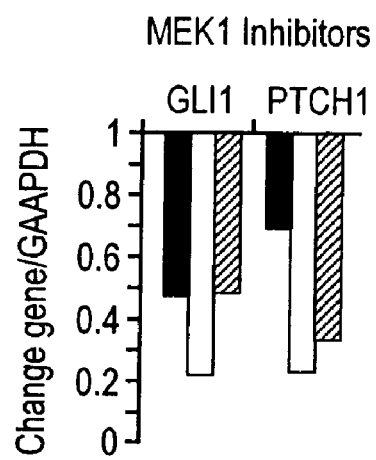
Figure 8C:
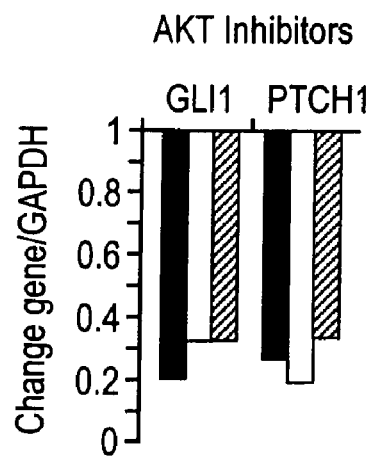

As expected, treatment with specific MEK1 (U0126) or AKT (SH6) inhibitors decreased BrdU incorporation after 48 h in one primary malignant melanoma culture Me-3 (Stecca, B. et al. Melanocyte proliferation and melanoma growth, recurrence and metastasis require sustained SONIC HEDGEHOG-GLI signaling. *Submitted.* (2006)) and two malignant melanoma cell lines, SK-Mel2 and WM-115 chosen for their known activated NRAS$^{Q61R}$ and BRAF$^{V600D}$ signaling status, respectively (Meier, F. et al. The RAS/RAF/MEK/ERK and PI3K/AKT signaling pathways present molecular targets for the effective treatment of advanced melanoma. *Front Biosci.* 10, 2986-3001 (2005); Davies, H. et al. Mutations of the BRAF gene in human cancer. *Nature* 417, 949-954 (2002)). (FIG. 8a). Propidium iodide FACS analyses of SH6 and U0126-treated SK-Mel2 cells showed a 50% and 30% decrease in the number of dividing cells (S/G2/M) as compared to control DMSO-treated cells at 24 h. This inhibition, however, also resulted in the rapid reduction of GLI1 and PTCH1 mRNA levels 4 h after treatment (FIG. 8b,c), similar to those seen with cyclopamine (Stecca, B. et al. Melanocyte proliferation and melanoma growth, recurrence and metastasis require sustained SONIC HEDGEHOG-GLI signaling. *Submitted.* (2006)), a small molecule that blocks the SHH-GLI pathway (Chen, J. K., Taipale, J., Cooper, M. K. & Beachy, P. A. Inhibition of Hedgehog signaling by direct binding of cyclopamine to Smoothened. *Genes Dev.* 16, 2743-2748 (2002)). Similar results were obtained with two other human melanoma cell lines (not shown). Because GLI1 is a strict target of HH signaling (e.g. Lee, J., Platt, K. A., Censullo, P. & Ruiz i Altaba, A. Gli1 is a target of Sonic hedgehog that induces ventral neural tube development. *Development* 124, 2537-2552 (1997)), this suggests that both MEK and AKT signaling affect SHH-GLI function.

Figure 8D:
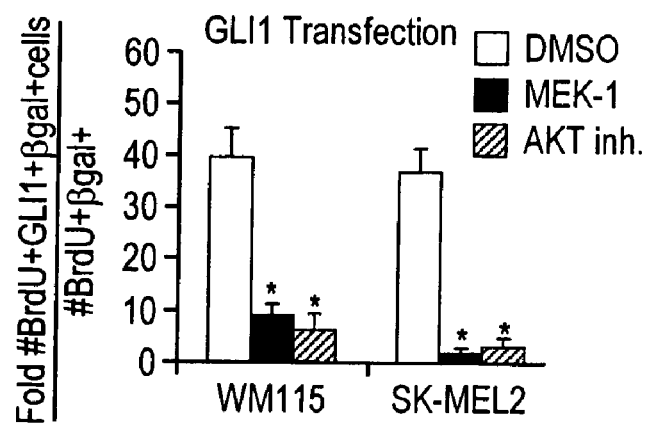

Expression of GLI1 through transfection in SK-Mel2 and WM-115 enhanced BrdU incorporation by ±6 fold (FIG. 8d). This effect was inhibited by inhibitors of MEK or AKT function (75→95% inhibition, FIG. 1d). MEK and AKT may thus affect SHH-GLI signaling at the level of GLI action, explaining the lower levels of GLI1 and PTCH1 mRNAs detected after inhibitor treatment (FIG. 8b,c) since GLI1 positively autoregulates and PCTH1 is a target of GLI1 (Dahmane, N. et al. The Sonic Hedgehog-Gli pathway regulates dorsal brain growth and tumorigenesis. *Development* 128, 5201-5212 (2001); Regl, G. et al. Human GLI2 and GLI1 are part of a positive feedback mechanism in Basal Cell Carcinoma. *Oncogene* 21, 5529-39 (2002); Agren, M., Kogerman, P., Kleman, M. I., Wessling, M. & Toftgard, R. Expression of the PTCH1 tumor suppressor gene is regulated by alternative promoters and a single functional Gli-binding site. *Gene.* 330, 101-114 (2004)).

Figure 8E:
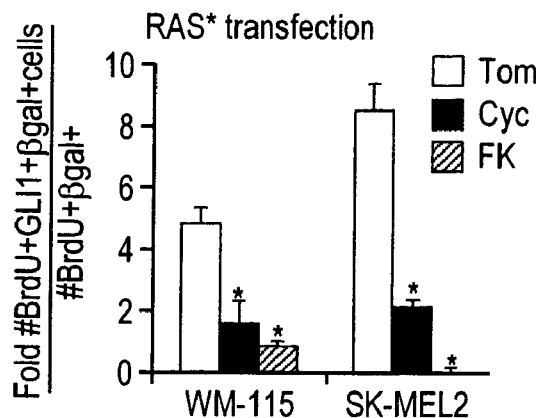

Transfection of oncogenic HRAS$^{V12G}$ or NRAS$^{Q61K}$, both of which induce melanoma in mice (Chin, L. et al. Essential role for oncogenic Ras in tumour maintenance. *Nature* 400, 468-472 (1999); Ackermann, J. et al. Metastasizing melanoma formation caused by expression of activated N-RasQ61K on an INK4a-deficient background. *Cancer Res.* 65, 4005-4011 (2005)), enhanced BrdU incorporation in melanoma cells by ±5-8.5 fold in WM-115 and SK-Mel2 cells (FIG. 8e and not shown). This increase was greatly diminished by treatment with cyclopamine (±65-75% inhibition, FIG. 8e). Cyclopamine treatment of melanoma cells specifically affects GLI function without non-specific effects (Stecca, B. et al. Melanocyte proliferation and melanoma growth, recurrence and metastasis require sustained SONIC HEDGEHOG-GLI signaling. *Submitted*. (2006)) and it did not alter the levels of p-ERK or p-AKT (not shown and Kessaris, N., Jamen, F., Rubin, L. L. & Richardson, W. D. Cooperation between sonic hedgehog and fibroblast growth factor/MAPK signalling pathways in neocortical precursors. *Development* 131, 1289-1298 (2004)). Oncogenic RAS signaling thus appears to require an active SHH-GLI pathway, possibly converging with it on the regulation of GLI function, as the PKA agonist forskolin, that inhibits SHH (Fan, C. M. et al. Long-range sclerotome induction by sonic hedgehog: direct role of the amino-terminal cleavage product and modulation by the cyclic AMP signaling pathway. *Cell* 81, 457-465 (1995)) and GLI1 activity (Sheng, T., Chi, S., Zhang, X. & Xie, J. Regulation of Gli1 localization by the cAMP/PKA signaling axis through a site near the nuclear localization signal. *J Biol Chem.* 281, 9-12 (2005)), blocked oncogenic RAS-induced proliferation in WM-115 and SK-Mel2 cells (±80% and 100% inhibition, FIG. 8e).

Figure 8F:
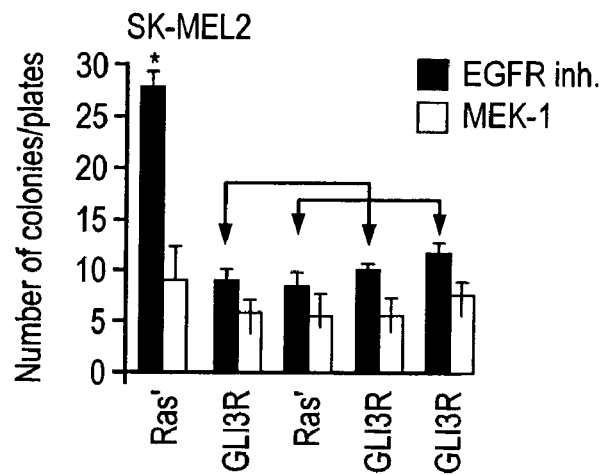
Figure 8G:
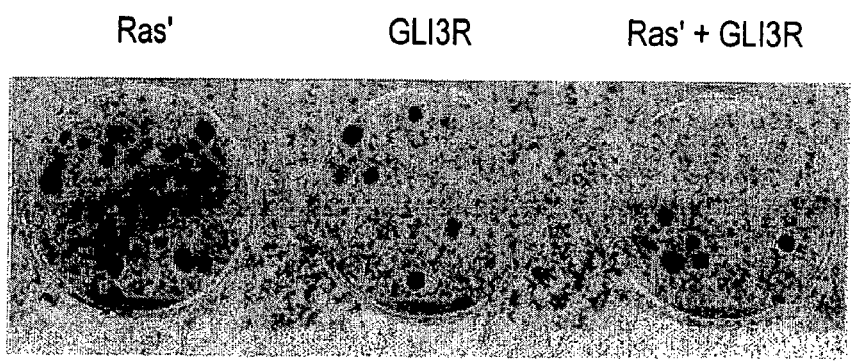

To further explore the requirement of GLI function for RAS activity, SK-Mel2 cells were transfected with oncogenic HRAS$^{V12G}$ and allowed to form colonies on plastic (FIG. 8*f, g*). Transfection of oncogenic RAS increased overall RAS action of these cells (FIG. 8e) and lead to an increase in the number of large colonies (Fujita, M. et al. Overexpression of mutant ras in human melanoma increases invasiveness, proliferation and anchorage-independent growth in vitro and induces tumour formation and cachexia in vivo. *Melanoma Res.* 9, 279-291 (1999)) over lacZ-(not shown) GLI3R-transfected cells (FIG. 8*f,g*). This was inhibited by coexpression of GLI3R or a different GLI repressor, Gli2R (FIG. 8*f,g*), which are pan-GLI dominant C'Δ repressor forms of human GLI3 and frog Gli2 (Ruiz i Altaba, A. Gli proteins encode context-dependent positive and negative functions: implications for development and disease. *Development* 126, 3205-3216 (1999)), supporting the requirement of positive GLI function for oncogenic RAS action.

Figure 9D:

NRAS$^{Q61K}$ Melanomas Harbor an Active Shh-Gli Pathway and Require its Activity The requirement of positive GLI function for RAS action in human melanomas raised the possibility that tumor induced by direct oncogenic activation of RAS signaling could require SHH-GLI pathway function. To test this idea primary and metastatic melanomas were collected from mice expressing oncogenic NRAS$^{Q61K}$ from the tyrosinase promoter (Ackermann, J. et al. Metastasizing melanoma formation caused by expression of activated N-RasQ61K on an INK4a-deficient background. *Cancer Res.* 65, 4005-4011 (2005)). NRAS$^{Q61K}$; Ink4a$^{-/-}$ mice develop numerous pigmented melanomas in the skin that metastasize to lymph nodes (FIG. 9*a,b*), with an Ink4a$^{-/-}$ background increasing their frequency (Ackermann, J. et al. Metastasizing melanoma formation caused by expression of activated N-RasQ61K on an INK4a-deficient background. *Cancer Res.* 65, 4005-4011 (2005)). Two large dermal primary melanomas and 20 lymph node metastases were dissected from two such mice and tested for the expression of the NRAS$^{Q61K}$ transgene and tyrosinase to identify tumors with high expression. 1 primary skin tumor and 11 lymph node metastases with high expression of NRAS$^{Q61K}$ (FIG. 9c) were then tested for the expression of Gli1 and Ptch1 by qPCR and compared with the expression in normal axillary, superficial cervical and inguinal lymph nodes (FIG. 9c). All melanomas showed elevated levels of Gli1 and Ptch1, but not Shh, indicating the presence of an active Shh-Gli pathway downstream of ligand action (FIG. 9c and not shown). In situ hybridization of frozen sections from primary and metastatic tumors confirmed expression of Gli1 and Ptch1 in tumor cells with heterogeneous levels (FIG. 9*d,e*).

Figure 9F:
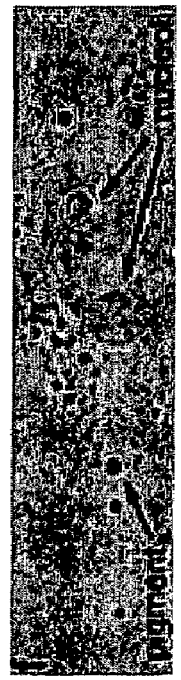
Figure 9E:
Figure 9G:
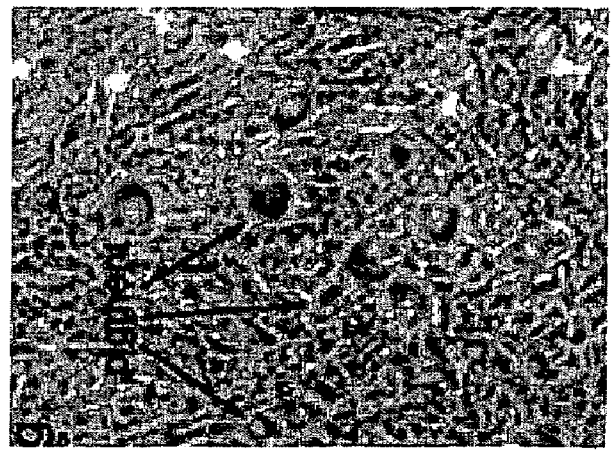
Figure 9H:
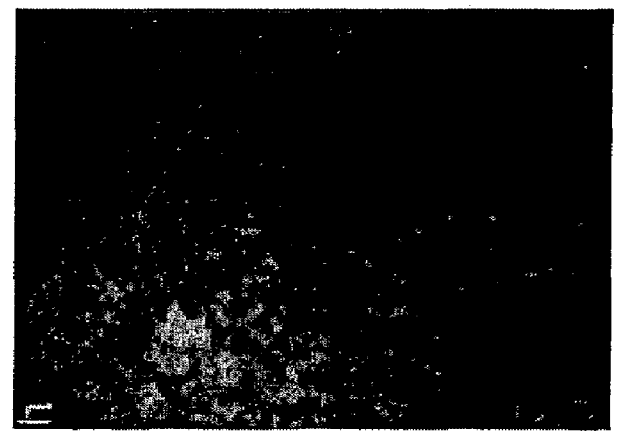
Figure 9I:
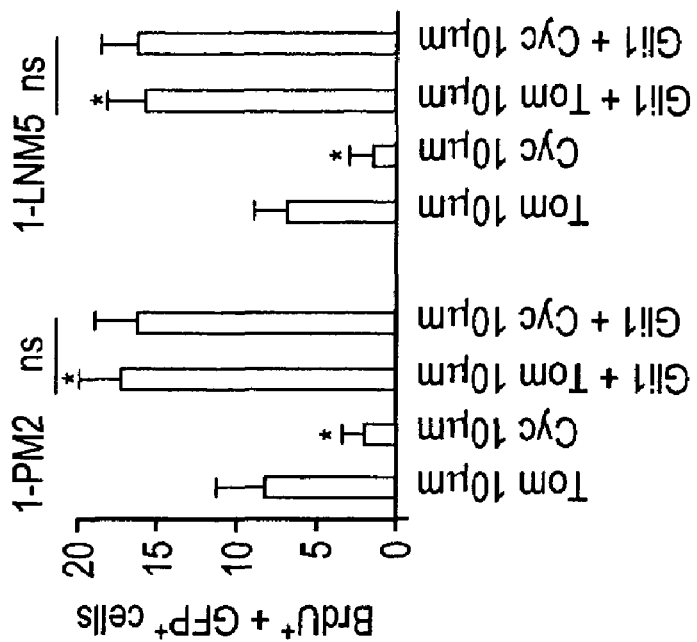

Cells from these tumors were cultured in vitro (0-1 passes) with >85% of cells displaying an elongated morphology with pigment and prominent nucleoli (FIG. 9*f,g*). Immunolabeling with the precursor/stem cell marker Nestin and the melanoma marker S100 showed heterogenous staining as reported (Ackermann, J. et al. Metastasizing melanoma formation caused by expression of activated N-RasQ61K on an INK4a-deficient background. *Cancer Res.* 65, 4005-4011 (2005)) (FIG. 9*h*). All cultures also maintained expression of NRAS, Gli1 and Ptch1 (not shown). To test for the requirement of Shh-Gli signaling, two melanoma primary cultures were first treated with cyclopamine, or tomatidine, after transfection of GFP-expressing plasmids plus a control plasmid or with a plasmid expressing GLI1 (FIG. 9i): treatment with cyclopamine, but not tomatidine, at 10 μM decreased the number of doubly BrdU+/GFP+ cells, expression of GLI1 increased the number of BrdU+/GFP+ cells and, importantly, it also abolished the inhibitory effect of cyclopamine, demonstrating its specific action as in human melanomas (Stecca, B. et al. Melanocyte proliferation and melanoma growth, recurrence and metastasis require sustained SONIC HEDGEHOG-GLI signaling. *Submitted*. (2006)).

Figure 9J:
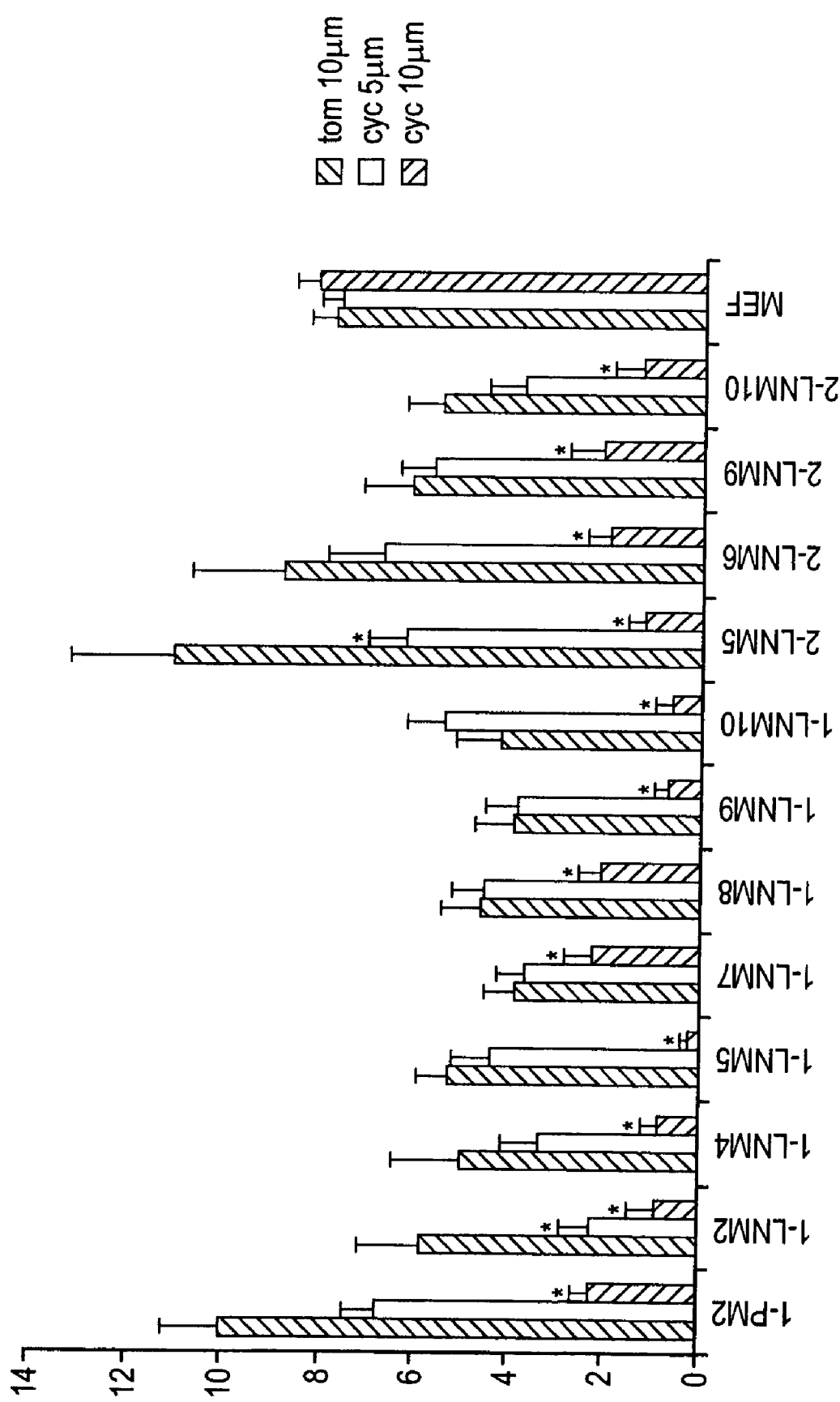

To test for a general requirement, all 12 primary cultures were then treated with cyclopamine. The proliferation of all cultures was inhibited by 10 μM treatment and one from each mouse also responded to 5 μM (FIG. 9*j*). Treatment with the inactive analog tomatidine had no effect (FIG. 9*j*). As control, cyclopamine did not affect the proliferation of mouse embryonic fibroblasts (MEF, FIG. 9*j*). These data suggest that all melanomas directly derived from the action of oncogenic RAS require SHH-GLI pathway function.

Oncogenic RAS-MEK/AKT Increase the Activity and Nuclear Localization of GLI1

Figure 10A:
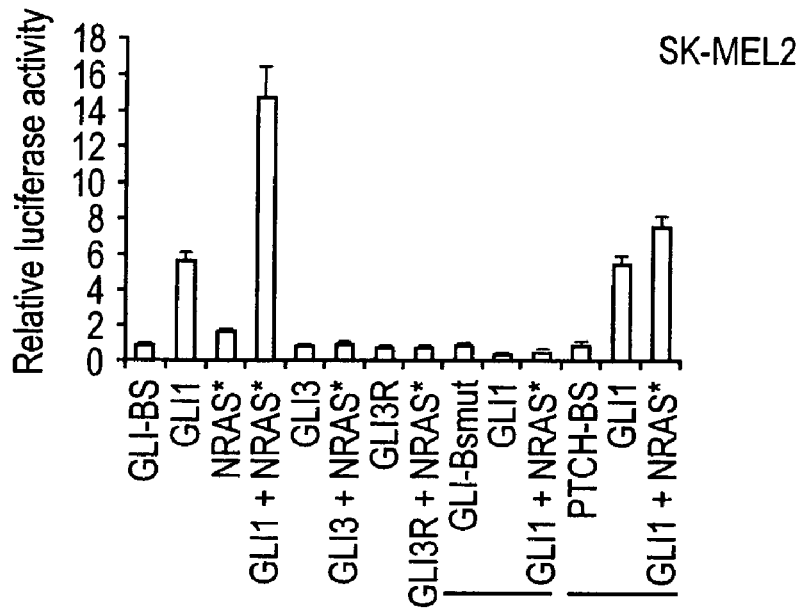
Figure 10B:
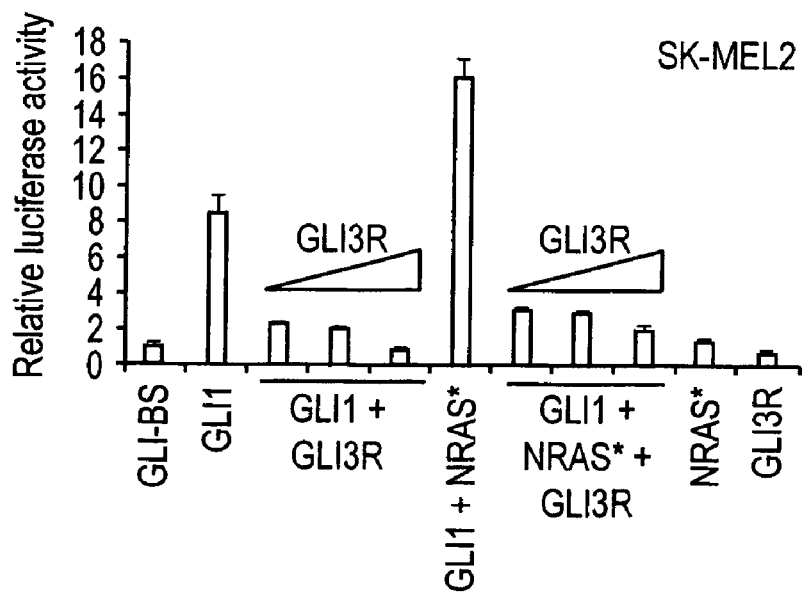
Figure 10C:
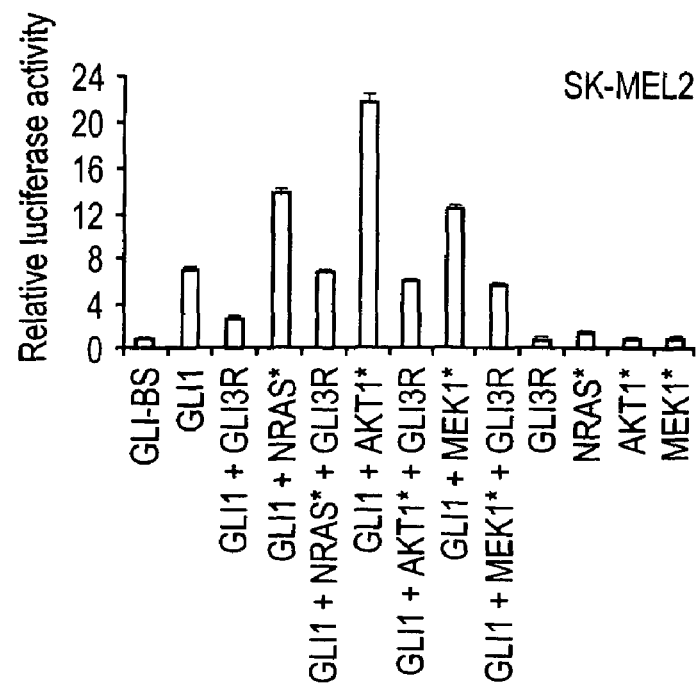
Figure 10D:
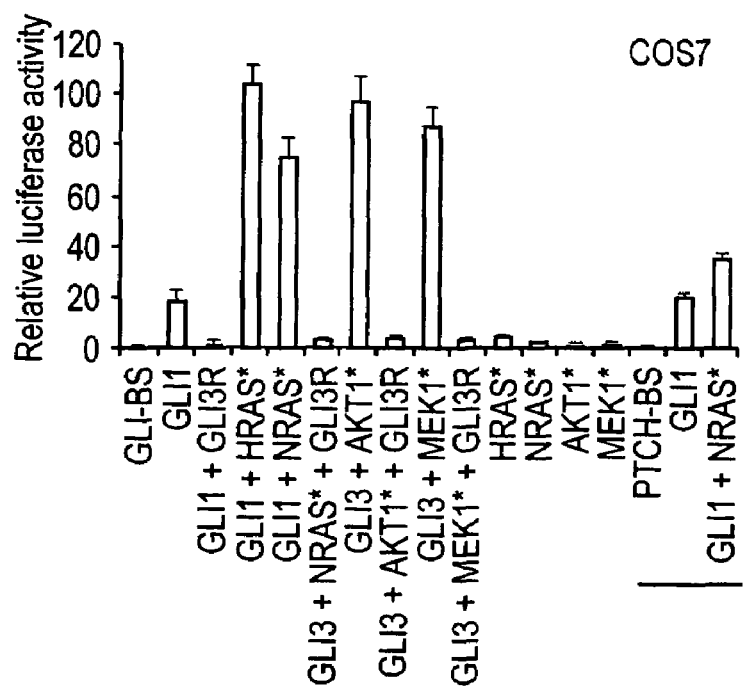

To directly test if oncogenic RAS-MEK/AKT signaling could act on positive GLI function, we tested for the effects of transfected NRAS$^{Q61K}$, HRAS$^{V12G}$, activated MEK1 (p45MAPKK$^{S222D}$) and activated AKT1 (N-myristoylated AKT1) (NRAS*, HRAS*, MEK1* and AKT1* in FIG. 10) on the induction of luciferase from a GLI reporter construct containing multiple GLI binding sites (Sasaki, H., Hui, C., Nakafuku, M. & Kondoh, H. A binding site for Gli proteins is essential for HNF-3beta floor plate enhancer activity in transgenics and can respond to Shh in vitro. *Development* 124, 1313-1322 (1997)) in human melanoma SK-Mel2 cells. These cells respond well to both GLI1 and oncogenic RAS (FIG. 8*d,e*) and harbor endogenous oncogenic NRAS$^{Q61R}$ signaling (Davies, H. et al. Mutations of the BRAF gene in human cancer. Nature 417, 949-954 (2002)), which can be further enhanced by expression of exogenous oncogenic HRAS or NRAS (FIG. 8e and not shown). Full-length GLI1, but not GLI3 or GLI3R induced a large increase (~6-fold) in luciferase activity over background levels (FIG. 10a). Expression of oncogenic NRAS$^{Q61K}$ or HRAS$^{V12G}$ alone induced a ~1.5-2 fold increase over background levels (FIG. 10*a,c*), possibly potentiating endogenous GLI activity. The transcriptional activity of full-length GLI1 but not that of GLI3, was enhanced ±2-2.5 fold by coexpression of NRAS$^{Q61K}$ (FIG. 10a). Oncogenic HRAS$^{V12G}$ stimulated GLI1 activity in a similar way (FIG. 10d and not shown). Oncogenic RAS did not endow dominant GLI3R with positive activity (FIG. 10a). Dominant active MEK-1 or dominant active AKT1 had similar effects to oncogenic RAS, with activated AKT1 having the strongest effects (~3-fold, FIG.

10c). The transcriptional activity of GLI1 alone or its enhanced activity by RAS-MEK/AKT were suppressed in a concentration-dependent manner by GLI3R (FIG. 10b,c). The effects of RAS on GLI1 transcriptional activity were equally observed in human MeWo melanoma cells (not shown) and were dependent on the presence of GLI binding sites (pControl series, FIG. 10a). In addition, oncogenic RAS also enhanced the activity of GLI1 by ~30% (FIG. 10a) from a PTCH1 reporter, harboring a single functional GLI binding site (Agren, M., Kogerman, P., Kleman, M. I., Wessling, M. & Toftgard, R. Expression of the PTCH1 tumor suppressor gene is regulated by alternative promoters and a single functional Gli-binding site. *Gene.* 330, 101-114 (2004)).

The activity of GLI1 is regulated by subcellular localization (Ruiz i Altaba, A. Gli proteins encode context-dependent positive and negative functions: implications for development and disease. *Development* 126, 3205-3216 (1999); Kogerman, P. et al. Mammalian suppressor-of-fused modulates nuclear-cytoplasmic shuttling of Gli-1. *Nat Cell Biol.* 1, 312-319 (1999); Di Marcotullio, L. et al. REN(KCTD11) is a suppressor of Hedgehog signaling and is deleted in human medulloblastoma. *Proc Natl Acad Sci USA* 101, 10833-10838 (2004)). To test if oncogenic RAS could regulate GLI1 nuclear localization, and in the absence of reliable antibodies to detect endogenous GLI proteins, SK-Mel2 melanoma cells were transfected with epitope-tagged GLI constructs (Ruiz i Altaba, A. Gli proteins encode context-dependent positive and negative functions: implications for development and disease. *Development* 126, 3205-3216 (1999)). GLI1 and GLI3 were both nuclear and cytoplasmic and coexpression of oncogenic NRAS$^{Q61K}$ or HRAS$^{V12G}$, which act near at the membrane, strongly enhanced nuclear localization of GLI1 but not that of GLI3 (FIG. 11a,b and not shown). Treatment of transfected SK-Mel2 cells, which harbor endogenous oncogenic NRAS$^{Q61K}$, with MEK or AKT inhibitors for 1 h had the reverse effect, increasing cytoplasmic localization of GLI1 (FIG. 11a,b). GLI3 was unaffected. Oncogenic RAS or the MEK or AKT inhibitors had no effect on the localization of the constitutively nuclear GLI3R (FIG. 11a,b and not shown). Dominant active MEK1 or dominant active AKT1 mimicked oncogenic RAS, enhancing nuclear accumulation of GLI1 (FIG. 11a,b).

Figure 11C:
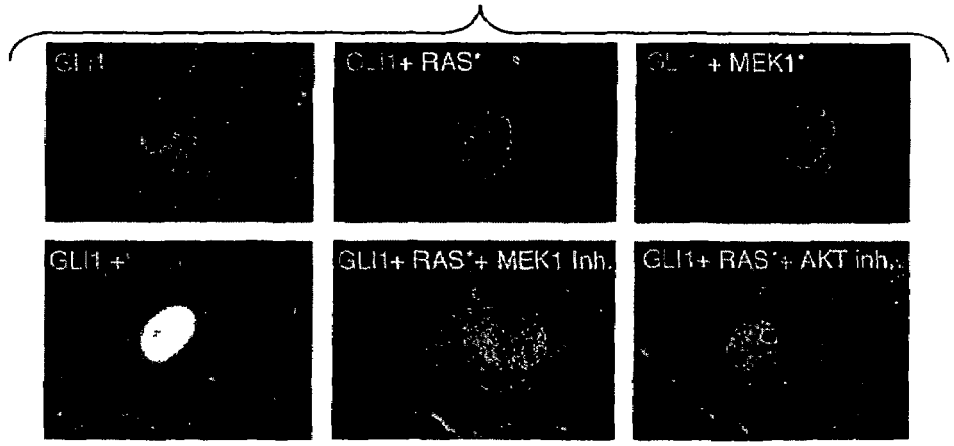

For a second test case using a transformed cell of a different species unrelated to oncogenic RAS-MEK/AKT signaling, we used monkey COS7 cells, which express SV40 large T antigen. These cells localize transfected GLI proteins largely to the cytoplasm (Ruiz i Altaba, A. Gli proteins encode context-dependent positive and negative functions: implications for development and disease. *Development* 126, 3205-3216 (1999)). In COS7 cells, transfection of oncogenic NRAS, as activated MEK1 and AKT1, induced the nuclear accumulation of Myc-tagged or HA-tagged GLI1 (FIG. 11c,d, not shown). The effects of oncogenic RAS on the nuclear accumulation of GLI1 were reversed by treatment with MEK or AKT inhibitors for 1 h (FIG. 11c,d). Oncogenic RAS-MEK/AKT also enhanced the transcriptional activity of GLI1 in COS7 cells by ±4-5 fold from the multimerized GLI binding site luciferase reporter (FIG. 10d), and by ±2 fold from a PTCH1 promoter-luciferase reporter (FIG. 10d, PTCH-BS series). GLI3R inhibited the enhancement of GLI1-mediated luciferase expression by oncogenic NRAS$^{Q61K}$, HRAS$^{V12G}$, and activated MEK1 and AKT1 in a concentration-dependent manner (FIG. 10d and not shown). Gli2 had a minor effect on luciferase reporters but an N'Δ construct behaved like GLI1. Since such a form is not known to exist in vivo we did not elaborate. The increase in luciferase activity by transfected NRAS$^{Q61K}$ over background (±3-4 fold RAS* over GLI-BS reporter alone; FIG. 10a-d) suggested activation of endogenous GLI1, itself a target of GLI1 activity. Indeed, NRAS$^{Q61K}$ enhanced endogenous Gli1 expression in COS7 cells (not shown). Together, the data indicate that the regulation of GLI1 by oncogenic RAS is conserved in different species and cells.

GLI1 is known to shuttle between nucleus and cytoplasm with nuclear export depending on a Crm-mediated mechanism, which can be blocked specifically with leptomycin B (LMB) yielding GLI1 fully nuclear and increasing its activity (Kogerman, P. et al. Mammalian suppressor-of-fused modulates nuclear-cytoplasmic shuttling of Gli-1. *Nat Cell Biol.* 1, 312-319 (1999)). Transfection of COS7 cells with GLI1 induced luciferase activity from a multimerized GLI reporter construct, and this was, as expected, increased ±3-fold by 4 h treatment with LMB (FIG. 11e). Co-expression of GLI1 and NRAS$^{Q61K}$ enhanced the activity of GLI1 by ±6-fold as compared with GLI1 alone (FIG. 11e). However, LMB treatment of cells coexpressing GLI1 and NRAS$^{Q61K}$ resulted in a further ±3-fold increase in GLI activity (FIG. 11e). The nuclear localization and enhanced activity of GLI1 by NRAS$^{Q61K}$ therefore does not appear to be related to a block of nuclear export, as LMB increases the activity of GLI1 alone or after enhancement by NRAS$^{Q61K}$.

Figure 12A:
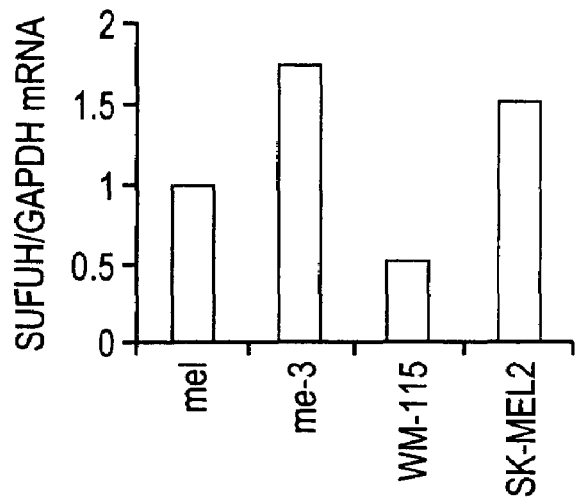
Figure 12B:
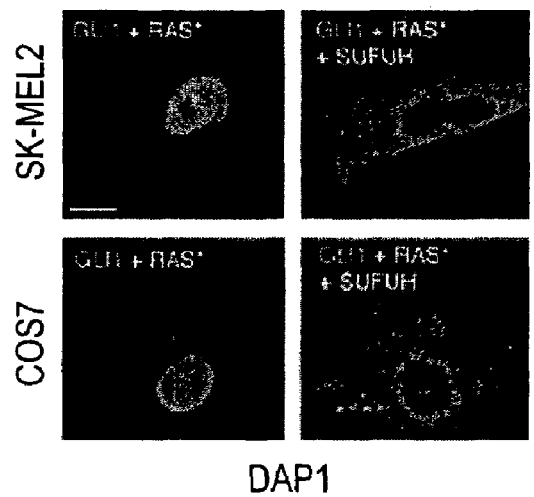
Figure 12C:
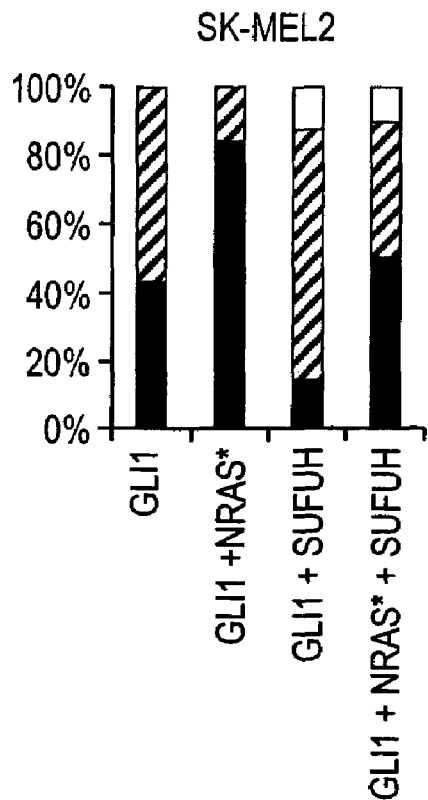
Figure 12D:
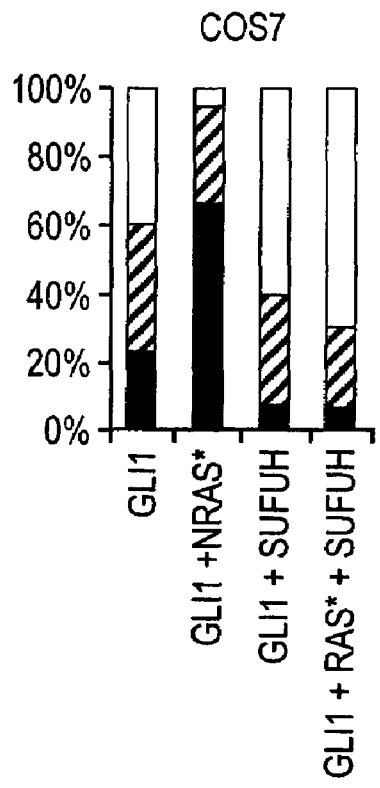
Figure 12E:
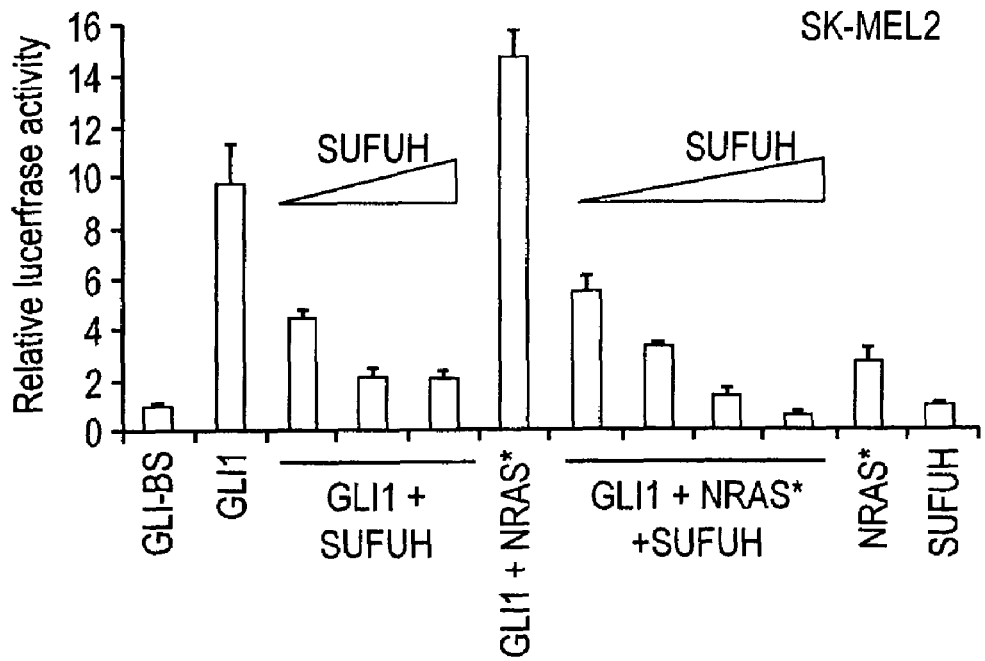
Figure 12F:
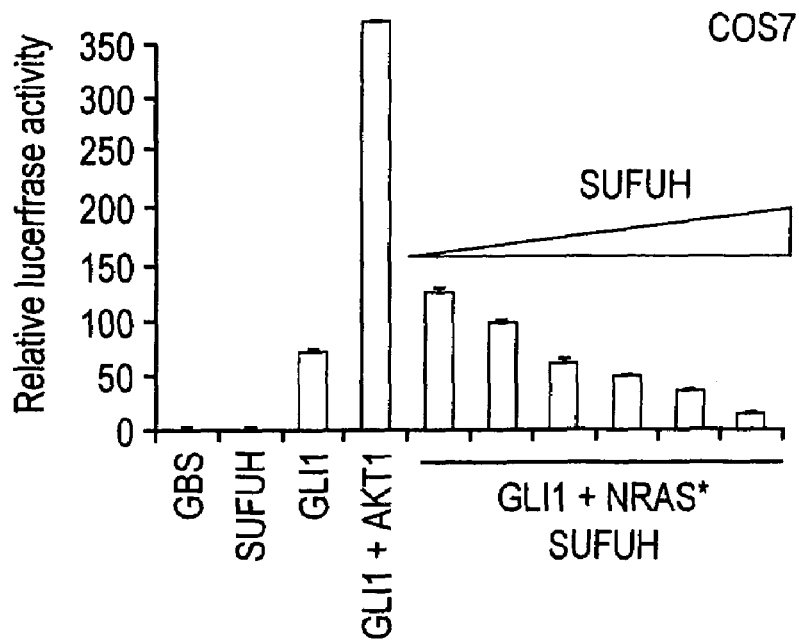
Figure 12G:
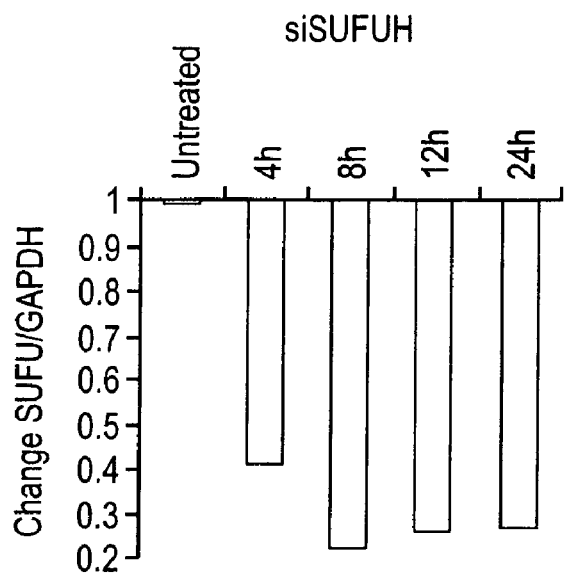

SUFUH Inhibits RAS-Mediated Enhancement of GLI1 Activity, Nuclear Localization and Melanoma Growth SUFUH is an essential negative regulator of SHH-GLI signaling known to inhibit the transcriptional activity of GLI proteins and to sequester them in the cytoplasm (Kogerman, P. et al. Mammalian suppressor-of-fused modulates nuclear-cytoplasmic shuttling of Gli-1. *Nat Cell Biol.* 1, 312-319 (1999); Ding, Q. et al. Mouse suppressor of fused is a negative regulator of sonic hedgehog signaling and alters the subcellular distribution of Gli1. *Curr Biol.* 9, 1119-1122 (1999); Svärd, J. et al. Genetic elimination of suppressor of fused reveals an essential repressor function in the Mammalian hedgehog signaling pathway. *Dev Cell.* 10, 187-197 (2006)) that we found variously expressed in human melanocytes, human and mouse melanomas and melanoma cell lines (FIG. 12a and not shown). In transfected SK-Mel2 and COS7 cells, SUFUH reversed the localization of nuclear GLI1 driven by oncogenic NRAS$^{Q61K}$, rendering it cytoplasmic (FIG. 12b-d). SUFUH also inhibited the transcriptional activity of GLI1, alone or after enhancement by cotransfected oncogenic NRAS$^{Q61K}$ in a concentration-dependent manner in both SK-Mel2 and COS7 cells (FIG. 12e,f).

Figure 12H:
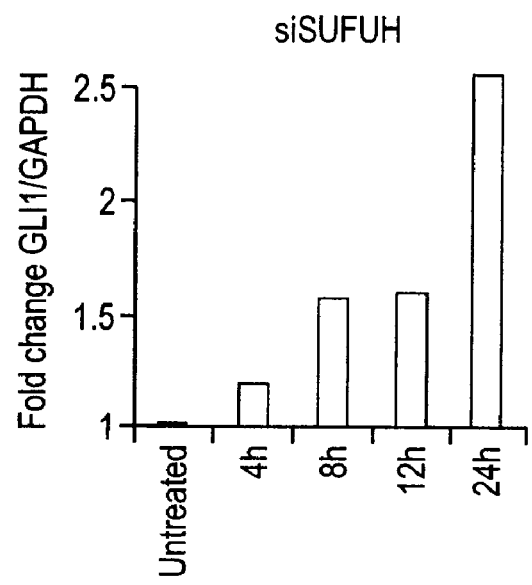
Figure 12I:
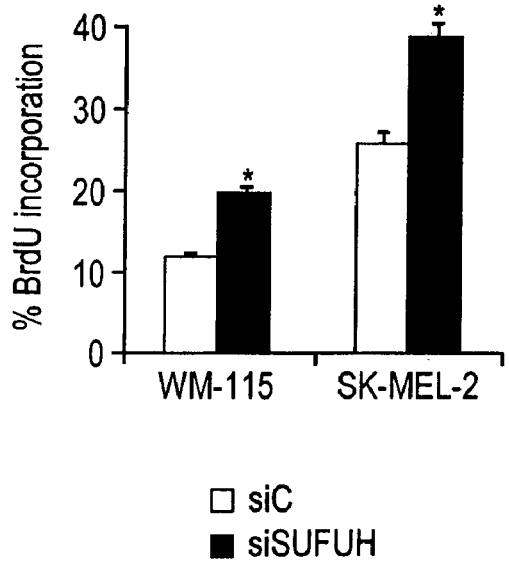
Figure 12J:
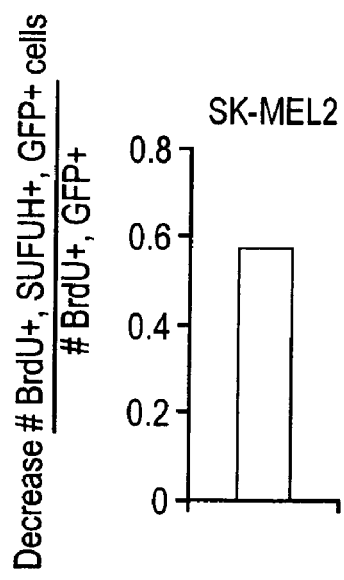

Direct testing of the role of SUFUH in human melanoma cells using two commercial, target-validated small interference RNAs (siRNAs) showed decreased SUFUH mRNA levels (FIG. 12g and not shown) and enhancement of GLI1 expression (FIG. 12h). This is consistent with the activation of Gli1 in Sufu$^{-/-}$ mice (Svärd, J. et al. Genetic elimination of suppressor of fused reveals an essential repressor function in the Mammalian hedgehog signaling pathway. *Dev Cell.* 10, 187-197 (2006)) and after its inhibition with siRNAs in a cell line (Varjosalo, M., Li, S. P. & Taipale, J. Divergence of Hedgehog Signal Transduction Mechanism between *Drosophila* and Mammals. *Dev Cell.* 10, 177-186 (2006)). Consequently, interference with SUFUH boosted melanoma cell proliferation by ±1.5-2-fold in WM-115 and SK-Mel2 cells (FIG. 12i). Conversely, elevating the levels of SUFUH by transfection of expressing plasmids into SK-Mel2 melanoma cells inhibited proliferation by ±45%, as assessed by BrdU incorporation after 48 h as compared with empty vector controls (FIG. 12j). Therefore, the balance and strength of SUFUH and RAS-MEK/AKT activities determines the behavior and function of GLI1, itself first induced by active SHH signaling, and hence melanoma growth. Moreover, RAS-MEK/AKT signaling does not directly act on GLI, but does prevent the inhibition of GLI by SUFUH. Therefore, based on the studies presented here, a method of inhibiting cellular proliferation or tumor cell formation by preventing the action of RAS on SUFUH/GLI is proposed.

Discussion

Two kinds of results have implicated SHH-GLI1 signaling in sporadic human cancers (Ruiz i Altaba, A. ed. *Hedgehog-Gli Signaling in Human Disease*. Austin: Landes Bioscience/Eurekah; New York: Springer Science+Business Media (2006)): i) Many types of sporadic tumors, including basal cell carcinomas, medulloblastomas, prostate cancer, melanomas and their metastases, consistently display an active pathway, and ii) these tumors require sustained pathway activity for continued growth (e.g. Stecca, B. et al. Melanocyte proliferation and melanoma growth, recurrence and metastasis require sustained SONIC HEDGEHOG-GLI signaling. *Submitted*. (2006); Sanchez, P. et al. Inhibition of prostate cancer proliferation by interference with SONIC HEDGEHOG-GLI1 signaling. *Proc. Natl. Acad. Sci. USA.* 101, 12561-12566 (2004); Dahmane, N. et al. The Sonic Hedgehog-Gli pathway regulates dorsal brain growth and tumorigenesis. *Development* 128, 5201-5212 (2001); Dahmane, N., Lee, J., Robins, P., Heller, P. & Ruiz i Altaba, A. Activation of the transcription factor Gli1 and the Sonic hedgehog signalling pathway in skin tumours. *Nature* 389, 876-881 (1997); Berman, D. M. et al. Medulloblastoma growth inhibition by hedgehog pathway blockade. *Science* 297, 1559-1561 (2002); Thayer, S. P. et al. Hedgehog is an early and late mediator of pancreatic cancer tumorigenesis. *Nature* 425, 851-856 (2003); Karhadkar, S. S. et al. Hedgehog signalling in prostate regeneration, neoplasia and metastasis. *Nature* 431, 707-712 (2004)). Here we show that GLI1 functions as a nodal point for the integration of SHH and RAS-MEK/AKT signaling in cancer.

Using melanomas as a tumor that requires both SHH-GLI signaling (Stecca, B. et al. Melanocyte proliferation and melanoma growth, recurrence and metastasis require sustained SONIC HEDGEHOG-GLI signaling. *Submitted*. (2006)) and oncogenic RAS-MEK/AKT function (Meier, F. et al. The RAS/RAF/MEK/ERK and PI3K/AKT signaling pathways present molecular targets for the effective treatment of advanced melanoma. *Front Biosci.* 10, 2986-3001 (2005)), we demonstrate that on one hand, the induction of GLI1 mRNA requires an active SHH pathway, but the levels, subcellular localization and transcriptional activity of GLI1 are modulated by RAS-MEK and AKT signaling, which are known to have multiple effects. On the other hand, the proliferative effects of RAS-MEK/AKT signaling on human melanomas depend on positive GLI activity, as these are inhibited by cyclopamine and GLI3R. We also show that SUFUH, an essential regulator of SHH-GLI signaling, modulates melanoma growth and that it can inhibit the action of GLI1 and compete the effects of oncogenic RAS.

We propose a model (FIG. 13) in which SHH signaling first induces GLI1 expression and blocks the formation of dominant GLI3R (Ruiz i Altaba, A. ed. *Hedgehog-Gli Signaling in Human Disease*. Austin: Landes Bioscience/Eurekah; New York: Springer Science+Business Media (2006)) but then GLI1 activity is enhanced by RAS-MEK/AKT signaling. Thus, ligand-dependent physiological PGF-RAS-MEK/AKT and SHH signaling are predicted to act together to modulate GLI function in a temporally, spatially and context-dependent controlled manner. This yields patterned growth and homeostasis. In contrast, combined oncogenic RTK-RAS-RAF/AKT signaling and SHH pathway activity shift GLI function to an active state, overwhelming or constitutively repressing the action of pathway inhibitors.

RAS-MEK/AKT function may directly potentiate GLI1 transcriptional activity and nuclear localization or/and repress the action of GLI antagonists. It could also enhance positive GLI function by rendering full-length GLI proteins nuclear, thereby enhancing GLI-GLI interactions (Nguyen, V., Chokas, A. L., Stecca, B. & Ruiz i Altaba, A. Cooperative requirement of the Gli proteins in neurogenesis. *Development* 132, 3267-3279 (2005)) and preventing their cytoplasmic processing or degradation. The difference in the induction from a multimerized GLI binding site reporter versus the PTCH1 reporter with a single functional binding site suggests that RAS action might favor expression of targets with multiple GLI binding sites. Positive autocrine same-pathway and cross-pathway feedback loops—triggered for example through the activation of PDGFR☐ by SHH-GLI signaling (this work Dahmane, N. et al. The Sonic Hedgehog-Gli pathway regulates dorsal brain growth and tumorigenesis. *Development* 128, 5201-5212 (2001); Xie, J. et al. A role of PDGFRalpha in basal cell carcinoma proliferation. *Proc. Natl. Acad. Sci. USA.* 98, 9255-9259 (2001))—may also contribute to tumor maintenance (e.g. Furge, K. A. et al. Suppression of Ras-mediated tumorigenicity and metastasis through inhibition of the Met receptor tyrosine kinase. *Proc Natl Acad Sci USA* 98, 10722-10727 (2001); Satyamoorthy, K. et al. Constitutive mitogen-activated protein kinase activation in melanoma is mediated by both BRAF mutations and autocrine growth factor stimulation. *Cancer Res.* 63, 756-759 (2003); Bardeesy, N. et al. Role of epidermal growth factor receptor signaling in RAS-driven melanoma. *Mol Cell Biol.* 25, 4176-4188 (2005)).

Expression of oncogenic RAS from a tyrosinase promoter induces melanoma in transgenic mice (Chin, L. et al. Essential role for oncogenic Ras in tumour maintenance. *Nature* 400, 468-472 (1999); Ackermann, J. et al. Metastasizing melanoma formation caused by expression of activated N-RasQ61K on an INK4a-deficient background. *Cancer Res.* 65, 4005-4011 (2005)) with sustained signaling being required for melanoma growth (Chin, L. et al. Essential role for oncogenic Ras in tumour maintenance. *Nature* 400, 468-472 (1999)). Both HRAS$^{V12G}$ and NRAS$^{Q61K}$ can induce cutaneous melanomas but only the latter metastasize (Chin, L. et al. Essential role for oncogenic Ras in tumour maintenance. *Nature* 400, 468-472 (1999); Ackermann, J. et al. Metastasizing melanoma formation caused by expression of activated N-RasQ61K on an INK4a-deficient background. *Cancer Res.* 65, 4005-4011 (2005)). Since both oncogenes engage the MEK and AKT cascades and behave similarly in our assays the difference could be due to background modifiers or expression levels. However, not all expressing cells in either case give rise to tumors. We propose that tumors develop in cells with oncogenic RAS-MEK/AKT activity that necessarily acquire sustained SHH-GLI pathway function. This is consistent with our demonstration that all NRAS$^{Q61K}$ mouse melanomas tested express Gli1 and require sustained signaling. Conversely, sustained RAS-MEK/AKT signaling may induce tumorigenesis from GLI1$^+$ cells, with sustained RAS function being required for sustained enhanced GLI activity. We have shown that GLI1$^+$ cells include a variety of progenitors in tissues such as granule cell precursors in the developing cerebellum and other dorsal brain regions (Dahmane, N. et al. The Sonic Hedgehog-Gli pathway regulates dorsal brain growth and tumorigenesis. *Development* 128, 5201-5212 (2001); Dahmane, N. & Ruiz i Altaba, A. Sonic hedgehog regulates the growth and patterning of the cerebellum. *Development* 126(14), 3089-3100 (1999)), brain stem cells (Palma, V. & Ruiz i Altaba, A. Hedgehog-GLI signaling regulates the behavior of cells with stem cell properties in the developing neocortex. *Development* 131, 337-345 (2004); Palma, V. et al. Sonic hedgehog controls stem cell behavior in the postnatal and adult brain. *Development* 132, 335-344 (2005)), epithelial cells of the human prostate gland (Sanchez, P. et al. Inhibition of prostate cancer proliferation by interference with SONIC HEDGEHOG-GLI1 signaling. *Proc. Natl. Acad. Sci. USA.* 101, 12561-12566 (2004)), and keratinocyte and melanocyte precursors in the human hair follicle (Stecca, B. et al. Melanocyte proliferation and melanoma growth, recurrence and metastasis require sustained SONIC HEDGEHOG-GLI signaling. *Submitted.* (2006); Dahmane, N., Lee, J., Robins, P., Heller, P. & Ruiz i Altaba, A. Activation of the transcription factor Gli1 and the Sonic hedgehog signalling pathway in skin tumours. *Nature* 389, 876-881 (1997)). Oncogenic RAS-MEK/AKT and sustained SHH-GLI signaling could thus cooperate to induce cancer from progenitor/stem cell populations.

Peptide growth factor-RAS-MEK/PI3K-AKT and SHH-GLI signaling pathways are involved in numerous aspects of development and homeostasis, and underlie a major part of human cancers. Our data provide a basis to explain a multitude of results in these contexts, including our previous finding that EGF and SHH signaling synergize in the control of the proliferation of neural stem cell lineages (Palma, V. & Ruiz i Altaba, A. Hedgehog-GLI signaling regulates the behavior of cells with stem cell properties in the developing neocortex. *Development* 131, 337-345 (2004); Palma, V. et al. Sonic hedgehog controls stem cell behavior in the postnatal and adult brain. *Development* 132, 335-344 (2005)). Other results that can be explained by our data include: i) SHH signaling requires PI3K-AKT activity in capillary morphogenesis (Kanda, S. et al. Sonic hedgehog induces capillary morphogenesis by endothelial cells through phosphoinositide 3-kinase. *J. Biol. Chem.* 278, 8244-8249 (2003)). ii) The in vitro oligodendrocyte-inducing activity of SHH depends on FGFR and MEK function (Kessaris, N., Jamen, F., Rubin, L. L. & Richardson, W. D. Cooperation between sonic hedgehog and fibroblast growth factor/MAPK signalling pathways in neocortical precursors. *Development* 131, 1289-1298 (2004)). iii) SHH and PI3K-AKT signaling synergize in cerebellar precursor proliferation (Kenney, A. M., Widlund, H. R. & Rowitch, D. H. Hedgehog and PI-3 kinase signaling converge on Nmyc1 to promote cell cycle progression in cerebellar neuronal precursors. *Development* 131, 217-228 (2004)). iv) Basal cell carcinoma cell proliferation and survival requires both SHH-GLI and MEK signaling (Dahmane, N., Lee, J., Robins, P., Heller, P. & Ruiz i Altaba, A. Activation of the transcription factor Gli1 and the Sonic hedgehog signalling pathway in skin tumours. *Nature* 389, 876-881 (1997); Xie, J. et al. A role of PDGFRalpha in basal cell carcinoma proliferation. *Proc. Natl. Acad. Sci. USA.* 98, 9255-9259 (2001); Xie, J. et al. Activating Smoothened mutations in sporadic basal-cell carcinoma. *Nature* 391, 90-92 (1998); Williams, J. A. et al. Identification of a small molecule inhibitor of the hedgehog signaling pathway: effects on basal cell carcinomalike lesions. *Proc Natl Acad Sci USA* 100, 4616-4621 (2003); Athar, M. et al. Inhibition of smoothened signaling prevents ultraviolet B-induced basal cell carcinomas through regulation of Fas expression and apoptosis. *Cancer Res.* 64, 7545-7552 (2004)). v) Medulloblastomas require both SHH-GLI (Dahmane, N. et al. The Sonic Hedgehog-Gli pathway regulates dorsal brain growth and tumorigenesis. *Development* 128, 5201-5212 (2001); Berman, D. M. et al. Medulloblastoma growth inhibition by hedgehog pathway blockade. *Science* 297, 1559-1561 (2002)) and PDGF-MEK (MacDonald, T. J. et al. Expression profiling of medulloblastoma: PDGFRA and the RAS/MAPK pathway as therapeutic targets for metastatic disease. *Nat Genet.* 29, 143-152 (2001)) signaling; and SHH synergizes with IGF2-AKT in the induction of medulloblastoma in mice (Rao, G. et al. Sonic hedgehog and insulin-like growth factor signaling synergize to induce medulloblastoma formation from nestin-expressing neural progenitors in mice. *Oncogene* 23, 6156-6162 (2004); Hartmann, W. et al. Insulin-like growth factor II is involved in the proliferation control of medulloblastoma and its cerebellar precursor cells. *Am. J. Pathol.* 166, 1153-1162 (2005). vi) Gliomas have been proposed to depend on SHH-GLI signaling (Dahmane, N. et al. The Sonic Hedgehog-Gli pathway regulates dorsal brain growth and tumorigenesis. *Development* 128, 5201-5212 (2001)) and commonly harbor mutations activating EGFR and/or inactivating PTEN, leading to RAS-MEK/AKT function (Maher, E. A. et al. Malignant glioma: genetics and biology of a grave matter. *Genes Dev.* 15, 1311-1333 (2001)). vii) The induction of rhabdomyosarcomas by SHH in mice requires IGF2-AKT activity (Kappler, R. et al. Molecular characterization of Patched-associated rhabdomyosarcoma. *J Pathol.* 200, 348-356 (2003)). We note, however, that the effects of RAS on GLI1 function are context-dependent as the differentiation of C3H10T1/2 by transfected GLI1 was impaired by oncogenic NRAS (not shown).

Tumors of different grades within a SHH-GLI-dependent cancer type, including cutaneous and metastatic melanomas (Stecca, B. et al. Melanocyte proliferation and melanoma growth, recurrence and metastasis require sustained SONIC HEDGEHOG-GLI signaling. *Submitted.* (2006)) as well as local and metastatic prostate cancers (Sanchez, P. et al. Inhibition of prostate cancer proliferation by interference with SONIC HEDGEHOG-GLI1 signaling. *Proc. Natl. Acad. Sci. USA.* 101, 12561-12566 (2004); Karhadkar, S. S. et al. Hedgehog signalling in prostate regeneration, neoplasia and metastasis. *Nature* 431, 707-712 (2004)), show a common dependency on SHH-GLI signaling. However, cell-intrinsic (Sanchez, P. et al. Inhibition of prostate cancer proliferation by interference with SONIC HEDGEHOG-GLI1 signaling. *Proc. Natl. Acad. Sci. USA.* 101, 12561-12566 (2004)) or ligand-dependent (Karhadkar, S. S. et al. Hedgehog signalling in prostate regeneration, neoplasia and metastasis. *Nature* 431, 707-712 (2004)) increases in signaling strength have been proposed to underlie tumor progression, which is sometimes correlated with increases in the expression or activity of pathway components (e.g. Stein, U. et al. GLI gene expression in bone and soft tissue sarcomas of adult patients correlates with tumor grade. *Cancer Res.* 59, 1890-1895 (1999); Grachtchouk, V. et al. The magnitude of hedgehog signaling activity defines skin tumor phenotype. *EMBO J.* 22, 2741-2751 (2003)). Our present findings on the modulation of GLI1 activity by oncogenic RAS-MEK/AKT in melanoma raises the possibility that the acquisition of oncogenic mutations that progressively activate these pathways during tumor progression (e.g. Meier, F. et al. The RAS/RAF/MEK/ERK and PI3K/AKT signaling pathways present molecular targets for the effective treatment of advanced melanoma. *Front Biosci.* 10, 2986-3001 (2005); Davies, H. et al. Mutations of the BRAF gene in human cancer. *Nature* 417, 949-954 (2002); Stahl, J. M. et al. Deregulated Akt3 activity promotes development of malignant melanoma. *Cancer Res.* 64, 7002-7010 (2004); Chudnovsky, Y., Khavari, P. A. & Adams, A. E. Melanoma genetics and the development of rational therapeutics. *J. Clin. Invest.* 115, 813-824 (2005); Tsao, H., Zhang, X., Fowlkes, K. & Haluska, F. G. Relative reciprocity of NRAS and PTEN/MMAC1 alterations in cutaneous melanoma cell lines. *Cancer Res.* 60, 1800-1804 (2000)) results in increasing, cell-intrinsic levels of positive GLI1 function in metastatic disease. Sequential, cell-autonomous, oncogene-driven increases in the level of nuclear, positive GLI1 transcriptional activity could therefore underlie progression of melanomas and other SHH-GLI-dependent cancers.

The many human cancers that depend on sustained SHH-GLI function, including melanoma, basal cell carcinomas, medulloblastoma, glioma, prostate and pancreas cancers (Ruiz i Altaba, A. ed. *Hedgehog-Gli Signaling in Human Disease*. Austin: Landes Bioscience/Eurekah; New York: Springer Science+Business Media (2006)) also involve RTK-RAS-MEK activity triggered by a variety of growth factors that include EGF, FGF, PDGF, IGF, HGF and Endothelin3; and PI3K-AKT activity often triggered by loss of PTEN (e.g. Meier, F. et al. The RAS/RAF/MEK/ERK and PI3K/AKT signaling pathways present molecular targets for the effective treatment of advanced melanoma. *Front Biosci.* 10, 2986-3001 (2005); Xie, J. et al. A role of PDGFRalpha in basal cell carcinoma proliferation. *Proc. Natl. Acad. Sci. USA.* 98, 9255-9259 (2001); MacDonald, T. J. et al. Expression profiling of medulloblastoma: PDGFRA and the RAS/MAPK pathway as therapeutic targets for metastatic disease. *Nat Genet.* 29, 143-152 (2001); Kappler, R. et al. Molecular characterization of Patched-associated rhabdomyosarcoma. *J Pathol.* 200, 348-356 (2003)). Thus, inhibiting positive GLI function through a strategy combining SHH-GLI pathway antagonists, or agonists of pathway inhibitors, plus agents leading to the inhibition of RAS-RAF-MEK and PI3K-AKT activities represents a wide-ranging, rational therapeutic goal.

Example 3

Synergistic Effect of an AKT Inhibitor or an MEK Inhibitor Combined with Cyclopamine on Proliferation of Tumor Cells Synergistic Effect of an AKT Inhibitor Plus Cyclopamine on Proliferation of Mewo Cells.

A study was conducted to determine whether the effective dose of cyclopamine could be lowered if this therapy was combined with the use of an AKT inhibitor, SH6. The effect of combination therapy on the proliferation of tumor cells is shown in FIG. 14, which is a histogram of the change in BrdU incorporation in Mewo Cells in the presence of suboptimal concentrations of an AKT inhibitor SH6 plus cyclopamine. Mewo cells were treated for 48 hours with either 5 µM of cyclopamine alone, or 20 µM of SH6 alone, or a combination of each at the given concentrations. Cell proliferation was assessed after incubation with BrdU as described. As shown in the figure, suboptimal doses of cyclopamine were significantly effective when combined with the AKT inhibitor, SH6.

Synergistic Effect of an MEK Inhibitor Plus Cyclopamine on Proliferation of WM115 Cells.

A study was conducted to determine whether the effective dose of cyclopamine could be lowered if this therapy was combined with the use of an MEK inhibitor, U0126. The effect of combination therapy on the proliferation of tumor cells is shown in FIG. 15, which is a histogram of the change in BrdU incorporation in WM115 cells in the presence of suboptimal concentrations of an MEK inhibitor U0126 plus cyclopamine. WM115 cells were treated for 48 hours with either 5 µM of cyclopamine alone, or 1 µM of U0126 alone, or a combination of each at the given concentrations. Cell proliferation was assessed after incubation with BrdU as described. As shown in the figure, suboptimal doses of cyclopamine were significantly effective when combined with the MEK inhibitor, U0126.

TABLE 1

Clinical data on melanoma samples.

| Sample | Gender[a] | Age | Type[b] | Localization | Breslow | Stage |
|---|---|---|---|---|---|---|
| 1 | M | 17 | BN | Lip | — | — |
| 2 | F | 39 | BN | Axilla | — | — |
| 3 | F | 69 | BN | Axilla | — | — |
| 4 | F | 28 | BN | Scalp | — | — |
| 5 | M | 28 | BN | Scalp | — | — |
| 6 | F | 30 | BN | Temple | — | — |
| 7 | F | 28 | BN | Hip | — | — |
| 8 | F | 40 | BN | Hip | — | — |
| 9 | M | 41 | BN | Cheek | — | — |
| 10 | F | 13 | BN | Neck | — | — |
| 11 | F | 40 | BN | Neck | — | — |
| 12 | M | 43 | AN | Abdomen | — | — |
| 13 | F | 40 | AN | Abdomen | — | — |
| 14 | n.a. | n.a. | AN | n.a. | — | — |
| 15 | M | 65 | PM | Thumb | 10 | II |
| 16 | F | 47 | PM | Back | 2.2 | III |
| 17 | M | 63 | LNM | LN sub-clavic | 1.7 | III |
| 18 | M | 37 | LNM | LN inguinal | 7 | III |
| 19 | M | 69 | LNM | LN inguinal | 3.3 | III |
| 20 | M | 26 | LNM | LN inguinal | 1.2 | III |
| 21 | M | 41 | LNM | LN obturator | 1.5 | III |
| 22 | M | 40 | LNM | LN prerenal | 0.91 | IV |
| 23 | M | 76 | CM | Back | 4 | III |
| 24 | F | 52 | Met. | Cervical | n.a. | IV |
| 25 | F | 45 | Met. | Brain | 4 | IV |
| 26 | M | 38 | Met. | Sub-cut | 4.6 | III |
| 27 | F | 47 | Met. | Sub-cut | 0.7 | IV |

[a]Gender. M: Male; F: Female
[b]Type. AN; Atypical Nevus; BN: Benign Nevus; CM: Cutaneous Metastasis; LNM: Lymph Node Metastasis; Met: Metastasis in other tissues; PM: Primary Melanoma.
n.a.: data not available. Preliminary analyses of 25 additional melanomas confirm ubiquitous GLI1 expression.

TABLE 2

Clinical data and results of melanoma samples subjected to in situ hybridization.
In situ hybridization samples

| | Gender[a] | Age | Type[b] | Site | Breslow | Stage | Expression | FIG. 2 |
|---|---|---|---|---|---|---|---|---|
| 28 | M | 49 | BN | Eyebrow | — | — | S/P/1/2/3* | |
| 29 | M | 42 | BN | Forehead | — | — | S/P/1/2/3* | top row |
| 30 | n.a. | n.a. | LNM | LN iliac | n.a. | n.a. | P/1/2/3* | |
| 31 | M | 80 | LNM | LN inguinal | n.a. | III | P/1/2/3* | |
| 32 | M | n.a. | LNM | LN axilla | n.a. | IV | S/P/1/2/3* | bottom row |
| 33 | F | 54 | CM | Back | 4.68 | III | S/P/1/2/3* | third row |
| 34 | F | 71 | CM | Skin inguinal | 3 | III | S/P/1/2/3* | |

TABLE 2-continued

Clinical data and results of melanoma samples subjected to in situ hybridization.

In situ hybridization samples

|    | Gender[a] | Age | Type[b] | Site    | Breslow | Stage | Expression  | FIG. 2     |
|----|-----------|-----|---------|---------|---------|-------|-------------|------------|
| 35 | F         | 75  | CM      | Leg     | 1.5     | III   | S/P/1/2/3*  |            |
| 36 | F         | 69  | CM      | Leg     | 8.8     | IV    | S/P/1/2/3*  |            |
| 37 | M         | 84  | CM      | Leg     | 2       | IV    | S/P/1/2/3*  | second row |
| 38 | M         | 40  | Met.    | Sub-cut | 0.91    | IV    | S/P/1/2/3*  |            |

*Detected expression of S = SHH; P = PTCH1; 1 = GLI1; 2 = GLI2; 3 = GLI3.
[a]Gender. M: Male; F: Female
[b]Type. BN: Benign Nevus; LNM: Lymph Node Metastasis; CM: Cutaneous Metastases; Met: Metastasis in other tissues
n.a.: data not available

TABLE 3

Clinical data of melanoma samples used for primary cultures.

Cell Cultures

| Sample | Name | Gender[a] | Age  | Type[b] | Site      | Breslow | Stage |
|--------|------|-----------|------|---------|-----------|---------|-------|
| 39     | Me-2 | M         | n.a. | LNM     | LN axilla | n.a.    | IV    |
| 40     | Me-1 | M         | 85   | CM      | Thigh     | 1.2     | III   |
| 41     | Me-3 | F         | 75   | CM      | Leg       | 1.5     | III   |
| 42     | Me-4 | F         | 69   | CM      | Leg       | 8.8     | IV    |
| 43     | Me-5 | M         | 84   | CM      | Leg       | 2       | IV    |

[a]Gender. M: Male; F: Female
[b]Type. CM: Cutaneous Metastasis; LNM: Lymph Node Metastasis.
n.a.: data not available

TABLE 4

| COMPOUND       | CELL TYPE               | $IC_{50}$        | REFERENCE NOS. |
|----------------|-------------------------|------------------|----------------|
| L-731,734      | Fibroblasts             | 1                | Kohl, et al., Science, 1993; 260: 1934-1937 |
| L-739,749      | Rat-1 fibroblasts       | 2.5              | Prendergast, GC, et al., Mol. Cell. Biol. 1994; 14: 4193-4202 |
|                |                         |                  | James G., et al., Proc Natl Acad Sci USA 1996; 93: 4454-4458 |
|                | JMML cells              | 1-10             | Emanuel, PD, et al., Blood. 2000; 95: 639-645 |
| B581           | NIG3T3 cells            | —                | Cox, AD., et al., J. Biol Chem, 1994; 269-19203-19206 |
| BZA-5B         | Rat-1 cells             | —                | James, GL., et al., Science, 1993; 260: 1937-1942 |
|                |                         |                  | James GL, et al., J. Biol. Chem. 1995; 270: 6221-6226 |
| BZA-2B         |                         |                  | James GL., et al., J. Biol. Chem. 1994; 269: 27705-27714 |
|                |                         |                  | James G., et al., Proc Natl Acad Sci USA 1996; 93: 4454-4458 |
| B956, B1086    | Human tumor cell lines  | 0.2-0.7          | Nagasu T. et al., Cancer Res. 1995; 55: 5310-5314 |
|                |                         | 3-7              |                |
|                |                         | 1.7-50           |                |
| SCH44342       | Cos cells               | —                | Bishop, WR, et al., J. Biol. Chem. 1995: 270: 30611-30618 |
|                | Various human tumor cell lines | 1         | Sepp-Lorenzino, L., et al., Cancer Res. 1995; 55: 5302-5309 |
| L-744,832      |                         | 1-10             | Emanuel, PD., et al., Blood. 2000; 95: 639-645 |
| Compound No. 46| NIH3T3                  | 0.19             | Leftheris, K., et al., J. Med. Chem. 1996; 39: 224-236 |
| FTI-277        | Glioma cell lines       | 2.0-15.5         | Bredel, M., et al., Neurosurgery. 1998; 43: 124-131 |
| Compound No. 10| Rat-1 cells             | 2.5-5            | DeSolms, S J., et al., J. Med. Chem 1998; 41: 2651-2656 |
| Compound 5m    | HIH3T3 cells            | 0.18             | McNamara, DJ., et al., J. Med. Chem. 1997; 40-3319-3322 |
| FTS*           | Rat-1 cells             | 30-40*           | Jansen, B., et al., Proc Natl Acad Sci USA 1999; 96: 14019-14024 |
|                | Human melanoma cell lines | 100*           |                |

Several Ftase inhibitors have been demonstrated to revert specifically the Ras-transformed phenotype and anchorage-independent growth in fibroblasts and human tumor cell lines. Cell growth inhibition may be a result of induction of apoptosis or arrest in the G1 phase of the cell cycle.
*FTS, S-farnesylthiosalicyclic acid, is an inhibitor of PPMTase.

TABLE 5

| COMPOUND | MODEL/TUMOR                | DOSE (mg/kg/d) | GROWTH INHIBITION | REF. NOS. |
|----------|----------------------------|----------------|-------------------|-----------|
| Manumycin| Nude mice/K-Ras fibrosarcoma |              | 70%               | Hara, M., et al., ProcNatlAcadSci USA 1993; 90: 2281-2285 |

TABLE 5-continued

| COMPOUND | MODEL/TUMOR | DOSE (mg/kg/d) | GROWTH INHIBITION | REF. NOS. |
|---|---|---|---|---|
| | Balb/c nude mice/pancreas (MIAPaCa-2) carcinoma | 1, 2, 5 | | Ito, T., et al., Jpn J Cancer Res 1996; 87: 113-116 |
| L-739,749 | Nude Harlan mice/Rat-1 cell tumors | 20 | 51%-66% | Kohl, NE, et al., ProcNatlAcadSci USA 1994; 91: 9141-9145 |
| B956, B1086 | Nude mice/bladder (EJ-1) Fibrosarcoma (HT1080) Colon (HCT 116) | 100 | | Nagasu, et al., Cancer Res 1995; 55: 5310-5314 |
| L-744,832 | MMTV-v-H-RAS transgenic mice/ Mammary, salivary Carcinoma | 10-40 40 | −5.4 vs 16.7 −7.7 vs 11.8 −9.9 vs 33.3 −12.3 vs 26.3 −10.2 vs 43.6 | Kohl, NE, et al., Nat Med 1995; 1: 792-797 Barrington, R E, et al., MolCellBiol. 1998; 18: 85-92 |
| FTI-276 FTI-277 | Nude Harlan Sprague-Dawley Mice/lung (A-549, Calu-1) tumors NIH3T3 | 10, 50, 100 50 | 75% 80% | Sun, J. et al., Cancer Res. 1995; 55: 4243-4247 |
| FTI-276 | A/J mice lung adenomas | 50 | 58% | Lantry LE, et al., Carcinogenesis 2000; 21: 113-116 |
| FTI-276 GGTI-297* | Nude Harlan Sprague-Dawley Mice/lung (A-549, Calu-1) | 70 | 70%-94% 56%-70% | Sun, J., et al., Oncogene 1998; 16: 1467-1473 |
| Compound no. 46 Compound no. 51 | Athymic Balb/c Rat-1 cells | 45 45 | T/C† = 154% T/C† = 142% | Leftheris K., et al., J. Med. Chem. 1996; 39: 224-236 |
| Compound 83b, 85b | Nude mice/colon (DLD-1, SW-260) H-Ras-CVLS fibroblasts H-Ras-CVLL fibroblasts | 10, 50 | 72% 95% 50% | Mallams, AK., et al., J.Med.Chem 1998; 41: 877-893 |
| SCH66336 | Nude mice/colon (DLD-1, HCT 116) Pancreas (MIA PaCa-2) NIH3T3 | 2, 5, 10, 40 | 76% 75% 100% | Njoroge, FG, et al., J.Med.Chem 1998; 41: 4890-4902 |
| Compound no. 4 | Nude mice/colon (DLD-1) | 10, 50 | 70% | Njoroge, FG, et al., J.Med.Chem 1998; 41: 4890-4902 |
| SCH66336 | Nude mice/lung (A549, HTB177) Pancreas (AsPC-1, HPAF-11) Hs 700T, MIA PaCa-2) Colon (HCT116, DLD-1) Prostate (DU-145) Urinary bladder (EJ) Wap-H-RAS transgenic Mice/mammary, salivary tumors | 40 2, 5, 10, 40 | 70%, 83% 72%, 67% 67%, 78% 84%, 76% 86% 100% 67%-86% | Liu M., et al., Cancer Res. 1998; 58: 4947-4956 |
| SCH59228 | Athymic mice/colon (DLD-1) H-Ras and K-Ras Fibroblast tumors | 10, 50 | >90% | Liu M., et al. Cancer Chemother Pharmacol. 1999; 43: 50-58 |
| L-744,832 | MMTV-N-RAS$^N$ transgenic Mice/lymphoid and mammary tumors | 40 | −0.7 vs 28.3 | Mangues, R., et al., Cancer Res. 1998; 58: 1253-1259 |
| L-744,832 | MMTV-TGFa/neu transgenic Mice/mammary tumors | 40 | −7.4 vs 19 | Norgaard, P. et al., ClinCancerRes. 1999; 5: 35-42 |
| Compound 5m | Nude mice/HIG3T3 | 150 | 88 | McNamara, DJ, et al., J.MedChem 1997; 40-3319-3322 |
| FTS* | SCID mice/melanoma (518A2, 607B) | 5* | 82-90 | Jansen, B., et al., ProcNatlAcadSci USA 1999; 96: 14019-14024 |

Several Ftase inhibitors have shown in vivo antitumor activity in mice. These inhibitors have been demonstrated to cause regression of tumors that depend on activated Ras in mouse xenograft and transgenic mouse models. The growth inhibition is given in percent of controls or as the comparison of the tumor mean growth rate (in mm3/day) in the presence or absence of the Ftase inhibitor. Cell growth inhibition may be a result of induction of apoptosis or arrest in the G1 phase of the cell cycle.
*FTS, S-farnesylthiosalicyclic acid, is an inhibitor of PPMTase.
†T/C indicates relative median survival time of treated (T) versus control (C) groups (% T/C values). The activity criterion for increased lifespan was a T/C of ≧125%.

TABLE 6

| Compound | Phase | Malignancy | Status | Protocol ID |
|---|---|---|---|---|
| R115777 | 1 | Solid advanced tumors | Completed | NCI-97-C-0086B |
| R115777 | 1 | Refractory solid tumors (children) | Active | CI-98-C-0141* |
| R115777 | 1 | Refractory or recurrent acute Leukemia or accelerated or blastic phase chronic myeloid leukemia | Active | MSGCC-9802 NCI-T99-0030* MSGCC-0398115 URCC-980300 |
| R115777 | 1 | Advanced cancer | Active | UTHSC-9785011335 NCI-V98-1501 JRF-R115777 SACI-IDD-98-03 |
| L-778,123 | 1 | Refractory or recurrent solid tumors or lymphomas | Active | MSKCC-98116 NCI-G99-1572* MERCK-003-04 |

TABLE 6-continued

| Compound | Phase Malignancy | Status | Protocol ID |
|---|---|---|---|
| SCH663361 | Advanced cancer | Active | MSKCC-99020<br>NCI-G99-1540*<br>SPRI-C98-564-01 |
| SCH6633611 | Metastatic adenocarcinoma of the pancreas | Active | MSKCC-98115<br>NCI-G99-1571*<br>SPRI-C98-545-12 |
| SCH6633611 | Metastatic adenocarcinoma of the pancreas | Active | CWRU-SCH-1298<br>NCI-G99-1534*<br>SPRI-C98-545-18 |
| SCH6633611 | Metastatic adenocarcinoma of the pancreas refractory to gemcitabine | Not yet active | UCLA-9906030<br>NCI-G99-1610*<br>SPRI-P00346 |
| SCH6633611<br>IND128 | Previously treated, inoperable, locally Advanced, or metastatic transitional cell carcinoma of the bladder | Not yet active | CAN-NCIC-IND128<br>SPRI-CAN-NCIC |

Three orally bioavailable Ftase inhibitors have entered several phase I/II clinical trials. Most of these trials are National Cancer Institute - sponsored (*). The malignancies comprise a wide variety of human colid tumors (eg. primary brain tumors such as gliomas, neurofibromas, neurofibrosarcomas and malignant schwannomas, neuroblastomas, Wilms tumors, germ cell tumors, adenocarcinomas of the pancreas) and hematopoietic diseases such as acute leukemias and chronic myeloid leukemia in acceleration and blastic phase.

What is claimed is:

1. A method for inhibiting the synthesis, expression or activity of a GLI protein in a cell comprising, contacting the cell with or introducing into the cell an inhibitor or antagonist of GLI synthesis or expression or activity, wherein the inhibitor or antagonist is the nucleic acid sequence set forth in SEQ ID NO: 1 wherein the contacting or introducing results in inhibition of synthesis, expression or activity of the GLI protein in the cell.

2. The method of claim 1, wherein the introducing further results in inhibition of cellular proliferation or inhibition of tumorigenesis.

3. The method of claim 2, wherein the inhibition of cellular proliferation occurs in a melanocyte, a benign or atypical nevus, a primary melanoma, or a metastatic melanoma.

4. The method of claim 1, wherein the cell is a tumor cell.

5. The method of claim 3, wherein the tumor cell is selected from the group consisting of a melanoma, a melanosarcoma and an amelanotic sarcoma.

* * * * *

SEQUENCE LISTING

<160> NUMBER OF SEQ ID NOS: 78

<210> SEQ ID NO 1
<211> LENGTH: 21
<212> TYPE: RNA
<213> ORGANISM: Artificial Sequence
<220> FEATURE:
<223> OTHER INFORMATION: synthetic

<400> SEQUENCE: 1
aacuccacag gcauacagga u                                              21

<210> SEQ ID NO 2
<211> LENGTH: 21
<212> TYPE: RNA
<213> ORGANISM: Artificial Sequence
<220> FEATURE:
<223> OTHER INFORMATION: synthetic

<400> SEQUENCE: 2
aagaucugga cagggaugac u                                              21

<210> SEQ ID NO 3
<211> LENGTH: 21
<212> TYPE: RNA
<213> ORGANISM: Artificial Sequence
<220> FEATURE:
<223> OTHER INFORMATION: synthetic

<400> SEQUENCE: 3
aaugaggaug aaaguccugg a                                              21

<210> SEQ ID NO 4
<211> LENGTH: 21
<212> TYPE: RNA
<213> ORGANISM: Artificial Sequence
<220> FEATURE:
<223> OTHER INFORMATION: synthetic

<400> SEQUENCE: 4
aacguacgcg gaauacaacg a                                              21

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gggatgatcc cacatcctca gtc                                              23

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
ctggagcagc cccccagt                                                    19

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
caccgctgct caaagagaa                                                   19

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
tctccacgcc actgtcatt                                                   19

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cgaacagatg tgagcgagaa                                                  20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ttgatcaatg aggccctctc                                                  20

<210> SEQ ID NO 11
<211> LENGTH: 19
<212> TYPE: DNA
<213> ORGANISM: Artificial Sequence
<220> FEATURE:
<223> OTHER INFORMATION: primer

```
<400> SEQUENCE: 11
ccacagaagc gctcctaca                                            19

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
ctgtaatttc gccccttcc                                            19

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
tccaaggcac atatccactg                                           20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
ccaggaaagt gaggaagtcg                                           20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cccacacttc aacagcacca                                           20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gctttgtcac aggactttgc                                           20

<210> SEQ ID NO 17
<211> LENGTH: 31
<212> TYPE: DNA
<213> ORGANISM: Artificial Sequence
<220> FEATURE:
<223> OTHER INFORMATION: primer

<400> SEQUENCE: 17
gcgactctcg agcatggaga attgtcacct g                              31

<210> SEQ ID NO 18
```

```
<211> LENGTH: 27
<212> TYPE: DNA
<213> ORGANISM: Artificial Sequence
<220> FEATURE:
<223> OTHER INFORMATION: primer

<400> SEQUENCE: 18
gcgctactcg agttcggttt tgatggt                                              27

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
agatgtagcc cttgtacctc a                                                    21

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
tttaagagct tccatttcta                                                      20

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
cttgccatgt ccaaaccag                                                       19

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
actcgctctc tgccctgtt                                                       19

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
cttcatggtg tggggctag                                                       19

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
```

```
tgtagtccgg gtggtctttc                                               20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gattccttcc aacccagaca                                               20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
gacaccgtgg tggtaggttc                                               20

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
gctacctatc cctgagcctg aa                                            22

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
gggcccaggg aacctgta                                                 18

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
gatcatcggg acagcaaagt g                                             21

<210> SEQ ID NO 30
<211> LENGTH: 23
<212> TYPE: DNA
<213> ORGANISM: Artificial Sequence
<220> FEATURE:
<223> OTHER INFORMATION: primer

<400> SEQUENCE: 30
tttctcataa gcaggtggag cat                                           23

<210> SEQ ID NO 31
<211> LENGTH: 18
<212> TYPE: DNA
```

```
<213> ORGANISM: Artificial Sequence
<220> FEATURE:
<223> OTHER INFORMATION: primer

<400> SEQUENCE: 31
ttcattgatg ccacaaca                                                 18

<210> SEQ ID NO 32
<211> LENGTH: 17
<212> TYPE: DNA
<213> ORGANISM: Artificial Sequence
<220> FEATURE:
<223> OTHER INFORMATION: primer

<400> SEQUENCE: 32
ccattggcag catcagc                                                  17

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
agcaaaaatg acccaccaat g                                             21

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
ggcctggatg gttcaggata                                               20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
accctatgaa cccagccatt                                               20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
tgctgtaacc tgaggtgctg                                               20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
ctctgaagct gagggtggag                                               20
```

-continued

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
ttctcccaat gaacgagacc                                               20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
gagcagatgc aacagcaaga                                               20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40
gtgtttggcc gtagtcaggt                                               20

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
tttgccaaca aggacagttg                                               20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ccctgagtcc catcatcact                                               20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
acctgtcctt ccaccaatca                                               20

<210> SEQ ID NO 44
<211> LENGTH: 20
<212> TYPE: DNA
<213> ORGANISM: Artificial Sequence
<220> FEATURE:

<223> OTHER INFORMATION: primer

<400> SEQUENCE: 44
ccccttaggc agagaggaat					20

<210> SEQ ID NO 45
<211> LENGTH: 19
<212> TYPE: DNA
<213> ORGANISM: Artificial Sequence
<220> FEATURE:
<223> OTHER INFORMATION: primer

<400> SEQUENCE: 45
gctgcctata gccagtgtc					19

<210> SEQ ID NO 46
<211> LENGTH: 19
<212> TYPE: DNA
<213> ORGANISM: Artificial Sequence
<220> FEATURE:
<223> OTHER INFORMATION: primer

<400> SEQUENCE: 46
gaagcaggtg caaagccag					19

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
ctccaggtta ccgctatcgt c					21

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
cacttggtcc gtctgttcct g					21

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
gcaggtttcg actgggtcta					20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
gaaggtgagg aagtcgctgt					20

```
<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
ccagaagcca atgcacctat                                                    20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
ataacagctc ccaccagtgc                                                    20

<210> SEQ ID NO 53
<211> LENGTH: 21
<212> TYPE: DNA
<213> ORGANISM: Artificial Sequence
<220> FEATURE:
<223> OTHER INFORMATION: primer

<400> SEQUENCE: 53
agtatgatga catcaagaag g                                                  21

<210> SEQ ID NO 54
<211> LENGTH: 21
<212> TYPE: DNA
<213> ORGANISM: Artificial Sequence
<220> FEATURE:
<223> OTHER INFORMATION: primer

<400> SEQUENCE: 54
atggtattca agagagtagg g                                                  21

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
atggtcctgg ctctgatgac                                                    20

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
tagccctgtg gttcttgtcc                                                    20

<210> SEQ ID NO 57
<211> LENGTH: 19
<212> TYPE: RNA
<213> ORGANISM: Artificial Sequence
<220> FEATURE:
<223> OTHER INFORMATION: synthetic
```

```
<400> SEQUENCE: 57
gcuugagagc guacaucug                                                19

<210> SEQ ID NO 58
<211> LENGTH: 21
<212> TYPE: RNA
<213> ORGANISM: Artificial Sequence
<220> FEATURE:
<223> OTHER INFORMATION: synthetic

<400> SEQUENCE: 58
aacguacgcg gaauacaacg a                                             21

<210> SEQ ID NO 59
<211> LENGTH: 1575
<212> TYPE: DNA
<213> ORGANISM: Homo sapiens

<400> SEQUENCE: 59
gcgaggcagc cagcgaggga gagagcgagc gggcgagccg gagcgaggaa gggaaagcgc     60
aagagagagc gcacacgcac acacccgccg cgcgcactcg cgcacggacc cgcacgggga    120
cagctcggaa gtcatcagtt ccatgggcga gatgctgctg ctggcgagat gtctgctgct    180
agtcctcgtc tcctcgctgc tggtatgctc gggactggcg tgcggaccgg cagggggtt    240 cgggaagagg aggcacccca aaaagctgac ccctttagcc tacaagcagt ttatccccaa    300
tgtggccgag aagaccctag cgccagcgg aaggtatgaa gggaagatct ccagaaactc    360
cgagcgattt aaggaactca ccccaatta caaccccgac atcatattta aggatgaaga    420
aaacaccgga gcggacaggc tgatgactca gaggtgtaag acaagttga acgctttggc    480 catctcggtg atgaaccagt ggccaggagt gaaactgcgg gtgaccgagg ctgggacga    540 agatggccac cactcagagg agtctctgca ctacgagggc cgcgcagtgg acatcaccac    600
gtctgaccgc gaccgcagca agtacggcat gctggcccgc ctggcggtgg aggccggctt    660
cgactgggtg tactacgagt ccaaggcaca tatccactgc tcggtgaaag cagagaactc    720
ggtggcggcc aaatcgggag gctgcttccc gggctcggcc acggtgcacc tggagcaggg    780
cggcaccaag ctggtgaagg acctgagccc cggggaccgc gtgctggcgg cggacgacca    840
gggccggctg ctctacagcg acttcctcac tttcctggac cgcgacgacg cgccaagaa    900 ggtcttctac gtgatcgaga cgcgggagc gcgcgagcgc ctgctgctca ccgccgcgca    960
cctgctcttt gtggcgccgc acaacgactc ggccaccggg gagcccgagg cgtcctcggg   1020
ctcggggccg ccttccgggg gcgcactggg gcctcgggcg ctgttcgcca gccgcgtgcg   1080
cccgggccag cgcgtgtacg tggtggccga gcgtgacggg gaccgccggc tcctgcccgc   1140
cgctgtgcac agcgtgaccc taagcgagga ggccgcgggc gcctacgcgc gctcacggc    1200 ccagggcacc attctcatca accgggtgct ggcctcgtgc tacgcggtca tcgaggagca   1260
cagctgggcg caccgggcct tcgcgcccct ccgcctggcg cacgcgctcc tggctgcact   1320
ggcgcccgcg cgcacggacc gcggcgggga cagcggcggc ggggaccgcg ggcggcg     1380 cggcagagta gccctaaccg ctccaggtgc tgccgacgct ccgggtgcgg gggccaccgc   1440
gggcatccac tggtactcgc agctgctcta ccaaataggc acctggctcc tggacagcga   1500
ggccctgcac ccgctgggca tggcggtcaa gtccagctga agccgggggg ccggggagg   1560 ggcgcgggag ggggc                                                   1575
```

<210> SEQ ID NO 60
<211> LENGTH: 462
<212> TYPE: PRT
<213> ORGANISM: Homo sapiens

<400> SEQUENCE: 60

```
Met Leu Leu Leu Ala Arg Cys Leu Leu Val Leu Val Ser Ser Leu
 1               5                  10                  15

Leu Val Cys Ser Gly Leu Ala Cys Gly Pro Gly Arg Gly Phe Gly
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380
```

```
Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
            405                 410                 415

Ala Pro Gly Ala Ala Asp Ala Pro Gly Ala Gly Ala Thr Ala Gly Ile
        420                 425                 430

His Trp Tyr Ser Gln Leu Leu Tyr Gln Ile Gly Thr Trp Leu Leu Asp
        435                 440                 445

Ser Glu Ala Leu His Pro Leu Gly Met Ala Val Lys Ser Ser
    450                 455                 460
```

<210> SEQ ID NO 61
<211> LENGTH: 1314
<212> TYPE: DNA
<213> ORGANISM: Mus musculus

<400> SEQUENCE: 61

```
atgctgctgc tgctggccag atgttttctg gtgatccttg cttcctcgct gctggtgtgc      60
cccgggctgg cctgtgggcc cggcaggggg tttggaaaga ggcggcaccc caaaaagctg     120
acccctttag cctacaagca gtttattccc aacgtagccg agaagaccct aggggccagc     180
ggcagatatg aagggaagat acaagaaac tccgaacgat ttaaggaact caccccaat      240
tacaaccccg acatcatatt taaggatgag gaaaacacgg agcagaccg gctgatgact      300
cagaggtgca agacaagtt aaatgccttg ccatctctg tgatgaacca gtggcctgga      360
gtgaagctgc gagtgaccga gggctgggat gaggacggcc atcattcaga ggagtctcta      420
cactatgagg tcgagcagt ggacatcacc acgtccgacc gggaccgcag caagtacggc      480
atgctggctc gcctggctgt ggaagcaggt ttcgactggg tctactatga atccaaagct      540
cacatccact gttctgtgaa agcagagaac tccgtggcgg ccaaatccgg cggctgtttc      600
ccgggatccg ccaccgtgca cctggagcag ggcggcacca agctggtgaa ggacttacgt      660
cccggagacc gcgtgctggc ggctgacgac cagggccggc tgctgtacag cgacttcctc      720
accttcctgg accgcgacga aggcgccaag aaggtcttct acgtgatcga dacgctggag      780
ccgcgcgagc gcctgctgct caccgccgcg cacctgctct cgtggcgcc gcacaacgac      840
tcggggccca cgcccgggcc aagcgcgctc tttgccagcc gcgtgcgccc cgggcagcgc      900
gtgtacgtgg tggctgaacg cggcggggac cgccggctgc tgcccgccgc ggtgcacagc      960
gtgacgctgc gagaggagga ggcgggcgcg tacgcgccgc tcacggcgca cggcaccatt     1020
ctcatcaacc gggtgctcgc ctcgtgctac gctgtcatcg aggagcacag ctgggcacac     1080
cgggccttcg cgccttttccg cctggcgcac gcgctgctgg ccgcgctggc acccgcccgc     1140
acggacggcg ggggcggggg cagcatccct gcagcgcaat ctgcaacgga agcgaggggc     1200
gcggagccga ctgcgggcat ccactggtac tcgcagctgc tctaccacat ggcacctgg      1260
ctgttggaca gcgagaccat gcatcccttg ggaatggcgg tcaagtccag ctga          1314
```

<210> SEQ ID NO 62
<211> LENGTH: 429
<212> TYPE: PRT
<213> ORGANISM: Mus musculus

<400> SEQUENCE: 62

```
Phe Leu Val Ile Leu Ala Ser Ser Leu Leu Val Cys Pro Gly Leu Ala
1               5                   10                  15

Cys Gly Pro Gly Arg Gly Phe Gly Lys Arg Arg His Pro Lys Lys Leu
```

-continued

```
                        20                  25                  30
Thr Pro Leu Ala Tyr Lys Gln Phe Ile Pro Asn Val Ala Glu Lys Thr
             35                  40                  45
Leu Gly Ala Ser Gly Arg Tyr Glu Gly Lys Ile Thr Arg Asn Ser Glu
 50                  55                  60
Arg Phe Lys Glu Leu Thr Pro Asn Tyr Asn Pro Asp Ile Ile Phe Lys
 65                  70                  75                  80
Asp Glu Asn Thr Gly Ala Asp Arg Leu Met Thr Gln Arg Cys Lys
                 85                  90                  95
Asp Lys Leu Asn Ala Leu Ala Ile Ser Val Met Asn Gln Trp Pro Gly
            100                 105                 110
Val Lys Leu Arg Val Thr Glu Gly Trp Asp Glu Asp Gly His His Ser
            115                 120                 125
Glu Glu Ser Leu His Tyr Glu Gly Arg Ala Val Asp Ile Thr Thr Ser
            130                 135                 140
Asp Arg Asp Arg Ser Lys Tyr Gly Met Leu Ala Arg Leu Ala Val Glu
145                 150                 155                 160
Ala Gly Phe Asp Trp Val Tyr Tyr Glu Ser Lys Ala His Ile His Cys
                165                 170                 175
Ser Val Lys Ala Glu Asn Ser Val Ala Ala Lys Ser Gly Gly Cys Phe
            180                 185                 190
Pro Gly Ser Ala Thr Val His Leu Glu Gln Gly Gly Thr Lys Leu Val
            195                 200                 205
Lys Asp Leu Arg Pro Gly Asp Arg Val Leu Ala Ala Asp Asp Gln Gly
210                 215                 220
Arg Leu Leu Tyr Ser Asp Phe Leu Thr Phe Leu Asp Arg Asp Glu Gly
225                 230                 235                 240
Ala Lys Lys Val Phe Tyr Val Ile Glu Thr Leu Glu Pro Arg Glu Arg
                245                 250                 255
Leu Leu Leu Thr Ala Ala His Leu Leu Phe Val Ala Pro His Asn Asp
            260                 265                 270
Ser Gly Pro Thr Pro Gly Pro Ser Ala Leu Phe Ala Ser Arg Val Arg
            275                 280                 285
Pro Gly Gln Arg Val Tyr Val Val Ala Glu Arg Gly Gly Asp Arg Arg
            290                 295                 300
Leu Leu Pro Ala Ala Val His Ser Val Thr Leu Arg Glu Glu Glu Ala
305                 310                 315                 320
Gly Ala Tyr Ala Pro Leu Thr Ala His Gly Thr Ile Leu Ile Asn Arg
                325                 330                 335
Val Leu Ala Ser Cys Tyr Ala Val Ile Glu Glu His Ser Trp Ala His
            340                 345                 350
Arg Ala Phe Ala Pro Phe Arg Leu Ala His Ala Leu Leu Ala Ala Leu
            355                 360                 365
Ala Pro Ala Arg Thr Asp Gly Gly Gly Gly Ser Ile Pro Ala Ala
            370                 375                 380
Gln Ser Ala Thr Glu Ala Arg Gly Ala Glu Pro Thr Ala Gly Ile His
385                 390                 395                 400
Trp Tyr Ser Gln Leu Leu Tyr His Ile Gly Thr Trp Leu Leu Asp Ser
                405                 410                 415
Glu Thr Met His Pro Leu Gly Met Ala Val Lys Ser Ser
            420                 425
```

<210> SEQ ID NO 63

<211> LENGTH: 1714
<212> TYPE: DNA
<213> ORGANISM: Rattus norvegicus

<400> SEQUENCE: 63

```
ttaaaatcag gctcttttg tcttttaatt gccgtctcga gacccaactc cgatgtgttc      60
cgttaccagc gaccggcagc ctgccatcgc agccctgtc tgggtgggga tcggagacaa     120
gtcccctgca gcaacagcag gcaaggttat ataggaagag aaagagccag gcagcgccag    180
agggaacgaa cgagccgagc gaggaaggga gagccgagcg caaggaggag cgcacacgca    240
cacacccgcg cgtaccagct cgcgcacaga ccggcgcggg gacggctcgc aagtcctcag    300
gttccgcgga cgagatgctg ctgctgctgg ccagatgttt tctggtggcc cttgcttcct    360
cgctgctggt gtgccccgga ctggcctgtg gcccggcag ggggtttgga aagaggcagc     420
accccaaaaa gctgacccct ttagcctaca agcagtttat ccccaacgta gccgagaaga    480
ccctagggc cagcggccga tatgaaggga agatcacaag aaactccgaa cgatttaagg     540
aactcacccc caattacaac cccgacatca tatttaagga tgaggaaaac actggagcag    600
accggctgat gactcagagg tgcaaagaca agttaaatgc cttggccatc tccgtgatga    660
accagtggcc tggagtgaag cttcgagtga ctgagggctg ggatgaggac ggccatcatt    720
cagaggagtc tctacactat gagggtcgag cagtggacat caccacgtct gacagggacc    780
gcagcaagta tggcatgctg gctcgcctgg ctgtggaggc tggattcgac tgggtctact    840
atgaatccaa agctcgcatc cactgctctg tgaaagcaga gaactccgtg gcggccaaat    900
ctgacggctg cttcccggga tcagccacag tgcacctgga gcagggtggc accaagttag    960
tgaaggatct aagtcccggg gaccgcgtgc tggcggctga cgaccagggc cggctgctgt   1020
acagcgactt cctcaccttc ctggaccgcg acgaaggtgc caagaaggtc ttctacgtga   1080
tcgagacgcg ggagccgcgg gagcgtctgc tgctcactgc cgcgcacctg ctcttcgtgg   1140
cgccgcacaa cgactccggg cccactccgg gaccgagccc actcttcgcc agccgcgtgc   1200
gtccggggca gcgcgtgtac gtggtggctg aacgcggcgg ggaccgccgg ctgctgcccg   1260
ccgcggtgca cagcgtaacg ctacgagagg aggcggcggg tgcgtacgcg ccgctcacgg   1320
cggacggcac cattctcatc aaccgggtgc tcgcctcgtg ctacgcagtc atcgaggagc   1380
acagctgggc acaccggcc ttcgcgccct tccgcctggc gcacgcgctg ctggccgcgc    1440
tggcaccccgc ccgcacggac ggcgggggcg ggggcagcat ccctgccccg caatctgtag   1500
cggaagcgag gggcgcaggg ccgcctgcgg gcatccactg gtactcgcag ctgctgtacc   1560
acattggcac ctggctgttg gacagcgaga ccctgcatcc cttgggaatg gcagtcaagt   1620
ccagctgaag tccgacggga ccgggcaggg ggcgtggggg cgggcgggcg ggaagcgact   1680
gccagataag caaccgggaa agcgcacgga agga                              1714
```

<210> SEQ ID NO 64
<211> LENGTH: 437
<212> TYPE: PRT
<213> ORGANISM: Rattus norvegicus

<400> SEQUENCE: 64

```
Met Leu Leu Leu Leu Ala Arg Cys Phe Leu Val Ala Leu Ala Ser Ser
 1               5                  10                  15

Leu Leu Val Cys Pro Gly Leu Ala Cys Gly Pro Gly Arg Gly Phe Gly
            20                  25                  30

Lys Arg Gln His Pro Lys Lys Leu Thr Pro Leu Ala Tyr Lys Gln Phe
```

```
                35                  40                  45
Ile Pro Asn Val Ala Glu Lys Thr Leu Gly Ala Ser Gly Arg Tyr Glu
 50                  55                  60
Gly Lys Ile Thr Arg Asn Ser Glu Arg Phe Lys Glu Leu Thr Pro Asn
 65                  70                  75                  80
Tyr Asn Pro Asp Ile Ile Phe Lys Asp Glu Asn Thr Gly Ala Asp
                 85                  90                  95
Arg Leu Met Thr Gln Arg Cys Lys Asp Lys Leu Asn Ala Leu Ala Ile
                100                 105                 110
Ser Val Met Asn Gln Trp Pro Gly Val Lys Leu Arg Val Thr Glu Gly
                115                 120                 125
Trp Asp Glu Asp Gly His His Ser Glu Glu Ser Leu His Tyr Glu Gly
            130                 135                 140
Arg Ala Val Asp Ile Thr Thr Ser Asp Arg Asp Arg Ser Lys Tyr Gly
145                 150                 155                 160
Met Leu Ala Arg Leu Ala Val Glu Ala Gly Phe Asp Trp Val Tyr Tyr
                165                 170                 175
Glu Ser Lys Ala Arg Ile His Cys Ser Val Lys Ala Glu Asn Ser Val
            180                 185                 190
Ala Ala Lys Ser Asp Gly Cys Phe Pro Gly Ser Ala Thr Val His Leu
            195                 200                 205
Glu Gln Gly Gly Thr Lys Leu Val Lys Asp Leu Ser Pro Gly Asp Arg
210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
                245                 250                 255
Glu Thr Arg Glu Pro Arg Glu Arg Leu Leu Leu Thr Ala Ala His Leu
            260                 265                 270
Leu Phe Val Ala Pro His Asn Asp Ser Gly Pro Thr Pro Gly Pro Ser
            275                 280                 285
Pro Leu Phe Ala Ser Arg Val Arg Pro Gly Gln Arg Val Tyr Val Val
            290                 295                 300
Ala Glu Arg Gly Gly Asp Arg Arg Leu Leu Pro Ala Ala Val His Ser
305                 310                 315                 320
Val Thr Leu Arg Glu Glu Ala Ala Gly Ala Tyr Ala Pro Leu Thr Ala
                325                 330                 335
Asp Gly Thr Ile Leu Ile Asn Arg Val Leu Ala Ser Cys Tyr Ala Val
            340                 345                 350
Ile Glu Glu His Ser Trp Ala His Arg Ala Phe Ala Pro Phe Arg Leu
            355                 360                 365
Ala His Ala Leu Leu Ala Ala Leu Ala Pro Ala Arg Thr Asp Gly Gly
            370                 375                 380
Gly Gly Gly Ser Ile Pro Ala Pro Gln Ser Val Ala Glu Ala Arg Gly
385                 390                 395                 400
Ala Gly Pro Pro Ala Gly Ile His Trp Tyr Ser Gln Leu Leu Tyr His
            405                 410                 415
Ile Gly Thr Trp Leu Leu Asp Ser Glu Thr Leu His Pro Leu Gly Met
            420                 425                 430
Ala Val Lys Ser Ser
            435

<210> SEQ ID NO 65
```

<211> LENGTH: 1546
<212> TYPE: DNA
<213> ORGANISM: Xenopus laevis

<400> SEQUENCE: 65

```
cgagcagaga ttgcccataa ttactgtctc gtctctacac ccccatgtgt tctgtgagcg      60
gggagctgca ccctggactt tctgcacctg ccttgcttgg gatcggtggc tagaggggtc     120
ggcgaggagg cacaaggttg ctggaagcag cagcgaagga gaacatcctc tgagcctttg     180
atgtaattgg cttcgctcgg acgagatgct ggttgcgaac tcgaatctct gttggctgct     240
gagcttcatc tgcaccctgg tgaccccccc tgggctggca tgtggacctg gccgaggcat     300
tggcaagagg agacacccca aaaaactcac ccctctcgcc tataagcagt tcatccccaa     360
cgtggcggag aagaccctgg gggccagcgg cagatacgaa ggaaagatta caaggaactc     420
ggattgcttt aaagaattaa ccccaatta taacccagat attatgttta aagacgagga     480
gagcaccggg gcggaccggc tcatgactca gagatgtaaa gacaaactga acgcactcgc     540
gatctccgtg atgaaccagt ggccgggggt gaagctgcgg gtgacggagg ggtgggatga     600
ggacgggcac cacttggagg agtcgctaca ttatgagggg agggcagtgg acatcactac     660
gtcggaccgg gaccgcagta aatacggaat gttgggccga ctggcggtgg aggccgggtt     720
cgactgggtc tattacgagt ccaaagctca tattcactgt tcggtcaaag cagagaactc     780
agtggcggcc aagtctggcg ggtgcttccc tgctggtgcc agggtgatgg tggaatttgg     840
tggcaccaaa gcggtgaaag acctgcgacc aggggaccgc gttctctcct ccgaccccca     900
agggaatctg ctctacagcg acttcctcat gttcatcgac caggagcgtg acgtcaagaa     960
gctcttttac gtcatcgaaa cgtctcgaga aaaaattcgg ttgaccgcgg cccatctact    1020
ttttgtggcc cagaccaagg tcaacggcac caggtcgttc aagtctgtct ttgccagcaa    1080
catccaacca ggagatctca tttatacagc agaatcccaa gaccatgacc ttgaagggcg    1140
gggaaagtgg agaaggttga tcttgaggga ggacactgga gcttatgcgc tctaactgc    1200
ccatgggact gtggttatag accaggtatt ggcctcctgc tatgcagtca ttgaggaaca    1260
cacctgggca cacctcgcat tgcgccact gaggtttggc atgagcctct cctcttatat    1320
ttaccccaga gactccagtc ctccatcagg ccttcagcct caccaccaag ttgaccttca    1380
gtctcaccat caagttgatc ttcagtctca ccaccaagtt gaccttcagt ctcaccacca    1440
acttgaaggc atccactggt actcccagct actgtatcag ataggactt ggcttttgga    1500
cagtagctcc ctgcacccac tgggcatggc aacgaaatcc agttga               1546
```

<210> SEQ ID NO 66
<211> LENGTH: 446
<212> TYPE: PRT
<213> ORGANISM: Xenopus laevis

<400> SEQUENCE: 66

```
Met Leu Val Ala Asn Ser Asn Leu Cys Trp Leu Leu Ser Phe Ile Cys
  1               5                  10                  15

Thr Leu Val Thr Pro Pro Gly Leu Ala Cys Gly Pro Gly Arg Gly Ile
             20                  25                  30

Gly Lys Arg Arg His Pro Lys Lys Leu Thr Pro Leu Ala Tyr Lys Gln
         35                  40                  45

Phe Ile Pro Asn Val Ala Glu Lys Thr Leu Gly Ala Ser Gly Arg Tyr
     50                  55                  60

Glu Gly Lys Ile Thr Arg Asn Ser Asp Cys Phe Lys Glu Leu Thr Pro
```

```
            65                  70                  75                  80
Asn Tyr Asn Pro Asp Ile Met Phe Lys Asp Glu Glu Ser Thr Gly Ala
                85                  90                  95

Asp Arg Leu Met Thr Gln Arg Cys Lys Asp Lys Leu Asn Ala Leu Ala
            100                 105                 110

Ile Ser Val Met Asn Gln Trp Pro Gly Val Lys Leu Arg Val Thr Glu
        115                 120                 125

Gly Trp Asp Glu Asp Gly His His Leu Glu Glu Ser Leu His Tyr Glu
    130                 135                 140

Gly Arg Ala Val Asp Ile Thr Thr Ser Asp Arg Asp Arg Ser Lys Tyr
145                 150                 155                 160

Gly Met Leu Gly Arg Leu Ala Val Glu Ala Gly Phe Asp Trp Val Tyr
                165                 170                 175

Tyr Glu Ser Lys Ala His Ile His Cys Ser Val Lys Ala Glu Asn Ser
            180                 185                 190

Val Ala Ala Lys Ser Gly Gly Cys Phe Pro Ala Gly Ala Arg Val Met
        195                 200                 205

Val Glu Phe Gly Gly Thr Lys Ala Val Lys Asp Leu Arg Pro Gly Asp
    210                 215                 220

Arg Val Leu Ser Ser Asp Pro Gln Gly Asn Leu Leu Tyr Ser Asp Phe
225                 230                 235                 240

Leu Met Phe Ile Asp Gln Glu Arg Asp Val Lys Lys Leu Phe Tyr Val
                245                 250                 255

Ile Glu Thr Ser Gln Arg Lys Ile Arg Leu Thr Ala Ala His Leu Leu
            260                 265                 270

Phe Val Ala Gln Thr Lys Val Asn Gly Thr Arg Ser Phe Lys Ser Val
        275                 280                 285

Phe Ala Ser Asn Ile Gln Pro Gly Asp Leu Ile Tyr Thr Ala Glu Ser
    290                 295                 300

Gln Asp His Asp Leu Glu Gly Arg Gly Lys Trp Arg Arg Leu Ile Leu
305                 310                 315                 320

Arg Glu Asp Thr Gly Ala Tyr Ala Pro Leu Thr Ala His Gly Thr Val
                325                 330                 335

Val Ile Asp Gln Val Leu Ala Ser Cys Tyr Ala Val Ile Glu Glu His
            340                 345                 350

Thr Trp Ala His Leu Ala Phe Ala Pro Leu Arg Phe Gly Met Ser Leu
        355                 360                 365

Ser Ser Tyr Ile Tyr Pro Arg Asp Ser Ser Pro Ser Gly Leu Gln
    370                 375                 380

Pro His His Gln Val Asp Leu Gln Ser His His Gln Val Asp Leu Gln
385                 390                 395                 400

Ser His His Gln Val Asp Leu Gln Ser His His Gln Leu Glu Gly Ile
                405                 410                 415

His Trp Tyr Ser Gln Leu Leu Tyr Gln Ile Gly Thr Trp Leu Leu Asp
            420                 425                 430

Ser Ser Ser Leu His Pro Leu Gly Met Ala Thr Lys Ser Ser
        435                 440                 445

<210> SEQ ID NO 67
<211> LENGTH: 1261
<212> TYPE: DNA
<213> ORGANISM: Homo sapiens

<400> SEQUENCE: 67
```

-continued

```
cccagcgctg caaggaccgc ctgaactcgc tggctatctc ggtgatgaac cagtggcccg    60
gtgtgaagct gcgggtgacc gagggctggg acgaggacgg ccaccactca gaggagtccc   120
tgcattatga gggccgcgcg gtggacatca ccacatcaga ccgcgaccgc aataagtatg   180
gactgctggc gcgcttggca gtggaggccg gctttgactg ggtgtattac gagtcaaagg   240
cccacgtgca ttgctccgtc aagtccgagc actcggccgc agcaacgacg ggcggctgct   300
tccctgccgg agcccaggta cgcctggaga gtggggcgcg tgtggccttg tcagccgtga   360
ggccgggaga ccgtgtgctg gccatggggg aggatgggag ccccaccttc agcgatgtgc   420
tcattttcct ggaccgcgag cctcacaggc tgagagcctt ccaggtcatc gagactcagg   480
acccccacg ccgcctggca ctcacacccg ctcacctgct ctttacggct gacaatcaca   540
cggagccggc agcccgcttc cgggccacat ttgccagcca cgtgcagcct ggccagtacg   600
tgctggtggc tggggtgcca ggcctgcagc ctgcccgcgt ggcagctgtc tctacacacg   660
tggccctcgg ggcctacgcc ccgctcacaa gcatgggac actggtggtg gaggatgtgg   720
tggcatcctg cttcgcggcc gtggctgacc accacctggc tcagttggcc ttctggcccc   780
tgagactctt tcacagcttg gcatggggca gctggacccc gggggagggt gtgcattggt   840
acccccagct gctctaccgc ctggggcgtc tcctgctaga gagggcagc ttccacccac   900
tgggcatgtc cggggcaggg agctgaaagg actccaccgc tgccctcctg gaactgctgt   960
actgggtcca gaagcctctc agccaggagg gagctggccc tggaagggac ctgagctggg  1020
ggacactggc cctgccatc tcctctgcca tgaagataca ccattgagac ttgactgggc  1080
aacaccagcg tcccccaccc ccgtcgtggt gtagtcatag agctgcaagc tgagctggcg  1140
aggggatggt tgttgacccc tctctcctag agaccttgag gctggcacgg cgactcccaa  1200
ctcagcctgc tctcactacg agttttcata ctctgcctcc cccattggga gggcccattc  1260
c                                                                 1261
```

<210> SEQ ID NO 68
<211> LENGTH: 293
<212> TYPE: PRT
<213> ORGANISM: Homo sapiens

<400> SEQUENCE: 68

```
Met Asn Gln Trp Pro Gly Val Lys Leu Arg Val Thr Glu Gly Trp Asp
  1               5                  10                  15
Glu Asp Gly His His Ser Glu Glu Ser Leu His Tyr Glu Gly Arg Ala
             20                  25                  30
Val Asp Ile Thr Thr Ser Asp Arg Asp Arg Asn Lys Tyr Gly Leu Leu
         35                  40                  45
Ala Arg Leu Ala Val Glu Ala Gly Phe Asp Trp Val Tyr Tyr Glu Ser
     50                  55                  60
Lys Ala His Val His Cys Ser Val Lys Ser Glu His Ser Ala Ala
 65                  70                  75                  80
Thr Thr Gly Gly Cys Phe Pro Ala Gly Ala Gln Val Arg Leu Glu Ser
                 85                  90                  95
Gly Ala Arg Val Ala Leu Ser Ala Val Arg Pro Gly Asp Arg Val Leu
            100                 105                 110
Ala Met Gly Glu Asp Gly Ser Pro Thr Phe Ser Asp Val Leu Ile Phe
        115                 120                 125
Leu Asp Arg Glu Pro His Arg Leu Arg Ala Phe Gln Val Ile Glu Thr
    130                 135                 140
```

```
Gln Asp Pro Pro Arg Arg Leu Ala Leu Thr Pro Ala His Leu Leu Phe
145                 150                 155                 160

Thr Ala Asp Asn His Thr Glu Pro Ala Ala Arg Phe Arg Ala Thr Phe
                165                 170                 175

Ala Ser His Val Gln Pro Gly Gln Tyr Val Leu Val Ala Gly Val Pro
            180                 185                 190

Gly Leu Gln Pro Ala Arg Val Ala Ala Val Ser Thr His Val Ala Leu
        195                 200                 205

Gly Ala Tyr Ala Pro Leu Thr Lys His Gly Thr Leu Val Val Glu Asp
    210                 215                 220

Val Val Ala Ser Cys Phe Ala Ala Val Ala Asp His His Leu Ala Gln
225                 230                 235                 240

Leu Ala Phe Trp Pro Leu Arg Leu Phe His Ser Leu Ala Trp Gly Ser
                245                 250                 255

Trp Thr Pro Gly Glu Gly Val His Trp Tyr Pro Gln Leu Leu Tyr Arg
                260                 265                 270

Leu Gly Arg Leu Leu Leu Glu Glu Gly Ser Phe His Pro Leu Gly Met
        275                 280                 285

Ser Gly Ala Gly Ser
    290

<210> SEQ ID NO 69
<211> LENGTH: 1277
<212> TYPE: DNA
<213> ORGANISM: Homo sapiens

<400> SEQUENCE: 69
```

| | | | | | |
|---|---|---|---|---|---|
| ccggcgcctc | atgacccagc | gctgcaagga | ccgcctgaac | tcgctggcta | tctcggtgat | 60 |
| gaaccagtgg | cccggtgtga | agctgcgggt | gaccgagggc | tgggacgagg | acggccacca | 120 |
| ctcagaggag | tccctgcatt | atgagggccg | cgcggtggac | atcaccacat | cagaccgcga | 180 |
| ccgcaataag | tatggactgc | tggcgcgctt | ggcagtggag | gccggctttg | actgggtgta | 240 |
| ttacgagtca | aaggcccacg | tgcattgctc | cgtcaagtcc | gagcactcgg | ccgcagccaa | 300 |
| gacgggcggc | tgcttccctg | ccggagccca | ggtacgcctg | agagtgggg | cgcgtgtggc | 360 |
| cttgtcagcc | gtgaggccgg | agaccgtgt | gctggccatg | ggggaggatg | ggagccccac | 420 |
| cttcagcgat | gtgctcattt | tcctggaccg | cgagccccac | aggctgagag | ccttccaggt | 480 |
| catcgagact | caggaccccc | cacgccgcct | ggcactcaca | cccgctcacc | tgctctttac | 540 |
| ggctgacaat | cacacggagc | cggcagcccg | cttccgggcc | acatttgcca | gccacgtgca | 600 |
| gcctggccag | tacgtgctgg | tggctggggt | gccaggcctg | cagcctgccc | gcgtggcagc | 660 |
| tgtctctaca | cacgtggccc | tcggggccta | cgccccgctc | acaaagcatg | gacactggt | 720 |
| ggtggaggat | gtggtggcat | cctgcttcgc | ggccgtggct | gaccaccacc | tggctcagtt | 780 |
| ggccttctgg | cccctgagac | tctttcacag | cttggcatgg | ggcagctgga | ccccggggga | 840 |
| gggtgtgcat | tggtaccccc | agctgctcta | ccgcctgggg | cgtctcctgc | tagaagaggg | 900 |
| cagcttccac | ccactgggca | tgtccgggc | agggagctga | aaggactcca | ccgctgccct | 960 |
| cctggaactg | ctgtactggg | tccagaagcc | tctcagccag | gagggagctg | ccctggaag | 1020 |
| ggacctgagc | tggggacac | tggctcctgc | catctcctct | gccatgaaga | tacaccattg | 1080 |
| agacttgact | gggcaacacc | agcgtccccc | accgcgtcg | tggtgtagtc | atagagctgc | 1140 |
| aagctgagct | ggcgagggga | tggttgttga | ccctctctc | ctagagacct | tgaggctggc | 1200 |
| acggcgactc | ccaactcagc | ctgctctcac | tacgagtttt | catactctgc | ctccccatt | 1260 | gggagggccc attcccc                                                          1277

<210> SEQ ID NO 70
<211> LENGTH: 312
<212> TYPE: PRT
<213> ORGANISM: Homo sapiens

<400> SEQUENCE: 70

Arg Arg Leu Met Thr Gln Arg Cys Lys Asp Arg Leu Asn Ser Leu Ala
 1               5                  10                  15

Ile Ser Val Met Asn Gln Trp Pro Gly Val Lys Leu Arg Val Thr Glu
            20                  25                  30

Gly Trp Asp Glu Asp Gly His His Ser Glu Glu Ser Leu His Tyr Glu
        35                  40                  45

Gly Arg Ala Val Asp Ile Thr Thr Ser Asp Arg Asp Arg Asn Lys Tyr
    50                  55                  60

Gly Leu Leu Ala Arg Leu Ala Val Glu Ala Gly Phe Asp Trp Val Tyr
65                  70                  75                  80

Tyr Glu Ser Lys Ala His Val His Cys Ser Val Lys Ser Glu His Ser
                85                  90                  95

Ala Ala Ala Lys Thr Gly Gly Cys Phe Pro Ala Gly Ala Gln Val Arg
            100                 105                 110

Leu Glu Ser Gly Ala Arg Val Ala Leu Ser Ala Val Arg Pro Gly Asp
        115                 120                 125

Arg Val Leu Ala Met Gly Glu Asp Gly Ser Pro Thr Phe Ser Asp Val
    130                 135                 140

Leu Ile Phe Leu Asp Arg Glu Pro His Arg Leu Arg Ala Phe Gln Val
145                 150                 155                 160

Ile Glu Thr Gln Asp Pro Pro Arg Arg Leu Ala Leu Thr Pro Ala His
                165                 170                 175

Leu Leu Phe Thr Ala Asp Asn His Thr Glu Pro Ala Ala Arg Phe Arg
            180                 185                 190

Ala Thr Phe Ala Ser His Val Gln Pro Gly Gln Tyr Val Leu Val Ala
        195                 200                 205

Gly Val Pro Gly Leu Gln Pro Ala Arg Val Ala Val Ser Thr His His
    210                 215                 220

Val Ala Leu Gly Ala Tyr Ala Pro Leu Thr Lys His Gly Thr Leu Val
225                 230                 235                 240

Val Glu Asp Val Val Ala Ser Cys Phe Ala Ala Val Ala Asp His His
                245                 250                 255

Leu Ala Gln Leu Ala Phe Trp Pro Leu Arg Leu Phe His Ser Leu Ala
            260                 265                 270

Trp Gly Ser Trp Thr Pro Gly Glu Gly Val His Trp Tyr Pro Gln Leu
        275                 280                 285

Leu Tyr Arg Leu Gly Arg Leu Leu Glu Glu Gly Ser Phe His Pro
    290                 295                 300

Leu Gly Met Ser Gly Ala Gly Ser
305                 310

<210> SEQ ID NO 71
<211> LENGTH: 1191
<212> TYPE: DNA
<213> ORGANISM: Mus musculus

<400> SEQUENCE: 71

```
atggctctgc cggccagtct gttgcccctg tgctgcttgg cactcttggc actatctgcc    60
cagagctgcg ggccgggccg aggaccggtt ggccggcggc gttatgtgcg caagcaactt   120
gtgcctctgc tatacaagca gtttgtgccc agtatgcccg agcggaccct gggcgcgagt   180
gggccagcgg aggggagggt aacaagggg tcggagcgct ccgggacct cgtacccaac    240
tacaaccccg acataatctt caaggatgag gagaacagcg gcgcagaccg cctgatgaca   300
gagcgttgca aagagcgggt gaacgctcta gccatcgcgg tgatgaacat gtggcccgga   360
gtacgcctac gtgtgactga aggctgggac gaggacggcc accacgcaca ggattcactc   420
cactacgaag gccgtgcctt ggacatcacc acgtctgacc gtgaccgtaa taagtatggt   480
tgttggcgc gcctagctgt ggaagccgga ttcgactggg tctactacga gtcccgcaac   540
cacatccacg tatcggtcaa agctgataac tcactggcgg tccgagccgg aggctgcttt   600
ccgggaaatg ccacggtgcg cttgcggagc ggcgaacgga aggggctgag ggaactacat   660
cgtggtgact gggtactggc cgctgatgca gcgggccgag tggtacccac gccagtgctg   720
ctcttcctgg accgggatct gcagcgccgc gcctcgttcg tggctgtgga accgagcgg    780
cctccgcgca aactgttgct cacacccctgg catctggtgt cgctgctcg cgggccagcg   840
cctgctccag gtgactttgc accggtgttc gcgcgccgct acgtgctgg cgactcggtg   900
ctggctcccg gcggggacgc gctccagccg gcgcgcgtag cccgcgtggc gcgcgaggaa   960
gccgtgggcg tgttcgcacc gctcactgcg cacgggacgc tgctggtcaa cgacgtcctc  1020
gcctcctgct acgcggttct agagagtcac cagtgggccc accgcgcctt cgcccctttg  1080
cggctgctgc acgcgctcgg ggctctgctc cctgggggtg cagtccagcc gactggcatg  1140
cattggtact ctcgcctcct ttaccgcttg gccgaggagt taatgggctg a           1191
```

<210> SEQ ID NO 72
<211> LENGTH: 396
<212> TYPE: PRT
<213> ORGANISM: Mus musculus

<400> SEQUENCE: 72

```
Met Ala Leu Pro Ala Ser Leu Leu Pro Leu Cys Cys Leu Ala Leu Leu
  1               5                  10                  15

Ala Leu Ser Ala Gln Ser Cys Gly Pro Gly Arg Gly Pro Val Gly Arg
             20                  25                  30

Arg Arg Tyr Val Arg Lys Gln Leu Val Pro Leu Leu Tyr Lys Gln Phe
         35                  40                  45

Val Pro Ser Met Pro Glu Arg Thr Leu Gly Ala Ser Gly Pro Ala Glu
     50                  55                  60

Gly Arg Val Thr Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
```

```
                165                 170                 175
Glu Ser Arg Asn His Ile His Val Ser Val Lys Ala Asp Asn Ser Leu
                180                 185                 190
Ala Val Arg Ala Gly Gly Cys Phe Pro Gly Asn Ala Thr Val Arg Leu
                195                 200                 205
Arg Ser Gly Glu Arg Lys Gly Leu Arg Glu Leu His Arg Gly Asp Trp
                210                 215                 220
Val Leu Ala Ala Asp Ala Ala Gly Arg Val Val Pro Thr Pro Val Leu
225                 230                 235                 240
Leu Phe Leu Asp Arg Asp Leu Gln Arg Ala Ser Phe Val Ala Val
                245                 250                 255
Glu Thr Glu Arg Pro Pro Arg Lys Leu Leu Leu Thr Pro Trp His Leu
                260                 265                 270
Val Phe Ala Ala Arg Gly Pro Ala Pro Ala Pro Gly Asp Phe Ala Pro
                275                 280                 285
Val Phe Ala Arg Arg Leu Arg Ala Gly Asp Ser Val Leu Ala Pro Gly
                290                 295                 300
Gly Asp Ala Leu Gln Pro Ala Arg Val Ala Arg Val Ala Arg Glu Glu
305                 310                 315                 320
Ala Val Gly Val Phe Ala Pro Leu Thr Ala His Gly Thr Leu Leu Val
                325                 330                 335
Asn Asp Val Leu Ala Ser Cys Tyr Ala Val Leu Glu Ser His Gln Trp
                340                 345                 350
Ala His Arg Ala Phe Ala Pro Leu Arg Leu Leu His Ala Leu Gly Ala
                355                 360                 365
Leu Leu Pro Gly Gly Ala Val Gln Pro Thr Gly Met His Trp Tyr Ser
                370                 375                 380
Arg Leu Leu Tyr Arg Leu Ala Glu Glu Leu Met Gly
385                 390                 395

<210> SEQ ID NO 73
<211> LENGTH: 3600
<212> TYPE: DNA
<213> ORGANISM: Homo sapiens

<400> SEQUENCE: 73
cccagactcc agccctggac cgcgcatccc gagcccagcg cccagacaga gtgtccccac    60
accctcctct gagacgccat gttcaactcg atgaccccac caccaatcag tagctatggc   120
gagccctgct gtctccggcc cctccccagt caggggccc ccagtgtggg gacagaagga   180
ctgtctggcc cgcccttctg ccaccaagct aacctcatgt ccggccccca cagttatggg   240
ccagccagag agaccaacag ctgcaccgag ggcccactct tttcttctcc ccggagtgca   300
gtcaagttga ccaagaagcg ggcactgtcc atctcacctc tgtcggatgc cagcctggac   360
ctgcagacgt tatccgcac ctcacccagc tccctcgtag ctttcatcaa ctcgcgatgc   420
acatctccag gaggctccta cggtcatctc tccattggca ccatgagccc atctctggga   480
ttcccagccc agatgaatca ccaaaaaggg ccctcgcctt cctttgggt ccagccttgt   540 ggtccccatg actctgcccg ggtgggatg atcccacatc ctcagtcccg ggacccttc   600 ccaacttgcc agctgaagtc tgagctggac atgctggttg gcaagtgccg ggaggaaccc   660
ttggaaggtg atatgtccag ccccaactcc acaggcatac aggatcccct gttggggatg   720
ctggatgggc gggaggacct cgagagagag gagaagcgtg agcctgaatc tgtgtatgaa   780
actgactgcc gttgggatgg ctgcagccag gaatttgact cccaagagca gctggtgcac   840
```

```
cacatcaaca gcgagcacat ccacggggag cggaaggagt tcgtgtgcca ctggggggc    900
tgctccaggg agctgaggcc cttcaaagcc cagtacatgc tggtggttca catgcgcaga    960
cacactggcg agaagccaca caagtgcacg tttgaagggt gccggaagtc atactcacgc   1020
ctcgaaaacc tgaagacgca cctgcggtca cacacgggtg agaagccata catgtgtgag   1080
cacgagggct gcagtaaagc cttcagcaat gccagtgacc gagccaagca ccagaatcgg   1140
acccattcca atgagaagcc gtatgtatgt aagctccctg gctgcaccaa acgctataca   1200
gatcctagct cgctgcgaaa acatgtcaag acagtgcatg gtcctgacgc ccatgtgacc   1260
aaacggcacc gtggggatgg cccctgcct cgggcaccat ccatttctac agtggagccc    1320
aagagggagc gggaaggagg tcccatcagg gaggaaagca gactgactgt gccagagggt   1380
gccatgaagc cacagccaag ccctggggcc cagtcatcct gcagcagtga ccactccccg   1440
gcagggagtg cagccaatac agacagtggt gtggaaatga ctggcaatgc agggggcagc   1500
actgaagacc tctccagctt ggacgaggga ccttgcattg ctggcactgg tctgtccact   1560
cttcgccgcc ttgagaacct caggctggac cagctacatc aactccggcc aatagggacc   1620
cggggtctca aactgcccag cttgtcccac accggtacca ctgtgtcccg ccgcgtgggc   1680
cccccagtct ctcttgaacg ccgcagcagc agctccagca gcatcagctc tgcctatact   1740
gtcagccgcc gctcctccct ggcctctcct ttcccccctg gctcccacc agagaatgga    1800
gcatcctccc tgcctggcct tatgcctgcc cagcactacc tgcttcgggc aagatatgct   1860
tcagccagag ggggtggtac ttcgcccact gcagcatcca gcctggatcg gataggtggt   1920
cttcccatgc ctccttggag aagccgagcc gagtatccag gatacaaccc caatgcaggg   1980
gtcacccgga gggccagtga cccagcccag gctgctgacc gtcctgctcc agctagagtc   2040
cagaggttca agagcctggg ctgtgtccat accccaccca ctgtggcagg gggaggacag   2100
aactttgatc cttacctccc aacctctgtc tactcaccac agcccccag catcactgag    2160
aatgctgcca tggatgctag agggctacag gaagagccag aagttgggac ctccatggtg   2220
ggcagtggtc tgaaccccta tatggacttc ccacctactg atactctggg atatggggga   2280
cctgaagggg cagcagctga gccttatgga gcgagggtc caggctctct gcctcttggg    2340
cctggtccac ccaccaacta tggcccaac cctgtcccc agcaggcctc atatcctgac     2400
cccacccaag aaacatgggg tgagttccct tcccactctg gctgtaccc aggccccaag    2460
gctctaggtg gaacctacag ccagtgtcct cgacttgaac attatggaca gtgcaagtc    2520
aagccagaac aggggtgccc agtggggtct gactccacag gactggcacc ctgcctcaat   2580
gcccacccca gtgagggcc cccacatcca cagcctctct tttcccatta ccccagccc    2640
tctcctcccc aatatctcca gtcaggcccc tataccccagc caccccctga ttatcttcct  2700
tcagaaccca ggccttgcct ggactttgat tccccccaccc attccacagg gcagctcaag  2760
gctcagcttg tgtgtaatta tgttcaatct caacaggagc tactgtggga gggtgggggc   2820
agggaagatg cccccgccca ggaaccttcc taccagagtc ccaagtttct gggggggttcc  2880
caggttagcc caagccgtgc taaagctcca gtgaacacat atggacctgg ctttggaccc   2940
aacttgccca tcacaagtc aggttcctat cccacccctt caccatgcca tgaaaattt     3000
gtagtggggg caaatagggc ttcacatagg gcagcagcac cacctcgact tctgcccca    3060
ttgcccactt gctatgggcc tctcaaagtg ggaggcacaa accccagctg tggtcatcct   3120
gaggtgggca ggctaggagg gggtcctgcc ttgtaccctc ctcccgaagg acaggtatgt   3180
```

| | | | | |
|---|---|---|---|---|
| aaccccctgg | actctcttga | tcttgacaac | actcagctgg | actttgtggc tattctggat | 3240 |
| gagcccagg | ggctgagtcc | tcctccttcc | catgatcagc | ggggcagctc tggacatacc | 3300 |
| ccacctccct | ctgggcccc | caacatggct | gtgggcaaca | tgagtgtctt actgagatcc | 3360 |
| ctacctgggg | aaacagaatt | cctcaactct | agtgcctaaa | gagtagggaa tctcatccat | 3420 |
| cacagatcgc | atttcctaag | gggtttctat | ccttccagaa | aaattggggg agctgcagtc | 3480 |
| ccctgcacaa | gatgcccag | ggatgggagg | tatgggctgg | gggctatgta tagtctgtat | 3540 |
| acgttttgag | gagaaatttg | ataatgacac | tgtttcctga | taataaagga actgcatcag | 3600 |

<210> SEQ ID NO 74
<211> LENGTH: 4909
<212> TYPE: DNA
<213> ORGANISM: Homo sapiens

<400> SEQUENCE: 74

| | | | | |
|---|---|---|---|---|
| gcgcccgccg | ccttacctga | ggccgccatc | cacgccggtt | gagtcgcgtt ctgccgcctc | 60 |
| ccgcctgtgg | tgcctcctga | actgcgtccg | ccgtctagtg | aagttcgtgg actcctacaa | 120 |
| taatgctata | aatgcataga | agaaaagaca | caggactgtg | aaagaaagtg atgatgcgat | 180 |
| gtctaaaacg | ttcaaggcac | cgcatctgtg | atcaagaata | catgtgctgc tttaccgaca | 240 |
| catcaaagag | caaggattgc | cacccaggac | gatgagcggc | tgagatggag acgtctgcct | 300 |
| cagccactgc | ctccgagaag | caagaagcca | aaagtgggat | cctggaggcc gctggcttcc | 360 |
| ccgacccggg | taaaaaggcc | tctcctttgg | tggtggctgc | agcggcagca gcagcggtag | 420 |
| ctgcccaagg | agcccagcct | tcaccttccc | ccaccccatc | aaccccgtgg cctaccagca | 480 |
| gattctgagc | cagcagaggg | gtctggggtc | agcctttgga | cacacaccac ccctgatcca | 540 |
| gccctcaccc | accttcctgg | cccagcagcc | catggccctc | acctccatca atgccacgcc | 600 |
| cacccagctc | agcagcagca | gcaactgtct | gagtgacacc | aaccagaaca agcagagcag | 660 |
| tgagtcggcc | gtcagcagca | ccgtcaaccc | tgtcgccatt | cacaagcgca gcaaggtcaa | 720 |
| gaccgagcct | gagggcctgc | ggccggcctc | ccctctggcg | ctgacgcagg agcagctggc | 780 |
| tgacctcaag | gaagatctgg | acagggatga | ctgtaagcag | gaggctgagg tggtcatcta | 840 |
| tgagaccaac | tgccactggg | aagactgcac | caaggagtac | gacacccagg agcagctggt | 900 |
| gcatcacatc | aacaacgagc | acatccacgg | ggagaagaag | gagtttgtgt gccgctggca | 960 |
| ggcctgcacg | cgggagcaga | agcccttcaa | ggcgcagtac | atgctggtgg tgcacatgcg | 1020 |
| gcgacacacg | ggcgagaagc | cccacaagtg | cacgttcgag | ggctgctcga aggcctactc | 1080 |
| ccgcctggag | aacctgaaga | cacacctgcg | gtcccacacc | ggggagaagc catatgtgtg | 1140 |
| tgagcacgag | ggctgcaaca | aagccttctc | caacgcctcg | gaccgcgcca agcaccagaa | 1200 |
| tcgcacccac | tccaacgaga | aaccctacat | ctgcaagatc | ccaggctgca ccaagagata | 1260 |
| cacagacccc | agctctctcc | ggaagcatgt | gaaaacggtc | cacggcccag atgcccacgt | 1320 |
| caccaagaag | cagcgcaatg | acgtgcacct | ccgcacaccg | ctgctcaaag agaatgggga | 1380 |
| cagtgaggcc | ggcacggagc | ctggcggccc | agagagcacc | gaggccagca gcaccagcca | 1440 |
| ggccgtggag | gactgcctgc | acgtcagagc | catcaagacc | gagagctccg gctgtgtca | 1500 |
| gtccagcccc | ggggcccagt | cgtcctgcag | cagcgagccc | tctcctctgg gcagtgcccc | 1560 |
| caacaatgac | agtggcgtgg | agatgccggg | gacggggccc | gggagcctgg gagacctgac | 1620 |
| ggcactggat | gacacacccc | caggggccga | cactcagcc | ctggctgccc cctccgctgg | 1680 |
| tggcctccag | ctgcgcaaac | acatgaccac | catgcaccgg | ttcgagcagc tcaagaagga | 1740 |

```
gaagctcaag tcactcaagg attcctgctc atgggccggg ccgactccac acacgcggaa   1800
caccaagctg cctcccctcc cgggaagtgg ctccatcctg gaaaacttca gtggcagtgg   1860
gggcggcggg cccgcggggc tgctgccgaa cccgcggctg tcggagctgt ccgcgagcga   1920
ggtgaccatg ctgagccagc tgcaggagcg ccgcgacagc tccaccagca cggtcagctc   1980
ggcctacacc gtgagccgcc gctcctccgg catctccccc tacttctcca gccgccgctc   2040
cagcgaggcc tcgcccctgg gcgccggccg cccgcacaac gcgagctccg ctgactccta   2100
cgaccccatc tccacggacg cgtcgcggcg ctcgagcgag gccagccagt gcagcggcgg   2160
ctccgggctg ctcaacctca cgccggcgca gcagtacagc ctgcgggcca agtacgcggc   2220
agccactggc ggcccccgc ccactccgct gccgggcctg gagcgcatga gcctgcggac   2280
caggctggcg ctgctggacg cggccgaggg cacgctgccc gccggctgcc cacgcccact   2340
ggggccgcgg cgtggcagcg acgggccgac ctatgccac ggccacgcgg gggctgcgcc   2400
cgccttcccc cacgaggctc caggcggcgg aaccaggcgg gccagcgacc ctgtgcggcg   2460
gcccgatgcc ctgtccctgc cgcgggtgca gcgcttccac agcacccaca acgtgaaccc   2520
cggcccgctg ccgcccctgtg ccgacaggcg aggcctccgc ctgcagagcc acccgagcac   2580
cgacggcggc ctggcccgcg gcgcctactc gccccggccg cctagcatca gcagaaacgt   2640
ggcgatggag gccgtggcgg caggagtgga cggcgcgggg cccgaggccg acctgggggct   2700
gccggaggac gacctggtgc ttccagacga cgtggtgcag tacatcaagg cgcacgccag   2760
tggcgctctg gacgagggca ccgggcaggt gtatcccacg gaaagcactg gcttctctga   2820
caacccaga ctaccagcc cggggctgca cggccagcgc aggatggtgg ctgcggactc   2880
caacgtgggc ccctccgccc ctatgctggg aggatgccag ttaggctttg gggcgccctc   2940
cagcctgaac aaaaataaca tgcctgtgca gtggaatgag gtgagctccg gcaccgtaga   3000
ctccctggcc agccaggtga agcctccacc ctttcctcag gcaacctgg cggtggtgca   3060
gcagaagcct gcctttggcc agtacccggg ctacagtccg caaggcctac aggctagccc   3120
tgggggcctg gacagcacgc agccacacct gcagccccgc agcggagccc ctcccaggg   3180
catccccagg gtaaactaca tgcagcagct gcgacagcca gtggcaggca gccagtgtcc   3240
tggcatgact accactatga gccccatgc ctgctatggc caagtccacc cccagctgag   3300
ccccagcacc atcagtgggg ccctcaacca gttcccccaa tcctgcagca acatgccagc   3360
caagccaggg catctggggc accctcagca gacagaagtg gcacctgacc ccaccacgat   3420
gggcaatcgc cacagggaac ttggggtccc caattcagcc ctggctggag tgccgccacc   3480
tcacccagtc cagagctacc cacagcagag ccatcacctg gcagcctcca tgagccagga   3540
gggctaccac caggtcccca gccttctgcc tgcccgccag cctggcttca tggagcccca   3600
aacaggcccg atggggtgg ctacagcagg ctttggccta gtgcagcccc ggcctcccct   3660
cgagcccagc cccactggcc gccaccgtgg ggtacgtgct gtgcagcagc agctggccta   3720
cgccagggcc acaggccatg ccatggctgc catgccgtcc agtcaggaaa cagcagaggc   3780
tgtgcccaag ggagcgatgg gcaacatggg gtcggtgcct cccagccgc ctccgcagga   3840
cgcaggtggg gccccggacc acagcatgct ctactactac ggccagatcc acatgtacga   3900
acaggatgga ggcctggaga acctcgggag ctgccaggtc atgcggtccc agccaccaca   3960
gccacaggct gtcaggaca gcatccagcc ccagccttg ccctcaccag ggtcaacca    4020
ggtgtccagc actgtggact cccagctcct ggaggccccc cagattgact tcgatgccat   4080
```

```
catggatgat ggcgatcact cgagtttgtt ctcgggtgct ctgagcccca gcctcctcca    4140
cagcctctcc cagaactcct cccgcctcac cacccccga aactccttga ccctgccctc      4200
catccccgca ggcatcagca acatggctgt cggggacatg agctccatgc tcaccagcct    4260
cgccgaggag agcaagttcc tgaacatgat gacctagagg cccgagcgcc tggtgctgag    4320
tgcacccgga ggggtcatcg ctgcccagag cctggggatt ccagctgtct tgtcttttc     4380 caaaaaagtg ttaaataggc ttgaggggtt gttgcgcaat ggccgcttca gatgacagat    4440
gttgtaagag aaggtttatg ggcatcctct ctggtctttt ggattattcc tcagaacaat    4500
gaaaaaagtc tccataggac aggaaggaat gcaaaactca tttacacagt gctttccagc    4560
ctttggtgct tacaggaccg cgctgttccg gcttcttcac ggctgacatt cggctaacga    4620
gggattactt tggccaaaac ctttcaaagg atatgcagaa agatggtagg gagcatttgg    4680
gtttgaatct gaatgctata ctggatactc tgctccggaa agatgagctt tttattctac    4740
tacttggaag gaaaggaat tcctctatga agcctaactc ttgaggtctc taacatacct     4800
tgtcatagag gaaaagcaca gattatacct ggatgattca ggagagtgta tatgaatgaa    4860
taaggcatcc aagtatatat gaatgaataa agtatgtaag tatcaccag              4909

<210> SEQ ID NO 75
<211> LENGTH: 5054
<212> TYPE: DNA
<213> ORGANISM: Homo sapiens

<400> SEQUENCE: 75
cgatactacg tgggcatttt tggtcgaaga gagctgaagt aatgagaaga catcatggag      60
gcccagtccc acagctccac gaccactgaa aagaaaaaag ttgagaattc catagtgaag     120
tgctccactc gaacagatgt gagcgagaaa gccgttgcct ccagcaccac ttctaatgag     180
gatgaaagtc ctggacagac ttatcacaga gagagaagaa acgcaatcac tatgcagcca     240
cagaatgtcc aggggctcag caaagtcagt gaggaacctt caacatcgag tgacgagagg     300
gcctcattga tcaagaaaga gatccatggg tccctgccac acgtggcgga gccctctgtg     360
ccgtaccgcg ggacggtgtt tgccatggac cccaggaatg gttacatgga gccccactac    420
caccctcctc atctttttcc tgccttccat cctcctgtac caattgatgc cagacatcat     480
gagggccgtt accattacga tccatctccg attcctccat gcatatgac ttccgcctta     540 tctagtagcc ctacgtatcc ggacctgccc ttcattagga tctccccaca ccggaaccc      600 gctgctgctt ccgagtctcc cttcagccct ccacatccct acattaatcc ctacatggac    660
tatatccgct ccttgcacag cagcccatcg ctctccatga tctcagcaac ccgtgggctg    720
agccctacag atgcgcccca tgcaggagtc agccagcag aatactatca tcagatggcc      780
ctgctaactg gccagcgcag cccctatgca gacattattc cctcagctgc caccgccggc    840
acgggggcca tccacatgga atatcttcat gctatggata gcaccagatt ctccagcccc    900
aggctgtcag ccaggccgag ccgaaaacgt acactgtcca tatcaccact ctccgatcat    960
agctttgacc ttcagaccat gataaggacg tctcccaact ccttggtcac gattctcaat   1020
aattcccgta gcagctcttc agcaagtggc tcctatggtc acttatctgc aagtgcaatc    1080
agccctgcct tgagcttcac ctactcttcc gcgcccgtct ctctccacat gcatcagcag   1140
atcctaagcc gacaacagag cttaggttca gcctttggac acagccctcc actcatccac   1200
cctgccccaa cttttccaac acagaggcct attccaggga tccctacggt tctgaacccc    1260
gtccaggtca gctccggccc ttctgagtcc tcacagaaca agcccacgag tgagtctgca    1320
```

-continued

```
gtgagcagca ctggtgaccc gatgcacaac aagaggtcca agatcaaacc cgatgaagac    1380
ctccccagcc cagggctcg ggggcagcag gaacagcccg aaggaacaac ccttgtcaag     1440
gaggaagggg acaaagatga aagcaaacag gagcctgaag tcatctatga gacaaactgc   1500
cactgggaag gctgcgcgag ggagttcgac acccaagagc agcttgtgca ccatataaat   1560
aacgaccata ttcatggaga gaagaaggag ttcgtgtgca ggtggctgga ctgctcaaga   1620
gagcagaaac ccttcaaagc ccagtatatg ttggtagtgc atatgagaag acacacgggc   1680
gagaagcctc acaaatgcac tttttgaaggt tgcacaaagg cctactcgag actagaaaac   1740
ttgaaaacac acttgagatc tcacactgga gagaaaccat acgtctgtga gcacgaaggt   1800
tgcaacaagg ctttctcaaa tgcctctgat cgcgccaaac accaaaacag aacgcattcc   1860
aatgagaaac catatgtgtg caaaatccca ggctgcacta agcgttacac agacccaagc   1920
tccctccgga acatgtgaa gacagtgcat ggcccagagg ctcatgtcac caagaagcag    1980
cgagggaca tccatcctcg gccgccaccc ccgagagatt ccggcagcca ttcacagtcc    2040
aggtcgcctg gccgaccgac tcagggagcc cttggtgagc agcaggacct cagcaacact   2100
acctcaaagc gggaagaatg cctccaggtg aaaaccgtca aggcagagaa gccaatgaca   2160
tctcagccaa gccctggtgg tcagtcttca tgcagcagcc aacagtcccc catcagcaac   2220
tattccaaca gtgggctcga gcttcctctg accgatggag gtagtatagg agacctcagt   2280
gccatcgatg aaaccccaat catggactca accatttcca ctgcaaccac agcccttgct   2340
ttgcaagcca ggagaaaccc ggcagggacc aaatggatgg agcacgtaaa actagaaagg   2400
ctaaaacaag tgaatggaat gtttccgcga ctgaacccca ttctaccccc taaagcccct   2460
gcggtctctc ctctcatagg aaatggcaca cagtccaaca cacctgcag cttgggtggg    2520
cccatgacgc ttctcccggg cagaagcgac ctctctgggg tggacgtcac tatgctgaac   2580
atgctcaaca aagggacag cagcgccagc accatcagct cggcctacct gagcagccgc    2640
cgctcctcag ggatctcgcc ctgcttctcc agccgccgct ccagcgaggc gtcacaggcc   2700
gagggccggc cgcagaacgt gagcgtggcc gactcctacg accccatctc caccgacgcc   2760
tcgcgccgct ccagcgaagc cagccagagc gacggcctgc ccagcctgct cagcctcacg   2820
cccgcccagc agtaccgcct caaggccaag tacgcggctg ccacaggagg gccgccgccg   2880
acgcccctgc ccaacatgga gaggatgagc ctgaagacgc gcctggcgct gctcgggat   2940
gccctcgagc ctggcgtggc cctgcctcca gttcatgccc cgaggaggtg cagcgacggg   3000
ggagcccacg gctacgggcg gcgccacctg cagccgcacg atgcgctggg ccacggcgtg   3060
aggagggcca gcgacccggt gcggacaggc tccgagggcc tggccctgcc tcgtgtgccg   3120
cgcttcagca gcctcagcag ctgcaacccc ccggcgatgg ccacgtccgc ggagaagcgc   3180
agtctcgtgc ttcagaatta cacgcggccc gagggcggcc agtcccgaaa cttccactcg   3240
tccccctgtc ctcccagcat caccgagaac gtcaccctgg agtccctgac catggacgct   3300
gatgccaacc tgaacgatga ggatttcctg ccggacgacg tggtgcagta tttaaattcc   3360
cagaaccaag cagggtacga gcagcacttc cccagcgccc tcccggacga cagcaaagtg   3420
ccccacgggc ccgtgacttt tgacgcgccc gggctgccag acagccacgc tggccagcag   3480
ttccatgccc tcgagcagcc ctgccccgag ggcagcaaaa ccgacctgcc cattcagtgg   3540
aacgaagtca gctccggaag cgccgacctg tcctcctcca agctcaagtg tgggccgcgg   3600
cccgctgtgc cgcagactcg cgcctttggg ttctgcaacg gcatggtcgt ccaccgcag    3660
```

```
aacccettga ggagcgggcc tgctgggggc tatcagaccc tcggggagaa cagcaacccc    3720
tacggtggcc cagagcactt gatgctccac aacagcccg gaagtggcac cagtggaaac    3780
gccttccatg aacagccctg taaggccccg cagtatggga actgtctcaa caggcagcca    3840
gtggcccctg gtgcactcga cggtgcctgt ggtgccggga ttcaagcctc aaagctgaag    3900
agcaccccca tgcaagggag cgggggccag ctgaatttcg gcctgccggt agcgccaaat    3960
gagtcagctg gcagcatggt gaatggcatg cagaaccagg acccagtggg acagggtac    4020
ctggctcacc agctcctcgg cgacagcatg cagcacccgg gggcaggccg ccccggtcag    4080
cagatgcttg gcagattag tgctacctca cacatcaaca tctaccaagg ccagagagc    4140
tgcctgccag gggctcacgg catgggcagc cagccgtcaa gcttggcagt tgtcagggc    4200
taccagccat gtgccagctt tgggggcagc aggcgccagg ctatgccgag ggacagcctt    4260
gctctgcagt caggacagct cagtgacaca agtcagacct gcagggtgaa tggtatcaag    4320
atggagatga agggcagcc ccatccgctg tgctctaatc tgcagaatta ctctggtcag    4380
ttctatgacc aaaccgtggg cttcagtcag caagacacga agctggttc attctctatt    4440
tcagacgcca gctgcctgct acaggggacc agcgccaaaa actctgagtt acttccccca    4500
ggtgctaatc aggtgacaag cacagtggac agcctcgaca gccatgacct ggaaggggta    4560
cagattgact tcgatgccat catagacgat ggggaccact ccagcctgat gtcggggcc    4620
ctgagcccaa gtatcattca gaaccttttcc catagctcct cccgcctcac cacgcctcgg    4680
gcgtccctcc cattcccagc gctgtccatg agcaccacca acatggctat cggggacatg    4740
agttctttgc tgacctcct agcggaagaa agcaaattcc ttgcagttat gcaataggct    4800
ttaggaaaaa aagactgcaa ccaacggaaa tcaataggag ttgaagagat taaactgact    4860
ttgtttggc tgttttttta gttctgtatg tattttagca atctcatctc acctaactga    4920
gatgtgtttc aattatattc cttttatgga aaaggactct gaaaaaccct aaagtattct    4980
agggagaaac tgtcttccat ttcagttttg aatcagtatt gttacactca aaccacccctc    5040
ttttaaaaaa aaaa                                                      5054
```

<210> SEQ ID NO 76
<211> LENGTH: 1106
<212> TYPE: PRT
<213> ORGANISM: Homo sapiens

<400> SEQUENCE: 76

Met Phe Asn Ser Met Thr Pro Pro Ile Ser Ser Tyr Gly Glu Pro
1               5                   10                  15

Cys Cys Leu Arg Pro Leu Pro Ser Gln Gly Ala Pro Ser Val Gly Thr
                20                  25                  30

Glu Gly Leu Ser Gly Pro Pro Phe Cys His Gln Ala Asn Leu Met Ser
            35                  40                  45

Gly Pro His Ser Tyr Gly Pro Ala Arg Glu Thr Asn Ser Cys Thr Glu
        50                  55                  60

Gly Pro Leu Phe Ser Ser Pro Arg Ser Ala Val Lys Leu Thr Lys Lys
65                  70                  75                  80

Arg Ala Leu Ser Ile Ser Pro Leu Ser Asp Ala Ser Leu Asp Leu Gln
                85                  90                  95

Thr Val Ile Arg Thr Ser Pro Ser Ser Leu Val Ala Phe Ile Asn Ser
                100                 105                 110

Arg Cys Thr Ser Pro Gly Gly Ser Tyr Gly His Leu Ser Ile Gly Thr
            115                 120                 125

```
Met Ser Pro Ser Leu Gly Phe Pro Ala Gln Met Asn His Gln Lys Gly
            130                 135                 140

Pro Ser Pro Ser Phe Gly Val Gln Pro Cys Gly Pro His Asp Ser Ala
145                 150                 155                 160

Arg Gly Gly Met Ile Pro His Pro Gln Ser Arg Gly Pro Phe Pro Thr
                    165                 170                 175

Cys Gln Leu Lys Ser Glu Leu Asp Met Leu Val Gly Lys Cys Arg Glu
                180                 185                 190

Glu Pro Leu Glu Gly Asp Met Ser Ser Pro Asn Ser Thr Gly Ile Gln
            195                 200                 205

Asp Pro Leu Leu Gly Met Leu Asp Gly Arg Glu Asp Leu Glu Arg Glu
210                 215                 220

Glu Lys Arg Glu Pro Glu Ser Val Tyr Glu Thr Asp Cys Arg Trp Asp
225                 230                 235                 240

Gly Cys Ser Gln Glu Phe Asp Ser Gln Glu Gln Leu Val His His Ile
                245                 250                 255

Asn Ser Glu His Ile His Gly Glu Arg Lys Glu Phe Val Cys His Trp
            260                 265                 270

Gly Gly Cys Ser Arg Glu Leu Arg Pro Phe Lys Ala Gln Tyr Met Leu
            275                 280                 285

Val Val His Met Arg Arg His Thr Gly Glu Lys Pro His Lys Cys Thr
290                 295                 300

Phe Glu Gly Cys Arg Lys Ser Tyr Ser Arg Leu Glu Asn Leu Lys Thr
305                 310                 315                 320

His Leu Arg Ser His Thr Gly Glu Lys Pro Tyr Met Cys Glu His Glu
                325                 330                 335

Gly Cys Ser Lys Ala Phe Ser Asn Ala Ser Asp Arg Ala Lys His Gln
            340                 345                 350

Asn Arg Thr His Ser Asn Glu Lys Pro Tyr Val Cys Lys Leu Pro Gly
            355                 360                 365

Cys Thr Lys Arg Tyr Thr Asp Pro Ser Ser Leu Arg Lys His Val Lys
370                 375                 380

Thr Val His Gly Pro Asp Ala His Val Thr Lys Arg His Arg Gly Asp
385                 390                 395                 400

Gly Pro Leu Pro Arg Ala Pro Ser Ile Ser Thr Val Glu Pro Lys Arg
                405                 410                 415

Glu Arg Glu Gly Gly Pro Ile Arg Glu Glu Ser Arg Leu Thr Val Pro
            420                 425                 430

Glu Gly Ala Met Lys Pro Gln Pro Ser Pro Gly Ala Gln Ser Ser Cys
            435                 440                 445

Ser Ser Asp His Ser Pro Ala Gly Ser Ala Ala Asn Thr Asp Ser Gly
    450                 455                 460

Val Glu Met Thr Gly Asn Ala Gly Gly Ser Thr Glu Asp Leu Ser Ser
465                 470                 475                 480

Leu Asp Glu Gly Pro Cys Ile Ala Gly Thr Gly Leu Ser Thr Leu Arg
                485                 490                 495

Arg Leu Glu Asn Leu Arg Leu Asp Gln Leu His Gln Leu Arg Pro Ile
            500                 505                 510

Gly Thr Arg Gly Leu Lys Leu Pro Ser Leu Ser His Thr Gly Thr Thr
            515                 520                 525

Val Ser Arg Arg Val Gly Pro Pro Val Ser Leu Glu Arg Arg Ser Ser
530                 535                 540
```

-continued

```
Ser Ser Ser Ser Ile Ser Ser Ala Tyr Thr Val Ser Arg Arg Ser Ser
545                 550                 555                 560

Leu Ala Ser Pro Phe Pro Gly Ser Pro Glu Asn Gly Ala Ser
                565                 570                 575

Ser Leu Pro Gly Leu Met Pro Ala Gln His Tyr Leu Leu Arg Ala Arg
            580                 585                 590

Tyr Ala Ser Ala Arg Gly Gly Gly Thr Ser Pro Thr Ala Ala Ser Ser
        595                 600                 605

Leu Asp Arg Ile Gly Gly Leu Pro Met Pro Pro Trp Arg Ser Arg Ala
    610                 615                 620

Glu Tyr Pro Gly Tyr Asn Pro Asn Ala Gly Val Thr Arg Arg Ala Ser
625                 630                 635                 640

Asp Pro Ala Gln Ala Ala Asp Arg Pro Ala Pro Ala Arg Val Gln Arg
                645                 650                 655

Phe Lys Ser Leu Gly Cys Val His Thr Pro Thr Val Ala Gly Gly
                660                 665                 670

Gly Gln Asn Phe Asp Pro Tyr Leu Pro Thr Ser Val Tyr Ser Pro Gln
            675                 680                 685

Pro Pro Ser Ile Thr Glu Asn Ala Ala Met Asp Ala Arg Gly Leu Gln
        690                 695                 700

Glu Glu Pro Glu Val Gly Thr Ser Met Val Gly Ser Gly Leu Asn Pro
705                 710                 715                 720

Tyr Met Asp Phe Pro Pro Thr Asp Thr Leu Gly Tyr Gly Gly Pro Glu
                725                 730                 735

Gly Ala Ala Ala Glu Pro Tyr Gly Ala Arg Gly Pro Gly Ser Leu Pro
            740                 745                 750

Leu Gly Pro Gly Pro Pro Thr Asn Tyr Gly Pro Asn Pro Cys Pro Gln
        755                 760                 765

Gln Ala Ser Tyr Pro Asp Pro Thr Gln Glu Thr Trp Gly Glu Phe Pro
770                 775                 780

Ser His Ser Gly Leu Tyr Pro Gly Pro Lys Ala Leu Gly Gly Thr Tyr
785                 790                 795                 800

Ser Gln Cys Pro Arg Leu Glu His Tyr Gly Gln Val Gln Val Lys Pro
                805                 810                 815

Glu Gln Gly Cys Pro Val Gly Ser Asp Ser Thr Gly Leu Ala Pro Cys
            820                 825                 830

Leu Asn Ala His Pro Ser Glu Gly Pro Pro His Pro Gln Pro Leu Phe
        835                 840                 845

Ser His Tyr Pro Gln Pro Ser Pro Gln Tyr Leu Gln Ser Gly Pro
        850                 855                 860

Tyr Thr Gln Pro Pro Asp Tyr Leu Pro Ser Glu Pro Arg Pro Cys
865                 870                 875                 880

Leu Asp Phe Asp Ser Pro Thr His Ser Thr Gly Gln Leu Lys Ala Gln
                885                 890                 895

Leu Val Cys Asn Tyr Val Gln Ser Gln Gln Glu Leu Leu Trp Glu Gly
            900                 905                 910

Gly Gly Arg Glu Asp Ala Pro Ala Gln Glu Pro Ser Tyr Gln Ser Pro
        915                 920                 925

Lys Phe Leu Gly Gly Ser Gln Val Ser Pro Ser Arg Ala Lys Ala Pro
        930                 935                 940

Val Asn Thr Tyr Gly Pro Gly Phe Gly Pro Asn Leu Pro Asn His Lys
945                 950                 955                 960

Ser Gly Ser Tyr Pro Thr Pro Ser Pro Cys His Glu Asn Phe Val Val
```

```
                965                 970                 975
Gly Ala Asn Arg Ala Ser His Arg Ala Ala Pro Pro Arg Leu Leu
            980                 985                 990
Pro Pro Leu Pro Thr Cys Tyr Gly Pro Leu Lys Val Gly Gly Thr Asn
            995                 1000                1005
Pro Ser Cys Gly His Pro Glu Val Gly Arg Leu Gly Gly Gly Pro Ala
        1010                1015                1020
Leu Tyr Pro Pro Pro Glu Gly Gln Val Cys Asn Pro Leu Asp Ser Leu
1025                1030                1035                1040
Asp Leu Asp Asn Thr Gln Leu Asp Phe Val Ala Ile Leu Asp Glu Pro
                1045                1050                1055
Gln Gly Leu Ser Pro Pro Ser His Asp Gln Arg Gly Ser Ser Gly
            1060                1065                1070
His Thr Pro Pro Pro Ser Gly Pro Asn Met Ala Val Gly Asn Met
            1075                1080                1085
Ser Val Leu Leu Arg Ser Leu Pro Gly Glu Thr Glu Phe Leu Asn Ser
            1090                1095                1100
Ser Ala
1105

<210> SEQ ID NO 77
<211> LENGTH: 1241
<212> TYPE: PRT
<213> ORGANISM: Homo sapiens

<400> SEQUENCE: 77

Met Ala Leu Thr Ser Ile Asn Ala Thr Pro Thr Gln Leu Ser Ser Ser
  1               5                  10                  15

Ser Asn Cys Leu Ser Asp Thr Asn Gln Asn Lys Ser Ser Glu Ser
             20                  25                  30

Ala Val Ser Ser Thr Val Asn Pro Val Ala Ile His Lys Arg Ser Lys
             35                  40                  45

Val Lys Thr Glu Pro Glu Gly Leu Arg Pro Ala Ser Pro Leu Ala Leu
 50                  55                  60

Thr Gln Glu Gln Leu Ala Asp Leu Lys Glu Asp Leu Asp Arg Asp Asp
 65                  70                  75                  80

Cys Lys Gln Glu Ala Glu Val Val Ile Tyr Glu Thr Asn Cys His Trp
                 85                  90                  95

Glu Asp Cys Thr Lys Glu Tyr Asp Thr Gln Glu Gln Leu Val His His
            100                 105                 110

Ile Asn Asn Glu His Ile His Gly Glu Lys Lys Glu Phe Val Cys Arg
            115                 120                 125

Trp Gln Ala Cys Thr Arg Glu Gln Lys Pro Phe Lys Ala Gln Tyr Met
130                 135                 140

Leu Val Val His Met Arg Arg His Thr Gly Glu Lys Pro His Lys Cys
145                 150                 155                 160

Thr Phe Glu Gly Cys Ser Lys Ala Tyr Ser Arg Leu Glu Asn Leu Lys
                165                 170                 175

Thr His Leu Arg Ser His Thr Gly Glu Lys Pro Tyr Val Cys Glu His
            180                 185                 190

Glu Gly Cys Asn Lys Ala Phe Ser Asn Ala Ser Asp Arg Ala Lys His
            195                 200                 205

Gln Asn Arg Thr His Ser Asn Glu Lys Pro Tyr Ile Cys Lys Ile Pro
    210                 215                 220
```

```
Gly Cys Thr Lys Arg Tyr Thr Asp Pro Ser Ser Leu Arg Lys His Val
225                 230                 235                 240

Lys Thr Val His Gly Pro Asp Ala His Val Thr Lys Lys Gln Arg Asn
            245                 250                 255

Asp Val His Leu Arg Thr Pro Leu Leu Lys Glu Asn Gly Asp Ser Glu
        260                 265                 270

Ala Gly Thr Glu Pro Gly Gly Pro Glu Ser Thr Glu Ala Ser Ser Thr
    275                 280                 285

Ser Gln Ala Val Glu Asp Cys Leu His Val Arg Ala Ile Lys Thr Glu
290                 295                 300

Ser Ser Gly Leu Cys Gln Ser Ser Pro Gly Ala Gln Ser Ser Cys Ser
305                 310                 315                 320

Ser Glu Pro Ser Pro Leu Gly Ser Ala Pro Asn Asn Asp Ser Gly Val
                325                 330                 335

Glu Met Pro Gly Thr Gly Pro Gly Ser Leu Gly Asp Leu Thr Ala Leu
            340                 345                 350

Asp Asp Thr Pro Pro Gly Ala Asp Thr Ser Ala Leu Ala Ala Pro Ser
        355                 360                 365

Ala Gly Gly Leu Gln Leu Arg Lys His Met Thr Thr Met His Arg Phe
370                 375                 380

Glu Gln Leu Lys Lys Glu Lys Leu Lys Ser Leu Lys Asp Ser Cys Ser
385                 390                 395                 400

Trp Ala Gly Pro Thr Pro His Thr Arg Asn Thr Lys Leu Pro Pro Leu
                405                 410                 415

Pro Gly Ser Gly Ser Ile Leu Glu Asn Phe Ser Gly Ser Gly Gly Gly
            420                 425                 430

Gly Pro Ala Gly Leu Leu Pro Asn Pro Arg Leu Ser Glu Leu Ser Ala
        435                 440                 445

Ser Glu Val Thr Met Leu Ser Gln Leu Gln Glu Arg Arg Asp Ser Ser
450                 455                 460

Thr Ser Thr Val Ser Ser Ala Tyr Thr Val Ser Arg Arg Ser Ser Gly
465                 470                 475                 480

Ile Ser Pro Tyr Phe Ser Arg Arg Ser Ser Glu Ala Ser Pro Leu
                485                 490                 495

Gly Ala Gly Arg Pro His Asn Ala Ser Ser Ala Asp Ser Tyr Asp Pro
            500                 505                 510

Ile Ser Thr Asp Ala Ser Arg Arg Ser Ser Glu Ala Ser Gln Cys Ser
        515                 520                 525

Gly Gly Ser Gly Leu Leu Asn Leu Thr Pro Ala Gln Gln Tyr Ser Leu
530                 535                 540

Arg Ala Lys Tyr Ala Ala Ala Thr Gly Gly Pro Pro Thr Pro Leu
545                 550                 555                 560

Pro Gly Leu Glu Arg Met Ser Leu Arg Thr Arg Leu Ala Leu Leu Asp
                565                 570                 575

Ala Ala Glu Gly Thr Leu Pro Ala Gly Cys Pro Arg Pro Leu Gly Pro
            580                 585                 590

Arg Arg Gly Ser Asp Gly Pro Thr Tyr Gly His Gly His Ala Gly Ala
        595                 600                 605

Ala Pro Ala Phe Pro His Glu Ala Pro Gly Gly Thr Arg Arg Ala
610                 615                 620

Ser Asp Pro Val Arg Arg Pro Asp Ala Leu Ser Leu Pro Arg Val Gln
625                 630                 635                 640

Arg Phe His Ser Thr His Asn Val Asn Pro Gly Pro Leu Pro Pro Cys
```

-continued

```
            645                 650                 655
Ala Asp Arg Arg Gly Leu Arg Leu Gln Ser His Pro Ser Thr Asp Gly
                660                 665                 670
Gly Leu Ala Arg Gly Ala Tyr Ser Pro Arg Pro Ser Ile Ser Glu
            675                 680                 685
Asn Val Ala Met Glu Ala Val Ala Ala Gly Val Asp Gly Ala Gly Pro
        690                 695                 700
Glu Ala Asp Leu Gly Leu Pro Glu Asp Asp Leu Val Leu Pro Asp Asp
705                 710                 715                 720
Val Val Gln Tyr Ile Lys Ala His Ala Ser Gly Ala Leu Asp Glu Gly
                725                 730                 735
Thr Gly Gln Val Tyr Pro Thr Glu Ser Thr Gly Phe Ser Asp Asn Pro
            740                 745                 750
Arg Leu Pro Ser Pro Gly Leu His Gly Gln Arg Arg Met Val Ala Ala
            755                 760                 765
Asp Ser Asn Val Gly Pro Ser Ala Pro Met Leu Gly Gly Cys Gln Leu
        770                 775                 780
Gly Phe Gly Ala Pro Ser Ser Leu Asn Lys Asn Asn Met Pro Val Gln
785                 790                 795                 800
Trp Asn Glu Val Ser Ser Gly Thr Val Asp Ser Leu Ala Ser Gln Val
                805                 810                 815
Lys Pro Pro Pro Phe Pro Gln Gly Asn Leu Ala Val Val Gln Gln Lys
            820                 825                 830
Pro Ala Phe Gly Gln Tyr Pro Gly Tyr Ser Pro Gln Gly Leu Gln Ala
        835                 840                 845
Ser Pro Gly Gly Leu Asp Ser Thr Gln Pro His Leu Gln Pro Arg Ser
850                 855                 860
Gly Ala Pro Ser Gln Gly Ile Pro Arg Val Asn Tyr Met Gln Gln Leu
865                 870                 875                 880
Arg Gln Pro Val Ala Gly Ser Gln Cys Pro Gly Met Thr Thr Thr Met
                885                 890                 895
Ser Pro His Ala Cys Tyr Gly Gln Val His Pro Gln Leu Ser Pro Ser
            900                 905                 910
Thr Ile Ser Gly Ala Leu Asn Gln Phe Pro Gln Ser Cys Ser Asn Met
        915                 920                 925
Pro Ala Lys Pro Gly His Leu Gly His Pro Gln Gln Thr Glu Val Ala
        930                 935                 940
Pro Asp Pro Thr Thr Met Gly Asn Arg His Arg Glu Leu Gly Val Pro
945                 950                 955                 960
Asn Ser Ala Leu Ala Gly Val Pro Pro His Pro Val Gln Ser Tyr
            965                 970                 975
Pro Gln Gln Ser His His Leu Ala Ala Ser Met Ser Gln Glu Gly Tyr
        980                 985                 990
His Gln Val Pro Ser Leu Leu Pro Ala Arg Gln Pro Gly Phe Met Glu
            995                 1000                1005
Pro Gln Thr Gly Pro Met Gly Val Ala Thr Ala Gly Phe Gly Leu Val
        1010                1015                1020
Gln Pro Arg Pro Pro Leu Glu Pro Ser Pro Thr Gly Arg His Arg Gly
1025                1030                1035                1040
Val Arg Ala Val Gln Gln Gln Leu Ala Tyr Ala Arg Ala Thr Gly His
                1045                1050                1055
Ala Met Ala Ala Met Pro Ser Ser Gln Glu Thr Ala Glu Ala Val Pro
            1060                1065                1070
```

-continued

```
Lys Gly Ala Met Gly Asn Met Gly Ser Val Pro Pro Gln Pro Pro Pro
        1075                1080                1085

Gln Asp Ala Gly Gly Ala Pro Asp His Ser Met Leu Tyr Tyr Tyr Gly
        1090                1095                1100

Gln Ile His Met Tyr Glu Gln Asp Gly Gly Leu Glu Asn Leu Gly Ser
1105                1110                1115                1120

Cys Gln Val Met Arg Ser Gln Pro Pro Gln Pro Gln Ala Cys Gln Asp
            1125                1130                1135

Ser Ile Gln Pro Gln Pro Leu Pro Ser Pro Gly Val Asn Gln Val Ser
            1140                1145                1150

Ser Thr Val Asp Ser Gln Leu Leu Glu Ala Pro Gln Ile Asp Phe Asp
            1155                1160                1165

Ala Ile Met Asp Asp Gly Asp His Ser Ser Leu Phe Ser Gly Ala Leu
            1170                1175                1180

Ser Pro Ser Leu Leu His Ser Leu Ser Gln Asn Ser Ser Arg Leu Thr
1185                1190                1195                1200

Thr Pro Arg Asn Ser Leu Thr Leu Pro Ser Ile Pro Ala Gly Ile Ser
            1205                1210                1215

Asn Met Ala Val Gly Asp Met Ser Ser Met Leu Thr Ser Leu Ala Glu
            1220                1225                1230

Glu Ser Lys Phe Leu Asn Met Met Thr
            1235                1240

<210> SEQ ID NO 78
<211> LENGTH: 1597
<212> TYPE: PRT
<213> ORGANISM: Homo sapiens
<220> FEATURE:
<221> NAME/KEY: VARIANT
<222> LOCATION: 1597
<223> OTHER INFORMATION: Xaa = Any Amino Acid

<400> SEQUENCE: 78

Met Glu Ala Gln Ser His Ser Ser Thr Thr Thr Glu Lys Lys Lys Val
 1               5                  10                  15

Glu Asn Ser Ile Val Lys Cys Ser Thr Arg Thr Asp Val Ser Glu Lys
            20                  25                  30

Ala Val Ala Ser Ser Thr Thr Ser Asn Glu Asp Glu Ser Pro Gly Gln
        35                  40                  45

Thr Tyr His Arg Glu Arg Arg Asn Ala Ile Thr Met Gln Pro Gln Asn
    50                  55                  60

Val Gln Gly Leu Ser Lys Val Ser Glu Glu Pro Ser Thr Ser Ser Asp
65                  70                  75                  80

Glu Arg Ala Ser Leu Ile Lys Lys Glu Ile His Gly Ser Leu Pro His
                85                  90                  95

Val Ala Glu Pro Ser Val Pro Tyr Arg Gly Thr Val Phe Ala Met Asp
            100                 105                 110

Pro Arg Asn Gly Tyr Met Glu Pro His Tyr His Pro Pro His Leu Phe
        115                 120                 125

Pro Ala Phe His Pro Pro Val Pro Ile Asp Ala Arg His His Glu Gly
    130                 135                 140

Arg Tyr His Tyr Asp Pro Ser Pro Ile Pro Pro Leu His Met Thr Ser
145                 150                 155                 160

Ala Leu Ser Ser Ser Pro Thr Tyr Pro Asp Leu Pro Phe Ile Arg Ile
                165                 170                 175
```

-continued

```
Ser Pro His Arg Asn Pro Ala Ala Ser Glu Ser Pro Phe Ser Pro
            180                 185                 190

Pro His Pro Tyr Ile Asn Pro Tyr Met Asp Tyr Ile Arg Ser Leu His
        195                 200                 205

Ser Ser Pro Ser Leu Ser Met Ile Ser Ala Thr Arg Gly Leu Ser Pro
    210                 215                 220

Thr Asp Ala Pro His Ala Gly Val Ser Pro Ala Glu Tyr Tyr His Gln
225                 230                 235                 240

Met Ala Leu Leu Thr Gly Gln Arg Ser Pro Tyr Ala Asp Ile Ile Pro
                245                 250                 255

Ser Ala Ala Thr Ala Gly Thr Gly Ala Ile His Met Glu Tyr Leu His
            260                 265                 270

Ala Met Asp Ser Thr Arg Phe Ser Ser Pro Arg Leu Ser Ala Arg Pro
        275                 280                 285

Ser Arg Lys Arg Thr Leu Ser Ile Ser Pro Leu Ser Asp His Ser Phe
    290                 295                 300

Asp Leu Gln Thr Met Ile Arg Thr Ser Pro Asn Ser Leu Val Thr Ile
305                 310                 315                 320

Leu Asn Asn Ser Arg Ser Ser Ser Ala Ser Gly Ser Tyr Gly His
                325                 330                 335

Leu Ser Ala Ser Ala Ile Ser Pro Ala Leu Ser Phe Thr Tyr Ser Ser
            340                 345                 350

Ala Pro Val Ser Leu His Met His Gln Gln Ile Leu Ser Arg Gln Gln
        355                 360                 365

Ser Leu Gly Ser Ala Phe Gly His Ser Pro Pro Leu Ile His Pro Ala
    370                 375                 380

Pro Thr Phe Pro Thr Gln Arg Pro Ile Pro Gly Ile Pro Thr Val Leu
385                 390                 395                 400

Asn Pro Val Gln Val Ser Ser Gly Pro Ser Glu Ser Ser Gln Asn Lys
                405                 410                 415

Pro Thr Ser Glu Ser Ala Val Ser Ser Thr Gly Asp Pro Met His Asn
            420                 425                 430

Lys Arg Ser Lys Ile Lys Pro Asp Glu Asp Leu Pro Ser Pro Gly Ala
        435                 440                 445

Arg Gly Gln Gln Glu Gln Pro Glu Gly Thr Thr Leu Val Lys Glu Glu
    450                 455                 460

Gly Asp Lys Asp Glu Ser Lys Gln Glu Pro Glu Val Ile Tyr Glu Thr
465                 470                 475                 480

Asn Cys His Trp Glu Gly Cys Ala Arg Glu Phe Asp Thr Gln Glu Gln
                485                 490                 495

Leu Val His Ile Asn Asn Asp His Ile His Gly Glu Lys Lys Glu
            500                 505                 510

Phe Val Cys Arg Trp Leu Asp Cys Ser Arg Glu Gln Lys Pro Phe Lys
        515                 520                 525

Ala Gln Tyr Met Leu Val Val His Met Arg Arg His Thr Gly Glu Lys
    530                 535                 540

Pro His Lys Cys Thr Phe Glu Gly Cys Thr Lys Ala Tyr Ser Arg Leu
545                 550                 555                 560

Glu Asn Leu Lys Thr His Leu Arg Ser His Thr Gly Glu Lys Pro Tyr
                565                 570                 575

Val Cys Glu His Glu Gly Cys Asn Lys Ala Phe Ser Asn Ala Ser Asp
            580                 585                 590

Arg Ala Lys His Gln Asn Arg Thr His Ser Asn Glu Lys Pro Tyr Val
```

-continued

```
            595                 600                 605
Cys Lys Ile Pro Gly Cys Thr Lys Arg Tyr Thr Asp Pro Ser Ser Leu
    610                 615                 620

Arg Lys His Val Lys Thr Val His Gly Pro Glu Ala His Val Thr Lys
625                 630                 635                 640

Lys Gln Arg Gly Asp Ile His Pro Arg Pro Pro Pro Arg Asp Ser
                645                 650                 655

Gly Ser His Ser Gln Ser Arg Ser Pro Gly Arg Pro Thr Gln Gly Ala
            660                 665                 670

Leu Gly Glu Gln Gln Asp Leu Ser Asn Thr Thr Ser Lys Arg Glu Glu
                675                 680                 685

Cys Leu Gln Val Lys Thr Val Lys Ala Glu Lys Pro Met Thr Ser Gln
    690                 695                 700

Pro Ser Pro Gly Gly Gln Ser Ser Cys Ser Ser Gln Gln Ser Pro Ile
705                 710                 715                 720

Ser Asn Tyr Ser Asn Ser Gly Leu Glu Leu Pro Leu Thr Asp Gly Gly
                725                 730                 735

Ser Ile Gly Asp Leu Ser Ala Ile Asp Glu Thr Pro Ile Met Asp Ser
            740                 745                 750

Thr Ile Ser Thr Ala Thr Thr Ala Leu Ala Leu Gln Ala Arg Arg Asn
    755                 760                 765

Pro Ala Gly Thr Lys Trp Met Glu His Val Lys Leu Glu Arg Leu Lys
770                 775                 780

Gln Val Asn Gly Met Phe Pro Arg Leu Asn Pro Ile Leu Pro Pro Lys
785                 790                 795                 800

Ala Pro Ala Val Ser Pro Leu Ile Gly Asn Gly Thr Gln Ser Asn Asn
                805                 810                 815

Thr Cys Ser Leu Gly Gly Pro Met Thr Leu Leu Pro Gly Arg Ser Asp
            820                 825                 830

Leu Ser Gly Val Asp Val Thr Met Leu Asn Met Leu Asn Arg Arg Asp
    835                 840                 845

Ser Ser Ala Ser Thr Ile Ser Ser Ala Tyr Leu Ser Ser Arg Arg Ser
850                 855                 860

Ser Gly Ile Ser Pro Cys Phe Ser Ser Arg Arg Ser Ser Glu Ala Ser
865                 870                 875                 880

Gln Ala Glu Gly Arg Pro Gln Asn Val Ser Val Ala Asp Ser Tyr Asp
                885                 890                 895

Pro Ile Ser Thr Asp Ala Ser Arg Arg Ser Ser Glu Ala Ser Gln Ser
            900                 905                 910

Asp Gly Leu Pro Ser Leu Leu Ser Leu Thr Pro Ala Gln Gln Tyr Arg
    915                 920                 925

Leu Lys Ala Lys Tyr Ala Ala Ala Thr Gly Gly Pro Pro Pro Thr Pro
930                 935                 940

Leu Pro Asn Met Glu Arg Met Ser Leu Lys Thr Arg Leu Ala Leu Leu
945                 950                 955                 960

Gly Asp Ala Leu Glu Pro Gly Val Ala Leu Pro Pro Val His Ala Pro
                965                 970                 975

Arg Arg Cys Ser Asp Gly Gly Ala His Gly Tyr Gly Arg Arg His Leu
            980                 985                 990

Gln Pro His Asp Ala Leu Gly His Gly Val Arg Arg Ala Ser Asp Pro
    995                 1000                1005

Val Arg Thr Gly Ser Glu Gly Leu Ala Leu Pro Arg Val Pro Arg Phe
    1010                1015                1020
```

```
Ser Ser Leu Ser Ser Cys Asn Pro Pro Ala Met Ala Thr Ser Ala Glu
1025                1030                1035                1040

Lys Arg Ser Leu Val Leu Gln Asn Tyr Thr Arg Pro Glu Gly Gly Gln
            1045                1050                1055

Ser Arg Asn Phe His Ser Ser Pro Cys Pro Pro Ser Ile Thr Glu Asn
            1060                1065                1070

Val Thr Leu Glu Ser Leu Thr Met Asp Ala Asp Ala Asn Leu Asn Asp
            1075                1080                1085

Glu Asp Phe Leu Pro Asp Asp Val Val Gln Tyr Leu Asn Ser Gln Asn
            1090                1095                1100

Gln Ala Gly Tyr Glu Gln His Phe Pro Ser Ala Leu Pro Asp Asp Ser
1105                1110                1115                1120

Lys Val Pro His Gly Pro Gly Asp Phe Asp Ala Pro Gly Leu Pro Asp
            1125                1130                1135

Ser His Ala Gly Gln Gln Phe His Ala Leu Glu Gln Pro Cys Pro Glu
            1140                1145                1150

Gly Ser Lys Thr Asp Leu Pro Ile Gln Trp Asn Glu Val Ser Ser Gly
            1155                1160                1165

Ser Ala Asp Leu Ser Ser Ser Lys Leu Lys Cys Gly Pro Arg Pro Ala
            1170                1175                1180

Val Pro Gln Thr Arg Ala Phe Gly Phe Cys Asn Gly Met Val Val His
1185                1190                1195                1200

Pro Gln Asn Pro Leu Arg Ser Gly Pro Ala Gly Gly Tyr Gln Thr Leu
            1205                1210                1215

Gly Glu Asn Ser Asn Pro Tyr Gly Gly Pro Glu His Leu Met Leu His
            1220                1225                1230

Asn Ser Pro Gly Ser Gly Thr Ser Gly Asn Ala Phe His Glu Gln Pro
            1235                1240                1245

Cys Lys Ala Pro Gln Tyr Gly Asn Cys Leu Asn Arg Gln Pro Val Ala
1250                1255                1260

Pro Gly Ala Leu Asp Gly Ala Cys Gly Ala Gly Ile Gln Ala Ser Lys
1265                1270                1275                1280

Leu Lys Ser Thr Pro Met Gln Gly Ser Gly Gly Gln Leu Asn Phe Gly
            1285                1290                1295

Leu Pro Val Ala Pro Asn Glu Ser Ala Gly Ser Met Val Asn Gly Met
            1300                1305                1310

Gln Asn Gln Asp Pro Val Gly Gln Gly Tyr Leu Ala His Gln Leu Leu
            1315                1320                1325

Gly Asp Ser Met Gln His Pro Gly Ala Gly Arg Pro Gly Gln Gln Met
            1330                1335                1340

Leu Gly Gln Ile Ser Ala Thr Ser His Ile Asn Ile Tyr Gln Gly Pro
1345                1350                1355                1360

Glu Ser Cys Leu Pro Gly Ala His Gly Met Gly Ser Gln Pro Ser Ser
            1365                1370                1375

Leu Ala Val Val Arg Gly Tyr Gln Pro Cys Ala Ser Phe Gly Gly Ser
            1380                1385                1390

Arg Arg Gln Ala Met Pro Arg Asp Ser Leu Ala Leu Gln Ser Gly Gln
            1395                1400                1405

Leu Ser Asp Thr Ser Gln Thr Cys Arg Val Asn Gly Ile Lys Met Glu
            1410                1415                1420

Met Lys Gly Gln Pro His Pro Leu Cys Ser Asn Leu Gln Asn Tyr Ser
1425                1430                1435                1440
```

-continued

```
Gly Gln Phe Tyr Asp Gln Thr Val Gly Phe Ser Gln Gln Asp Thr Lys
                1445                1450                1455

Ala Gly Ser Phe Ser Ile Ser Asp Ala Ser Cys Leu Leu Gln Gly Thr
            1460                1465                1470

Ser Ala Lys Asn Ser Glu Leu Leu Ser Pro Gly Ala Asn Gln Val Thr
        1475                1480                1485

Ser Thr Val Asp Ser Leu Asp Ser His Asp Leu Glu Gly Val Gln Ile
    1490                1495                1500

Asp Phe Asp Ala Ile Ile Asp Asp Gly Asp His Ser Ser Leu Met Ser
1505                1510                1515                1520

Gly Ala Leu Ser Pro Ser Ile Ile Gln Asn Leu Ser His Ser Ser Ser
                1525                1530                1535

Arg Leu Thr Thr Pro Arg Ala Ser Leu Pro Phe Pro Val Ala Val His
            1540                1545                1550

Glu His His Gln His Gly Tyr Arg Gly His Glu Phe Phe Ala Asp Leu
        1555                1560                1565

Pro Ser Gly Arg Lys Gln Ile Pro Cys Ser Tyr Ala Ile Gly Phe Arg
    1570                1575                1580

Lys Lys Arg Leu Gln Pro Thr Glu Ile Asn Arg Ser Xaa
1585                1590                1595
```